US012458691B2

(12) United States Patent
Kwong et al.

(10) Patent No.: US 12,458,691 B2
(45) Date of Patent: Nov. 4, 2025

(54) HIV-1 ENV FUSION PEPTIDE IMMUNOGENS AND THEIR USE

(71) Applicant: The United States of America, as represented by the Secretary, Department of Health and Human Services, Bethesda, MD (US)

(72) Inventors: Peter Kwong, Washington, DC (US); Rui Kong, Bethesda, MD (US); Tongqing Zhou, Boyds, MD (US); John Mascola, Rockville, MD (US); Kai Xu, Bethesda, MD (US); Cheng Cheng, Bethesda, MD (US); Gwo-Yu Chuang, Rockville, MD (US); Kevin Liu, Bethesda, MD (US); Baoshan Zhang, Bethesda, MD (US); Li Ou, Potomac, MD (US); Wing-Pui Kong, Germantown, MD (US)

(73) Assignee: The United States of America, as represented by the Secretary Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/164,988

(22) Filed: Feb. 6, 2023

(65) Prior Publication Data

US 2023/0338507 A1 Oct. 26, 2023

Related U.S. Application Data

(63) Continuation of application No. 16/338,964, filed as application No. PCT/US2017/054959 on Oct. 3, 2017, now Pat. No. 11,602,559.

(Continued)

(51) Int. Cl.
*C12N 7/00* (2006.01)
*A61K 39/21* (2006.01)
(Continued)

(52) U.S. Cl.
CPC .......... *A61K 39/21* (2013.01); *A61K 47/6415* (2017.08); *A61K 47/643* (2017.08);
(Continued)

(58) Field of Classification Search
None
See application file for complete search history.

(56) References Cited

U.S. PATENT DOCUMENTS 6,932,971 B2 8/2005 Bachmann et al.
9,175,070 B2 11/2015 Mascola et al.
(Continued)

FOREIGN PATENT DOCUMENTS

WO WO 1989/009785 10/1989
WO WO8909785 * 10/1989
(Continued)

OTHER PUBLICATIONS

Koniev et al., "Developments and recent advancements in the field of endogenous amino acid selective bond forming reactions for bioconjugation," Chem. Soc. Rev. 44: 5495 (Year: 2015).*
(Continued)

*Primary Examiner* — M Franco G Salvoza
(74) *Attorney, Agent, or Firm* — Klarquist Sparkman, LLP

(57) ABSTRACT

Embodiments of immunogens based on the HIV-1 Env fusion peptide and methods of their use and production are disclosed. Nucleic acid molecules encoding the immunogens are also provided. In several embodiments, the immunogens can be used to generate an immune response to
(Continued)

HIV-1 Env in a subject, for example, to treat or prevent an HIV-1 infection in the subject.

20 Claims, 69 Drawing Sheets

Specification includes a Sequence Listing.

Related U.S. Application Data

(60) Provisional application No. 62/403,266, filed on Oct. 3, 2016.

(51) Int. Cl.
*A61K 47/64* (2017.01)
*A61P 31/18* (2006.01)
*C07K 14/005* (2006.01)
*A61K 39/00* (2006.01)

(52) U.S. Cl.
CPC ............ *A61K 47/646* (2017.08); *A61P 31/18* (2018.01); *C07K 14/005* (2013.01); *C12N 7/00* (2013.01); *A61K 2039/545* (2013.01); *A61K 2039/6037* (2013.01); *A61K 2039/6081* (2013.01); *C07K 2319/40* (2013.01); *C07K 2319/55* (2013.01); *C12N 2740/16023* (2013.01); *C12N 2740/16134* (2013.01); *C12N 2740/16171* (2013.01)

(56) References Cited

U.S. PATENT DOCUMENTS

2005/0271676 A1 12/2005 Sette et al.
2012/0258126 A1 10/2012 Scholler et al.

FOREIGN PATENT DOCUMENTS

WO WO 1993/015750 8/1993
WO WO 1997/014436 4/1997
WO WO 2000/040616 7/2000
WO WO 2001/024810 4/2001
WO WO 2006/077601 7/2006
WO WO-2010037402 A1 * 4/2010 ............ A61K 39/00
WO WO 2012/055985 5/2012
WO WO 2012/101235 8/2012
WO WO 2014/093702 6/2014

OTHER PUBLICATIONS

Haynes et al., "Conversion of an immunogenic human immunodeficiency virus (HIV) envelope synthetic peptide to a tolerogen in chimpanzees by the fusogenic domain of HIV gp41 envelope protein," *Journal of Experimental Medicine* 177.3: 717-727, 1993.
Kong et al., "Fusion peptide of HIV-1 as a site of vulnerability to neutralizing antibody," *Science* 352.6287: 828-833, 2016, including supplementary materials.
Kwong et al. "Rational design of vaccines to elicit broadly neutralizing antibodies to HIV-1," *Cold Spring Harbor Perspectives in Medicine* 1.1: a007278, 2011.
Ou et al., "Preclinical Development of a Fusion Peptide Conjugate as an HIV Vaccine Immunogen," *Scientific Reports* 10.1: 3032, Feb. 2020, including supplemental information (21 pages).
Pancera et al. "Structure and immune recognition of trimeric pre-fusion HIV-1 Env," *Nature* 514.7523: 455-461, 2014.
Reimer et al., "Matrix-MTM Adjuvant Induces Local Recruitment, Activation and Maturation of Central Immune Cells in Absence of Antigen," *PLoS One* 7.7: e41451, 2012.
Wegmann et al., "The Carbomer-Lecithin Adjuvant Adjuplex has Potent Immunoactivating Properties and Elicits Protective Adaptive Immunity against Influenza Virus Challenge in Mice," *Clinical and Vaccine Immunology* 22.9: 1004-1012, 2015.

* cited by examiner

FIG. 3A

| Class | Antibody | Heavy | | | | Light | | | |
|---|---|---|---|---|---|---|---|---|---|
| | | HV | HJ | HV ident (%) | CDR H3 | KV | KJ | KV ident (%) | CDR L3 |
| **Mouse 1868** | | | | | | | | | |
| vFP1 | vFP1.01 | HV1-15*01 | HJ1*03 | 94.5 | LRNYWYFDV SEQ ID NO: 159 | KV1-117*01 | KJ2*01 | 95.6 | FQGSHVPYT SEQ ID NO: 166 |
| vFP1 | vFP1.02 | HV1-15*01 | HJ1*03 | 94.5 | LRNYWYFDV SEQ ID NO: 159 | KV1-117*01 | KJ2*01 | 95.9 | FQGSHVPYT SEQ ID NO: 166 |
| vFP1 | vFP2.01 | HV1-15*01 | HJ2*01 | 96.5 | LKRFYYFDY SEQ ID NO: 160 | KV1-117*01 | KJ4*01 | 93.2 | FQGSHVPYT SEQ ID NO: 166 |
| vFP1 | vFP3.01 | HV1-15*01 | HJ2*01 | 95.2 | LKRFYYFDY SEQ ID NO: 160 | KV1-117*01 | KJ4*01 | 95.6 | FQGSHFPFT SEQ ID NO: 167 |
| vFP1 | vFP4.01 | HV1-12*01 | HJ1*03 | 94.6 | LLPKWYFDV SEQ ID NO: 161 | KV1-117*01 | KJ2*01 | 96.9 | FQGSHVPYT SEQ ID NO: 166 |
| vFP5 | vFP5.01 | HV3-6*01 | HJ3*01 | 94.9 | EGNYRAY SEQ ID NO: 162 | KV6-23*01 | KJ5*01 | 93.2 | QQYSSYPLT SEQ ID NO: 168 |
| vFP6 | vFP6.01 | HV1-7*01 | HJ2*01 | 93.1 | GYVAFHY SEQ ID NO: 163 | KV2-112*01 | KJ4*01 | 97.6 | QQLVQHPFT SEQ ID NO: 169 |
| **Mouse 2586** | | | | | | | | | |
| vFP1 | vFP7.01 | HV1-15*01 | HJ1*03 | 96.5 | LRLYGYFDV SEQ ID NO: 164 | KV1-117*01 | KJ2*01 | 99.0 | FQGSHIPYT SEQ ID NO: 170 |
| vFP1 | vFP7.02 | HV1-15*01 | HJ1*03 | 96.9 | LRLYGYFDV SEQ ID NO: 164 | KV1-117*01 | KJ2*01 | 98.6 | FQGSHVPYT SEQ ID NO: 166 |
| vFP1 | vFP7.03 | HV1-15*01 | HJ1*03 | 96.5 | LRLYWYFDV SEQ ID NO: 165 | KV1-117*01 | KJ2.01 | 99.3 | FQGSHVPYT SEQ ID NO: 166 |
| vFP1 | vFP7.04 | HV1-15*01 | HJ1*03 | 97.9 | LRLYWYFDV SEQ ID NO: 165 | KV1-117*01 | KJ2*01 | 98.0 | FQGSHVPYT SEQ ID NO: 166 |
| vFP1 | vFP7.05 | HV1-15*01 | HJ1*03 | 96.2 | LRLYWYFDV SEQ ID NO: 165 | KV1-117*01 | KJ2*01 | 96.6 | FQGSHVPYT SEQ ID NO: 166 |

FIG. 4A
1868-vFP1.01 – 8.2% breadth
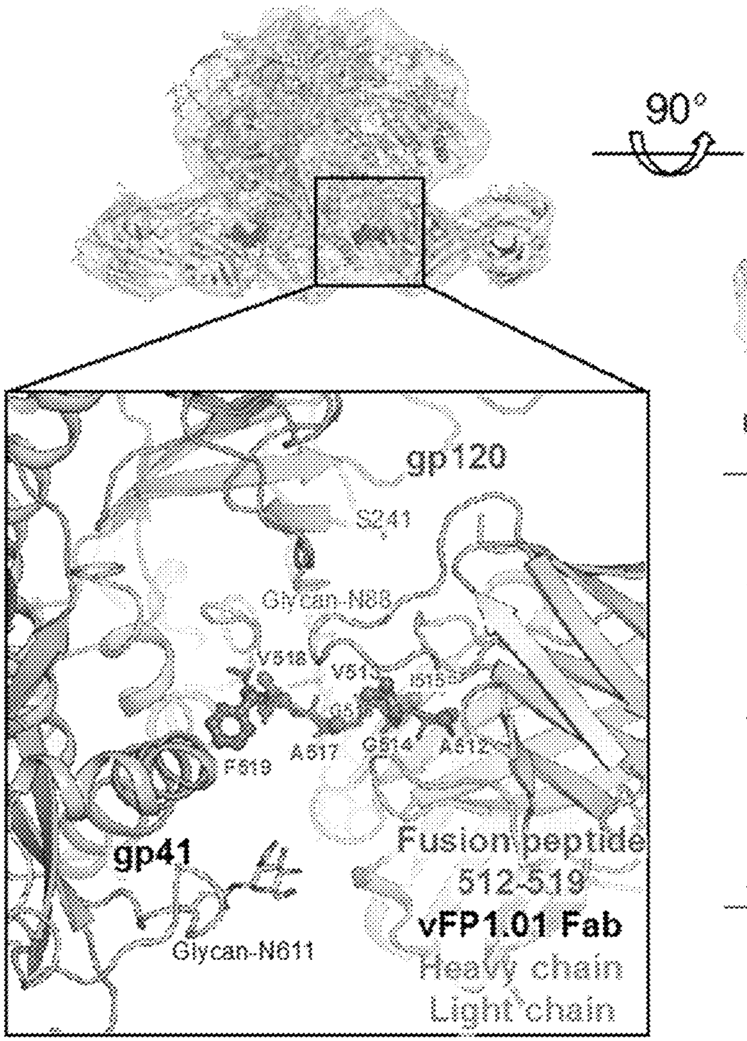
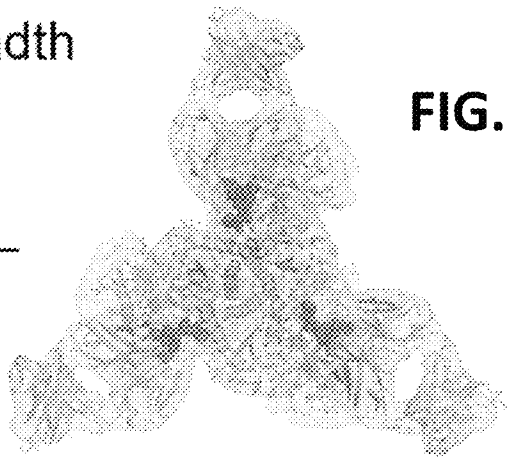
| Fusion peptide sequence | | Fusion peptide recognition and surface area | | |
|---|---|---|---|---|
| | | vFP1.01 contact area (Å²) | Accessible surface area (Å²) | Buried surface (%) |
| ✹ | A - 512 | 155.7 | 155.7 | 100.0 |
| ✹ | V | 133.1 | 133.1 | 100.0 |
| ● | G | 42.1 | 43.4 | 97.0 |
| ✹ | I | 188.2 | 191.6 | 98.2 |
| ● | G | 33.1 | 68.8 | 48.1 |
| ✹ | A | 40.6 | 58.9 | 68.8 |
| ● | V | 7.7 | 141.2 | 5.4 |
| ✹ | F - 519 | 9.0 | 253.8 | 3.5 |
✹ Main chain and side chain contact
● Main chain-only contact with vFP1.01

1868-vFP5.01 – 1.0% breadth

| Fusion peptide sequence | Fusion peptide recognition and surface area | | |
|---|---|---|---|
| | vFP5.01 contact area (Å$^2$) | Accessible surface area (Å$^2$) | Buried surface (%) |
| ✹ A - 512 | 35.3 | 108.6 | 32.5 |
| ✹ V | 153.9 | 153.9 | 100.0 |
| ● G | 46.0 | 46.0 | 100.0 |
| ✹ I | 174.7 | 174.7 | 100.0 |
| ● G | 38.4 | 55.7 | 69.1 |
| ✹ A | 24.5 | 35.0 | 70.1 |
| ✹ V | 17.1 | 146.5 | 11.7 |
| ✹ F - 519 | 129.7 | 233.2 | 55.6 |

✹ Main chain and side chain contact

● Main chain-only contact with vFP5.01

| | vFP1.01 | vFP5.01 | VRC34.01 |
|---|---|---|---|
| vFP1.01 | - | **60%** | **64%** |
| vFP5.01 | 24° | - | **48%** |
| VRC34.01 | 152° | 130° | - |

Fv domain overlap (%) and rotation (°)

FIG. 5A

| Immunization regimens | | | | | | | | SVA MLV | | | BG505 WT | | | BG505 Δ611 glycan | | | BG505 Δ88+Δ611 glycans | | | Hybridoma-identified antibodies |
|---|---|---|---|---|---|---|---|---|---|---|---|---|---|---|---|---|---|---|---|---|
| Mouse ID | Trimer prime | FP immunization | | | | Trimer Boost | Days post-prime | ID50 | ID80 | Max % Neut | ID50 | ID80 | Max % Neut | ID50 | ID80 | Max % Neut | ID50 | ID80 | Max % Neut | Cross-clade ΔGlycan-only Non-neutralizing |
| 2703 | T1 | FP6 | FP6 | FP6 | | | 71 | <20 | <20 | 36 | <20 | <20 | 41 | 221 | <20 | 79 | 471 | 48 | 85 | vFP12.01-06 |
| 2706 | T1 | FP7 | FP7 | FP7 | | | 71 | <20 | <20 | 50 | <20 | <20 | 36 | 66 | <20 | 75 | 210 | 27 | 63 | vFP13.01-03, vFP14.01-02 |
| 2711 | T1 | FP9 | FP9 | FP9 | | | 74 | <20 | <20 | 49 | <20 | <20 | 36 | 441 | 74 | 90 | 834 | 139 | 94 | vFP15.01-07 |
| 2712 | T1 | FP10 | FP10 | FP10 | | | 80 | 195 | <20 | 81 | 150 | <20 | 70 | 155 | 49 | 81 | 202 | 54 | 86 | vFP16.01-02 |
| 2713 | T1 | FP10 | FP10 | FP10 | | | 80 | 128 | <20 | 74 | 156 | <20 | 68 | 169 | 21 | 81 | 162 | 53 | 86 | vFP17.01 |
| 2714 | T1 | FP10 | FP10 | FP10 | | | 78 | 90 | <20 | 63 | 110 | <20 | 73 | 269 | 41 | 91 | 282 | 78 | 92 | vFP18.01-02, vFP19.01-02 |
| 2716 | T1 | FP8 | FP7 | FP6 | | T2 | 91 | <20 | <20 | 35 | 155 | 38 | 66 | 33,118 | 8,844 | 100 | 77,279 | 17,983 | 99 | vFP20.01 |
| 2717 | T1 | FP8 | FP7 | FP6 | | | 74 | <20 | <20 | 38 | <20 | <20 | 40 | 251 | 48 | 89 | 574 | 68 | 89 | vFP21.01 |
| 2718 | T1 | FP8 | FP9 | FP10 | | T2 | 92 | <20 | <20 | 45 | 20 | <20 | 50 | 1,732 | 187 | 95 | 4,292 | 382 | 95 | vFP22.01 |
| 2719 | T1 | FP8 | FP9 | FP10 | | | 78 | <20 | <20 | 35 | <20 | <20 | 47 | 123 | 22 | 82 | 241 | 67 | 94 | vFP23.01-03, vFP24.01, vFP25.01-18 |
| 2787 | T1 | FP8 | FP8 | FP8 | | | 68 | <20 | <20 | 34 | <20 | <20 | 44 | 178 | <20 | 61 | 314 | 25 | 82 | vFP26.01-04 |
| 2788 | T1 | FP8 | FP8 | FP8 | FP8 | | 90 | <20 | <20 | 33 | <20 | <20 | 25 | 89 | <20 | 78 | 167 | <20 | 80 | vFP27.01 |
| 2789 | T1 | FP8 | FP8 | FP8 | FP8 | | 91 | <20 | <20 | 39 | <20 | <20 | 36 | 250 | 28 | 84 | 342 | 67 | 91 | vFP28.01, vFP29.01 |
| 2790 | T1 | FP8 | FP8 | | | T2 | 68 | <20 | <20 | 34 | <20 | <20 | 41 | 1,649 | 54 | 87 | 772 | 148 | 95 | vFP30.01-02 |
| 2791 | T1 | FP8 | FP8 | | | T2 | 69 | <20 | <20 | 42 | 39 | <20 | 62 | 3,174 | 416 | 96 | 4,636 | 855 | 97 | vFP31.01 |
| 2792 | T1 | FP8 | FP8 | | | T2 | 69 | <20 | <20 | 35 | 29 | <20 | 57 | 1,243 | 297 | 98 | 3,808 | 789 | 98 | vFP32.01-07 |

Key:
FP6 = AVGIGA (residues 1-6, SEQ ID NO: 1)
FP7 = AVGIGAV (residues 1-7, SEQ ID NO: 1)
FP8 = AVGIGAVF (residues 1-8, SEQ ID NO: 1)
FP9 = AVGIGAVFL (residues 1-9, SEQ ID NO: 1)
FP10 = AVGIGAVFLG (SEQ ID NO: 1)
T1 = BG505 SOSIP
T2 = BG505 DS-SOSIP

| ID50 | ID80 |
|---|---|
| <40 | <20 |
| 40-100 | 20-100 |
| 100-1000 | |
| 1000-10000 | |
| 10000-100000 | |

FIG. 5C

IC50(µg/ml)

| Clade | A | A | B | B | C | A | AE | BC | C | C | # Neut (10 isolates) |
|---|---|---|---|---|---|---|---|---|---|---|---|
| Glycan missing | Complete | Complete | Complete | Complete | Complete | 241 | 241 & 611 | 448 | 241 | 241 | |
| Viral name | KER2008.12 | Q23.17 | 3988.25 | BL01.DG | 286.36 | BG505.W6M.C2 | CNE56 | CNE19 | 25710-2.43 | 0077.V1.C16 | |
| N123-VRC34.01 | 0.028 | 0.083 | 0.026 | 0.046 | 4.11 | 0.569 | >50 | 0.043 | 0.128 | 0.721 | 9 |
| 1868-vFP1.01 | 19.1 | 3.01 | >50 | >50 | >50 | 21.9 | 4.49 | 2.96 | 0.756 | 7.1 | 7 |
| 2703-vFP12.01 | >50 | 13.9 | 5.01 | >50 | >50 | >50 | 25.8 | >50 | >50 | >50 | 3 |
| 2703-vFP12.02 | >50 | 11.3 | 36.1 | >50 | >50 | >50 | 8.04 | 7.53 | 8.13 | 33.5 | 6 |
| 2703-vFP12.04 | 11.4 | 4.31 | 3.58 | 8.18 | 35.8 | 6.96 | 0.831 | 3.9 | 0.786 | 8.47 | 10 |
| 2703-vFP12.06 | 36.1 | 26.2 | 5.67 | 32.6 | >50 | 16.3 | 6.6 | 5.96 | 6.45 | >50 | 8 |
| 2711-vFP15.01 | 45.5 | 24.5 | >50 | >50 | 40.3 | 44.9 | 6.07 | 9.61 | 2.97 | >50 | 7 |
| 2711-vFP15.02 | 4.15 | 1.55 | 6.68 | 32.3 | 20 | 9.24 | 2.85 | 2.38 | 1.51 | 13.2 | 10 |
| 2711-vFP15.03 | 3.97 | 14.4 | >50 | >50 | 10.9 | 21.2 | 27.6 | 0.922 | 0.562 | 23.8 | 8 |
| 2711-vFP15.04 | 19.8 | 5.16 | >50 | >50 | >50 | 36.1 | 3.79 | 4.66 | 1.73 | 23.3 | 7 |
| 2711-vFP15.05 | 23 | 6.39 | 4.75 | >50 | 13.7 | 17.9 | 7.38 | 3.34 | 2.09 | 23.5 | 9 |
| 2711-vFP15.07 | 2.01 | 5.91 | 45.2 | >50 | 18.2 | >50 | 6.52 | 3.82 | 0.751 | 6.84 | 6 |
| 2712-vFP16.02 | 1.44 | 0.84 | 6.72 | 3.26 | 2.67 | 2.64 | 1.06 | 0.203 | 0.355 | 1.29 | 10 |
| 2713-vFP17.01 | >50 | >50 | 7.2 | 12.3 | >50 | 18.8 | 18.3 | 4.05 | 1.46 | 23.7 | 7 |
| 2716-vFP20.01 | 2.84 | 1.67 | 1.16 | 3.81 | 8.56 | 2.47 | 1.82 | 0.644 | 0.608 | 4.39 | 10 |
| 2787-vFP26.02 | >50 | 15.1 | 8.51 | >50 | >50 | 26.5 | 17.1 | 23.1 | 3.95 | 18.5 | 7 |
| 2787-vFP26.03 | 3.96 | 27.7 | >50 | 22.7 | >50 | 39.2 | 8.43 | 0.539 | 0.574 | 9.46 | 8 |
| 2787-vFP26.04 | 4.25 | 2.91 | 8.42 | 19.8 | 20.8 | 6.04 | 10.6 | 1.3 | 1.23 | 15.2 | 10 |
| 2788-vFP27.01 | 1.84 | 6.9 | 9.55 | >50 | 24.8 | 16.4 | 11 | 1.45 | 1.03 | 28.2 | 9 |
| 2790-vFP30.01 | 5.48 | 3.18 | 9.71 | 7.39 | 40.2 | 1.73 | 4.17 | 2.12 | 2.03 | 7.26 | 10 |
| 2791-vFP31.01 | 7.05 | 1.92 | 14.8 | 17.3 | 36.9 | 21.5 | 3.92 | 1.27 | 1.14 | 9.7 | 10 |
| 2792-vFP32.01 | 35.9 | 30.4 | >50 | 35.3 | >50 | 9.38 | 10.7 | 2.86 | 3.13 | 11.2 | 8 |
| 2792-vFP32.03 | >50 | 33.1 | >50 | 2.33 | >50 | 0.751 | 1.11 | 7.93 | 1.27 | 2.53 | 7 |
| 2792-vFP32.04 | 34.3 | 4.75 | >50 | 8.55 | >50 | 17.2 | 4.46 | 2.36 | 1.03 | 26.7 | 8 |
| 2792-vFP32.06 | 20.2 | 44.8 | >50 | >50 | >50 | 24.6 | 10.8 | 2.4 | 2.42 | 44.2 | 7 |
| 2792-vFP32.07 | >50 | 8.49 | >50 | 2.86 | >50 | 1.67 | 1.17 | 10.7 | 1.14 | 2.93 | 7 |

| Clade | | | A | | A | | B | | B | | C | | A | | AE | | BC | | C | | C | |
|---|---|---|---|---|---|---|---|---|---|---|---|---|---|---|---|---|---|---|---|---|---|---|
| Glycan missing | | | Complete | | Complete | | Complete | | Complete | | Complete | | 241 | | 241/611 | | 448 | | 241 | | 241 | |
| Viruses | SVA-MLV | | KER2008.12 | | Q23.17 | | 3988.25 | | BL01.DG | | 286.36 | | BG505 WT | | CNE56 | | CNE19 | | 25710-2.43 | | 0077.V1.C16 | |
| Mouse ID | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 |
| 2716 | <20 | <20 | 60 | <20 | 242 | <20 | 339 | 22 | 158 | 46 | 90 | <20 | 155 | 38 | 822 | 222 | 277 | 39 | 843 | 174 | 157 | 41 |
| 2718 | <20 | <20 | 28 | <20 | 41 | <20 | 40 | <20 | 36 | <20 | 26 | <20 | 20 | <20 | 59 | <20 | 32 | <20 | 119 | 32 | 35 | <20 |
| 2790 | <20 | <20 | 22 | <20 | 37 | <20 | 42 | <20 | 43 | <20 | 23 | <20 | <20 | <20 | 22 | <20 | 65 | <20 | 76 | <20 | 23 | <20 |
| 2791 | <20 | <20 | 39 | <20 | 61 | <20 | 69 | <20 | 73 | <20 | 45 | <20 | 39 | <20 | 75 | 25 | 61 | <20 | 134 | 26 | 45 | <20 |
| 2792 | <20 | <20 | 26 | <20 | 37 | <20 | 43 | <20 | 69 | 21 | 36 | <20 | 29 | <20 | 48 | 21 | 50 | <20 | 157 | 40 | 34 | <20 |

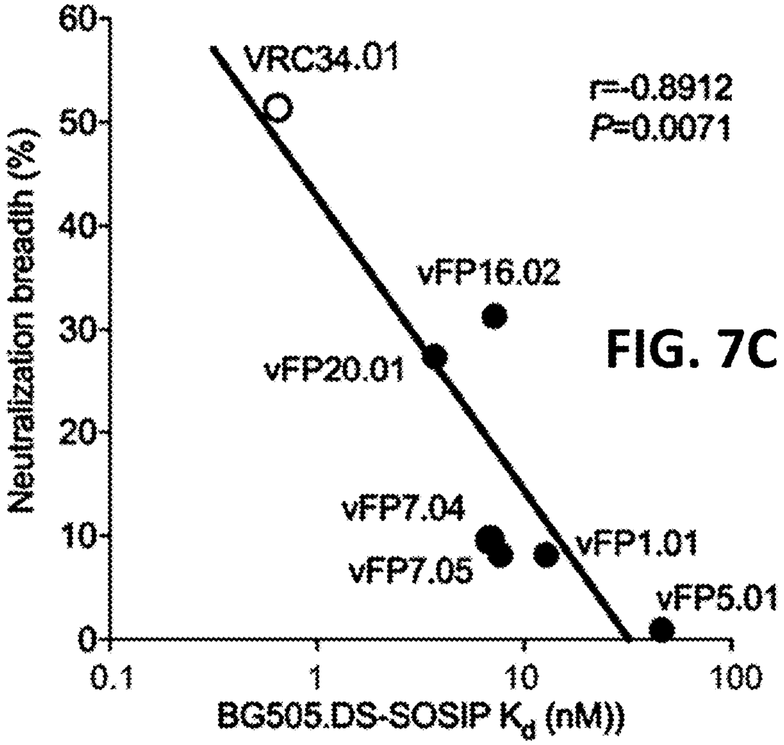
FIG. 7C
FIG. 7D
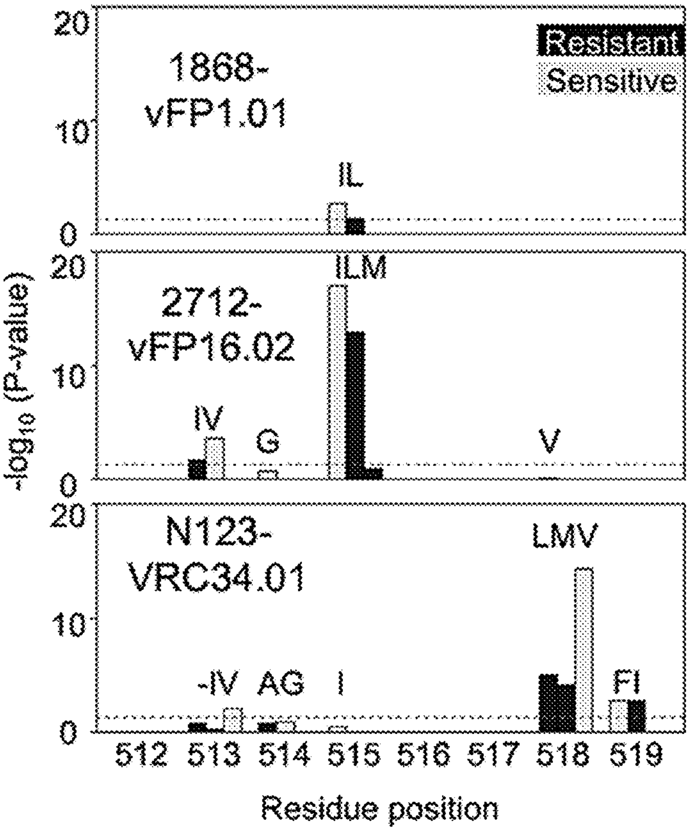

FIG. 7E

| | Residue 512-516 | Identical sequences in 208 HIV-1 isolates | Accumulative coverage (%) |
|---|---|---|---|
| Res. 1-5 of SEQ ID NO: 1 | AVGIG | 101 | 48.6 |
| Res. 1-5 of SEQ ID NO: 2 | AVGLG | 38 | 66.8 |
| Res. 1-5 of SEQ ID NO: 7 | AIGLG | 15 | 74.0 |
| Res. 1-5 of SEQ ID NO: 4 | AVGTIG | 9 | 78.4 |
| SEQ ID NO: 173 | AVGMG | 7 | 81.7 |
| Res. 1-4 of SEQ ID NO: 12 | AALG | 6 | 84.6 |
| SEQ ID NO: 174 | AIGMG | 4 | 86.5 |
| SEQ ID NO: 175 | AVVGLG | 3 | 88.0 |
| SEQ ID NO: 176 | TVGIG | 2 | 88.9 |
| SEQ ID NO: 177 | AVTMG | 2 | 89.9 |
| SEQ ID NO: 178 | AVTLG | 2 | 90.9 |
| SEQ ID NO: 179 | AVGTLG | 2 | 91.8 |
| SEQ ID NO: 180 | AVGMA | 2 | 92.8 |
| SEQ ID NO: 181 | AVGFG | 2 | 93.8 |
| SEQ ID NO: 182 | EVTLG | 1 | 94.2 |
| SEQ ID NO: 183 | DLGLG | 1 | 94.7 |
| SEQ ID NO: 184 | AVVELG | 1 | 95.2 |
| SEQ ID NO: 185 | AVTIG | 1 | 95.7 |
| SEQ ID NO: 186 | AVGVG | 1 | 96.2 |
| SEQ ID NO: 187 | AVGMLG | 1 | 96.6 |
| SEQ ID NO: 188 | AVGIVG | 1 | 97.1 |
| SEQ ID NO: 189 | AVGGIG | 1 | 97.6 |
| SEQ ID NO: 190 | AVGGFG | 1 | 98.1 |
| SEQ ID NO: 191 | AMGIG | 1 | 98.6 |
| SEQ ID NO: 192 | AIGIG | 1 | 99.0 |
| SEQ ID NO: 193 | AAIG | 1 | 99.5 |
| SEQ ID NO: 194 | AAGIG | 1 | 100.0 |

FIG. 7F

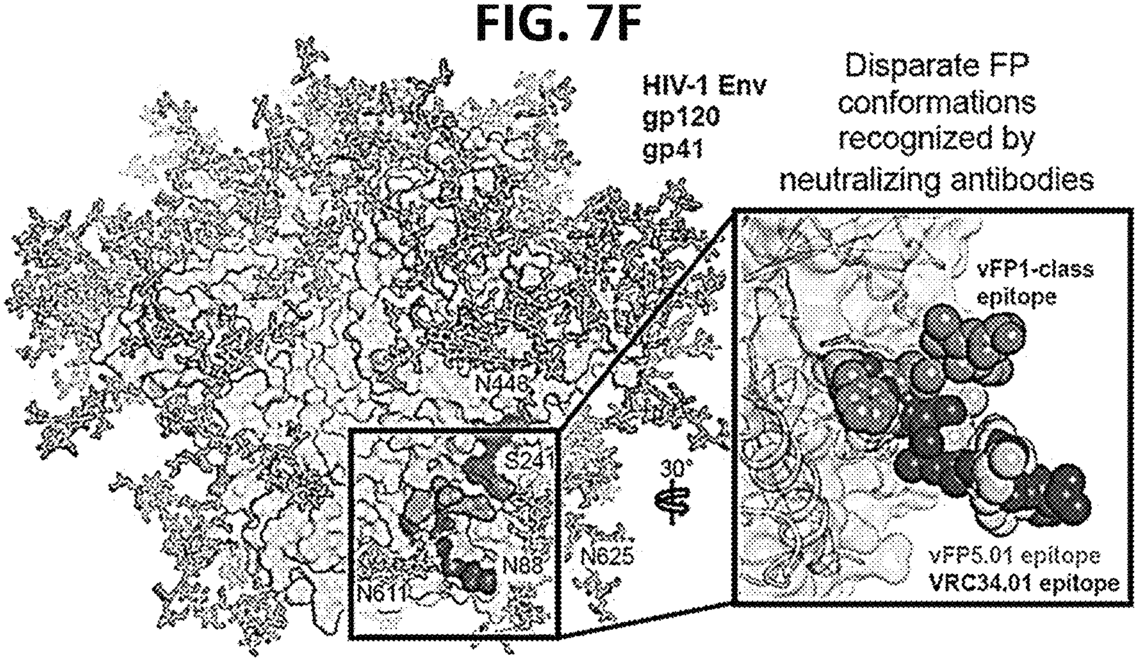

FIG. 8A $$\textit{Antigenicity score} = \sum_{i=1}^{N} w_i \times Fn_i \times \left(\frac{Fn_i}{Fn_i + Fp_i}\right)$$

where $\sum_{i=1}^{N} w_i = 1$ $w_i$: weight for epitope *i*

$Fn_i$: Fraction of neutralizing antibody binding to epitope *i*

$Fp_i$: Fraction of poorly/non-neutralizing antibody binding to epitope *i*

N: Number of epitopes

FIG. 8C

| Construct | Scaffold configuration (EM) | Apparent $K_D$ value (nM, with IgG avidity) | | | | | | |
|---|---|---|---|---|---|---|---|---|
| | | VRC34.01 | VRC34.05 | PGT151 | CH07 | ACS202 | VRC01 | 447-52D |
| FP-KLH | KLH particle | <0.001 | <0.001 | <0.001 | N.B. | <0.001 | N.B. | N.B. |
| FP-1M6T | Monomer | 5.6 | N.B. | N.B. | N.B. | N.B. | N.B. | N.B. |
| FP-1Y12 | Dimer/Oligomer | 3.7 | N.B. | <0.001 | N.B. | N.B. | N.B. | N.B. |
| FP-3HSH | Trimer | <0.001 | 25.4 | 47.2 | N.B. | N.B. | N.B. | N.B. |
| FP-1SLF | Tetramer | <0.001 | 70.9 | 87.1 | N.B. | N.B. | N.B. | N.B. |
| SOSIP.664 | Env Trimer | <0.001 | 0.8 | <0.001 | N.B. | <0.001 | <0.001 | N.B. |
| DS SOSIP | Env Trimer | <0.001 | 0.6 | <0.001 | N.B. | <0.001 | <0.001 | N.B. |

N.B., apparent $K_D$>2000nM

FIG. 8D

>FP-3HSH (SEQ ID NO: 78)

MDSKGSSQKGSRLLLLLVVSNLLLPQGVLAAVGIGAVFLGGGGSSGVRLWATRQAMLGQVHEVPEGWLIF
VAEQEELYVRVQNGFRKVQLEARTPLPRGGGSLEVLFQGPGSGSAWSHPQFEKGSGHHHHHHHH**

>FP-1SLF (SEQ ID NO: 195)

MDSKGSSQKGSRLLLLLVVSNLLLPQGVLAAVGIGAVFLGITGTWYNQLGSTFIVTAGADGALTGTYESA
VGNAESRYVLTGRYDSAPATDGSGTALGWTVAWKNNYRNAHSATTWSGQYVGGAEARINTQWLLTSGTTE
ANAWKSTLVGHDTFTKVKPSAASGGLVPRGSHHHHHHSAWSHPQFEK**

FIG. 8G
Physical stability of fusion peptide-coupled KLH
| Retained fractional VRC34.01 reactivity | | | | | | |
|---|---|---|---|---|---|---|
| Temp (°C) | | pH | | Freeze Thaw | Osmolality (mM) | |
| 50 | 70 | 3.5 | 10 | | 10 | 3000 |
| 1.0 | 1.0 | 0.0 | 0.9 | 1.1 | 1.0 | 0.9 |
FIG. 8H
FP-KLH only
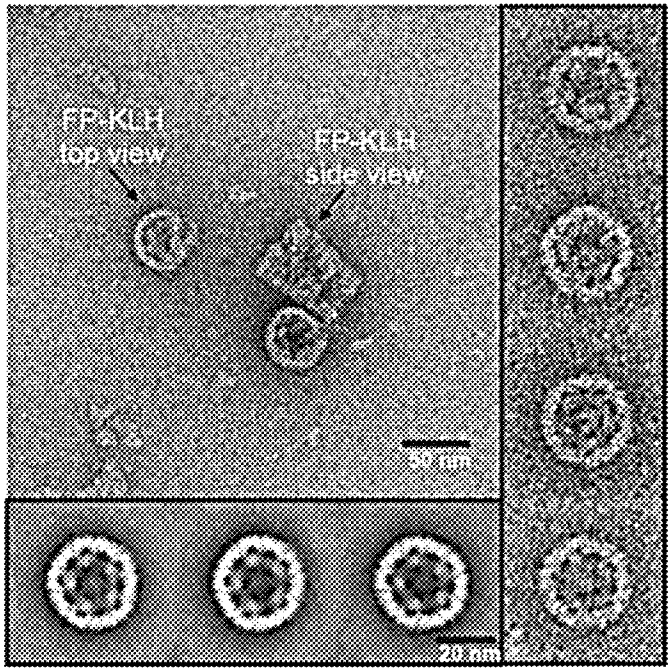
FP-KLH in complex with VRC34.01 fab
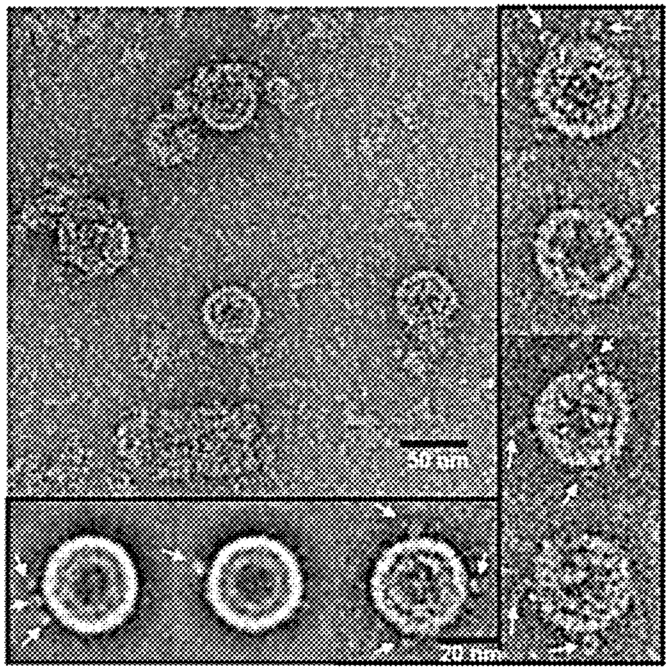

FIG. 9A

| Viruses | | Mice sera | | | | | |
|---|---|---|---|---|---|---|---|
| | | 1868 | 1882 | 1883 | 1884 | 2586 | 2602 |
| SVA-MLV | ID50 | 50 | 23 | 25 | <20 | 23 | <20 |
| | ID80 | <20 | <20 | <20 | <20 | <20 | <20 |
| BG505 WT | ID50 | <20 | <20 | <20 | <20 | <20 | 60 |
| | ID80 | <20 | <20 | <20 | <20 | <20 | <20 |
| BG505 Δ611 glycan | ID50 | 108 | 95 | 62 | 89 | 78 | 275 |
| | ID80 | 20 | <20 | <20 | <20 | <20 | 22 |
| BG505 Δ88+Δ611 glycans | ID50 | 493 | 320 | 239 | 205 | 239 | 575 |
| | ID80 | 65 | 26 | 29 | 26 | <20 | 55 |

| ID50 | ID80 |
|---|---|
| <40 | <20 |
| 40-100 | 20-100 |
| 100-1000 | |

FIG. 9B

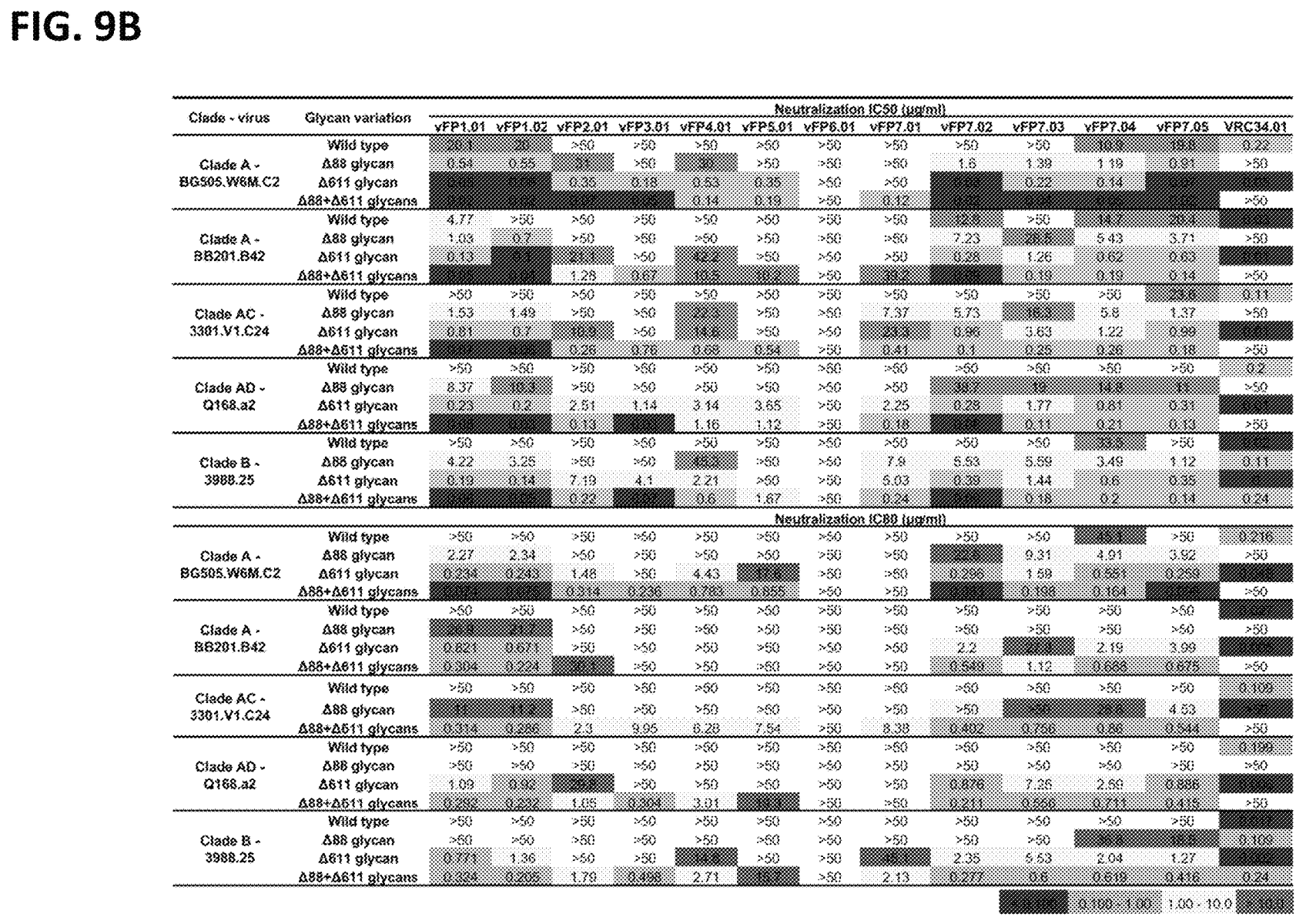

| Clade - virus | Glycan variation | vFP1.01 | vFP1.02 | vFP2.01 | vFP3.01 | vFP4.01 | vFP5.01 | vFP6.01 | vFP7.01 | vFP7.02 | vFP7.03 | vFP7.04 | vFP7.05 | VRC34.01 |
|---|---|---|---|---|---|---|---|---|---|---|---|---|---|---|
| | | Neutralization IC50 (µg/ml) | | | | | | | | | | | | |
| Clade A - BG505.W6M.C2 | Wild type | 20.1 | 20 | >50 | >50 | >50 | >50 | >50 | >50 | >50 | >50 | 10.9 | 19.8 | 0.22 |
| | Δ88 glycan | 0.54 | 0.55 | 31 | >50 | 30 | >50 | >50 | >50 | 1.6 | 1.39 | 1.19 | 0.91 | >50 |
| | Δ611 glycan | [illegible] | [illegible] | 0.35 | 0.18 | 0.53 | 0.35 | >50 | >50 | [illegible] | 0.22 | 0.14 | [illegible] | [illegible] |
| | Δ88+Δ611 glycans | [illegible] | [illegible] | [illegible] | [illegible] | 0.14 | 0.19 | >50 | 0.12 | [illegible] | [illegible] | [illegible] | [illegible] | >50 |
| Clade A - BB201.B42 | Wild type | 4.77 | >50 | >50 | >50 | >50 | >50 | >50 | >50 | 12.9 | >50 | 14.7 | 20.4 | [illegible] |
| | Δ88 glycan | 1.03 | 0.7 | >50 | >50 | >50 | >50 | >50 | >50 | 7.23 | 20.5 | 5.43 | 3.71 | >50 |
| | Δ611 glycan | 0.13 | [illegible] | 21.1 | >50 | 42.2 | >50 | >50 | >50 | 0.28 | 1.26 | 0.62 | 0.63 | [illegible] |
| | Δ88+Δ611 glycans | [illegible] | [illegible] | 1.28 | 0.67 | 10.5 | 18.2 | >50 | 18.2 | [illegible] | 0.19 | 0.19 | 0.14 | >50 |
| Clade AC - 3301.V1.C24 | Wild type | >50 | >50 | >50 | >50 | >50 | >50 | >50 | >50 | >50 | >50 | >50 | 23.8 | 0.11 |
| | Δ88 glycan | 1.53 | 1.49 | >50 | >50 | 22.3 | >50 | >50 | 7.37 | 5.73 | 16.3 | 5.8 | 1.37 | >50 |
| | Δ611 glycan | 0.81 | 0.7 | 10.9 | >50 | 14.6 | >50 | >50 | 23.3 | 0.96 | 3.63 | 1.22 | 0.99 | [illegible] |
| | Δ88+Δ611 glycans | [illegible] | [illegible] | 0.26 | 0.76 | 0.68 | 0.54 | >50 | 0.41 | 0.1 | 0.26 | 0.36 | 0.18 | >50 |
| Clade AD - Q168.a2 | Wild type | >50 | >50 | >50 | >50 | >50 | >50 | >50 | >50 | >50 | >50 | >50 | >50 | 0.2 |
| | Δ88 glycan | 8.37 | 10.3 | >50 | >50 | >50 | >50 | >50 | >50 | 38.7 | 19 | 14.8 | 11 | >50 |
| | Δ611 glycan | 0.23 | 0.2 | 2.51 | 1.14 | 3.14 | 3.65 | >50 | 2.25 | 0.28 | 1.77 | 0.81 | 0.31 | [illegible] |
| | Δ88+Δ611 glycans | [illegible] | [illegible] | 0.13 | [illegible] | 1.16 | 1.12 | >50 | 0.18 | [illegible] | 0.11 | 0.21 | 0.13 | >50 |
| Clade B - 3988.25 | Wild type | >50 | >50 | >50 | >50 | >50 | >50 | >50 | >50 | >50 | >50 | 33.5 | >50 | [illegible] |
| | Δ88 glycan | 4.22 | 3.25 | >50 | >50 | 48.3 | >50 | >50 | 7.9 | 5.53 | 5.59 | 3.49 | 1.12 | 0.11 |
| | Δ611 glycan | 0.19 | 0.14 | 7.19 | 4.1 | 2.21 | >50 | >50 | 5.03 | 0.39 | 1.44 | 0.6 | 0.35 | [illegible] |
| | Δ88+Δ611 glycans | [illegible] | [illegible] | 0.33 | [illegible] | 0.6 | 1.67 | >50 | 0.24 | [illegible] | 0.18 | 0.2 | 0.14 | 0.24 |
| | | Neutralization IC80 (µg/ml) | | | | | | | | | | | | |
| Clade A - BG505.W6M.C2 | Wild type | >50 | >50 | >50 | >50 | >50 | >50 | >50 | >50 | >50 | >50 | 45.1 | >50 | 0.216 |
| | Δ88 glycan | 2.27 | 2.34 | >50 | >50 | >50 | >50 | >50 | >50 | 22.5 | 9.31 | 4.91 | 3.92 | >50 |
| | Δ611 glycan | 0.234 | 0.243 | 1.48 | >50 | 4.43 | 17.6 | >50 | >50 | 0.296 | 1.59 | 0.561 | 0.259 | [illegible] |
| | Δ88+Δ611 glycans | [illegible] | [illegible] | 0.314 | 0.236 | 0.783 | 0.855 | >50 | >50 | [illegible] | 0.198 | 0.164 | [illegible] | >50 |
| Clade A - BB201.B42 | Wild type | >50 | >50 | >50 | >50 | >50 | >50 | >50 | >50 | >50 | >50 | >50 | >50 | [illegible] |
| | Δ88 glycan | 26.8 | 21.7 | >50 | >50 | >50 | >50 | >50 | >50 | >50 | >50 | >50 | >50 | >50 |
| | Δ611 glycan | 0.821 | 0.671 | >50 | >50 | >50 | >50 | >50 | >50 | 2.2 | 27.9 | 2.19 | 3.99 | [illegible] |
| | Δ88+Δ611 glycans | 0.304 | 0.224 | [illegible] | >50 | >50 | >50 | >50 | >50 | 0.549 | 1.12 | 0.668 | 0.675 | >50 |
| Clade AC - 3301.V1.C24 | Wild type | >50 | >50 | >50 | >50 | >50 | >50 | >50 | >50 | >50 | >50 | >50 | >50 | 0.109 |
| | Δ88 glycan | 11 | 11.2 | >50 | >50 | >50 | >50 | >50 | >50 | >50 | [illegible] | 26.6 | 4.53 | [illegible] |
| | Δ88+Δ611 glycans | 0.314 | 0.286 | 2.3 | 9.95 | 6.28 | 7.54 | >50 | 8.38 | 0.402 | 0.756 | 0.86 | 0.544 | >50 |
| Clade AD - Q168.a2 | Wild type | >50 | >50 | >50 | >50 | >50 | >50 | >50 | >50 | >50 | >50 | >50 | >50 | 0.199 |
| | Δ88 glycan | >50 | >50 | >50 | >50 | >50 | >50 | >50 | >50 | >50 | >50 | >50 | >50 | >50 |
| | Δ611 glycan | 1.09 | 0.92 | [illegible] | >50 | >50 | >50 | >50 | >50 | 0.876 | 7.26 | 2.59 | 0.886 | [illegible] |
| | Δ88+Δ611 glycans | 0.292 | 0.232 | 1.05 | 0.304 | 3.01 | [illegible] | >50 | >50 | 0.211 | 0.556 | 0.711 | 0.415 | >50 |
| Clade B - 3988.25 | Wild type | >50 | >50 | >50 | >50 | >50 | >50 | >50 | >50 | >50 | >50 | >50 | >50 | [illegible] |
| | Δ88 glycan | >50 | >50 | >50 | >50 | >50 | >50 | >50 | >50 | >50 | >50 | [illegible] | [illegible] | 0.109 |
| | Δ611 glycan | 0.771 | 1.36 | >50 | >50 | [illegible] | >50 | >50 | [illegible] | 2.35 | 5.53 | 2.04 | 1.27 | [illegible] |
| | Δ88+Δ611 glycans | 0.324 | 0.205 | 1.79 | 0.498 | 2.71 | [illegible] | >50 | 2.13 | 0.277 | 0.6 | 0.619 | 0.416 | 0.24 |

Legend: < 0.100 | 0.100 - 1.00 | 1.00 - 10.0 | > 10.0

FP-competed sera neutralization

Summary of the effect of FP-competition to sera neutralization $ID_{50}$

| Serum | Mock media | Fusion peptide | | | Control peptide | | |
|---|---|---|---|---|---|---|---|
| | ID50 | ID50 | Fold change | % inhibition | ID50 | Fold change | % inhibition |
| 2716 | 610 | 33 | 18.5 | 95% | 633 | 1.0 | -4% |
| 2718 | 68 | 27 | 2.5 | 60% | 61 | 1.1 | 10% |
| 2790 | 55 | 38 | 1.4 | 31% | 36 | 1.5 | 35% |
| 2791 | 141 | 31 | 4.5 | 78% | 61 | 2.3 | 57% |
| 2792 | 118 | 48 | 2.5 | 59% | 128 | 0.9 | -8% |

| | Immunizations | | | | | | | BG505.N88Q.N611Q | |
|---|---|---|---|---|---|---|---|---|---|
| Group # | 1 | 2 | 3 | 4 | 5 | 6 | Animal ID | ID50 | ID80 |
| 1 | T1 | FP6 | FP7 | FP8 | T2 | T2 | 4441 | 2029 | 280 |
| | | | | | | | 4442 | 136 | <20 |
| | | | | | | | 4443 | 2087 | 348 |
| | | | | | | | 4444 | 4011 | 488 |
| | | | | | | | 4445 | 176 | <20 |
| 2 | T1 | FP8 | FP8 | FP8 | T2 | T2 | 4446 | 1398 | 222 |
| | | | | | | | 4447 | 87 | <20 |
| | | | | | | | 4448 | 1127 | 325 |
| | | | | | | | 4449 | 329 | 82 |
| | | | | | | | 4450 | 1312 | 302 |
| 3 | T1 | KLH only | KLH only | KLH only | T2 | T2 | 4451 | <20 | <20 |
| | | | | | | | 4452 | <20 | <20 |
| | | | | | | | 4453 | <20 | <20 |
| | | | | | | | 4454 | <20 | <20 |
| | | | | | | | 4455 | <20 | <20 |

Key:
FP6 = AVGIGA-KLH (residues 1-6, SEQ ID NO: 1)
FP7 = AVGIGAV-KLH (residues 1-7, SEQ ID NO: 1)
FP8 = AVGIGAVF-KLH (residues 1-8, SEQ ID NO: 1)
T1 = BG505 SOSIP
T2 = BG505 DS-SOSIP

| ID50 | ID80 |
|---|---|
| <40 | <20 |
| 40-100 | 20-100 |
| 100-1000 | |
| 1000-10000 | |

vFP1.01 in complex
with fusion peptide

FIG. 11A

| Mouse ID | Immunization | | | SVA-MLV | | BG505 WT | | BG505 Δ611 glycan | | BG505 Δ88+Δ611 glycans | | Hybridoma-identified antibodies |
|---|---|---|---|---|---|---|---|---|---|---|---|---|
| | 1 | 2 | 3 | ID50 | ID80 | ID50 | ID80 | ID50 | ID80 | ID50 | ID80 | (All vFP1 class) |
| **2586** | FP8 | FP8 | | 23 | <20 | <20 | <20 | 78 | <20 | 239 | <20 | *vFP7.01-vFP7.03, vFP7.04-vFP7.07, vFP7.08* |
| **2602** | FP8 | FP8 | | <20 | <20 | 60 | <20 | 275 | 22 | 575 | 55 | *vFP8.01, vFP8.02, vFP8.03* |
| **1868** | T1 | FP8 | FP8 | 50 | <20 | <20 | <20 | 108 | 20 | 493 | 65 | *vFP1.01-vFP1.02, vFP2.01, vFP3.01, vFP4.01* |
| **1882** | T1 | FP8 | FP8 | 23 | <20 | <20 | <20 | 95 | <20 | 320 | 26 | *vFP9.01* |
| **1883** | T1 | FP8 | FP8 | 25 | <20 | <20 | <20 | 62 | <20 | 239 | 29 | *vFP10.01-vFP10.05, vFP11.01* |

Key:
FP8 = AVGIGAVF-KLH (residues 1-8, SEQ ID NO: 1)
T1 = BG505 SOSIP

| ID50 | ID80 |
|---|---|
| <40 | <20 |
| 40-100 | 20-100 |
| 100-1000 | |

FIG. 12A

| Ligand | BG505.DS-SOSIP | | | BG505.DS-SOSIP.Δ88 | | | BG505.DS-SOSIP.Δ611 | | | Fusion peptide | | |
|---|---|---|---|---|---|---|---|---|---|---|---|---|
| mAb | ka (1/Ms) | kd (1/s) | $K_D$ (M/l) | ka (1/Ms) | kd (1/s) | $K_D$ (M/l) | ka (1/Ms) | kd (1/s) | $K_D$ (M/l) | ka (1/Ms) | kd (1/s) | $K_D$ (M/l) |
| **vFP1.01** | 4.73E+04 | 6.07E-04 | 1.28E-08 | 1.45E+05 | 3.04E-04 | 2.10E-09 | 9.02E+04 | 4.47E-04 | 4.96E-09 | 1.89E+05 | 1.35E-03 | 7.15E-09 |
| **vFP1.02** | 3.80E+04 | 4.77E-04 | 1.25E-08 | 1.01E+05 | 1.14E-04 | 1.13E-09 | 6.62E+04 | 3.89E-04 | 5.87E-09 | 1.66E+05 | 1.36E-03 | 8.19E-09 |
| **vFP2.01** | 2.43E+04 | 6.61E-04 | 2.72E-08 | 5.38E+04 | 4.24E-04 | 7.87E-09 | 3.69E+04 | 9.15E-04 | 2.48E-08 | 9.53E+04 | 1.48E-03 | 1.56E-08 |
| **vFP3.01** | 4.34E+04 | 2.20E-03 | 5.07E-08 | 7.64E+04 | 2.23E-03 | 2.95E-08 | 6.49E+04 | 1.47E-03 | 2.26E-08 | 1.91E+05 | 2.76E-03 | 1.44E-08 |
| **vFP4.01** | 1.93E+04 | 4.36E-04 | 2.26E-08 | 4.99E+04 | 1.92E-04 | 3.85E-09 | 2.92E+04 | 3.90E-04 | 1.33E-08 | 1.04E+05 | 1.02E-03 | 9.82E-09 |
| **vFP5.01** | 6.75E+04 | 3.10E-03 | 4.62E-08 | 2.23E+05 | 3.66E-03 | 1.64E-08 | 1.24E+05 | 1.88E-03 | 1.51E-08 | 3.88E+05 | 2.06E-03 | 5.29E-09 |
| **vFP6.01** | 1.12E+04 | 1.04E-02 | 9.28E-07 | 6.55E+04 | 5.72E-03 | 8.74E-08 | 1.55E+05 | 2.61E-02 | 1.69E-07 | 6.65E+05 | 3.48E-03 | 5.23E-09 |
| **vFP7.01** | 1.90E+05 | 5.14E-03 | 2.71E-08 | 3.00E+05 | 1.34E-03 | 4.46E-09 | 2.25E+05 | 3.12E-03 | 1.39E-08 | 4.79E+06 | 2.54E-03 | 5.30E-10 |
| **vFP7.02** | 7.22E+04 | 1.97E-03 | 2.72E-08 | 1.90E+05 | 1.19E-03 | 6.26E-09 | 1.34E+05 | 1.02E-03 | 7.61E-09 | 3.29E+06 | 1.48E-03 | 4.50E-10 |
| **vFP7.03** | 4.22E+04 | 6.10E-04 | 1.44E-08 | 8.83E+04 | 1.59E-04 | 1.80E-09 | 6.25E+04 | 5.59E-04 | 8.94E-09 | 1.26E+06 | 1.25E-03 | 9.94E-10 |
| **vFP7.04** | 5.07E+04 | 3.48E-04 | 6.86E-09 | 8.20E+04 | 1.32E-04 | 1.61E-09 | 5.55E+04 | 3.10E-04 | 5.59E-09 | 1.11E+06 | 8.94E-04 | 8.05E-10 |
| **vFP7.05** | 5.71E+04 | 4.38E-04 | 7.68E-09 | 1.59E+05 | 3.29E-04 | 2.07E-09 | 9.59E+04 | 4.11E-04 | 4.28E-09 | 2.52E+06 | 7.68E-04 | 3.05E-10 |
| **vFP16.02** | 5.82E+04 | 4.18E-04 | 7.19E-09 | 1.79E+05 | 3.11E-04 | 1.74E-09 | 1.41E+05 | 2.96E-04 | 2.10E-09 | 9.87E+05 | 1.05E-03 | 1.06E-09 |
| **vFP20.01** | 5.99E+04 | 2.22E-04 | 3.71E-09 | 1.49E+05 | 6.33E-05 | 4.26E-10 | 1.57E+05 | 1.47E-04 | 9.34E-10 | 5.88E+05 | 9.61E-04 | 1.64E-09 |
| **VRC34** | 5.25E+05 | 3.40E-04 | 6.48E-10 | 1.63E+06 | 3.27E-03 | 2.00E-09 | 1.59E+06 | 7.09E-04 | 4.46E-10 | 1.50E+06 | 9.24E-03 | 6.17E-09 |

V-gene signature of vFP1 class antibodies

ANA HEp2 staining assay

Numbers in red are autoreactivity scores

ANA HEp2 staining score

| mAb | Score | | Interpretation |
|---|---|---|---|
| | 21-Sep-16 | 22-Sep-16 | |
| vFP1.01 | 0 | 0 | Not reactive |
| vFP5.01 | 0 | 0 | Not reactive |
| vFP16.02 | 0 | 0 | Not reactive |
| vFP20.01 | 0 | 0 | Not reactive |
| VRC34.01 | 0 | 0 | Not reactive |
| VRC01-LS | 0 | 0 | Not reactive |
| 4E10 | 1 | 1 | Autoreactive |
| VRC07-523-LS | 2 | 2 | Autoreactive |
| VRC07-G54W | 3 | 3 | Autoreactive |

FIG. 13D

Anti-cardiolipin ELISA

| mAb | OD | | GPL units | | Interpretation |
|---|---|---|---|---|---|
| | 100 µg/ml | 33 µg/ml | 100 µg/ml | | |
| vFP1.01 | 0.21 | 0.10 | 20.62 | 8.18 | Not reactive |
| vFP5.01 | 0.06 | 0.05 | 3.40 | 2.80 | Not reactive |
| vFP16.02 | 0.04 | 0.04 | -4.08 | -4.56 | Not reactive |
| vFP20.01 | 0.23 | 0.09 | 8.86 | -0.62 | Not reactive |
| VRC34.01 | 0.04 | 0.04 | 2.03 | 1.96 | Not reactive |
| VRC01-LS | 0.09 | 0.06 | 7.05 | 3.98 | Not reactive |
| 4E10 | 1.48 | 1.48 | 164.32 | 164.26 | Reactive |
| VRC07-523-LS | 0.11 | 0.06 | 9.49 | 4.20 | Not reactive |
| VRC07-G54W | 0.31 | 0.13 | 31.87 | 11.96 | Not reactive |

GPL color score

| | |
|---|---|
| <15 | Negative |
| 15-20 | indeterminate |
| 20-80 | low to medium positive |
| >80 | high positive |

FIG. 13F

Neutralization assay with guinea pig FP immunization study week 28 sera

| Clade | A | | A | | B | | B | | C | | AE | | BC | | C | | C | | A | | A | | A | | A | |
|---|---|---|---|---|---|---|---|---|---|---|---|---|---|---|---|---|---|---|---|---|---|---|---|---|---|---|
| Glycan missing | Complete | | Complete | | Complete | | Complete | | Complete | | 241+611 | | 448 | | 241 | | 241 | | 241 | | 88+241 | | 241+611 | | 88+241+611 | |
| Viruses | KER2008.12 | | Q23.17 | | 3988.25 | | BL01.DG | | 286.36 | | CNE56 | | CNE19 | | 25710-2.43 | | 0077.V1.C16 | | BG505 | | BG505 Δ88 | | BG505 Δ611 | | BG505 Δ88+611 | |
| Guinea Pig ID | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 |
| CGP701-1 | <20 | <20 | <20 | <20 | <20 | <20 | <20 | <20 | <20 | <20 | 70 | <20 | <20 | <20 | 45 | <20 | <20 | <20 | 81 | <20 | 145 | 22 | 6,149 | 953 | [illegible] | 8,365 |
| CGP701-2 | <20 | <20 | <20 | <20 | <20 | <20 | <20 | <20 | <20 | <20 | <20 | <20 | <20 | <20 | <20 | <20 | <20 | <20 | 2,065 | 389 | 1,287 | 257 | 6,857 | 999 | [illegible] | 870 |
| CGP701-3 | <20 | <20 | <20 | <20 | <20 | <20 | <20 | <20 | <20 | <20 | 58 | <20 | <20 | <20 | 72 | <20 | <20 | <20 | 161 | 71 | 226 | 46 | 3,406 | 1,062 | [illegible] | 6,195 |
| CGP701-4 | <20 | <20 | <20 | <20 | <20 | <20 | <20 | <20 | <20 | <20 | <20 | <20 | <20 | <20 | 33 | <20 | <20 | <20 | 36 | <20 | 23 | <20 | 2,295 | 534 | [illegible] | 2,922 |
| CGP701-5 | 161 | <20 | 151 | <20 | 128 | <20 | 148 | <20 | <20 | <20 | 141 | <20 | 275 | 37 | 496 | 104 | <20 | <20 | 106 | 25 | 433 | 104 | 4,997 | 1,471 | [illegible] | 5,418 |

<20
20-100
100-1000
1000-10000
[illegible]

FIG. 13H

Sera

Neutralization assay with NHP FP immunization study week 26 sera

| Clade | A | | A | | B | | B | | C | | AE | | BC | | C | | C | | A | | A | | A | | A | |
|---|---|---|---|---|---|---|---|---|---|---|---|---|---|---|---|---|---|---|---|---|---|---|---|---|---|---|
| Glycan missing | Complete | | Complete | | Complete | | Complete | | Complete | | 241+611 | | 448 | | 241 | | 241 | | 241 | | 88+241 | | 241+611 | | 88+241+611 | |
| Viruses | KER2008.12 | | Q23.17 | | 3988.25 | | BL01.DG | | 286.36 | | CNE56 | | CNE19 | | 25710-2.43 | | 0077.V1.C16 | | BG505 | | BG505 Δ88 | | BG505 Δ611 | | BG505 Δ88+611 | |
| NHP ID | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 | ID50 | ID80 |
| DF3R, CNHP7 4-1 | <20 | <20 | <20 | <20 | 23 | <20 | <20 | <20 | 20 | <20 | 24 | <20 | <20 | <20 | <20 | <20 | <20 | <20 | <20 | <20 | <20 | <20 | 60 | <20 | 323 | 67 |
| DFPE, CNHP7 4-2 | <20 | <20 | <20 | <20 | <20 | <20 | <20 | <20 | <20 | <20 | <20 | <20 | <20 | <20 | 32 | <20 | <20 | <20 | <20 | <20 | <20 | <20 | 266 | 59 | 1,701 | 349 |
| DF1W, CNHP7 4-3 | <20 | <20 | <20 | <20 | <20 | <20 | <20 | <20 | <20 | <20 | <20 | <20 | <20 | <20 | <20 | <20 | <20 | <20 | <20 | <20 | <20 | <20 | 91 | 34 | 754 | 103 |
| DF4B, CNHP7 4-4 | <20 | <20 | <20 | <20 | <20 | <20 | <20 | <20 | <20 | <20 | <20 | <20 | <20 | <20 | <20 | <20 | <20 | <20 | <20 | <20 | <20 | <20 | 275 | 36 | 636 | 55 |
| 0PV, CNHP7 4-5 | <20 | <20 | 42 | <20 | 63 | <20 | <20 | <20 | <20 | <20 | <20 | <20 | 30 | <20 | 76 | 23 | <20 | <20 | <20 | <20 | <20 | <20 | 1,479 | 384 | 5,977 | 1,440 |

<20
20-100
100-1000
1000-10000

FIG. 14A

| | vFP1.01 | vFP1.02 | vFP2.01 | vFP3.01 | vFP4.01 | vFP5.01 | vFP6.01 | vFP7.01 | vFP7.02 | vFP7.03 | vFP7.04 | vFP7.05 | vFP16.02 | vFP20.01 | VRC34.01 |
|---|---|---|---|---|---|---|---|---|---|---|---|---|---|---|---|
| 512 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| 513 | 0.93 | 0.97 | 0.69 | 0.70 | 0.44 | 0.59 | 0.83 | 0.90 | 0.97 | 1.02 | 1.04 | 1.02 | 1.01 | 0.99 | 0.05 |
| 514 | 0.24 | 0.23 | 0.06 | 0.04 | 0.01 | 0.41 | 0.72 | 0.06 | 0.10 | 0.04 | 0.00 | 0.00 | 0.66 | 0.48 | 0.72 |
| 515 | 0.44 | 0.44 | 0.10 | 0.04 | 0.05 | 0.07 | 0.47 | 0.25 | 0.32 | 0.27 | 0.29 | 0.23 | 0.69 | 0.66 | 0.03 |
| 516 | 1.03 | 1.07 | 1.01 | 1.05 | 0.75 | 0.56 | 0.78 | 0.99 | 0.99 | 0.99 | 1.02 | 1.00 | 0.98 | 0.99 | 0.01 |
| 517 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| 518 | 0.96 | 1.06 | 1.03 | 1.00 | 1.02 | 0.92 | 0.39 | 1.01 | 1.03 | 1.06 | 1.02 | 1.06 | 1.03 | 1.02 | 0.73 |
| 519 | 0.93 | 1.03 | 0.98 | 1.02 | 1.03 | 0.14 | 0.30 | 0.98 | 1.02 | 1.04 | 1.02 | 1.03 | 1.03 | 1.01 | 0.80 |
| 520 | 0.99 | 1.06 | 1.01 | 1.07 | 1.05 | 1.01 | 1.01 | 1.03 | 1.03 | 1.05 | 1.01 | 1.04 | 1.05 | 1.05 | 1.02 |
| 521 | 0.98 | 1.08 | 1.02 | 1.09 | 1.01 | 0.99 | 1.02 | 1.03 | 1.02 | 1.02 | 1.02 | 1.00 | 1.00 | 1.00 | 0.85 |

< 0.25 | 0.25 - 0.50 | 0.50 - 0.75 | > 0.75

Binding of indicated antibodies to alanine mutants normalized to binding to the wild-type FP sequence.

FIG. 14B

| | vFP1.01 | vFP1.02 | vFP2.01 | vFP3.01 | vFP4.01 | vFP5.01 | vFP6.01 | vFP7.01 | vFP7.02 | vFP7.03 | vFP7.04 | vFP7.05 | vFP16.02 | vFP20.01 | VRC34.01 |
|---|---|---|---|---|---|---|---|---|---|---|---|---|---|---|---|
| 512 | 0.98 | 1.03 | 0.85 | 1.09 | 0.85 | 0.91 | 0.60 | 0.81 | 0.94 | 0.88 | 0.98 | 0.96 | 1.00 | 0.97 | 0.52 |
| 513 | 0.12 | 0.08 | 0.06 | 0.03 | 0.04 | 0.43 | 0.59 | 0.13 | 0.14 | 0.17 | 0.30 | 0.27 | 0.51 | 0.34 | 0.00 |
| 514 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| 515 | 0.05 | 0.03 | 0.02 | 0.02 | 0.01 | 0.01 | 0.12 | 0.04 | 0.01 | 0.01 | 0.01 | 0.01 | 0.03 | 0.03 | 0.00 |
| 516 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| 517 | 0.83 | 0.96 | 0.93 | 0.93 | 0.96 | 0.86 | 0.93 | 0.94 | 0.92 | 0.94 | 0.97 | 0.94 | 0.97 | 0.98 | 0.75 |
| 518 | 0.98 | 1.02 | 0.96 | 0.86 | 1.01 | 0.71 | 0.11 | 0.95 | 0.98 | 1.00 | 0.98 | 0.99 | 1.02 | 1.00 | 0.49 |
| 519 | 0.95 | 0.97 | 0.84 | 0.95 | 0.88 | 0.09 | 0.39 | 0.87 | 0.92 | 0.90 | 0.89 | 0.90 | 0.92 | 0.91 | 0.49 |
| 520 | 0.99 | 1.06 | 0.97 | 1.09 | 1.03 | 1.07 | 0.95 | 0.97 | 0.99 | 1.00 | 0.98 | 1.00 | 1.01 | 1.00 | 1.01 |
| 521 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |

< 0.25 | 0.25 - 0.50 | 0.50 - 0.75 | > 0.75

Binding of indicated antibodies to glycine mutants normalized to binding to the wild-type sequence.

FIG. 15

| $IC_{50}$<50 μg/ml | 1868-vFP1.01 | 1868-vFP5.01 | 2586-vFP7.04 | 2586-vFP7.05 | 2712-vFP16.02 | 2716-vFP20.01 | N123-VRC34.01 |
|---|---|---|---|---|---|---|---|
| Neutralization breadth on 208 virus panel | 8.17% | 0.96% | 9.62% | 8.17% | 31.3% | 27.4% | 51.4% |
| Neutralization breadth on global virus panel | 8.33% | 0% | 8.33% | 16.7% | 41.7% | 41.7% | 75.0% |
| Neutralization breadth against tier 2 isolates | 7.69% | 0% | 8.33% | 8.33% | 28.9% | 25.0% | 50.0% |
| Neutralization breadth on FP8-sequence viruses | 20.7% | 1.72% | 22.4% | 17.2% | 72.4% | 74.1% | 94.8% |

| $IC_{50}$<100 μg/ml | 1868-vFP1.01 | 1868-vFP5.01 | 2586-vFP7.04 | 2586-vFP7.05 | 2712-vFP16.02 | 2716-vFP20.01 | N123-VRC34.01 |
|---|---|---|---|---|---|---|---|
| Neutralization breadth on 208 virus panel | 9.62% | 1.92% | 11.1% | 8.65% | 36.5% | 32.2% | 51.92% |
| Neutralization breadth on global virus panel | 16.7% | 0% | 8.33% | 16.7% | 41.7% | 50.0% | 75.0% |
| Neutralization breadth against tier 2 isolates | 7.69% | 0% | 10.3% | 8.97% | 34.0% | 28.9% | 50.6% |
| Neutralization breadth on FP8-sequence viruses | 25.9% | 3.45% | 27.6% | 19.0% | 81.0% | 82.8% | 94.8% |

FIG. 16 vFP7.04

| Residue number | Amino acid type | Adjusted P-value | Sensitive / Resistant |
|---|---|---|---|
| 515 | Ile | 0.0003 | Sensitive |
| 515 | Leu | 0.0100 | Resistant |

vFP20.01

| Residue number | Amino acid type | Adjusted P-value | Sensitive / Resistant |
|---|---|---|---|
| 513 | Val | 0.0014 | Sensitive |
| 515 | Ile | $1.73e^{-16}$ | Sensitive |
| 515 | Leu | $2.47e^{-11}$ | Resistant |
| 518 | Val | 0.0168 | Sensitive |

vFP7.05

| Residue number | Amino acid type | Adjusted P-value | Sensitive / Resistant |
|---|---|---|---|
| 515 | Ile | 0.0019 | Sensitive |
| 515 | Leu | 0.0347 | Resistant |

vFP1.01

| Residue number | *N*-glycan sequon | Adjusted P-value | Sensitive / Resistant |
|---|---|---|---|
| 241 | Yes | 0.0244 | Resistant |

VRC34.01

| Residue number | *N*-glycan sequon | Adjusted P-value | Sensitive / Resistant |
|---|---|---|---|
| 448 | Yes | 0.0327 | Resistant |

vFP7.04

| Residue number | *N*-glycan sequon | Adjusted P-value | Sensitive / Resistant |
|---|---|---|---|
| 241 | Yes | 0.0466 | Resistant |

vFP7.05

| Residue number | *N*-glycan sequon | Adjusted P-value | Sensitive / Resistant |
|---|---|---|---|
| 241 | Yes | 0.0244 | Resistant |

vFP16.02

| Residue number | *N*-glycan sequon | Adjusted P-value | Sensitive / Resistant |
|---|---|---|---|

vFP20.01

| Residue number | *N*-glycan sequon | Adjusted P-value | Sensitive / Resistant |
|---|---|---|---|

FIG. 17
Scaffold 1M6T
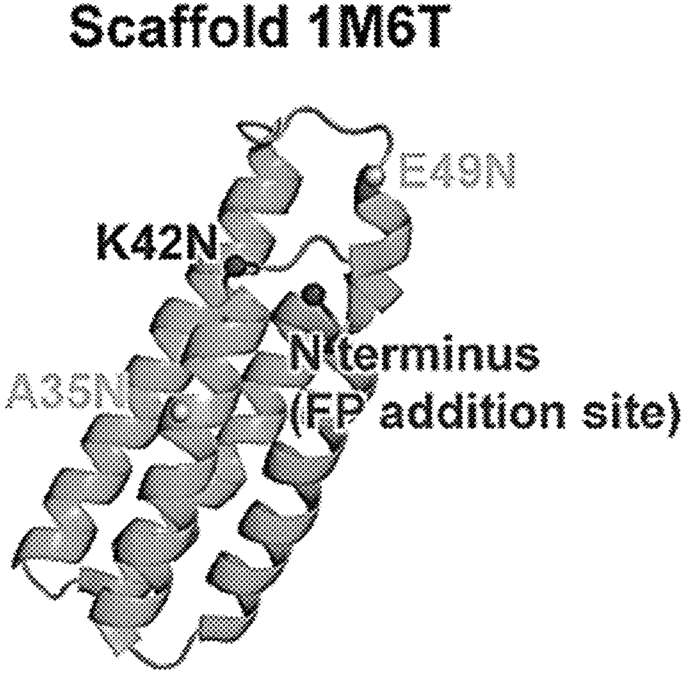
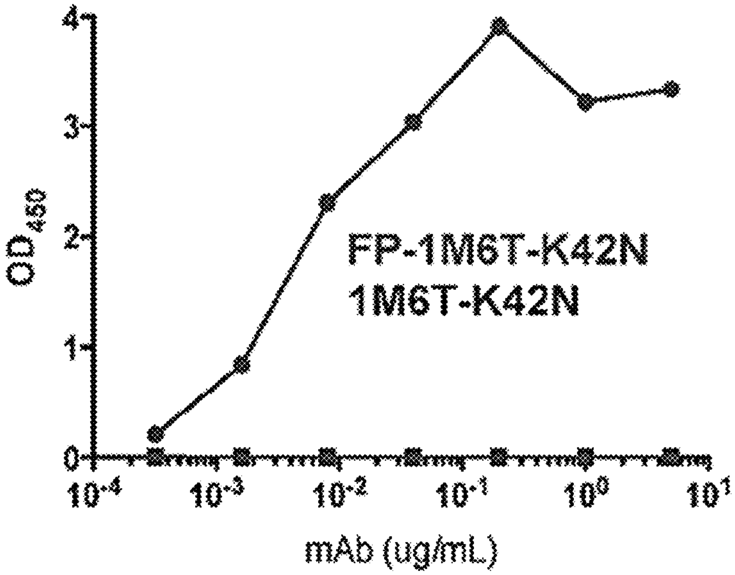

FIG. 18A

HIV FP on Nanoparticles: Lumazine Synthase

Lumazine Synthase
(60 copies, d ~ 16nm)

- FP at N terminal
- NxS/T mutation on one of the loops

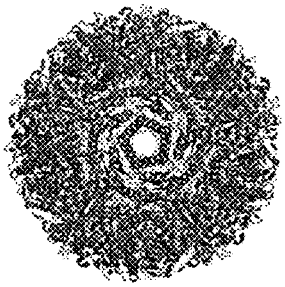

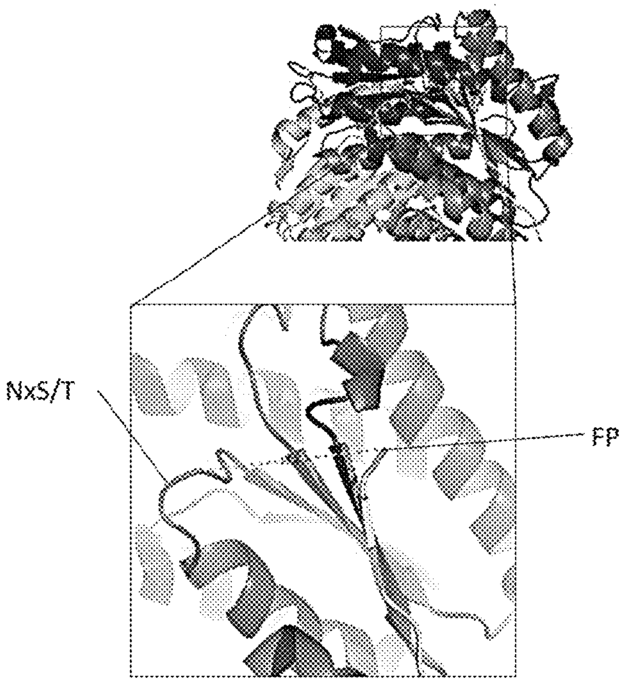

Constructs:

1. HIV_FP 1hqk D71N D73S
2. HIV_FP 1hqk G12N R14S

FIG. 18B

Antigenicity of FP nanoparticles

| Immunogen | SEQ ID NO | N123-VRC34.01 | N123-VRC34.05 | Anti-strep |
|---|---|---|---|---|
| HIV_FP_1hqk_G12N_R14S | 102 | 0.986 | 0.2069 | 1.2082 |
| HIV_FP-LS | 101 | 2.9289 | 2.2687 | 3.4076 |
| HIV_FP_3egm_N148S_HIS1 | 114 | 0.434 | 0.0865 | 0.0738 |
| HIV_FP 3egm-2 N148S_HIS1 | 115 | 0.2585 | 0.0684 | 0.0727 |
| HIV_FP_3egm_N148S | 112 | 2.4349 | 1.6502 | 0.0767 |
| HIV_FP 3egm-2 N148S | 113 | 2.5944 | 1.5273 | 0.0722 |
| HIV_FP_3egm_Q69N | 118 | 0.3849 | 0.2124 | 0.0682 |
| HIV_FP_3egm_S72N_HIS1 | 120 | 0.9051 | 0.1111 | 0.0679 |
| HIV_FP_3egm_S72N | 119 | 0.0708 | 0.0687 | 0.1951 |
| HIV_FP_3egm_H96N_HIS1 | 122 | 2.4607 | 1.0042 | 0.3171 |
| HIV_FP_3egm_H96N | 121 | 1.9871 | 1.335 | 0.0652 |

Purification of FP-1HQK lumazine synthase nanoparticles
FIG. 18C
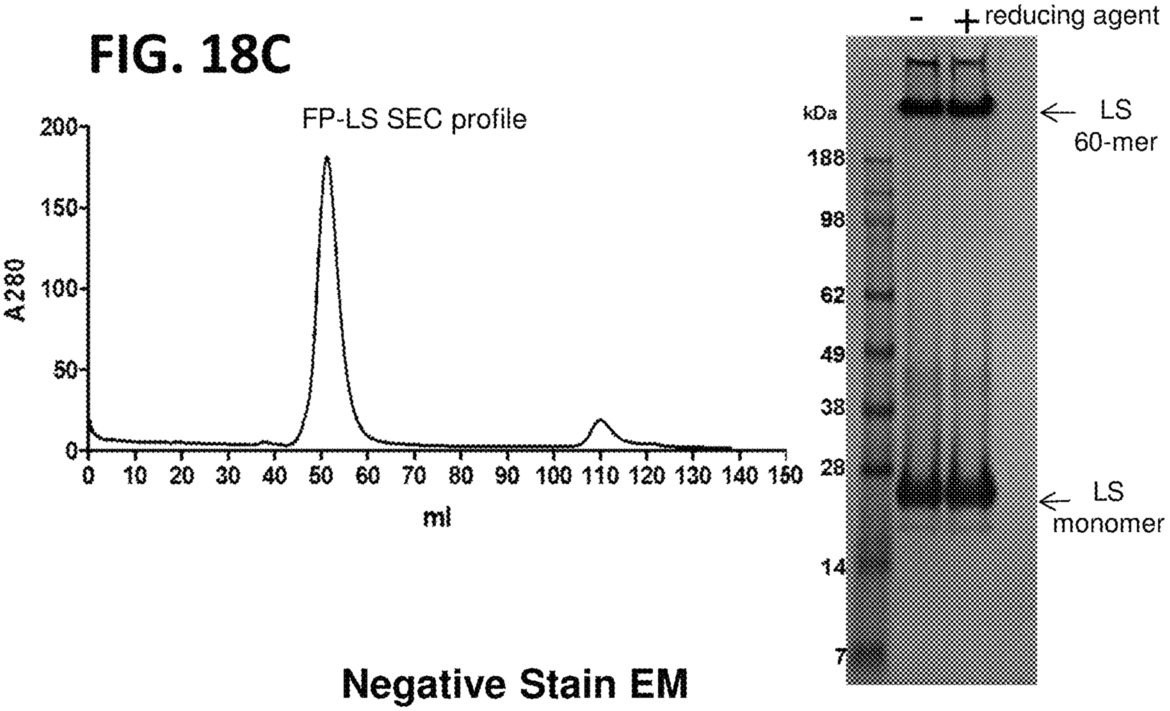
Negative Stain EM
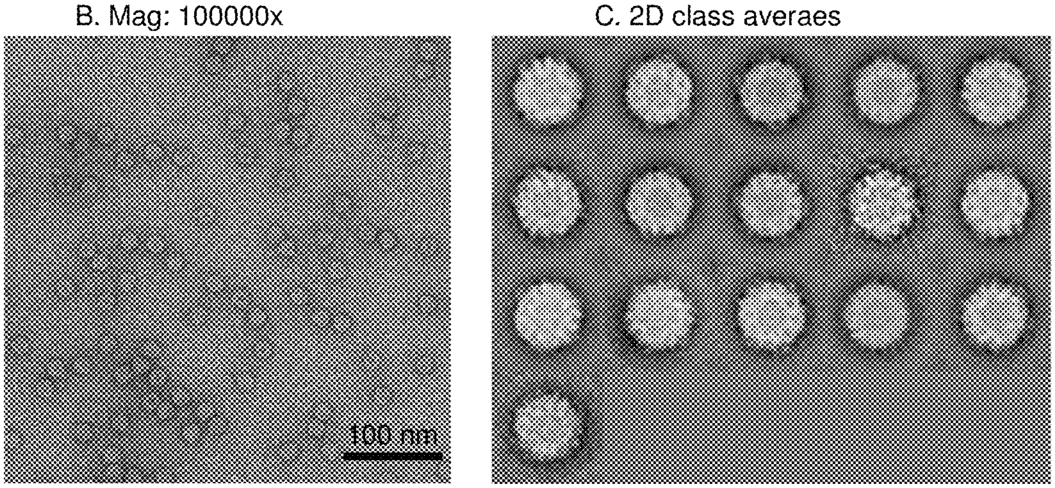
FIG. 18D
| Construct | Scaffold configuration (EM) | Apparent $K_D$ value (nM) | | | | | |
|---|---|---|---|---|---|---|---|
| | | N123-VRC34.01 | N123-VRC34.05 | PGT151 | CH07 | FP1.01 | FP1.05 |
| FP-LS | 60-mer Nano particle | <0.001 | 0.002 | <0.001 | N.B. | <0.001 | <0.001 |
| FP-KLH | KLH particle | <0.001 | <0.001 | <0.001 | N.B | N.D. | N.D. |
| FP-1M6T | Monomer | 5.6 | N.B. | N.B. | N.B. | N.D. | N.D. |

FIG. 19A

| Name | Fusion peptide | Carrier |
|---|---|---|
| KLH1 | AVGIGAVF (res. 1-8 of SEQ ID NO: 1) | KLH |
| KLH2 | AVGLGAVF (res. 1-8 of SEQ ID NO: 2) | KLH |
| KLH3 | AIGLGAMF (res. 1-8 of SEQ ID NO: 7) | KLH |
| KLH4 | AVGTIGAMF (res. 1-9 of SEQ ID NO: 4) | KLH |
| CRM1 | AVGIGAVF (res. 1-8 of SEQ ID NO: 1) | CRM197 |
| CRM2 | AVGLGAVF (res. 1-8 of SEQ ID NO: 2) | CRM197 |
| CRM3 | AIGLGAMF (res. 1-8 of SEQ ID NO: 7) | CRM197 |
| CRM4 | AVGTIGAMF (res. 1-9 of SEQ ID NO: 4) | CRM197 |
| TTHc1 | AVGIGAVF (res. 1-8 of SEQ ID NO: 1) | TTHc |
| TTHc2 | AVGLGAVF (res. 1-8 of SEQ ID NO: 2) | TTHc |
| TTHc3 | AIGLGAMF (res. 1-8 of SEQ ID NO: 7) | TTHc |
| TTHc4 | AVGTIGAMF (res. 1-9 of SEQ ID NO: 4) | TTHc |
| HID1 | AVGIGAVF (res. 1-8 of SEQ ID NO: 1) | HiD |
| HID2 | AVGLGAVF (res. 1-8 of SEQ ID NO: 2) | HiD |
| HID3 | AIGLGAMF (res. 1-8 of SEQ ID NO: 7) | HiD |
| HID4 | AVGTIGAMF (res. 1-9 of SEQ ID NO: 4) | HiD |

FIG. 19B

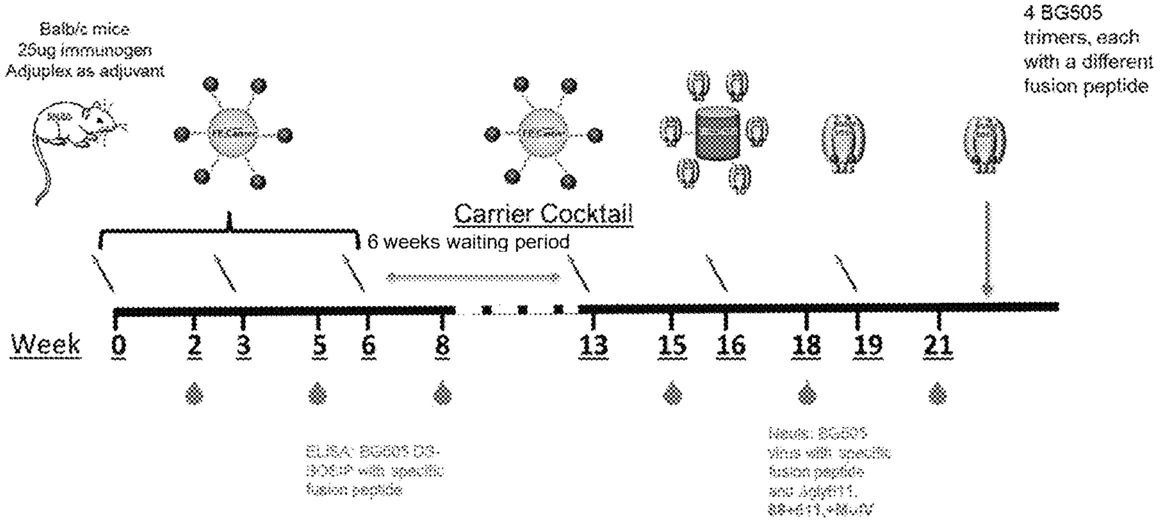

Immunize with specific FP-carrier on Weeks 0, 3, 6
Immunize with FP-carrier cocktail on Week 13 (KLH1-4, CRM1-4, TT1-4, or HID1-4)
Immunize with BG505.DS-SOSIP.664 with FP sequence corresponding to initial FP-carrier on Weeks 16, 19
Blood draws on Weeks 2, 5, 8, 15, 18, 21

FP-Carrier Immunogens Elicit High Titers Against FP-1M6T After 2 Immunizations (Week 5)

FP-Carrier Immunogens Elicit High Titers Against FP-carrier After 2 Immunizations (Week 5)

FP-Carrier Immunogens Start to Elicit Titers against Trimer after 3 Immunizations with FP-carrier

HIV-1 Env Trimer boost enhances Titers against Trimer

ELISA Binding to BG505.SOSIP.664 HIV-1 Env trimer of sera from week 21, post 6th immunization, after 1st trimer boost

Conjugation Chemistry: MBS and Sulfo-SIAB Crosslinkers

FIG. 21A

Guinea Pig Immunization Protocol

| Group | Immunogen Weeks 0, 4, 16 | Immunogen week 24 | Immunogen week 28 | Immunogen week 32 | Immunogen week 36 | Immunogen week 40 | Immunogen week 48 |
|---|---|---|---|---|---|---|---|
| 625 | CH505 FP degly3 (SEQ ID NO: 146 | FP7-KLH | FP6-KLH | FP5-KLH | FP4-KLH | BG505 SOSIP_DS (SEQ ID NO: 155) | CH505 SOSIP_DS (SEQ ID NO: 158) |
| 626 | CH505 FP delgy4 (SEQ ID NO: 145 | FP8-KLH | FP7-KLH | FP6-KLH | FP5-KLH | BG505 SOSIP_DS (SEQ ID NO: 155) | CH505 SOSIP_DS (SEQ ID NO: 158) |
| 611 | CH505 SOSIP_DS (SEQ ID NO: 158) | FP8-KLH | FP7-KLH | FP6-KLH | FP8-KLH | BG505 SOSIP_DS (SEQ ID NO: 155) | CH505 SOSIP_DS (SEQ ID NO: 158) |

FP4, FP5, FP6, FP7, FP8 refer to peptides with the first 4, 5, 6, 7, or 8 amino acids of the HIV-1 Env fusion peptide (from the N-terminus) sequence set forth as AVGIGAVFLG (SEQ ID NO: 1).

KLH: Keyhole Limpet Hemocyanin.

Immunogens were administered to Guinea pigs at 25 µg/dose with ADJUPLEX™ as adjuvant.

FIG. 21B

Neutralization using Sera from Immunized Guinea Pigs

| ID50 | Virus | BG505.W6M.C2 | | | | | | BG505.W6M.C2.N88Q.SG3 | | | | | | BG505.W6M.C2.N611Q.SG3 | | | | | |
|---|---|---|---|---|---|---|---|---|---|---|---|---|---|---|---|---|---|---|---|
| Group | Animal | wk 18 | wk 30 | wk 34 | Wk 38 | Wk 42 | Wk 52 | wk 18 | wk 30 | wk 34 | Wk 38 | Wk 42 | Wk 52 | wk 18 | wk 30 | Wk 34 | Wk 38 | Wk 42 | Wk 52 |
| 625 | 1 | <20 | <20 | <20 | <20 | <20 | 34 | <20 | <20 | <20 | <20 | <20 | 38 | 265 | 821 | 2,679 | 725 | 2,010 | 1,360 |
| | 2 | <20 | <20 | <20 | <20 | <20 | 43 | <20 | <20 | <20 | <20 | 36 | 54 | 475 | 167 | 1,211 | 245 | 1,042 | 4,125 |
| | 3 | <20 | <20 | <20 | <20 | <20 | 28 | <20 | <20 | <20 | <20 | <20 | 78 | 26 | 1,232 | 4,619 | 1,056 | 1,104 | 3,190 |
| | 4 | 64 | <20 | <20 | 78 | 129 | 278 | 51 | <20 | <20 | <20 | 60 | 247 | 184 | 87 | 111 | 367 | 462 | 1,138 |
| | 5 | 25 | <20 | <20 | <20 | 26 | 48 | 38 | 23 | <20 | <20 | 26 | 76 | 3,410 | 357 | 577 | 747 | 759 | 1,182 |
| 626 | 6 | <20 | <20 | <20 | <20 | <20 | 55 | 20 | <20 | <20 | <20 | <20 | 62 | 125 | 41 | 78 | 234 | 570 | 2,390 |
| | 7 | 64 | 21 | <20 | 36 | 209 | 516 | 74 | 42 | <20 | 74 | 131 | 296 | 325 | 130 | 2,218 | 977 | 1,662 | 2,681 |
| | 8 | 41 | <20 | <20 | 31 | 50 | 177 | 34 | <20 | <20 | 47 | 46 | 259 | 534 | 240 | 273 | 223 | 1,389 | 4,168 |
| | 9 | <20 | <20 | <20 | <20 | <20 | 80 | 32 | <20 | <20 | <20 | <20 | 139 | 176 | 286 | 258 | 219 | 2,670 | 4,022 |
| | 10 | <20 | <20 | <20 | <20 | <20 | 66 | <20 | <20 | <20 | 26 | 32 | 128 | 66 | 463 | 8,676 | 6,518 | 5,643 | 4,332 |
| 611 | 11 | <20 | 21 | <20 | <20 | 86 | 406 | <20 | 49 | <20 | <20 | 118 | 904 | 507 | 166 | 255 | 140 | 2,278 | 4,960 |
| | 12 | <20 | <20 | <20 | <20 | <20 | <20 | <20 | <20 | <20 | <20 | <20 | <20 | <20 | <20 | 90 | 169 | 401 | 419 |
| | 13 | 24 | <20 | <20 | 41 | 163 | 491 | 77 | 28 | <20 | 22 | 217 | 883 | 208 | 175 | 1,762 | 932 | 3,464 | 6,058 |
| | 14 | <20 | <20 | <20 | <20 | <20 | <20 | <20 | <20 | <20 | <20 | <20 | <20 | <20 | 21 | 58 | 98 | 123 | 316 |
| | 15 | <20 | <20 | <20 | <20 | <20 | <20 | <20 | <20 | <20 | <20 | <20 | <20 | <20 | <20 | <20 | 77 | 94 | 76 |

| ID50 | Virus | BG505.W6M.C2.N88Q.N611Q.SG3 | | | | | | CH0505s.T/F | | | | | CNE56 | | HxB2.DG.SG3 | 25710-2.43 | | CNE19 | | 0077.V1.C16 |
|---|---|---|---|---|---|---|---|---|---|---|---|---|---|---|---|---|---|---|---|---|
| Group | Animal | wk 18 | wk 30 | wk 34 | Wk 38 | Wk 42 | Wk 52 | wk 18 | wk 30 | wk 34 | Wk 38 | wk 52 | Wk 42 | Wk 52 | wk 52 | Wk 42 | wk 52 | Wk 42 | Wk 52 | Wk 42 |
| 625 | 16 | 235 | 2,465 | 5,509 | 2,868 | 5,387 | 5,512 | <20 | <20 | <20 | <20 | <20 | 20 | <20 | <20 | 70 | 95 | <20 | <20 | <20 |
| | 17 | 2,110 | 426 | 2,931 | 1,005 | 3,100 | 16,699 | <20 | <20 | <20 | <20 | 25 | 39 | 45 | 68 | 84 | 272 | 32 | 155 | <20 |
| | 18 | 332 | 7,757 | 14,250 | 11,631 | 5,580 | 16,460 | <20 | <20 | <20 | <20 | 239 | <20 | <20 | 104 | 43 | 136 | <20 | <20 | <20 |
| | 19 | 581 | 149 | 389 | 391 | 521 | 1,414 | <20 | <20 | <20 | <20 | 243 | <20 | <20 | <20 | 42 | 98 | <20 | <20 | <20 |
| | 20 | 1,582 | 331 | 822 | 523 | 1,369 | 1,603 | <20 | <20 | <20 | <20 | <20 | <20 | <20 | <20 | <20 | <20 | <20 | <20 | <20 |
| 626 | 21 | 167 | 78 | 1,321 | 2,222 | 867 | 2,832 | <20 | <20 | <20 | <20 | <20 | <20 | <20 | <20 | <20 | <20 | <20 | <20 | <20 |
| | 22 | 262 | 117 | 14,871 | 9,779 | 1,720 | 3,704 | <20 | <20 | <20 | <20 | <20 | <20 | <20 | <20 | 51 | 61 | <20 | <20 | <20 |
| | 23 | 990 | 160 | 234 | 396 | 1,136 | 5,613 | <20 | <20 | <20 | <20 | <20 | <20 | <20 | <20 | <20 | <20 | <20 | <20 | <20 |
| | 24 | 197 | 242 | 435 | 528 | 2,860 | 8,020 | <20 | <20 | <20 | <20 | 27 | <20 | <20 | <20 | <20 | <20 | <20 | <20 | <20 |
| | 25 | 275 | 2,227 | 21,492 | 26,507 | 18,317 | 20,316 | <20 | <20 | <20 | <20 | 88 | 75 | 102 | 128 | 124 | 526 | 22 | 50 | 42 |
| 611 | 26 | 447 | 225 | 280 | 385 | 1,786 | 5,340 | 150 | 75 | 128 | 61 | 262 | <20 | <20 | 26 | <20 | <20 | <20 | <20 | <20 |
| | 27 | <20 | 73 | 1,499 | 1,894 | 1,479 | 2,183 | <20 | <20 | <20 | <20 | 81 | <20 | <20 | <20 | 24 | 129 | <20 | <20 | <20 |
| | 28 | 152 | 233 | 3,226 | 3,030 | 2,483 | 6,161 | 325 | 99 | 167 | 202 | 490 | <20 | <20 | <20 | <20 | <20 | <20 | <20 | <20 |
| | 29 | <20 | 40 | 239 | 336 | 558 | 2,569 | <20 | <20 | <20 | <20 | <20 | <20 | <20 | <20 | <20 | 39 | <20 | <20 | <20 |
| | 30 | <20 | <20 | 130 | 609 | 480 | 794 | <20 | <20 | <20 | <20 | 216 | <20 | <20 | <20 | <20 | 50 | <20 | 41 | <20 |

FIG. 21C

Neutralization using Sera from Immunized Guinea Pigs

| | CLADE | A | | | | | A | | | | | A | | | | |
|---|---|---|---|---|---|---|---|---|---|---|---|---|---|---|---|---|
| ID50 | Virus | BG505.W6M.C2 | | | | | BG505.W6M.C2.N88Q.SG3 | | | | | BG505.W6M.C2.N611Q.SG3 | | | | |
| Group | Animal | wk 18 | wk 30 | wk 34 | Wk 38 | Wk 42 | wk 18 | wk 30 | wk 34 | Wk 38 | Wk 42 | wk 18 | wk 30 | wk 34 | Wk 38 | Wk 42 |
| 625 | 6 | <20 | <20 | <20 | <20 | <20 | <20 | <20 | <20 | <20 | <20 | 265 | 821 | 2,679 | 725 | 2,010 |
| | 7 | <20 | <20 | <20 | <20 | <20 | <20 | <20 | <20 | <20 | 36 | 475 | 167 | 1,211 | 245 | 1,042 |
| | 8 | <20 | <20 | <20 | <20 | <20 | <20 | <20 | <20 | <20 | <20 | 26 | 1,232 | 4,619 | 1,056 | 1,104 |
| | 9 | 64 | <20 | <20 | 78 | 129 | 51 | <20 | <20 | <20 | 60 | 184 | 87 | 111 | 367 | 462 |
| | 10 | 25 | <20 | <20 | <20 | 26 | 38 | 23 | <20 | <20 | 26 | 3,410 | 357 | 577 | 747 | 759 |
| 626 | 6 | <20 | <20 | <20 | <20 | <20 | 20 | <20 | <20 | <20 | <20 | 125 | 41 | 78 | 234 | 570 |
| | 7 | 64 | 21 | <20 | 36 | 209 | 74 | 42 | <20 | 74 | 131 | 325 | 130 | 2,218 | 977 | 1,662 |
| | 8 | 41 | <20 | <20 | 31 | 50 | 34 | <20 | <20 | 47 | 46 | 534 | 240 | 273 | 223 | 1,389 |
| | 9 | <20 | <20 | <20 | <20 | <20 | 32 | <20 | <20 | <20 | <20 | 176 | 286 | 258 | 219 | 2,670 |
| | 10 | <20 | <20 | <20 | <20 | <20 | <20 | <20 | <20 | 26 | 32 | 66 | 463 | 8,676 | 6,518 | 5,643 |
| 611 | 6 | <20 | 21 | <20 | <20 | 86 | <20 | 49 | <20 | <20 | 118 | 507 | 166 | 255 | 140 | 2,278 |
| | 7 | <20 | <20 | <20 | <20 | <20 | <20 | <20 | <20 | <20 | <20 | <20 | <20 | 90 | 169 | 401 |
| | 8 | 24 | <20 | <20 | 41 | 163 | 77 | 28 | <20 | 22 | 217 | 208 | 175 | 1,762 | 932 | 3,464 |
| | 9 | <20 | <20 | <20 | <20 | <20 | <20 | <20 | <20 | <20 | <20 | <20 | 21 | 58 | 98 | 123 |
| | 10 | <20 | <20 | <20 | <20 | <20 | <20 | <20 | <20 | <20 | <20 | <20 | <20 | <20 | 77 | 94 |

| | | A | | | | | C | | | | AE | C | C | BC |
|---|---|---|---|---|---|---|---|---|---|---|---|---|---|---|
| ID50 | Virus | BG505.W6M.C2.N88Q.N611Q.SG3 | | | | | MW965.26 | | | | CNE56 | 25710-2.43 | 0077.V1.C16 | CNE19 |
| Group | Animal | wk 18 | wk 30 | wk 34 | Wk 38 | Wk 42 | wk 18 | wk 30 | wk 34 | Wk 38 | Wk 42 | wk 52 | Wk 42 | Wk 42 |
| 625 | 6 | 235 | 2,465 | 5,509 | 2,868 | 5,387 | 10,031 | 2,403 | 4,887 | 5,765 | 3,461 | 20 | 70 | <20 |
| | 7 | 2,110 | 426 | 2,931 | 1,005 | 3,100 | 65,385 | 11,240 | 26,534 | 25,433 | 50,047 | 39 | 84 | <20 |
| | 8 | 332 | 7,757 | 14,250 | 11,631 | 5,580 | 1,684 | 1,176 | 948 | 1,246 | 1,837 | <20 | 43 | <20 |
| | 9 | 581 | 149 | 389 | 391 | 521 | 1,867 | 1,027 | 1,042 | 1,688 | 846 | <20 | 42 | <20 |
| | 10 | 1,582 | 331 | 822 | 523 | 1,369 | 16,553 | 3,287 | 2,895 | 3,743 | 1,626 | <20 | <20 | <20 |
| 626 | 6 | 167 | 78 | 1,321 | 2,222 | 867 | 13,311 | 3,797 | 9,454 | 9,412 | 7,267 | <20 | <20 | <20 |
| | 7 | 262 | 117 | 14,871 | 9,779 | 1,720 | 270,936 | 24,304 | 40,528 | 39,099 | 14,509 | <20 | 51 | <20 |
| | 8 | 990 | 160 | 234 | 396 | 1,136 | 29,084 | 7,699 | 13,583 | 11,830 | 5,754 | <20 | <20 | <20 |
| | 9 | 197 | 242 | 435 | 528 | 2,860 | 19,570 | 5,810 | 6,887 | 9,324 | 4,309 | <20 | <20 | <20 |
| | 10 | 275 | 2,227 | 21,492 | 26,507 | 18,317 | 7,864 | 2,743 | 3,057 | 2,562 | 1,529 | 75 | 124 | 42 |
| 611 | 6 | 447 | 225 | 280 | 385 | 1,786 | 24 | 23 | <20 | <20 | 49 | <20 | <20 | <20 |
| | 7 | <20 | 73 | 1,499 | 1,894 | 1,479 | 4,549 | 1,296 | 1,555 | 1,620 | 3,220 | <20 | 24 | <20 |
| | 8 | 152 | 233 | 3,226 | 3,030 | 2,483 | 2,350 | 882 | 918 | 983 | 925 | <20 | <20 | <20 |
| | 9 | <20 | 40 | 239 | 336 | 558 | 78 | 101 | 88 | 58 | 331 | <20 | <20 | <20 |
| | 10 | <20 | <20 | 130 | 609 | 480 | <20 | 32 | <20 | 28 | 128 | <20 | <20 | <20 |

SEQUENCE LISTING

```
Sequence total quantity: 198
SEQ ID NO: 1            moltype = AA  length = 10
FEATURE                 Location/Qualifiers
source                  1..10
                        mol_type = protein
                        organism = human immunodeficiency virus
SEQUENCE: 1
AVGIGAVFLG                                                         10

SEQ ID NO: 2            moltype = AA  length = 10
FEATURE                 Location/Qualifiers
source                  1..10
                        mol_type = protein
                        organism = human immunodeficiency virus
SEQUENCE: 2
AVGLGAVFLG                                                         10

SEQ ID NO: 3            moltype = AA  length = 10
FEATURE                 Location/Qualifiers
source                  1..10
                        mol_type = protein
                        organism = human immunodeficiency virus
SEQUENCE: 3
AVGIGAMIFG                                                         10
```

```
SEQ ID NO: 4            moltype = AA  length = 11
FEATURE                 Location/Qualifiers
source                  1..11
                        mol_type = protein
                        organism = human immunodeficiency virus
SEQUENCE: 4
AVGTIGAMFL G                                                        11

SEQ ID NO: 5            moltype = AA  length = 10
FEATURE                 Location/Qualifiers
source                  1..10
                        mol_type = protein
                        organism = human immunodeficiency virus
SEQUENCE: 5
AVGIGAMFLG                                                          10

SEQ ID NO: 6            moltype = AA  length = 10
FEATURE                 Location/Qualifiers
source                  1..10
                        mol_type = protein
                        organism = human immunodeficiency virus
SEQUENCE: 6
AVGIGALFLG                                                          10

SEQ ID NO: 7            moltype = AA  length = 10
FEATURE                 Location/Qualifiers
source                  1..10
                        mol_type = protein
                        organism = human immunodeficiency virus
SEQUENCE: 7
AIGLGAMFLG                                                          10

SEQ ID NO: 8            moltype = AA  length = 10
FEATURE                 Location/Qualifiers
source                  1..10
                        mol_type = protein
                        organism = human immunodeficiency virus
SEQUENCE: 8
AVGLGAVFIG                                                          10

SEQ ID NO: 9            moltype = AA  length = 10
FEATURE                 Location/Qualifiers
source                  1..10
                        mol_type = protein
                        organism = human immunodeficiency virus
SEQUENCE: 9
AVGIGAVLLG                                                          10

SEQ ID NO: 10           moltype = AA  length = 10
FEATURE                 Location/Qualifiers
source                  1..10
                        mol_type = protein
                        organism = human immunodeficiency virus
SEQUENCE: 10
AVGIGAVFIG                                                          10

SEQ ID NO: 11           moltype = AA  length = 10
FEATURE                 Location/Qualifiers
source                  1..10
                        mol_type = protein
                        organism = human immunodeficiency virus
SEQUENCE: 11
AIGLGALFLG                                                          10

SEQ ID NO: 12           moltype = AA  length = 9
FEATURE                 Location/Qualifiers
source                  1..9
                        mol_type = protein
                        organism = human immunodeficiency virus
SEQUENCE: 12
AALGAVFLG                                                           9

SEQ ID NO: 13           moltype = AA  length = 161
FEATURE                 Location/Qualifiers
REGION                  1..161
                        note = Epitope Scaffold Protein
source                  1..161
                        mol_type = protein
```

```
                         organism = synthetic construct
SEQUENCE: 13
AVDMFIKIGD VKGESKDKTH AEEIDVLAWS WGMSQSGSMH MGGGGGAGKV NVQDLSFTKY  60
IDKSTPNLMM ACSSGKHYPQ AKLTIRKAGG ENQVEYLIIT LKEVLVSSVS TGGSGGEDRL  120
TENVTLNFAQ VQVDYQPQKA DGAKDGGPVK YGWNIRQNVQ A                      161

SEQ ID NO: 14            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 14
AVDMFIKIGD VKGESKDKTH NSTIDVLAWS WGMSQSGSMH MGGGGGAGKV NVQDLSFTKY  60
IDKSTPNLMM ACSSGKHYPQ AKLTIRKAGG ENQVEYLIIT LKEVLVSSVS TGGSGGEDRL  120
TENVTLNFAQ VQVDYQPQKA DGAKDGGPVK YGWNIRQNVQ A                      161

SEQ ID NO: 15            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 15
AVDMFIKIGD VKGESKDKTH AEEIDVLAWS WGMSQSGSMH MGGGGGAGKV NVQDLSFTKY  60
IDKSTPNLMM ACSSGKHYPQ AKLTIRKAGG ENQVEYLIIT LKEVLVSSVS TGGSGGEDRL  120
TENVTLNFAQ VQVDYQPQNS TGAKDGGPVK YGWNIRQNVQ A                      161

SEQ ID NO: 16            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 16
AVDMFIKIGD VKGESKDKTH NSTIDVLAWS WGMSQSGSMH MGGGGGAGKV NVQDLSFTKY  60
IDKSTPNLMM ACSSGKHYPQ AKLTIRKAGG ENQVEYLIIT LKEVLVSSVS TGGSGGEDRL  120
TENVTLNFAQ VQVDYQPQNS TGAKDGGPVK YGWNIRQNVQ A                      161

SEQ ID NO: 17            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 17
AVDMFIKIGD VKGESKDKTH AEEIDVLAWS WGMSQSGSMH MGGGGGAGKV NVQDLSFTKY  60
IDKSTPNLMM ACSSGKHYPQ AKLTIRKACG ENQVEYLIIT LKEVLVSSVS TGGSGGEDRL  120
TENVTLNFAQ VQVDYQPQKA DGAKDGGPVK YGWNICQNVQ A                      161

SEQ ID NO: 18            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 18
AVDMFIKIGD VKGESKDKTH AEEIDVLAWS WGMSQSGSMH MGGGGGAGKV NVQDLSFTKY  60
IDKSTPNLMM ACSSGKHYPQ AKLTIRKACG ENQVEYLIIT LKEVLVSSVS TGGSGGEDRL  120
TENVTLNFAQ VQVDYQPQNS TGAKDGGPVK YGWNICQNVQ A                      161

SEQ ID NO: 19            moltype = AA  length = 161
FEATURE                  Location/Qualifiers
REGION                   1..161
                         note = Epitope Scaffold Protein
source                   1..161
                         mol_type = protein
                         organism = synthetic construct
SEQUENCE: 19
AVDMFIKIGD VKGESKDKTH NSTIDVLAWS WGMSQSGSMH MGGGGGAGKV NVQDLSFTKY  60
IDKSTPNLMM ACSSGKHYPQ AKLTIRKACG ENQVEYLIIT LKEVLVSSVS TGGSGGEDRL  120
TENVTLNFAQ VQVDYQPQKA DGAKDGGPVK YGWNICQNVQ A                      161

SEQ ID NO: 20            moltype = AA  length = 161
```

```
FEATURE                 Location/Qualifiers
REGION                  1..161
                        note = Epitope Scaffold Protein
source                  1..161
                        mol_type = protein
                        organism = synthetic construct
SEQUENCE: 20
AVDMFIKIGD VKGESKDKTH NSTIDVLAWS WGMSQSGSMH MGGGGGAGKV NVQDLSFTKY  60
IDKSTPNLMM ACSSGKHYPQ AKLTIRKACG ENQVEYLIIT LKEVLVSSVS TGGSGGEDRL  120
TENVTLNFAQ VQVDYQPQNS TGAKDGGPVK YGWNICQNVQ A                     161

SEQ ID NO: 21           moltype = AA  length = 106
FEATURE                 Location/Qualifiers
REGION                  1..106
                        note = Epitope Scaffold Protein
source                  1..106
                        mol_type = protein
                        organism = synthetic construct
SEQUENCE: 21
ADLEDNWETL NDNLKVIEKA DNAAQVKDAL TKMRNASLDA QKATPPKLED KSPDSPEMKD  60
FRHGFDILVG QIDDALKLAN EGKVKEAQAA AEQLKTTRNA YIQKYL                106

SEQ ID NO: 22           moltype = AA  length = 106
FEATURE                 Location/Qualifiers
REGION                  1..106
                        note = Epitope Scaffold Protein
source                  1..106
                        mol_type = protein
                        organism = synthetic construct
SEQUENCE: 22
ADLEDNWETL NDNLKVIEKA DNAAQVKDAL TKMRAAALDA QNATPPKLED KSPDSPEMKD  60
FRHGFDILVG QIDDALKLAN EGKVKEAQAA AEQLKTTRNA YIQKYL                106

SEQ ID NO: 23           moltype = AA  length = 106
FEATURE                 Location/Qualifiers
REGION                  1..106
                        note = Epitope Scaffold Protein
source                  1..106
                        mol_type = protein
                        organism = synthetic construct
SEQUENCE: 23
ADLEDNWETL NDNLKVIEKA DNAAQVKDAL TKMRAAALDA QKATPPKLND TSPDSPEMKD  60
FRHGFDILVG QIDDALKLAN EGKVKEAQAA AEQLKTTRNA YIQKYL                106

SEQ ID NO: 24           moltype = AA  length = 106
FEATURE                 Location/Qualifiers
REGION                  1..106
                        note = Epitope Scaffold Protein
source                  1..106
                        mol_type = protein
                        organism = synthetic construct
SEQUENCE: 24
ADLEDNWETL NDNLKVIEKA DNAAQVKDAL TKMRAAALDA QKATPPKLED KSPDSPEMKD  60
FRHGFDILVG QIDDALKLAN EGKVKEAQAA AEQLKTTRNA YIQKYL                106

SEQ ID NO: 25           moltype = AA  length = 54
FEATURE                 Location/Qualifiers
REGION                  1..54
                        note = Epitope Scaffold Protein
source                  1..54
                        mol_type = protein
                        organism = synthetic construct
SEQUENCE: 25
SGVRLWATRQ AMLGQVHEVP EGWLIFVAEQ EELYVRVQNG FRKVQLEART PLPR       54

SEQ ID NO: 26           moltype = AA  length = 54
FEATURE                 Location/Qualifiers
REGION                  1..54
                        note = Epitope Scaffold Protein
source                  1..54
                        mol_type = protein
                        organism = synthetic construct
SEQUENCE: 26
SGVRLWATRQ NMTGQVHEVP EGWLIFVAEQ EELYVRVQNG FRKVQLEART PLPR       54

SEQ ID NO: 27           moltype = AA  length = 54
FEATURE                 Location/Qualifiers
REGION                  1..54
                        note = Epitope Scaffold Protein
```

```
source                  1..54
                        mol_type = protein
                        organism = synthetic construct
SEQUENCE: 27
SGVRLWATRQ AMLGNVTEVP EGWLIFVAEQ EELYVRVQNG FRKVQLEART PLPR        54

SEQ ID NO: 28           moltype = AA  length = 54
FEATURE                 Location/Qualifiers
REGION                  1..54
                        note = Epitope Scaffold Protein
source                  1..54
                        mol_type = protein
                        organism = synthetic construct
SEQUENCE: 28
SGVRLWATRQ AMLGQVHNVS EGWLIFVAEQ EELYVRVQNG FRKVQLEART PLPR        54

SEQ ID NO: 29           moltype = AA  length = 127
FEATURE                 Location/Qualifiers
REGION                  1..127
                        note = Epitope Scaffold Protein
source                  1..127
                        mol_type = protein
                        organism = synthetic construct
SEQUENCE: 29
AEAGITGTWY NQLGSTFIVT AGADGALTGT YESAVGNAES RYVLTGRYDS APATDGSGTA  60
LGWTVAWKNN YRNAHSATTW SGQYVGGAEA RINTQWLLTS GTTEANAWKS TLVGHDTFTK  120
VKNSSAS                                                            127

SEQ ID NO: 30           moltype = AA  length = 126
FEATURE                 Location/Qualifiers
REGION                  1..126
                        note = Epitope Scaffold Protein
source                  1..126
                        mol_type = protein
                        organism = synthetic construct
SEQUENCE: 30
EAGITGTWYN QLGSTFIVTA GADGALTGTY ESAVGNAESR YVLTGRYDSA PATDGSGTAL  60
GWTVAWKNNY RNAHSATTWS GQYVGGNESR INTQWLLTSG TTEANAWKST LVGHDTFTKV  120
KPSAAS                                                             126

SEQ ID NO: 31           moltype = AA  length = 126
FEATURE                 Location/Qualifiers
REGION                  1..126
                        note = Epitope Scaffold Protein
source                  1..126
                        mol_type = protein
                        organism = synthetic construct
SEQUENCE: 31
EAGITGTWYN QLGSTFIVTA GADGALTGTY ESAVGNAESR YVLTGRYDSA PATDGSGTAL  60
GWTVAWKNNY RNAHSATTWS GQYVGGAEAR INTQWLLTSG TNESNAWKST LVGHDTFTKV  120
KPSAAS                                                             126

SEQ ID NO: 32           moltype = AA  length = 176
FEATURE                 Location/Qualifiers
REGION                  1..176
                        note = Epitope Scaffold Protein
source                  1..176
                        mol_type = protein
                        organism = synthetic construct
SEQUENCE: 32
AVGIGAVFLG GGGGGAVDMF IKIGDVKGES KDKTHAEEID VLAWSWGMSQ SGSMHMGGGG  60
GAGKVNVQDL SFTKYIDKST PNLMMACSSG KHYPQAKLTI RKAGGENQVE YLIITLKEVL  120
VSSVSTGGSG GEDRLTENVT LNFAQVQVDY QPQKADGAKD GGPVKYGWNI RQNVQA      176

SEQ ID NO: 33           moltype = AA  length = 191
FEATURE                 Location/Qualifiers
REGION                  1..191
                        note = Epitope Scaffold Protein
source                  1..191
                        mol_type = protein
                        organism = synthetic construct
SEQUENCE: 33
AVGIGAVFLG GGGGGAVGIG AVFLGGGGGG AVDMFIKIGD VKGESKDKTH AEEIDVLAWS  60
WGMSQSGSMH MGGGGGAGKV NVQDLSFTKY IDKSTPNLMM ACSSGKHYPQ AKLTIRKAGG  120
ENQVEYLIIT LKEVLVSSVS TGGSGGEDRL TENVTLNFAQ VQVDYQPQKA DGAKDGGPVK  180
YGWNIRQNVQ A                                                       191

SEQ ID NO: 34           moltype = AA  length = 176
FEATURE                 Location/Qualifiers
```

```
REGION                  1..176
                        note = Epitope Scaffold Protein
source                  1..176
                        mol_type = protein
                        organism = synthetic construct
SEQUENCE: 34
AVGIGAVFLG GGGGGAVDMF IKIGDVKGES KDKTHNSTID VLAWSWGMSQ SGSMHMGGGG  60
GAGKVNVQDL SFTKYIDKST PNLMMACSSG KHYPQAKLTI RKAGGENQVE YLIITLKEVL  120
VSSVSTGGSG GEDRLTENVT LNFAQVQVDY QPQKADGAKD GGPVKYGWNI RQNVQA      176

SEQ ID NO: 35           moltype = AA  length = 176
FEATURE                 Location/Qualifiers
REGION                  1..176
                        note = Epitope Scaffold Protein
source                  1..176
                        mol_type = protein
                        organism = synthetic construct
SEQUENCE: 35
AVGIGAVFLG GGGGGAVDMF IKIGDVKGES KDKTHAEEID VLAWSWGMSQ SGSMHMGGGG  60
GAGKVNVQDL SFTKYIDKST PNLMMACSSG KHYPQAKLTI RKAGGENQVE YLIITLKEVL  120
VSSVSTGGSG GEDRLTENVT LNFAQVQVDY QPQNSTGAKD GGPVKYGWNI RQNVQA      176

SEQ ID NO: 36           moltype = AA  length = 176
FEATURE                 Location/Qualifiers
REGION                  1..176
                        note = Epitope Scaffold Protein
source                  1..176
                        mol_type = protein
                        organism = synthetic construct
SEQUENCE: 36
AVGIGAVFLG GGGGGAVDMF IKIGDVKGES KDKTHNSTID VLAWSWGMSQ SGSMHMGGGG  60
GAGKVNVQDL SFTKYIDKST PNLMMACSSG KHYPQAKLTI RKAGGENQVE YLIITLKEVL  120
VSSVSTGGSG GEDRLTENVT LNFAQVQVDY QPQNSTGAKD GGPVKYGWNI RQNVQA      176

SEQ ID NO: 37           moltype = AA  length = 191
FEATURE                 Location/Qualifiers
REGION                  1..191
                        note = Epitope Scaffold Protein
source                  1..191
                        mol_type = protein
                        organism = synthetic construct
SEQUENCE: 37
AVGIGAVFLG GGGGGAVGIG AVFLGGGGGG AVDMFIKIGD VKGESKDKTH NSTIDVLAWS  60
WGMSQSGSMH MGGGGGAGKV NVQDLSFTKY IDKSTPNLMM ACSSGKHYPQ AKLTIRKAGG  120
ENQVEYLIIT LKEVLVSSVS TGGSGGEDRL TENVTLNFAQ VQVDYQPQKA DGAKDGGPVK  180
YGWNIRQNVQ A                                                      191

SEQ ID NO: 38           moltype = AA  length = 191
FEATURE                 Location/Qualifiers
REGION                  1..191
                        note = Epitope Scaffold Protein
source                  1..191
                        mol_type = protein
                        organism = synthetic construct
SEQUENCE: 38
AVGIGAVFLG GGGGGAVGIG AVFLGGGGGG AVDMFIKIGD VKGESKDKTH AEEIDVLAWS  60
WGMSQSGSMH MGGGGGAGKV NVQDLSFTKY IDKSTPNLMM ACSSGKHYPQ AKLTIRKAGG  120
ENQVEYLIIT LKEVLVSSVS TGGSGGEDRL TENVTLNFAQ VQVDYQPQNS TGAKDGGPVK  180
YGWNIRQNVQ A                                                      191

SEQ ID NO: 39           moltype = AA  length = 191
FEATURE                 Location/Qualifiers
REGION                  1..191
                        note = Epitope Scaffold Protein
source                  1..191
                        mol_type = protein
                        organism = synthetic construct
SEQUENCE: 39
AVGIGAVFLG GGGGGAVGIG AVFLGGGGGG AVDMFIKIGD VKGESKDKTH NSTIDVLAWS  60
WGMSQSGSMH MGGGGGAGKV NVQDLSFTKY IDKSTPNLMM ACSSGKHYPQ AKLTIRKAGG  120
ENQVEYLIIT LKEVLVSSVS TGGSGGEDRL TENVTLNFAQ VQVDYQPQNS TGAKDGGPVK  180
YGWNIRQNVQ A                                                      191

SEQ ID NO: 40           moltype = AA  length = 176
FEATURE                 Location/Qualifiers
REGION                  1..176
                        note = Epitope Scaffold Protein
source                  1..176
                        mol_type = protein
```

```
                       organism = synthetic construct
SEQUENCE: 40
AVGIGAVFLG GGGGGAVDMF IKIGDVKGES KDKTHAEEID VLAWSWGMSQ SGSMHMGGGG  60
GAGKVNVQDL SFTKYIDKST PNLMMACSSG KHYPQAKLTI RKACGENQVE YLIITLKEVL  120
VSSVSTGGSG GEDRLTENVT LNFAQVQVDY QPQKADGAKD GGPVKYGWNI CQNVQA      176

SEQ ID NO: 41          moltype = AA  length = 191
FEATURE                Location/Qualifiers
REGION                 1..191
                       note = Epitope Scaffold Protein
source                 1..191
                       mol_type = protein
                       organism = synthetic construct
SEQUENCE: 41
AVGIGAVFLG GGGGGAVGIG AVFLGGGGGG AVDMFIKIGD VKGESKDKTH AEEIDVLAWS  60
WGMSQSGSMH MGGGGGAGKV NVQDLSFTKY IDKSTPNLMM ACSSGKHYPQ AKLTIRKACG  120
ENQVEYLIIT LKEVLVSSVS TGGSGGEDRL TENVTLNFAQ VQVDYQPQKA DGAKDGGPVK  180
YGWNICQNVQ A                                                       191

SEQ ID NO: 42          moltype = AA  length = 176
FEATURE                Location/Qualifiers
REGION                 1..176
                       note = Epitope Scaffold Protein
source                 1..176
                       mol_type = protein
                       organism = synthetic construct
SEQUENCE: 42
AVGIGAVFLG GGGGGAVDMF IKIGDVKGES KDKTHNSTID VLAWSWGMSQ SGSMHMGGGG  60
GAGKVNVQDL SFTKYIDKST PNLMMACSSG KHYPQAKLTI RKACGENQVE YLIITLKEVL  120
VSSVSTGGSG GEDRLTENVT LNFAQVQVDY QPQKADGAKD GGPVKYGWNI CQNVQA      176

SEQ ID NO: 43          moltype = AA  length = 176
FEATURE                Location/Qualifiers
REGION                 1..176
                       note = Epitope Scaffold Protein
source                 1..176
                       mol_type = protein
                       organism = synthetic construct
SEQUENCE: 43
AVGIGAVFLG GGGGGAVDMF IKIGDVKGES KDKTHAEEID VLAWSWGMSQ SGSMHMGGGG  60
GAGKVNVQDL SFTKYIDKST PNLMMACSSG KHYPQAKLTI RKACGENQVE YLIITLKEVL  120
VSSVSTGGSG GEDRLTENVT LNFAQVQVDY QPQNSTGAKD GGPVKYGWNI CQNVQA      176

SEQ ID NO: 44          moltype = AA  length = 176
FEATURE                Location/Qualifiers
REGION                 1..176
                       note = Epitope Scaffold Protein
source                 1..176
                       mol_type = protein
                       organism = synthetic construct
SEQUENCE: 44
AVGIGAVFLG GGGGGAVDMF IKIGDVKGES KDKTHNSTID VLAWSWGMSQ SGSMHMGGGG  60
GAGKVNVQDL SFTKYIDKST PNLMMACSSG KHYPQAKLTI RKACGENQVE YLIITLKEVL  120
VSSVSTGGSG GEDRLTENVT LNFAQVQVDY QPQNSTGAKD GGPVKYGWNI CQNVQA      176

SEQ ID NO: 45          moltype = AA  length = 191
FEATURE                Location/Qualifiers
REGION                 1..191
                       note = Epitope Scaffold Protein
source                 1..191
                       mol_type = protein
                       organism = synthetic construct
SEQUENCE: 45
AVGIGAVFLG GGGGGAVGIG AVFLGGGGGG AVDMFIKIGD VKGESKDKTH NSTIDVLAWS  60
WGMSQSGSMH MGGGGGAGKV NVQDLSFTKY IDKSTPNLMM ACSSGKHYPQ AKLTIRKACG  120
ENQVEYLIIT LKEVLVSSVS TGGSGGEDRL TENVTLNFAQ VQVDYQPQKA DGAKDGGPVK  180
YGWNICQNVQ A                                                       191

SEQ ID NO: 46          moltype = AA  length = 191
FEATURE                Location/Qualifiers
REGION                 1..191
                       note = Epitope Scaffold Protein
source                 1..191
                       mol_type = protein
                       organism = synthetic construct
SEQUENCE: 46
AVGIGAVFLG GGGGGAVGIG AVFLGGGGGG AVDMFIKIGD VKGESKDKTH AEEIDVLAWS  60
WGMSQSGSMH MGGGGGAGKV NVQDLSFTKY IDKSTPNLMM ACSSGKHYPQ AKLTIRKACG  120
ENQVEYLIIT LKEVLVSSVS TGGSGGEDRL TENVTLNFAQ VQVDYQPQNS TGAKDGGPVK  180
```

```
YGWNICQNVQ A                                                    191

SEQ ID NO: 47          moltype = AA  length = 191
FEATURE                Location/Qualifiers
REGION                 1..191
                       note = Epitope Scaffold Protein
source                 1..191
                       mol_type = protein
                       organism = synthetic construct
SEQUENCE: 47
AVGIGAVFLG GGGGGAVGIG AVFLGGGGGG AVDMFIKIGD VKGESKDKTH NSTIDVLAWS  60
WGMSQSGSMH MGGGGGAGKV NVQDLSFTKY IDKSTPNLMM ACSSGKHYPQ AKLTIRKACG  120
ENQVEYLIIT LKEVLVSSVS TGGSGGEDRL TENVTLNFAQ VQVDYQPQNS TGAKDGGPVK  180
YGWNICQNVQ A                                                    191

SEQ ID NO: 48          moltype = AA  length = 118
FEATURE                Location/Qualifiers
REGION                 1..118
                       note = Epitope Scaffold Protein
source                 1..118
                       mol_type = protein
                       organism = synthetic construct
SEQUENCE: 48
AVGIGAVFLG GGADLEDNWE TLNDNLKVIE KADNAAQVKD ALTKMRNASL DAQKATPPKL  60
EDKSPDSPEM KDFRHGFDIL VGQIDDALKL ANEGKVKEAQ AAAEQLKTTR NAYIQKYL    118

SEQ ID NO: 49          moltype = AA  length = 118
FEATURE                Location/Qualifiers
REGION                 1..118
                       note = Epitope Scaffold Protein
source                 1..118
                       mol_type = protein
                       organism = synthetic construct
SEQUENCE: 49
AVGIGAVFLG GGADLEDNWE TLNDNLKVIE KADNAAQVKD ALTKMRAAAL DAQNATPPKL  60
EDKSPDSPEM KDFRHGFDIL VGQIDDALKL ANEGKVKEAQ AAAEQLKTTR NAYIQKYL    118

SEQ ID NO: 50          moltype = AA  length = 118
FEATURE                Location/Qualifiers
REGION                 1..118
                       note = Epitope Scaffold Protein
source                 1..118
                       mol_type = protein
                       organism = synthetic construct
SEQUENCE: 50
AVGIGAVFLG GGADLEDNWE TLNDNLKVIE KADNAAQVKD ALTKMRAAAL DAQKATPPKL  60
NDTSPDSPEM KDFRHGFDIL VGQIDDALKL ANEGKVKEAQ AAAEQLKTTR NAYIQKYL    118

SEQ ID NO: 51          moltype = AA  length = 118
FEATURE                Location/Qualifiers
REGION                 1..118
                       note = Epitope Scaffold Protein
source                 1..118
                       mol_type = protein
                       organism = synthetic construct
SEQUENCE: 51
AVGIGAVFLG GGADLEDNWE TLNDNLKVIE KADNAAQVKD ALTKMRAAAL DAQKATPPKL  60
EDKSPDSPEM KDFRHGFDIL VGQIDDALKL ANEGKVKEAQ AAAEQLKTTR NAYIQKYL    118

SEQ ID NO: 52          moltype = AA  length = 68
FEATURE                Location/Qualifiers
REGION                 1..68
                       note = Epitope Scaffold Protein
source                 1..68
                       mol_type = protein
                       organism = synthetic construct
SEQUENCE: 52
AVGIGAVFLG GGGSSGVRLW ATRQAMLGQV HEVPEGWLIF VAEQEELYVR VQNGFRKVQL  60
EARTPLPR                                                        68

SEQ ID NO: 53          moltype = AA  length = 68
FEATURE                Location/Qualifiers
REGION                 1..68
                       note = Epitope Scaffold Protein
source                 1..68
                       mol_type = protein
                       organism = synthetic construct
SEQUENCE: 53
AVGIGAVFLG GGGSSGVRLW ATRQNMTGQV HEVPEGWLIF VAEQEELYVR VQNGFRKVQL  60
```

```
EARTPLPR                                                          68

SEQ ID NO: 54           moltype = AA  length = 68
FEATURE                 Location/Qualifiers
REGION                  1..68
                        note = Epitope Scaffold Protein
source                  1..68
                        mol_type = protein
                        organism = synthetic construct
SEQUENCE: 54
AVGIGAVFLG GGGSSGVRLW ATRQAMLGNV TEVPEGWLIF VAEQEELYVR VQNGFRKVQL  60
EARTPLPR                                                          68

SEQ ID NO: 55           moltype = AA  length = 68
FEATURE                 Location/Qualifiers
REGION                  1..68
                        note = Epitope Scaffold Protein
source                  1..68
                        mol_type = protein
                        organism = synthetic construct
SEQUENCE: 55
AVGIGAVFLG GGGSSGVRLW ATRQAMLGQV HNVSEGWLIF VAEQEELYVR VQNGFRKVQL  60
EARTPLPR                                                          68

SEQ ID NO: 56           moltype = AA  length = 135
FEATURE                 Location/Qualifiers
REGION                  1..135
                        note = Epitope Scaffold Protein
source                  1..135
                        mol_type = protein
                        organism = synthetic construct
SEQUENCE: 56
AVGIGAVFAE AGITGTWYNQ LGSTFIVTAG ADGALTGTYE SAVGNAESRY VLTGRYDSAP  60
ATDGSGTALG WTVAWKNNYR NAHSATTWSG QYVGGAEARI NTQWLLTSGT TEANAWKSTL  120
VGHDTFTKVK NSSAS                                                  135

SEQ ID NO: 57           moltype = AA  length = 134
FEATURE                 Location/Qualifiers
REGION                  1..134
                        note = Epitope Scaffold Protein
source                  1..134
                        mol_type = protein
                        organism = synthetic construct
SEQUENCE: 57
AVGIGAVFEA GITGTWYNQL GSTFIVTAGA DGALTGTYES AVGNAESRYV LTGRYDSAPA  60
TDGSGTALGW TVAWKNNYRN AHSATTWSGQ YVGGNESRIN TQWLLTSGTT EANAWKSTLV  120
GHDTFTKVKP SAAS                                                   134

SEQ ID NO: 58           moltype = AA  length = 133
FEATURE                 Location/Qualifiers
REGION                  1..133
                        note = Epitope Scaffold Protein
source                  1..133
                        mol_type = protein
                        organism = synthetic construct
SEQUENCE: 58
AVGIGAVEAG ITGTWYNQLG STFIVTAGAD GALTGTYESA VGNAESRYVL TGRYDSAPAT  60
DGSGTALGWT VAWKNNYRNA HSATTWSGQY VGGAEARINT QWLLTSGTNE SNAWKSTLVG  120
HDTFTKVKPS AAS                                                    133

SEQ ID NO: 59           moltype = AA  length = 218
FEATURE                 Location/Qualifiers
REGION                  1..218
                        note = Epitope Scaffold Protein
source                  1..218
                        mol_type = protein
                        organism = synthetic construct
SEQUENCE: 59
MDSKGSSQKG SRLLLLLVVS NLLLPQGVLA AVGIGAVFLG GGGGGAVDMF IKIGDVKGES  60
KDKTHAEEID VLAWSWGMSQ SGSMHMGGGG GAGKVNVQDL SFTKYIDKST PNLMMACSSG  120
KHYPQAKLTI RKAGGENQVE YLIITLKEVL VSSVSTGGSG GEDRLTENVT LNFAQVQVDY  180
QPQKADGAKD GGPVKYGWNI RQNVQAGGGS HHHHHHHH                          218

SEQ ID NO: 60           moltype = AA  length = 233
FEATURE                 Location/Qualifiers
REGION                  1..233
                        note = Epitope Scaffold Protein
source                  1..233
                        mol_type = protein
```

```
                         organism = synthetic construct
SEQUENCE: 60
MDSKGSSQKG SRLLLLLVVS NLLLPQGVLA AVGIGAVFLG GGGGGAVGIG AVFLGGGGGG  60
AVDMFIKIGD VKGESKDKTH AEEIDVLAWS WGMSQSGSMH MGGGGGAGKV NVQDLSFTKY  120
IDKSTPNLMM ACSSGKHYPQ AKLTIRKAGG ENQVEYLIIT LKEVLVSSVS TGGSGGEDRL  180
TENVTLNFAQ VQVDYQPQKA DGAKDGGPVK YGWNIRQNVQ AGGGSHHHHH HHH         233

SEQ ID NO: 61            moltype = AA  length = 218
FEATURE                  Location/Qualifiers
REGION                   1..218
                         note = Epitope Scaffold Protein
source                   1..218
                         mol_type = protein
                         organism = synthetic construct
SEQUENCE: 61
MDSKGSSQKG SRLLLLLVVS NLLLPQGVLA AVGIGAVFLG GGGGGAVDMF IKIGDVKGES  60
KDKTHNSTID VLAWSWGMSQ SGSMHMGGGG GAGKVNVQDL SFTKYIDKST PNLMMACSSG  120
KHYPQAKLTI RKAGGENQVE YLIITLKEVL VSSVSTGGSG GEDRLTENVT LNFAQVQVDY  180
QPQKADGAKD GGPVKYGWNI RQNVQAGGGS HHHHHHHH                          218

SEQ ID NO: 62            moltype = AA  length = 218
FEATURE                  Location/Qualifiers
REGION                   1..218
                         note = Epitope Scaffold Protein
source                   1..218
                         mol_type = protein
                         organism = synthetic construct
SEQUENCE: 62
MDSKGSSQKG SRLLLLLVVS NLLLPQGVLA AVGIGAVFLG GGGGGAVDMF IKIGDVKGES  60
KDKTHAEEID VLAWSWGMSQ SGSMHMGGGG GAGKVNVQDL SFTKYIDKST PNLMMACSSG  120
KHYPQAKLTI RKAGGENQVE YLIITLKEVL VSSVSTGGSG GEDRLTENVT LNFAQVQVDY  180
QPQNSTGAKD GGPVKYGWNI RQNVQAGGGS HHHHHHHH                          218

SEQ ID NO: 63            moltype = AA  length = 218
FEATURE                  Location/Qualifiers
REGION                   1..218
                         note = Epitope Scaffold Protein
source                   1..218
                         mol_type = protein
                         organism = synthetic construct
SEQUENCE: 63
MDSKGSSQKG SRLLLLLVVS NLLLPQGVLA AVGIGAVFLG GGGGGAVDMF IKIGDVKGES  60
KDKTHNSTID VLAWSWGMSQ SGSMHMGGGG GAGKVNVQDL SFTKYIDKST PNLMMACSSG  120
KHYPQAKLTI RKAGGENQVE YLIITLKEVL VSSVSTGGSG GEDRLTENVT LNFAQVQVDY  180
QPQNSTGAKD GGPVKYGWNI RQNVQAGGGS HHHHHHHH                          218

SEQ ID NO: 64            moltype = AA  length = 233
FEATURE                  Location/Qualifiers
REGION                   1..233
                         note = Epitope Scaffold Protein
source                   1..233
                         mol_type = protein
                         organism = synthetic construct
SEQUENCE: 64
MDSKGSSQKG SRLLLLLVVS NLLLPQGVLA AVGIGAVFLG GGGGGAVGIG AVFLGGGGGG  60
AVDMFIKIGD VKGESKDKTH NSTIDVLAWS WGMSQSGSMH MGGGGGAGKV NVQDLSFTKY  120
IDKSTPNLMM ACSSGKHYPQ AKLTIRKAGG ENQVEYLIIT LKEVLVSSVS TGGSGGEDRL  180
TENVTLNFAQ VQVDYQPQKA DGAKDGGPVK YGWNIRQNVQ AGGGSHHHHH HHH         233

SEQ ID NO: 65            moltype = AA  length = 233
FEATURE                  Location/Qualifiers
REGION                   1..233
                         note = Epitope Scaffold Protein
source                   1..233
                         mol_type = protein
                         organism = synthetic construct
SEQUENCE: 65
MDSKGSSQKG SRLLLLLVVS NLLLPQGVLA AVGIGAVFLG GGGGGAVGIG AVFLGGGGGG  60
AVDMFIKIGD VKGESKDKTH AEEIDVLAWS WGMSQSGSMH MGGGGGAGKV NVQDLSFTKY  120
IDKSTPNLMM ACSSGKHYPQ AKLTIRKAGG ENQVEYLIIT LKEVLVSSVS TGGSGGEDRL  180
TENVTLNFAQ VQVDYQPQNS TGAKDGGPVK YGWNIRQNVQ AGGGSHHHHH HHH         233

SEQ ID NO: 66            moltype = AA  length = 233
FEATURE                  Location/Qualifiers
REGION                   1..233
                         note = Epitope Scaffold Protein
source                   1..233
                         mol_type = protein
                         organism = synthetic construct
```

```
SEQUENCE: 66
MDSKGSSQKG SRLLLLLVVS NLLLPQGVLA AVGIGAVFLG GGGGGAVGIG AVFLGGGGGG  60
AVDMFIKIGD VKGESKDKTH NSTIDVLAWS WGMSQSGSMH MGGGGGAGKV NVQDLSFTKY  120
IDKSTPNLMM ACSSGKHYPQ AKLTIRKAGG ENQVEYLIIT LKEVLVSSVS TGGSGGEDRL  180
TENVTLNFAQ VQVDYQPQNS TGAKDGGPVK YGWNIRQNVQ AGGGSHHHHH HHH         233

SEQ ID NO: 67          moltype = AA  length = 218
FEATURE                Location/Qualifiers
REGION                 1..218
                       note = Epitope Scaffold Protein
source                 1..218
                       mol_type = protein
                       organism = synthetic construct
SEQUENCE: 67
MDSKGSSQKG SRLLLLLVVS NLLLPQGVLA AVGIGAVFLG GGGGGAVDMF IKIGDVKGES  60
KDKTHAEEID VLAWSWGMSQ SGSMHMGGGG GAGKVNVQDL SFTKYIDKST PNLMMACSSG  120
KHYPQAKLTI RKACGENQVE YLIITLKEVL VSSVSTGGSG GEDRLTENVT LNFAQVQVDY  180
QPQKADGAKD GGPVKYGWNI CQNVQAGGGS HHHHHHHH                          218

SEQ ID NO: 68          moltype = AA  length = 233
FEATURE                Location/Qualifiers
REGION                 1..233
                       note = Epitope Scaffold Protein
source                 1..233
                       mol_type = protein
                       organism = synthetic construct
SEQUENCE: 68
MDSKGSSQKG SRLLLLLVVS NLLLPQGVLA AVGIGAVFLG GGGGGAVGIG AVFLGGGGGG  60
AVDMFIKIGD VKGESKDKTH AEEIDVLAWS WGMSQSGSMH MGGGGGAGKV NVQDLSFTKY  120
IDKSTPNLMM ACSSGKHYPQ AKLTIRKACG ENQVEYLIIT LKEVLVSSVS TGGSGGEDRL  180
TENVTLNFAQ VQVDYQPQKA DGAKDGGPVK YGWNICQNVQ AGGGSHHHHH HHH         233

SEQ ID NO: 69          moltype = AA  length = 218
FEATURE                Location/Qualifiers
REGION                 1..218
                       note = Epitope Scaffold Protein
source                 1..218
                       mol_type = protein
                       organism = synthetic construct
SEQUENCE: 69
MDSKGSSQKG SRLLLLLVVS NLLLPQGVLA AVGIGAVFLG GGGGGAVDMF IKIGDVKGES  60
KDKTHNSTID VLAWSWGMSQ SGSMHMGGGG GAGKVNVQDL SFTKYIDKST PNLMMACSSG  120
KHYPQAKLTI RKACGENQVE YLIITLKEVL VSSVSTGGSG GEDRLTENVT LNFAQVQVDY  180
QPQKADGAKD GGPVKYGWNI CQNVQAGGGS HHHHHHHH                          218

SEQ ID NO: 70          moltype = AA  length = 218
FEATURE                Location/Qualifiers
REGION                 1..218
                       note = Epitope Scaffold Protein
source                 1..218
                       mol_type = protein
                       organism = synthetic construct
SEQUENCE: 70
MDSKGSSQKG SRLLLLLVVS NLLLPQGVLA AVGIGAVFLG GGGGGAVDMF IKIGDVKGES  60
KDKTHAEEID VLAWSWGMSQ SGSMHMGGGG GAGKVNVQDL SFTKYIDKST PNLMMACSSG  120
KHYPQAKLTI RKACGENQVE YLIITLKEVL VSSVSTGGSG GEDRLTENVT LNFAQVQVDY  180
QPQNSTGAKD GGPVKYGWNI CQNVQAGGGS HHHHHHHH                          218

SEQ ID NO: 71          moltype = AA  length = 218
FEATURE                Location/Qualifiers
REGION                 1..218
                       note = Epitope Scaffold Protein
source                 1..218
                       mol_type = protein
                       organism = synthetic construct
SEQUENCE: 71
MDSKGSSQKG SRLLLLLVVS NLLLPQGVLA AVGIGAVFLG GGGGGAVDMF IKIGDVKGES  60
KDKTHNSTID VLAWSWGMSQ SGSMHMGGGG GAGKVNVQDL SFTKYIDKST PNLMMACSSG  120
KHYPQAKLTI RKACGENQVE YLIITLKEVL VSSVSTGGSG GEDRLTENVT LNFAQVQVDY  180
QPQNSTGAKD GGPVKYGWNI CQNVQAGGGS HHHHHHHH                          218

SEQ ID NO: 72          moltype = AA  length = 233
FEATURE                Location/Qualifiers
REGION                 1..233
                       note = Epitope Scaffold Protein
source                 1..233
                       mol_type = protein
                       organism = synthetic construct
SEQUENCE: 72
```

```
MDSKGSSQKG SRLLLLLVVS NLLLPQGVLA AVGIGAVFLG GGGGGAVGIG AVFLGGGGGG  60
AVDMFIKIGD VKGESKDKTH NSTIDVLAWS WGMSQSGSMH MGGGGGAGKV NVQDLSFTKY  120
IDKSTPNLMM ACSSGKHYPQ AKLTIRKACG ENQVEYLIIT LKEVLVSSVS TGGSGGEDRL  180
TENVTLNFAQ VQVDYQPQKA DGAKDGGPVK YGWNICQNVQ AGGGSHHHHH HHH         233

SEQ ID NO: 73          moltype = AA  length = 233
FEATURE                Location/Qualifiers
REGION                 1..233
                       note = Epitope Scaffold Protein
source                 1..233
                       mol_type = protein
                       organism = synthetic construct
SEQUENCE: 73
MDSKGSSQKG SRLLLLLVVS NLLLPQGVLA AVGIGAVFLG GGGGGAVGIG AVFLGGGGGG  60
AVDMFIKIGD VKGESKDKTH AEEIDVLAWS WGMSQSGSMH MGGGGGAGKV NVQDLSFTKY  120
IDKSTPNLMM ACSSGKHYPQ AKLTIRKACG ENQVEYLIIT LKEVLVSSVS TGGSGGEDRL  180
TENVTLNFAQ VQVDYQPQNS TGAKDGGPVK YGWNICQNVQ AGGGSHHHHH HHH         233

SEQ ID NO: 74          moltype = AA  length = 233
FEATURE                Location/Qualifiers
REGION                 1..233
                       note = Epitope Scaffold Protein
source                 1..233
                       mol_type = protein
                       organism = synthetic construct
SEQUENCE: 74
MDSKGSSQKG SRLLLLLVVS NLLLPQGVLA AVGIGAVFLG GGGGGAVGIG AVFLGGGGGG  60
AVDMFIKIGD VKGESKDKTH NSTIDVLAWS WGMSQSGSMH MGGGGGAGKV NVQDLSFTKY  120
IDKSTPNLMM ACSSGKHYPQ AKLTIRKACG ENQVEYLIIT LKEVLVSSVS TGGSGGEDRL  180
TENVTLNFAQ VQVDYQPQNS TGAKDGGPVK YGWNICQNVQ AGGGSHHHHH HHH         233

SEQ ID NO: 75          moltype = AA  length = 184
FEATURE                Location/Qualifiers
REGION                 1..184
                       note = Epitope Scaffold Protein
source                 1..184
                       mol_type = protein
                       organism = synthetic construct
SEQUENCE: 75
MDSKGSSQKG SRLLLLLVVS NLLLPQGVLA AVGIGAVFLG GGADLEDNWE TLNDNLKVIE  60
KADNAAQVKD ALTKMRNASL DAQKATPPKL EDKSPDSPEM KDFRHGFDIL VGQIDDALKL  120
ANEGKVKEAQ AAAEQLKTTR NAYIQKYLGG GSLEVLFQGP GSGSAWSHPQ FEKGSGHHHH  180
HHHH                                                              184

SEQ ID NO: 76          moltype = AA  length = 184
FEATURE                Location/Qualifiers
REGION                 1..184
                       note = Epitope Scaffold Protein
source                 1..184
                       mol_type = protein
                       organism = synthetic construct
SEQUENCE: 76
MDSKGSSQKG SRLLLLLVVS NLLLPQGVLA AVGIGAVFLG GGADLEDNWE TLNDNLKVIE  60
KADNAAQVKD ALTKMRAAAL DAQNATPPKL EDKSPDSPEM KDFRHGFDIL VGQIDDALKL  120
ANEGKVKEAQ AAAEQLKTTR NAYIQKYLGG GSLEVLFQGP GSGSAWSHPQ FEKGSGHHHH  180
HHHH                                                              184

SEQ ID NO: 77          moltype = AA  length = 184
FEATURE                Location/Qualifiers
REGION                 1..184
                       note = Epitope Scaffold Protein
source                 1..184
                       mol_type = protein
                       organism = synthetic construct
SEQUENCE: 77
MDSKGSSQKG SRLLLLLVVS NLLLPQGVLA AVGIGAVFLG GGADLEDNWE TLNDNLKVIE  60
KADNAAQVKD ALTKMRAAAL DAQKATPPKL NDTSPDSPEM KDFRHGFDIL VGQIDDALKL  120
ANEGKVKEAQ AAAEQLKTTR NAYIQKYLGG GSLEVLFQGP GSGSAWSHPQ FEKGSGHHHH  180
HHHH                                                              184

SEQ ID NO: 78          moltype = AA  length = 134
FEATURE                Location/Qualifiers
REGION                 1..134
                       note = Epitope Scaffold Protein
source                 1..134
                       mol_type = protein
                       organism = synthetic construct
SEQUENCE: 78
MDSKGSSQKG SRLLLLLVVS NLLLPQGVLA AVGIGAVFLG GGGSSGVRLW ATRQAMLGQV  60
```

```
HEVPEGWLIF VAEQEELYVR VQNGFRKVQL EARTPLPRGG GSLEVLFQGP GSGSAWSHPQ  120
FEKGSGHHHH HHHH                                                   134

SEQ ID NO: 79          moltype = AA  length = 134
FEATURE                Location/Qualifiers
REGION                 1..134
                       note = Epitope Scaffold Protein
source                 1..134
                       mol_type = protein
                       organism = synthetic construct
SEQUENCE: 79
MDSKGSSQKG SRLLLLLVVS NLLLPQGVLA AVGIGAVFLG GGGSSGVRLW ATRQNMTGQV  60
HEVPEGWLIF VAEQEELYVR VQNGFRKVQL EARTPLPRGG GSLEVLFQGP GSGSAWSHPQ  120
FEKGSGHHHH HHHH                                                   134

SEQ ID NO: 80          moltype = AA  length = 134
FEATURE                Location/Qualifiers
REGION                 1..134
                       note = Epitope Scaffold Protein
source                 1..134
                       mol_type = protein
                       organism = synthetic construct
SEQUENCE: 80
MDSKGSSQKG SRLLLLLVVS NLLLPQGVLA AVGIGAVFLG GGGSSGVRLW ATRQAMLGNV  60
TEVPEGWLIF VAEQEELYVR VQNGFRKVQL EARTPLPRGG GSLEVLFQGP GSGSAWSHPQ  120
FEKGSGHHHH HHHH                                                   134

SEQ ID NO: 81          moltype = AA  length = 134
FEATURE                Location/Qualifiers
REGION                 1..134
                       note = Epitope Scaffold Protein
source                 1..134
                       mol_type = protein
                       organism = synthetic construct
SEQUENCE: 81
MDSKGSSQKG SRLLLLLVVS NLLLPQGVLA AVGIGAVFLG GGGSSGVRLW ATRQAMLGQV  60
HNVSEGWLIF VAEQEELYVR VQNGFRKVQL EARTPLPRGG GSLEVLFQGP GSGSAWSHPQ  120
FEKGSGHHHH HHHH                                                   134

SEQ ID NO: 82          moltype = AA  length = 173
FEATURE                Location/Qualifiers
REGION                 1..173
                       note = Recombinant Protein Nanoparticle Sequence
source                 1..173
                       mol_type = protein
                       organism = synthetic construct
SEQUENCE: 82
ESQVRQQFSK DIEKLLNEQV NKEMQSSNLY MSMSSWCYTH SLDGAGLFLF DHAAEEYEHA  60
KKLIIFLNEN NVPVQLTSIS APEHKFEGLT QIFQKAYEHE QHISESINNI VDHAIKSKDH  120
ATFNFLQWYV AEQHEEEVLF KDILDKIELI GNENHGLYLA DQYVKGIAKS RKS         173

SEQ ID NO: 83          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 83
MLSKDIIKLL NEQVNKEMQS SNLYMSMSSW CYTHSLDGAG LFLFDHAAEE YEHAKKLIIF  60
LNENNVPVQL TSISAPHHKF HGLTHIFHKA YHHEQHISES INNIVDHAIK SKDHATFNFL  120
QWYVAEQHEE EVLFKDILDK IELIGNENHG LYLADQYVKG IAKSRKS               167

SEQ ID NO: 84          moltype = AA  length = 154
FEATURE                Location/Qualifiers
REGION                 1..154
                       note = Recombinant Protein Nanoparticle Sequence
source                 1..154
                       mol_type = protein
                       organism = synthetic construct
SEQUENCE: 84
MQIYEGKLTA EGLRFGIVAS RFNHALVDRL VEGAIDAIVR HGGREEDITL VRVPGSWEIP  60
VAAGELARKE DIDAVIAIGV LIRGATPHFD YIASEVSKGL ADLSLELRKP ITFGVITADT  120
LEQAIERAGT KHGNKGWEAA LSAIEMANLF KSLR                              154

SEQ ID NO: 85          moltype = AA  length = 265
FEATURE                Location/Qualifiers
REGION                 1..265
                       note = Recombinant Protein Nanoparticle Sequence
```

```
source                  1..265
                        mol_type = protein
                        organism = synthetic construct
SEQUENCE: 85
MEFLKRSFAP LTEKQWQEID NRAREIFKTQ LYGRKFVDVE GPYGWEYAAH PLGEVEVLSD  60
ENEVVKWGLR KSLPLIELRA TFTLDLWELD NLERGKPNVD LSSLEETVRK VAEFEDEVIF  120
RGCEKSGVKG LLSFEERKIE CGSTPKDLLE AIVRALSIFS KDGIEGPYTL VINTDRWINF  180
LKEEAGHYPL EKRVEECLRG GKIITTPRIE DALVVSERGG DFKLILGQDL SIGYEDREKD  240
AVRLFITETF TFQVVNPEAL ILLKF                                       265

SEQ ID NO: 86           moltype = AA  length = 265
FEATURE                 Location/Qualifiers
REGION                  1..265
                        note = Recombinant Protein Nanoparticle Sequence
source                  1..265
                        mol_type = protein
                        organism = synthetic construct
SEQUENCE: 86
MEFLKRSFAP LTEKQWQEID NRAREIFKTQ LYGRKFVDVE GPYGWEYAAH PLGEVEVLSD  60
ENEVVKWGLR KSLPLIELRA TFTLDLWELD NLERGKPNVD LSSLEETVRK VAEFEDEVIF  120
RGCEKSGVKG LLSFEERKIE CGSTPKDLLE AIVRALSIFS KDGIEGPYTL VINTDRWINF  180
LKEEAGHYPL EKRVEECLRG GKIITTPRIE DALVVSERGG DFKLILGQDL SIGYEDREKD  240
AVRLFITETF TFQVVNPEAL ILLKF                                       265

SEQ ID NO: 87           moltype = AA  length = 154
FEATURE                 Location/Qualifiers
REGION                  1..154
                        note = Recombinant Protein Nanoparticle Sequence
source                  1..154
                        mol_type = protein
                        organism = synthetic construct
SEQUENCE: 87
MQIYEGKLTA ENLSFGIVAS RFNHALVDRL VEGAIDAIVR HGGREEDITL VRVPGSWEIP  60
VAAGELARKE DIDAVIAIGV LIRGATPHFD YIASEVSKGL ADLSLELRKP ITFGVITADT  120
LEQAIERAGT KHGNKGWEAA LSAIEMANLF KSLR                             154

SEQ ID NO: 88           moltype = AA  length = 154
FEATURE                 Location/Qualifiers
REGION                  1..154
                        note = Recombinant Protein Nanoparticle Sequence
source                  1..154
                        mol_type = protein
                        organism = synthetic construct
SEQUENCE: 88
MQIYEGKLTA EGLRFGIVAS RFNHALVDRL VEGAIDAIVR HGGREEDITL VRVPGSWEIP  60
VAAGELARKE NISAVIAIGV LIRGATPHFD YIASEVSKGL ADLSLELRKP ITFGVITADT  120
LEQAIERAGT KHGNKGWEAA LSAIEMANLF KSLR                             154

SEQ ID NO: 89           moltype = AA  length = 163
FEATURE                 Location/Qualifiers
REGION                  1..163
                        note = Recombinant Protein Nanoparticle Sequence
source                  1..163
                        mol_type = protein
                        organism = synthetic construct
SEQUENCE: 89
DIIKLLNEQV NKEMQSSNLY MSMSSWCYTH SLDGAGLFLF DHAAEEYEHA KKLIIFLNEN  60
NVPVQLTSIS APHHKFHGLT HIFHKAYHHE QHISESINNI VDHAIKSKDH ATFNFLQWYV  120
AEQHEEEVLF KDILDKIELI GNENHGLYLA DQYVKGIAKS RKS                   163

SEQ ID NO: 90           moltype = AA  length = 163
FEATURE                 Location/Qualifiers
REGION                  1..163
                        note = Recombinant Protein Nanoparticle Sequence
source                  1..163
                        mol_type = protein
                        organism = synthetic construct
SEQUENCE: 90
DIIKLLNEQV NNETQSSNLY MSMSSWCYTH SLDGAGLFLF DHAAEEYEHA KKLIIFLNEN  60
NVPVQLTSIS APHHKFHGLT HIFHKAYHHE QHISESINNI VDHAIKSKDH ATFNFLQWYV  120
AEQHEEEVLF KDILDKIELI GNENHGLYLA DQYVKGIAKS RKS                   163

SEQ ID NO: 91           moltype = AA  length = 163
FEATURE                 Location/Qualifiers
REGION                  1..163
                        note = Recombinant Protein Nanoparticle Sequence
source                  1..163
                        mol_type = protein
                        organism = synthetic construct
```

```
SEQUENCE: 91
DIIKLLNEQV NKEMQSSNLY MSMSSWCYTH SLDGAGLFLF DHAAEEYEHA KKLIIFLNEN  60
NVPVQLTSIS APHHKFHGLT HIFHKAYHHE QHISESINNI TDHAIKSKDH ATFNFLQWYV  120
AEQHEEEVLF KDILDKIELI GNENHGLYLA DQYVKGIAKS RKS                   163

SEQ ID NO: 92          moltype = AA  length = 163
FEATURE                Location/Qualifiers
REGION                 1..163
                       note = Recombinant Protein Nanoparticle Sequence
source                 1..163
                       mol_type = protein
                       organism = synthetic construct
SEQUENCE: 92
DIIKLLNEQV NNETQSSNLY MSMSSWCYTH SLDGAGLFLF DHAAEEYEHA KKLIIFLNEN  60
NVPVQLTSIS APHHKFHGLT HIFHKAYHHE QHISESINNI TDHAIKSKDH ATFNFLQWYV  120
AEQHEEEVLF KDILDKIELI GNENHGLYLA DQYVKGIAKS RKS                   163

SEQ ID NO: 93          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 93
MLSKDIIKLL NEQVNKEMQS SNLYMSMSSW CYTHSLDGAG LFLFDHAAEE YEHAKKLIIF  60
LNENNVPVQL TSISAPHHKF HGLTHIFHKA YHHEQHISES INNIVDHAIK SKDHATFNFL  120
QWYVAEQHEE EVLFKDILDK IELIGNESHG LYLADQYVKG IAKSRKS               167

SEQ ID NO: 94          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 94
MLSKDIIKLL NEQVNKEMQS SNLYMSMSSW CYTHSLDGAG LFLFDHAAEE YEHAKKLIIF  60
LNENNVPVQL TSISHHHHHH EGLTQIFQKA YEHEQHISES INNIVDHAIK SKDHATFNFL  120
QWYVAEQHEE EVLFKDILDK IELIGNESHG LYLADQYVKG IAKSRKS               167

SEQ ID NO: 95          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 95
MLSKDIIKLL NEQVNKEMQS SNLYMSMSSW CYTHSLDGAG LFLFDHAAEE YEHAKKLIIF  60
LNENNVHHHH HHISAPEHNF SGLTQIFQKA YEHEQHISES INNIVDHAIK SKDHATFNFL  120
QWYVAEQHEE EVLFKDILDK IELIGNENHG LYLADQYVKG IAKSRKS               167

SEQ ID NO: 96          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 96
MLSKDIIKLL NEQVNKEMQS SNLYMSMSSW CYTHSLDGAG LFLFDHAAEE YEHAKKLIIF  60
LNENNVPVNL TSISHHHHHH EGLTQIFQKA YEHEQHISES INNIVDHAIK SKDHATFNFL  120
QWYVAEQHEE EVLFKDILDK IELIGNENHG LYLADQYVKG IAKSRKS               167

SEQ ID NO: 97          moltype = AA  length = 167
FEATURE                Location/Qualifiers
REGION                 1..167
                       note = Recombinant Protein Nanoparticle Sequence
source                 1..167
                       mol_type = protein
                       organism = synthetic construct
SEQUENCE: 97
MLSKDIIKLL NEQVNKEMQS SNLYMSMSSW CYTHSLDGAG LFLFDHAAEE YEHAKKLIIF  60
LNENNVPVNL TSISAPHHKF HGLTHIFHKA YHHEQHISES INNIVDHAIK SKDHATFNFL  120
QWYVAEQHEE EVLFKDILDK IELIGNENHG LYLADQYVKG IAKSRKS               167

SEQ ID NO: 98          moltype = AA  length = 165
FEATURE                Location/Qualifiers
```

```
REGION                  1..165
                        note = Recombinant Protein Nanoparticle Sequence
source                  1..165
                        mol_type = protein
                        organism = synthetic construct
SEQUENCE: 98
MLSKDIIKLL NEQVNKEMQS SNLYMSMSSW CYTHSLDGAG LFLFDHAAEE YEHAKKLIIF  60
LNENNVPVQL TNISHHHHHH EGLTQIFQKA YEQHISESIN NIVDHAIKSK DHATFNFLQW  120
YVAEQHEEEV LFKDILDKIE LIGNENHGLY LADQYVKGIA KSRKS                 165

SEQ ID NO: 99           moltype = AA  length = 167
FEATURE                 Location/Qualifiers
REGION                  1..167
                        note = Recombinant Protein Nanoparticle Sequence
source                  1..167
                        mol_type = protein
                        organism = synthetic construct
SEQUENCE: 99
MLSKDIIKLL NEQVNKEMQS SNLYMSMSSW CYTHSLDGAG LFLFDHAAEE YEHAKKLIIF  60
LNENNVPVQL TSISAPHHKF HGLTHIFHKA YHHEQNISES INNIVDHAIK SKDHATFNFL  120
QWYVAEQHEE EVLFKDILDK IELIGNENHG LYLADQYVKG IAKSRKS               167

SEQ ID NO: 100          moltype = AA  length = 167
FEATURE                 Location/Qualifiers
REGION                  1..167
                        note = Recombinant Protein Nanoparticle Sequence
source                  1..167
                        mol_type = protein
                        organism = synthetic construct
SEQUENCE: 100
MLSKDIIKLL NEQVNKEMQS SNLYMSMSSW CYTHSLDGAG LFLFDHAAEE YEHAKKLIIF  60
LNENNVPVQL TSISHHHHHH EGLTQIFQKA YEHEQNISES INNIVDHAIK SKDHATFNFL  120
QWYVAEQHEE EVLFKDILDK IELIGNENHG LYLADQYVKG IAKSRKS               167

SEQ ID NO: 101          moltype = AA  length = 166
FEATURE                 Location/Qualifiers
REGION                  1..166
                        note = Recombinant Protein Nanoparticle Sequence
source                  1..166
                        mol_type = protein
                        organism = synthetic construct
SEQUENCE: 101
AVGIGAVFLG SGMQIYEGKL TAEGLSFGIV ASRFNHALVD RLVEGAIDAI VRHGGREEDI  60
TLVRVPGSWE IPVAAGELAR KEDIDAVIAI GVLIRGATPH FDYIASEVSK GLADLSLELR  120
KPITFGVITA DTLEQAIERA GTKHGNKGWE AALSAIEMAN LFKSLR                166

SEQ ID NO: 102          moltype = AA  length = 166
FEATURE                 Location/Qualifiers
REGION                  1..166
                        note = Recombinant Protein Nanoparticle Sequence
source                  1..166
                        mol_type = protein
                        organism = synthetic construct
SEQUENCE: 102
AVGIGAVFLG SGMQIYEGKL TAENLSFGIV ASRFNHALVD RLVEGAIDAI VRHGGREEDI  60
TLVRVPGSWE IPVAAGELAR KEDIDAVIAI GVLIRGATPH FDYIASEVSK GLADLSLELR  120
KPITFGVITA DTLEQAIERA GTKHGNKGWE AALSAIEMAN LFKSLR                166

SEQ ID NO: 103          moltype = AA  length = 168
FEATURE                 Location/Qualifiers
REGION                  1..168
                        note = Recombinant Protein Nanoparticle Sequence
source                  1..168
                        mol_type = protein
                        organism = synthetic construct
SEQUENCE: 103
AVGIGAVFLG SGSAMQIYEG KLTAEGLRFG IVASRFNHAL VDRLVEGAID AIVRHGGREE  60
DITLVRVPGS WEIPVAAGEL ARKENISAVI AIGVLIRGAT PHFDYIASEV SKGLADLSLE  120
LRKPITFGVI TADTLEQAIE RAGTKHGNKG WEAALSAIEM ANLFKSLR              168

SEQ ID NO: 104          moltype = AA  length = 175
FEATURE                 Location/Qualifiers
REGION                  1..175
                        note = Recombinant Protein Nanoparticle Sequence
source                  1..175
                        mol_type = protein
                        organism = synthetic construct
SEQUENCE: 104
AVGIGAVFLS GGDIIKLLNE QVNKEMQSSN LYMSMSSWCY THSLDGAGLF LFDHAAEEYE  60
```

```
HAKKLIIFLN ENNVPVQLTS ISAPHHKFHG LTHIFHKAYH HEQHISESIN NIVDHAIKSK  120
DHATFNFLQW YVAEQHEEEV LFKDILDKIE LIGNENHGLY LADQYVKGIA KSRKS       175

SEQ ID NO: 105          moltype = AA  length = 187
FEATURE                 Location/Qualifiers
REGION                  1..187
                        note = Recombinant Protein Nanoparticle Sequence
source                  1..187
                        mol_type = protein
                        organism = synthetic construct
SEQUENCE: 105
AVGIGAVFLS GGAVGIGAVF LSGGDIIKLL NEQVNKEMQS SNLYMSMSSW CYTHSLDGAG  60
LFLFDHAAEE YEHAKKLIIF LNENNVPVQL TSISAPHHKF HGLTHIFHKA YHHEQHISES  120
INNIVDHAIK SKDHATFNFL QWYVAEQHEE EVLFKDILDK IELIGNENHG LYLADQYVKG  180
IAKSRKS                                                            187

SEQ ID NO: 106          moltype = AA  length = 175
FEATURE                 Location/Qualifiers
REGION                  1..175
                        note = Recombinant Protein Nanoparticle Sequence
source                  1..175
                        mol_type = protein
                        organism = synthetic construct
SEQUENCE: 106
AVGIGAVFLS GGDIIKLLNE QVNNETQSSN LYMSMSSWCY THSLDGAGLF LFDHAAEEYE  60
HAKKLIIFLN ENNVPVQLTS ISAPHHKFHG LTHIFHKAYH HEQHISESIN NIVDHAIKSK  120
DHATFNFLQW YVAEQHEEEV LFKDILDKIE LIGNENHGLY LADQYVKGIA KSRKS       175

SEQ ID NO: 107          moltype = AA  length = 175
FEATURE                 Location/Qualifiers
REGION                  1..175
                        note = Recombinant Protein Nanoparticle Sequence
source                  1..175
                        mol_type = protein
                        organism = synthetic construct
SEQUENCE: 107
AVGIGAVFLS GGDIIKLLNE QVNKEMQSSN LYMSMSSWCY THSLDGAGLF LFDHAAEEYE  60
HAKKLIIFLN ENNVPVQLTS ISAPHHKFHG LTHIFHKAYH HEQHISESIN NITDHAIKSK  120
DHATFNFLQW YVAEQHEEEV LFKDILDKIE LIGNENHGLY LADQYVKGIA KSRKS       175

SEQ ID NO: 108          moltype = AA  length = 187
FEATURE                 Location/Qualifiers
REGION                  1..187
                        note = Recombinant Protein Nanoparticle Sequence
source                  1..187
                        mol_type = protein
                        organism = synthetic construct
SEQUENCE: 108
AVGIGAVFLS GGAVGIGAVF LSGGDIIKLL NEQVNNETQS SNLYMSMSSW CYTHSLDGAG  60
LFLFDHAAEE YEHAKKLIIF LNENNVPVQL TSISAPHHKF HGLTHIFHKA YHHEQHISES  120
INNIVDHAIK SKDHATFNFL QWYVAEQHEE EVLFKDILDK IELIGNENHG LYLADQYVKG  180
IAKSRKS                                                            187

SEQ ID NO: 109          moltype = AA  length = 187
FEATURE                 Location/Qualifiers
REGION                  1..187
                        note = Recombinant Protein Nanoparticle Sequence
source                  1..187
                        mol_type = protein
                        organism = synthetic construct
SEQUENCE: 109
AVGIGAVFLS GGAVGIGAVF LSGGDIIKLL NEQVNKEMQS SNLYMSMSSW CYTHSLDGAG  60
LFLFDHAAEE YEHAKKLIIF LNENNVPVQL TSISAPHHKF HGLTHIFHKA YHHEQHISES  120
INNITDHAIK SKDHATFNFL QWYVAEQHEE EVLFKDILDK IELIGNENHG LYLADQYVKG  180
IAKSRKS                                                            187

SEQ ID NO: 110          moltype = AA  length = 187
FEATURE                 Location/Qualifiers
REGION                  1..187
                        note = Recombinant Protein Nanoparticle Sequence
source                  1..187
                        mol_type = protein
                        organism = synthetic construct
SEQUENCE: 110
AVGIGAVFLS GGAVGIGAVF LSGGDIIKLL NEQVNNETQS SNLYMSMSSW CYTHSLDGAG  60
LFLFDHAAEE YEHAKKLIIF LNENNVPVQL TSISAPHHKF HGLTHIFHKA YHHEQHISES  120
INNITDHAIK SKDHATFNFL QWYVAEQHEE EVLFKDILDK IELIGNENHG LYLADQYVKG  180
IAKSRKS                                                            187
```

```
SEQ ID NO: 111          moltype = AA  length = 187
FEATURE                 Location/Qualifiers
REGION                  1..187
                        note = Recombinant Protein Nanoparticle Sequence
source                  1..187
                        mol_type = protein
                        organism = synthetic construct
SEQUENCE: 111
AVGIGAVFLS GGAVGIGAVF LSGGDIIKLL NEQVNNETQS SNLYMSMSSW CYTHSLDGAG  60
LFLFDHAAEE YEHAKKLIIF LNENNVPVQL TSISAPHHKF HGLTHIFHKA YHHEQHISES  120
INNITDHAIK SKDHATFNFL QWYVAEQHEE EVLFKDILDK IELIGNENHG LYLADQYVKG  180
IAKSRKS                                                            187

SEQ ID NO: 112          moltype = AA  length = 181
FEATURE                 Location/Qualifiers
REGION                  1..181
                        note = Recombinant Protein Nanoparticle Sequence
source                  1..181
                        mol_type = protein
                        organism = synthetic construct
SEQUENCE: 112
AVGIGAVFLG SQDPMLSKDI IKLLNEQVNK EMQSSNLYMS MSSWCYTHSL DGAGLFLFDH  60
AAEEYEHAKK LIIFLNENNV PVQLTSISAP HHKFHGLTHI FHKAYHHEQH ISESINNIVD  120
HAIKSKDHAT FNFLQWYVAE QHEEEVLFKD ILDKIELIGN ESHGLYLADQ YVKGIAKSRK  180
S                                                                  181

SEQ ID NO: 113          moltype = AA  length = 181
FEATURE                 Location/Qualifiers
REGION                  1..181
                        note = Recombinant Protein Nanoparticle Sequence
source                  1..181
                        mol_type = protein
                        organism = synthetic construct
SEQUENCE: 113
AVGIGAVFLG SGDPMLSKDI IKLLNEQVNK EMQSSNLYMS MSSWCYTHSL DGAGLFLFDH  60
AAEEYEHAKK LIIFLNENNV PVQLTSISAP HHKFHGLTHI FHKAYHHEQH ISESINNIVD  120
HAIKSKDHAT FNFLQWYVAE QHEEEVLFKD ILDKIELIGN ESHGLYLADQ YVKGIAKSRK  180
S                                                                  181

SEQ ID NO: 114          moltype = AA  length = 181
FEATURE                 Location/Qualifiers
REGION                  1..181
                        note = Recombinant Protein Nanoparticle Sequence
source                  1..181
                        mol_type = protein
                        organism = synthetic construct
SEQUENCE: 114
AVGIGAVFLG SQDPMLSKDI IKLLNEQVNK EMQSSNLYMS MSSWCYTHSL DGAGLFLFDH  60
AAEEYEHAKK LIIFLNENNV PVQLTSISHH HHHHEGLTQI FQKAYEHEQH ISESINNIVD  120
HAIKSKDHAT FNFLQWYVAE QHEEEVLFKD ILDKIELIGN ESHGLYLADQ YVKGIAKSRK  180
S                                                                  181

SEQ ID NO: 115          moltype = AA  length = 181
FEATURE                 Location/Qualifiers
REGION                  1..181
                        note = Recombinant Protein Nanoparticle Sequence
source                  1..181
                        mol_type = protein
                        organism = synthetic construct
SEQUENCE: 115
AVGIGAVFLG SGDPMLSKDI IKLLNEQVNK EMQSSNLYMS MSSWCYTHSL DGAGLFLFDH  60
AAEEYEHAKK LIIFLNENNV PVQLTSISHH HHHHEGLTQI FQKAYEHEQH ISESINNIVD  120
HAIKSKDHAT FNFLQWYVAE QHEEEVLFKD ILDKIELIGN ESHGLYLADQ YVKGIAKSRK  180
S                                                                  181

SEQ ID NO: 116          moltype = AA  length = 180
FEATURE                 Location/Qualifiers
REGION                  1..180
                        note = Recombinant Protein Nanoparticle Sequence
source                  1..180
                        mol_type = protein
                        organism = synthetic construct
SEQUENCE: 116
AVGIGAVFLG QDPMLSKDII KLLNEQVNKE MQSSNLYMSM SSWCYTHSLD GAGLFLFDHA  60
AEEYEHAKKL IIFLNENNVH HHHHHISAPE HNFSGLTQIF QKAYEHEQHI SESINNIVDH  120
AIKSKDHATF NFLQWYVAEQ HEEEVLFKDI LDKIELIGNE NHGLYLADQY VKGIAKSRKS  180

SEQ ID NO: 117          moltype = AA  length = 177
FEATURE                 Location/Qualifiers
```

```
REGION                  1..177
                        note = Recombinant Protein Nanoparticle Sequence
source                  1..177
                        mol_type = protein
                        organism = synthetic construct
SEQUENCE: 117
AVGIGAVFLG MLSKDIIKLL NEQVNKEMQS SNLYMSMSSW CYTHSLDGAG LFLFDHAAEE  60
YEHAKKLIIF LNENNVHHHH HHISAPEHNF SGLTQIFQKA YEHEQHISES INNIVDHAIK  120
SKDHATFNFL QWYVAEQHEE EVLFKDILDK IELIGNENHG LYLADQYVKG IAKSRKS     177

SEQ ID NO: 118          moltype = AA  length = 177
FEATURE                 Location/Qualifiers
REGION                  1..177
                        note = Recombinant Protein Nanoparticle Sequence
source                  1..177
                        mol_type = protein
                        organism = synthetic construct
SEQUENCE: 118
AVGIGAVFLG MLSKDIIKLL NEQVNKEMQS SNLYMSMSSW CYTHSLDGAG LFLFDHAAEE  60
YEHAKKLIIF LNENNVPVNL TSISHHHHHH EGLTQIFQKA YEHEQHISES INNIVDHAIK  120
SKDHATFNFL QWYVAEQHEE EVLFKDILDK IELIGNENHG LYLADQYVKG IAKSRKS     177

SEQ ID NO: 119          moltype = AA  length = 177
FEATURE                 Location/Qualifiers
REGION                  1..177
                        note = Recombinant Protein Nanoparticle Sequence
source                  1..177
                        mol_type = protein
                        organism = synthetic construct
SEQUENCE: 119
AVGIGAVFLG MLSKDIIKLL NEQVNKEMQS SNLYMSMSSW CYTHSLDGAG LFLFDHAAEE  60
YEHAKKLIIF LNENNVPVNL TSISAPHHKF HGLTHIFHKA YHHEQHISES INNIVDHAIK  120
SKDHATFNFL QWYVAEQHEE EVLFKDILDK IELIGNENHG LYLADQYVKG IAKSRKS     177

SEQ ID NO: 120          moltype = AA  length = 177
FEATURE                 Location/Qualifiers
REGION                  1..177
                        note = Recombinant Protein Nanoparticle Sequence
source                  1..177
                        mol_type = protein
                        organism = synthetic construct
SEQUENCE: 120
AVGIGAVFLG SGMLSKDIIK LLNEQVNKEM QSSNLYMSMS SWCYTHSLDG AGLFLFDHAA  60
EEYEHAKKLI IFLNENNVPV QLTNISHHHH HHEGLTQIFQ KAYEQHISES INNIVDHAIK  120
SKDHATFNFL QWYVAEQHEE EVLFKDILDK IELIGNENHG LYLADQYVKG IAKSRKS     177

SEQ ID NO: 121          moltype = AA  length = 179
FEATURE                 Location/Qualifiers
REGION                  1..179
                        note = Recombinant Protein Nanoparticle Sequence
source                  1..179
                        mol_type = protein
                        organism = synthetic construct
SEQUENCE: 121
AVGIGAVFLG SGMLSKDIIK LLNEQVNKEM QSSNLYMSMS SWCYTHSLDG AGLFLFDHAA  60
EEYEHAKKLI IFLNENNVPV QLTSISAPHH KFHGLTHIFH KAYHHEQNIS ESINNIVDHA  120
IKSKDHATFN FLQWYVAEQH EEEVLFKDIL DKIELIGNEN HGLYLADQYV KGIAKSRKS   179

SEQ ID NO: 122          moltype = AA  length = 179
FEATURE                 Location/Qualifiers
REGION                  1..179
                        note = Recombinant Protein Nanoparticle Sequence
source                  1..179
                        mol_type = protein
                        organism = synthetic construct
SEQUENCE: 122
AVGIGAVFLG SGMLSKDIIK LLNEQVNKEM QSSNLYMSMS SWCYTHSLDG AGLFLFDHAA  60
EEYEHAKKLI IFLNENNVPV QLTSISHHHH HHEGLTQIFQ KAYEHEQNIS ESINNIVDHA  120
IKSKDHATFN FLQWYVAEQH EEEVLFKDIL DKIELIGNEN HGLYLADQYV KGIAKSRKS   179

SEQ ID NO: 123          moltype = AA  length = 220
FEATURE                 Location/Qualifiers
REGION                  1..220
                        note = Recombinant Protein Nanoparticle Sequence
source                  1..220
                        mol_type = protein
                        organism = synthetic construct
SEQUENCE: 123
MDSKGSSQKG SRLLLLLVVS NLLLPQGVVG AVGIGAVFLG SGMQIYEGKL TAENLSFGIV  60
```

```
ASRFNHALVD RLVEGAIDAI VRHGGREEDI TLVRVPGSWE IPVAAGELAR KEDIDAVIAI  120
GVLIRGATPH FDYIASEVSK GLADLSLELR KPITFGVITA DTLEQAIERA GTKHGNKGWE  180
AALSAIEMAN LFKSLRGGLV PRGSHHHHHH SAWSHPQFEK                        220

SEQ ID NO: 124          moltype = AA  length = 220
FEATURE                 Location/Qualifiers
REGION                  1..220
                        note = Recombinant Protein Nanoparticle Sequence
source                  1..220
                        mol_type = protein
                        organism = synthetic construct
SEQUENCE: 124
MDSKGSSQKG SRLLLLLVVS NLLLPQGVVG AVGIGAVFLG SGMQIYEGKL TAENLSFGIV  60
ASRFNHALVD RLVEGAIDAI VRHGGREEDI TLVRVPGSWE IPVAAGELAR KEDIDAVIAI  120
GVLIRGATPH FDYIASEVSK GLADLSLELR KPITFGVITA DTLEQAIERA GTKHGNKGWE  180
AALSAIEMAN LFKSLRGGLV PRGSHHHHHH SAWSHPQFEK                        220

SEQ ID NO: 125          moltype = AA  length = 222
FEATURE                 Location/Qualifiers
REGION                  1..222
                        note = Recombinant Protein Nanoparticle Sequence
source                  1..222
                        mol_type = protein
                        organism = synthetic construct
SEQUENCE: 125
MDSKGSSQKG SRLLLLLVVS NLLLPQGVVG AVGIGAVFLG SGSAMQIYEG KLTAEGLRFG  60
IVASRFNHAL VDRLVEGAID AIVRHGGREE DITLVRVPGS WEIPVAAGEL ARKENISAVI  120
AIGVLIRGAT PHFDYIASEV SKGLADLSLE LRKPITFGVI TADTLEQAIE RAGTKHGNKG  180
WEAALSAIEM ANLFKSLRGG LVPRGSHHHH HHSAWSHPQF EK                     222

SEQ ID NO: 126          moltype = AA  length = 211
FEATURE                 Location/Qualifiers
REGION                  1..211
                        note = Recombinant Protein Nanoparticle Sequence
source                  1..211
                        mol_type = protein
                        organism = synthetic construct
SEQUENCE: 126
MDSKGSSQKG SRLLLLLVVS NLLLPQGVVG AVGIGAVFLG SQDPMLSKDI IKLLNEQVNK  60
EMQSSNLYMS MSSWCYTHSL DGAGLFLFDH AAEEYEHAKK LIIFLNENNV PVQLTSISAP  120
HHKFHGLTHI FHKAYHHEQH ISESINNIVD HAIKSKDHAT FNFLQWYVAE QHEEEVLFKD  180
ILDKIELIGN ESHGLYLADQ YVKGIAKSRK S                                 211

SEQ ID NO: 127          moltype = AA  length = 211
FEATURE                 Location/Qualifiers
REGION                  1..211
                        note = Recombinant Protein Nanoparticle Sequence
source                  1..211
                        mol_type = protein
                        organism = synthetic construct
SEQUENCE: 127
MDSKGSSQKG SRLLLLLVVS NLLLPQGVVG AVGIGAVFLG SGDPMLSKDI IKLLNEQVNK  60
EMQSSNLYMS MSSWCYTHSL DGAGLFLFDH AAEEYEHAKK LIIFLNENNV PVQLTSISAP  120
HHKFHGLTHI FHKAYHHEQH ISESINNIVD HAIKSKDHAT FNFLQWYVAE QHEEEVLFKD  180
ILDKIELIGN ESHGLYLADQ YVKGIAKSRK S                                 211

SEQ ID NO: 128          moltype = AA  length = 211
FEATURE                 Location/Qualifiers
REGION                  1..211
                        note = Recombinant Protein Nanoparticle Sequence
source                  1..211
                        mol_type = protein
                        organism = synthetic construct
SEQUENCE: 128
MDSKGSSQKG SRLLLLLVVS NLLLPQGVVG AVGIGAVFLG SQDPMLSKDI IKLLNEQVNK  60
EMQSSNLYMS MSSWCYTHSL DGAGLFLFDH AAEEYEHAKK LIIFLNENNV PVQLTSISHH  120
HHHHEGLTQI FQKAYEHEQH ISESINNIVD HAIKSKDHAT FNFLQWYVAE QHEEEVLFKD  180
ILDKIELIGN ESHGLYLADQ YVKGIAKSRK S                                 211

SEQ ID NO: 129          moltype = AA  length = 211
FEATURE                 Location/Qualifiers
REGION                  1..211
                        note = Recombinant Protein Nanoparticle Sequence
source                  1..211
                        mol_type = protein
                        organism = synthetic construct
SEQUENCE: 129
MDSKGSSQKG SRLLLLLVVS NLLLPQGVVG AVGIGAVFLG SGDPMLSKDI IKLLNEQVNK  60
EMQSSNLYMS MSSWCYTHSL DGAGLFLFDH AAEEYEHAKK LIIFLNENNV PVQLTSISHH  120
```

```
HHHHEGLTQI FQKAYEHEQH ISESINNIVD HAIKSKDHAT FNFLQWYVAE QHEEEVLFKD  180
ILDKIELIGN ESHGLYLADQ YVKGIAKSRK S                                 211

SEQ ID NO: 130         moltype = AA  length = 210
FEATURE                Location/Qualifiers
REGION                 1..210
                       note = Recombinant Protein Nanoparticle Sequence
source                 1..210
                       mol_type = protein
                       organism = synthetic construct
SEQUENCE: 130
MDSKGSSQKG SRLLLLLVVS NLLLPQGVVG AVGIGAVFLG QDPMLSKDII KLLNEQVNKE  60
MQSSNLYMSM SSWCYTHSLD GAGLFLFDHA AEEYEHAKKL IIFLNENNVH HHHHHISAPE  120
HNFSGLTQIF QKAYEHEQHI SESINNIVDH AIKSKDHATF NFLQWYVAEQ HEEEVLFKDI  180
LDKIELIGNE NHGLYLADQY VKGIAKSRKS                                   210

SEQ ID NO: 131         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 131
MDSKGSSQKG SRLLLLLVVS NLLLPQGVVG AVGIGAVFLG MLSKDIIKLL NEQVNKEMQS  60
SNLYMSMSSW CYTHSLDGAG LFLFDHAAEE YEHAKKLIIF LNENNVHHHH HHISAPEHNF  120
SGLTQIFQKA YEHEQHISES INNIVDHAIK SKDHATFNFL QWYVAEQHEE EVLFKDILDK  180
IELIGNENHG LYLADQYVKG IAKSRKS                                      207

SEQ ID NO: 132         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 132
MDSKGSSQKG SRLLLLLVVS NLLLPQGVVG AVGIGAVFLG MLSKDIIKLL NEQVNKEMQS  60
SNLYMSMSSW CYTHSLDGAG LFLFDHAAEE YEHAKKLIIF LNENNVPVNL TSISHHHHHH  120
EGLTQIFQKA YEHEQHISES INNIVDHAIK SKDHATFNFL QWYVAEQHEE EVLFKDILDK  180
IELIGNENHG LYLADQYVKG IAKSRKS                                      207

SEQ ID NO: 133         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 133
MDSKGSSQKG SRLLLLLVVS NLLLPQGVVG AVGIGAVFLG MLSKDIIKLL NEQVNKEMQS  60
SNLYMSMSSW CYTHSLDGAG LFLFDHAAEE YEHAKKLIIF LNENNVPVNL TSISAPHHKF  120
HGLTHIFHKA YHHEQHISES INNIVDHAIK SKDHATFNFL QWYVAEQHEE EVLFKDILDK  180
IELIGNENHG LYLADQYVKG IAKSRKS                                      207

SEQ ID NO: 134         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 134
MDSKGSSQKG SRLLLLLVVS NLLLPQGVVG AVGIGAVFLG SGMLSKDIIK LLNEQVNKEM  60
QSSNLYMSMS SWCYTHSLDG AGLFLFDHAA EEYEHAKKLI IFLNENNVPV QLTNISHHHH  120
HHEGLTQIFQ KAYEQHISES INNIVDHAIK SKDHATFNFL QWYVAEQHEE EVLFKDILDK  180
IELIGNENHG LYLADQYVKG IAKSRKS                                      207

SEQ ID NO: 135         moltype = AA  length = 209
FEATURE                Location/Qualifiers
REGION                 1..209
                       note = Recombinant Protein Nanoparticle Sequence
source                 1..209
                       mol_type = protein
                       organism = synthetic construct
SEQUENCE: 135
MDSKGSSQKG SRLLLLLVVS NLLLPQGVVG AVGIGAVFLG SGMLSKDIIK LLNEQVNKEM  60
QSSNLYMSMS SWCYTHSLDG AGLFLFDHAA EEYEHAKKLI IFLNENNVPV QLTSISAPHH  120
KFHGLTHIFH KAYHHEQNIS ESINNIVDHA IKSKDHATFN FLQWYVAEQH EEEVLFKDIL  180
```

```
DKIELIGNEN HGLYLADQYV KGIAKSRKS                                  209

SEQ ID NO: 136         moltype = AA  length = 209
FEATURE                Location/Qualifiers
REGION                 1..209
                       note = Recombinant Protein Nanoparticle Sequence
source                 1..209
                       mol_type = protein
                       organism = synthetic construct
SEQUENCE: 136
MDSKGSSQKG SRLLLLLVVS NLLLPQGVVG AVGIGAVFLG SGMLSKDIIK LLNEQVNKEM  60
QSSNLYMSMS SWCYTHSLDG AGLFLFDHAA EEYEHAKKLI IFLNENNVPV QLTSISHHHH  120
HHEGLTQIFQ KAYEHEQNIS ESINNIVDHA IKSKDHATFN FLQWYVAEQH EEEVLFKDIL  180
DKIELIGNEN HGLYLADQYV KGIAKSRKS                                  209

SEQ ID NO: 137         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 137
MDSKGSSQKG SRLLLLLVVS NLLLPQGVLA AVGIGAVFLS GGDIIKLLNE QVNKEMQSSN  60
LYMSMSSWCY THSLDGAGLF LFDHAAEEYE HAKKLIIFLN ENNVPVQLTS ISAPHHKFHG  120
LTHIFHKAYH HEQHISESIN NIVDHAIKSK DHATFNFLQW YVAEQHEEEV LFKDILDKIE  180
LIGNENHGLY LADQYVKGIA KSRKSGS                                    207

SEQ ID NO: 138         moltype = AA  length = 219
FEATURE                Location/Qualifiers
REGION                 1..219
                       note = Recombinant Protein Nanoparticle Sequence
source                 1..219
                       mol_type = protein
                       organism = synthetic construct
SEQUENCE: 138
MDSKGSSQKG SRLLLLLVVS NLLLPQGVLA AVGIGAVFLS GGAVGIGAVF LSGGDIIKLL  60
NEQVNKEMQS SNLYMSMSSW CYTHSLDGAG LFLFDHAAEE YEHAKKLIIF LNENNVPVQL  120
TSISAPHHKF HGLTHIFHKA YHHEQHISES INNIVDHAIK SKDHATFNFL QWYVAEQHEE  180
EVLFKDILDK IELIGNENHG LYLADQYVKG IAKSRKSGS                       219

SEQ ID NO: 139         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 139
MDSKGSSQKG SRLLLLLVVS NLLLPQGVLA AVGIGAVFLS GGDIIKLLNE QVNNETQSSN  60
LYMSMSSWCY THSLDGAGLF LFDHAAEEYE HAKKLIIFLN ENNVPVQLTS ISAPHHKFHG  120
LTHIFHKAYH HEQHISESIN NIVDHAIKSK DHATFNFLQW YVAEQHEEEV LFKDILDKIE  180
LIGNENHGLY LADQYVKGIA KSRKSGS                                    207

SEQ ID NO: 140         moltype = AA  length = 207
FEATURE                Location/Qualifiers
REGION                 1..207
                       note = Recombinant Protein Nanoparticle Sequence
source                 1..207
                       mol_type = protein
                       organism = synthetic construct
SEQUENCE: 140
MDSKGSSQKG SRLLLLLVVS NLLLPQGVLA AVGIGAVFLS GGDIIKLLNE QVNKEMQSSN  60
LYMSMSSWCY THSLDGAGLF LFDHAAEEYE HAKKLIIFLN ENNVPVQLTS ISAPHHKFHG  120
LTHIFHKAYH HEQHISESIN NITDHAIKSK DHATFNFLQW YVAEQHEEEV LFKDILDKIE  180
LIGNENHGLY LADQYVKGIA KSRKSGS                                    207

SEQ ID NO: 141         moltype = AA  length = 219
FEATURE                Location/Qualifiers
REGION                 1..219
                       note = Recombinant Protein Nanoparticle Sequence
source                 1..219
                       mol_type = protein
                       organism = synthetic construct
SEQUENCE: 141
MDSKGSSQKG SRLLLLLVVS NLLLPQGVLA AVGIGAVFLS GGAVGIGAVF LSGGDIIKLL  60
NEQVNNETQS SNLYMSMSSW CYTHSLDGAG LFLFDHAAEE YEHAKKLIIF LNENNVPVQL  120
TSISAPHHKF HGLTHIFHKA YHHEQHISES INNIVDHAIK SKDHATFNFL QWYVAEQHEE  180
EVLFKDILDK IELIGNENHG LYLADQYVKG IAKSRKSGS                       219
```

```
SEQ ID NO: 142         moltype = AA  length = 219
FEATURE                Location/Qualifiers
REGION                 1..219
                       note = Recombinant Protein Nanoparticle Sequence
source                 1..219
                       mol_type = protein
                       organism = synthetic construct
SEQUENCE: 142
MDSKGSSQKG SRLLLLLVVS NLLLPQGVLA AVGIGAVFLS GGAVGIGAVF LSGGDIIKLL  60
NEQVNKEMQS SNLYMSMSSW CYTHSLDGAG LFLFDHAAEE YEHAKKLIIF LNENNVPVQL  120
TSISAPHHKF HGLTHIFHKA YHHEQHISES INNITDHAIK SKDHATFNFL QWYVAEQHEE  180
EVLFKDILDK IELIGNENHG LYLADQYVKG IAKSRKSGS                         219

SEQ ID NO: 143         moltype = AA  length = 219
FEATURE                Location/Qualifiers
REGION                 1..219
                       note = Recombinant Protein Nanoparticle Sequence
source                 1..219
                       mol_type = protein
                       organism = synthetic construct
SEQUENCE: 143
MDSKGSSQKG SRLLLLLVVS NLLLPQGVLA AVGIGAVFLS GGAVGIGAVF LSGGDIIKLL  60
NEQVNNETQS SNLYMSMSSW CYTHSLDGAG LFLFDHAAEE YEHAKKLIIF LNENNVPVQL  120
TSISAPHHKF HGLTHIFHKA YHHEQHISES INNITDHAIK SKDHATFNFL QWYVAEQHEE  180
EVLFKDILDK IELIGNENHG LYLADQYVKG IAKSRKSGS                         219

SEQ ID NO: 144         moltype = AA  length = 219
FEATURE                Location/Qualifiers
REGION                 1..219
                       note = Recombinant Protein Nanoparticle Sequence
source                 1..219
                       mol_type = protein
                       organism = synthetic construct
SEQUENCE: 144
MDSKGSSQKG SRLLLLLVVS NLLLPQGVLA AVGIGAVFLS GGAVGIGAVF LSGGDIIKLL  60
NEQVNNETQS SNLYMSMSSW CYTHSLDGAG LFLFDHAAEE YEHAKKLIIF LNENNVPVQL  120
TSISAPHHKF HGLTHIFHKA YHHEQHISES INNITDHAIK SKDHATFNFL QWYVAEQHEE  180
EVLFKDILDK IELIGNENHG LYLADQYVKG IAKSRKSGS                         219

SEQ ID NO: 145         moltype = AA  length = 623
FEATURE                Location/Qualifiers
REGION                 1..623
                       note = Recombinant HIV-1 Env protein
source                 1..623
                       mol_type = protein
                       organism = synthetic construct
SEQUENCE: 145
AENLWVTVYY GVPVWKEAKT TLFCASDAKA YEKEVHNVWA THACVPTDPN PQEMVLKQVT  60
ENFNMWKNDM VDQMHEDVIS LWDQSLKPCV KLTPLCVTLN CTNATASNSS IIEGMKNCSF  120
NITTELRDKR EKKNALFYKL DIVQLDGNSS QYRLINCNTS VCTQACPKVS FDPIPIHYCA  180
PAGYAILKCN QKTFTGTGPC NQVSTVQCTH GIKPVVSTQL LLNGSLAEGE IIIRSENITN  240
NVKTIIVHLN ESVKIECTRP NNKTRTSIRI GPGQAFYATG QVIGDIREAY CNINESKWNE  300
TLQRVSKKLK EYFPHKNITF QPSSGGDLEI TTHSFNCGGE FFYCNTSSLF NRTYMANSTD  360
MANSTETNST RTITIHCRIK QIINMWQEVG RCMYAPPIAG NITCISNITG LLLTRDGGKN  420
NTETFRPGGG NMKDNWRSEL YKYKVVKIEP LGVAPTRCKR RVVGRRRRRR AVGIGAVFLG  480
FLGAAGSTMG AASMTLTVQA RNLLSGIVQQ QSNLLRAPEA QQHLLKLTVW GIKQLQARVL  540
AVERYLRDQQ LLGIWGCSGK LICCTNVPWQ SSWSNRNLSE IWDNMTWLQW DKEISNYTQI  600
IYGLLEESQN QQEKNEQDLL ALD                                          623

SEQ ID NO: 146         moltype = AA  length = 623
FEATURE                Location/Qualifiers
REGION                 1..623
                       note = Recombinant HIV-1 Env protein
source                 1..623
                       mol_type = protein
                       organism = synthetic construct
SEQUENCE: 146
AENLWVTVYY GVPVWKEAKT TLFCASDAKA YEKEVHNVWA THACVPTDPN PQEMVLKNVT  60
ENFNMWKNDM VDQMHEDVIS LWDQSLKPCV KLTPLCVTLN CTNATASNSS IIEGMKNCSF  120
NITTELRDKR EKKNALFYKL DIVQLDGNSS QYRLINCNTS VCTQACPKVS FDPIPIHYCA  180
PAGYAILKCN QKTFTGTGPC NQVSTVQCTH GIKPVVSTQL LLNGSLAEGE IIIRSENITN  240
NVKTIIVHLN ESVKIECTRP NNKTRTSIRI GPGQAFYATG QVIGDIREAY CNINESKWNE  300
TLQRVSKKLK EYFPHKNITF QPSSGGDLEI TTHSFNCGGE FFYCNTSSLF NRTYMANSTD  360
MANSTETNST RTITIHCRIK QIINMWQEVG RCMYAPPIAG NITCISNITG LLLTRDGGKN  420
NTETFRPGGG NMKDNWRSEL YKYKVVKIEP LGVAPTRCKR RVVGRRRRRR AVGIGAVFLG  480
FLGAAGSTMG AASMTLTVQA RNLLSGIVQQ QSNLLRAPEA QQHLLKLTVW GIKQLQARVL  540
AVERYLRDQQ LLGIWGCSGK LICCTNVPWQ SSWSNRNLSE IWDNMTWLQW DKEISNYTQI  600
IYGLLEESQN QQEKNEQDLL ALD                                          623
```

```
SEQ ID NO: 147          moltype = AA  length = 4
FEATURE                 Location/Qualifiers
REGION                  1..4
                        note = Furin cleavage site sequence
source                  1..4
                        mol_type = protein
                        organism = synthetic construct
SEQUENCE: 147
REKR                                                              4

SEQ ID NO: 148          moltype = AA  length = 6
FEATURE                 Location/Qualifiers
REGION                  1..6
                        note = Furin cleavage site sequence
source                  1..6
                        mol_type = protein
                        organism = synthetic construct
SEQUENCE: 148
RRRRRR                                                            6

SEQ ID NO: 149          moltype = AA  length = 10
FEATURE                 Location/Qualifiers
REGION                  1..10
                        note = Peptide linker
source                  1..10
                        mol_type = protein
                        organism = synthetic construct
SEQUENCE: 149
GGSGGGGSGG                                                        10

SEQ ID NO: 150          moltype = AA  length = 27
FEATURE                 Location/Qualifiers
REGION                  1..27
                        note = Transmembrane domain
source                  1..27
                        mol_type = protein
                        organism = synthetic construct
SEQUENCE: 150
KIFIMIVGGL IGLRIVFAVL SVIHRVR                                     27

SEQ ID NO: 151          moltype = AA  length = 23
FEATURE                 Location/Qualifiers
REGION                  1..23
                        note = Transmembrane domain
source                  1..23
                        mol_type = protein
                        organism = synthetic construct
SEQUENCE: 151
ILAIYSTVAS SLVLLVSLGA ISF                                         23

SEQ ID NO: 152          moltype = AA  length = 29
FEATURE                 Location/Qualifiers
REGION                  1..29
                        note = Transmembrane domain
source                  1..29
                        mol_type = protein
                        organism = synthetic construct
SEQUENCE: 152
IITIGSICMV VGIISLILQI GNIISIWVS                                   29

SEQ ID NO: 153          moltype = AA  length = 26
FEATURE                 Location/Qualifiers
REGION                  1..26
                        note = Foldon Domain
source                  1..26
                        mol_type = protein
                        organism = synthetic construct
SEQUENCE: 153
GYIPEAPRDG QAYVRKDGEW VLLSTF                                      26

SEQ ID NO: 154          moltype = AA  length = 856
FEATURE                 Location/Qualifiers
source                  1..856
                        mol_type = protein
                        organism = human immunodeficiency virus
SEQUENCE: 154
MRVKEKYQHL WRWGWRWGTM LLGMLMICSA TEKLWVTVYY GVPVWKEATT TLFCASDAKA  60
YDTEVHNVWA THACVPTDPN PQEVVLVNVT ENFNMWKNDM VEQMHEDIIS LWDQSLKPCV  120
```

```
KLTPLCVSLK CTDLKNDTNT NSSSGRMIME KGEIKNCSFN ISTSIRGKVQ KEYAFFYKLD  180
IIPIDNDTTS YKLTSCNTSV ITQACPKVSF EPIPIHYCAP AGFAILKCNN KTFNGTGPCT  240
NVSTVQCTHG IRPVVSTQLL LNGSLAEEEV VIRSVNFTDN AKTIIVQLNT SVEINCTRPN  300
NNTRKRIRIQ RGPGRAFVTI GKIGNMRQAH CNISRAKWNN TLKQIASKLR EQFGNNKTII  360
FKQSSGGDPE IVTHSFNCGG EFFYCNSTQL FNSTWFNSTW STEGSNNTEG SDTITLPCRI  420
KQIINMWQKV GKAMYAPPIS GQIRCSSNIT GLLLTRDGGN SNNESEIFRP GGGDMRDNWR  480
SELYKYKVVK IEPLGVAPTK AKRRVVQREK RAVGIGALFL GFLGAAGSTM GAASMTLTVQ  540
ARQLLSGIVQ QQNNLLRAIE AQQHLLQLTV WGIKQLQARI LAVERYLKDQ QLLGIWGCSG  600
KLICTTAVPW NASWSNKSLE QIWNHTTWME WDREINNYTS LIHSLIEESQ NQQEKNEQEL  660
LELDKWASLW NWFNITNWLW YIKLFIMIVG GLVGLRIVFA VLSIVNRVRQ GYSPLSFQTH  720
LPTPRGPDRP EGIEEEGGER DRDRSIRLVN GSLALIWDDL RSLCLFSYHR LRDLLLIVTR  780
IVELLGRRGW EALKYWWNLL QYWSQELKNS AVSLLNATAI AVAEGTDRVI EVVQGACRAI  840
RHIPRRIRQG LERILL                                                  856

SEQ ID NO: 155          moltype = AA  length = 634
FEATURE                 Location/Qualifiers
REGION                  1..634
                        note = Recombinant HIV-1 Env protein
source                  1..634
                        mol_type = protein
                        organism = synthetic construct
SEQUENCE: 155
AENLWVTVYY GVPVWKDAET TLFCASDAKA YETEKHNVWA THACVPTDPN PQEIHLENVT  60
EEFNMWKNNM VEQMHTDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA CTQACPKVSF  180
EPIPIHYCAP AGFAILKCKD KKFNGTGPCP SVSTVQCTHG IKPVVSTQLL LNGSLAEEEV  240
MIRSENITNN AKNILVQFNT PVQINCTRPN NNTRKSIRIG PGQAFYATGD IIGDIRQAHC  300
NVSKATWNET LGKVVKQLRK HFGNNTIIRF ANSSGGDLEV TTHSFNCGGE FFYCNTSGLF  360
NSTWISNTSV QGSNSTGSND SITLPCRIKQ IINMWQRIGQ CMYAPPIQGV IRCVSNITGL  420
ILTRDGGSTN STTETFRPGG GDMRDNWRSE LYKYKVVKIE PLGVAPTRCK RRVVGRRRRR  480
RAVGIGAVFL GFLGAAGSTM GAASMTLTVQ ARNLLSGIVQ QQSNLLRAPE AQQHLLKLTV  540
WGIKQLQARV LAVERYLRDQ QLLGIWGCSG KLICCTNVPW NSSWSNRNLS EIWDNMTWLQ  600
WDKEISNYTQ IIYGLLEESQ NQQEKNEQDL LALD                              634

SEQ ID NO: 156          moltype = AA  length = 623
FEATURE                 Location/Qualifiers
REGION                  1..623
                        note = Recombinant HIV-1 Env protein
source                  1..623
                        mol_type = protein
                        organism = synthetic construct
SEQUENCE: 156
AENLWVTVYY GVPVWKEAKT TLFCASDAKA YEKEVHNVWA THACVPTDPN PQEMVLKQVT  60
ENFNMWKNDM VDQMHEDVIS LWDQSLKPCV KLTPLCVTLN CTNATASNSS IIEGMKNCSF  120
NITTELRDKR EKKNALFYKL DIVQLDGNSS QYRLINCNTS VCTQACPKVS FDPIPIHYCA  180
PAGYAILKCN QKTFTGTGPC NQVSTVQCTH GIKPVVSTQL LLNGSLAEGE IIIRSENITN  240
NVKTIIVHLN ESVKIECTRP NNKTRTSIRI GPGQAFYATG QVIGDIREAY CNINESKWNE  300
TLQRVSKKLK EYFPHKNITF QPSSGGDLEI TTHSFNCGGE FFYCNTSSLF NRTYMANSTD  360
MANSTETNST RTITIHCRIK QIINMWQEVG RCMYAPPIAG NITCISNITG LLLTRDGGKN  420
NTETFRPGGG NMKDNWRSEL YKYKVVKIEP LGVAPTRCKR RVVGRRRRRR AVGIGAVFLG  480
FLGAAGSTMG AASMTLTVQA RNLLSGIVQQ QSNLLRAPEA QQHLLKLTVW GIKQLQARVL  540
AVERYLRDQQ LLGIWGCSGK LICCTNVPWQ SSWSNRNLSE IWDNMTWLQW DKEISNYTQI  600
IYGLLEESQN QQEKNEQDLL ALD                                          623

SEQ ID NO: 157          moltype = AA  length = 623
FEATURE                 Location/Qualifiers
REGION                  1..623
                        note = Recombinant HIV-1 Env protein
source                  1..623
                        mol_type = protein
                        organism = synthetic construct
SEQUENCE: 157
AENLWVTVYY GVPVWKEAKT TLFCASDAKA YEKEVHNVWA THACVPTDPN PQEMVLKNVT  60
ENFNMWKNDM VDQMHEDVIS LWDQSLKPCV KLTPLCVTLN CTNATASNSS IIEGMKNCSF  120
NITTELRDKR EKKNALFYKL DIVQLDGNSS QYRLINCNTS VCTQACPKVS FDPIPIHYCA  180
PAGYAILKCN QKTFTGTGPC NQVSTVQCTH GIKPVVSTQL LLNGSLAEGE IIIRSENITN  240
NVKTIIVHLN ESVKIECTRP NNKTRTSIRI GPGQAFYATG QVIGDIREAY CNINESKWNE  300
TLQRVSKKLK EYFPHKNITF QPSSGGDLEI TTHSFNCGGE FFYCNTSSLF NRTYMANSTD  360
MANSTETNST RTITIHCRIK QIINMWQEVG RCMYAPPIAG NITCISNITG LLLTRDGGKN  420
NTETFRPGGG NMKDNWRSEL YKYKVVKIEP LGVAPTRCKR RVVGRRRRRR AVGIGAVFLG  480
FLGAAGSTMG AASMTLTVQA RNLLSGIVQQ QSNLLRAPEA QQHLLKLTVW GIKQLQARVL  540
AVERYLRDQQ LLGIWGCSGK LICCTNVPWQ SSWSNRNLSE IWDNMTWLQW DKEISNYTQI  600
IYGLLEESQN QQEKNEQDLL ALD                                          623

SEQ ID NO: 158          moltype = AA  length = 623
FEATURE                 Location/Qualifiers
REGION                  1..623
                        note = Recombinant HIV-1 Env protein
source                  1..623
```

```
                        mol_type = protein
                        organism = synthetic construct
SEQUENCE: 158
AENLWVTVYY GVPVWKEAKT TLFCASDAKA YEKEVHNVWA THACVPTDPN PQEMVLKNVT  60
ENFNMWKNDM VDQMHEDVIS LWDQSLKPCV KLTPLCVTLN CTNATASNSS IIEGMKNCSF  120
NITTELRDKR EKKNALFYKL DIVQLDGNSS QYRLINCNTS VCTQACPKVS FDPIPIHYCA  180
PAGYAILKCN NKTFTGTGPC NNVSTVQCTH GIKPVVSTQL LLNGSLAEGE IIIRSENITN  240
NVKTIIVHLN ESVKIECTRP NNKTRTSIRI GPGQAFYATG QVIGDIREAY CNINESKWNE  300
TLQRVSKKLK EYFPHKNITF QPSSGGDLEI TTHSFNCGGE FFYCNTSSLF NRTYMANSTD  360
MANSTETNST RTITIHCRIK QIINMWQEVG RCMYAPPIAG NITCISNITG LLLTRDGGKN  420
NTETFRPGGG NMKDNWRSEL YKYKVVKIEP LGVAPTRCKR RVVGRRRRRR AVGIGAVFLG  480
FLGAAGSTMG AASMTLTVQA RNLLSGIVQQ QSNLLRAPEA QQHLLKLTVW GIKQLQARVL  540
AVERYLRDQQ LLGIWGCSGK LICCTNVPWN SSWSNRNLSE IWDNMTWLQW DKEISNYTQI  600
IYGLLEESQN QQEKNEQDLL ALD                                            623

SEQ ID NO: 159          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 159
LRNYWYFDV                                                            9

SEQ ID NO: 160          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 160
LKRFYYFDY                                                            9

SEQ ID NO: 161          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 161
LLPKWYFDV                                                            9

SEQ ID NO: 162          moltype = AA  length = 7
FEATURE                 Location/Qualifiers
REGION                  1..7
                        note = Recombinant antibody CDR sequence
source                  1..7
                        mol_type = protein
                        organism = synthetic construct
SEQUENCE: 162
EGNYRAY                                                              7

SEQ ID NO: 163          moltype = AA  length = 7
FEATURE                 Location/Qualifiers
REGION                  1..7
                        note = Recombinant antibody CDR sequence
source                  1..7
                        mol_type = protein
                        organism = synthetic construct
SEQUENCE: 163
GYVAFHY                                                              7

SEQ ID NO: 164          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 164
LRLYGYFDV                                                            9

SEQ ID NO: 165          moltype = AA  length = 9
FEATURE                 Location/Qualifiers
REGION                  1..9
                        note = Recombinant antibody CDR sequence
```

```
source                  1..9
                        mol_type = protein
                        organism = synthetic construct
SEQUENCE: 165
LRLYWYFDV                                                         9

SEQ ID NO: 166          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 166
FQGSHVPYT                                                         9

SEQ ID NO: 167          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 167
FQGSHFPFT                                                         9

SEQ ID NO: 168          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 168
QQYSSYPLT                                                         9

SEQ ID NO: 169          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 169
QQLVQHPFT                                                         9

SEQ ID NO: 170          moltype = AA  length = 9
FEATURE                 Location/Qualifiers
REGION                  1..9
                        note = Recombinant antibody CDR sequence
source                  1..9
                        mol_type = protein
                        organism = synthetic construct
SEQUENCE: 170
FQGSHIPYT                                                         9

SEQ ID NO: 171          moltype = AA  length = 109
FEATURE                 Location/Qualifiers
REGION                  1..109
                        note = Recombinant antibody variable domain sequence
source                  1..109
                        mol_type = protein
                        organism = synthetic construct
SEQUENCE: 171
QVQLQQSGAE LVRPGASVTL SCKASGYTFT DYEMHWVKQT PVHGLEWIGA IDPETGGTAY  60
NQKFKGKAIL TADKSSSTAY MELRSLTSED SAVYYCTRWG TGTTVTVSS             109

SEQ ID NO: 172          moltype = AA  length = 111
FEATURE                 Location/Qualifiers
REGION                  1..111
                        note = Recombinant antibody variable domain sequence
source                  1..111
                        mol_type = protein
                        organism = synthetic construct
SEQUENCE: 172
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP PFGGGTKLEI K          111

SEQ ID NO: 173          moltype = AA  length = 5
```

```
FEATURE                 Location/Qualifiers
source                  1..5
                        mol_type = protein
                        organism = human immunodeficiency virus
SEQUENCE: 173
AVGMG                                                                5

SEQ ID NO: 174          moltype = AA  length = 5
FEATURE                 Location/Qualifiers
source                  1..5
                        mol_type = protein
                        organism = human immunodeficiency virus
SEQUENCE: 174
AIGMG                                                                5

SEQ ID NO: 175          moltype = AA  length = 6
FEATURE                 Location/Qualifiers
source                  1..6
                        mol_type = protein
                        organism = human immunodeficiency virus
SEQUENCE: 175
AVVGLG                                                               6

SEQ ID NO: 176          moltype = AA  length = 5
FEATURE                 Location/Qualifiers
source                  1..5
                        mol_type = protein
                        organism = human immunodeficiency virus
SEQUENCE: 176
TVGAG                                                                5

SEQ ID NO: 177          moltype = AA  length = 5
FEATURE                 Location/Qualifiers
source                  1..5
                        mol_type = protein
                        organism = human immunodeficiency virus
SEQUENCE: 177
AVTMG                                                                5

SEQ ID NO: 178          moltype = AA  length = 5
FEATURE                 Location/Qualifiers
source                  1..5
                        mol_type = protein
                        organism = human immunodeficiency virus
SEQUENCE: 178
AVTLG                                                                5

SEQ ID NO: 179          moltype = AA  length = 6
FEATURE                 Location/Qualifiers
source                  1..6
                        mol_type = protein
                        organism = human immunodeficiency virus
SEQUENCE: 179
AVGTLG                                                               6

SEQ ID NO: 180          moltype = AA  length = 5
FEATURE                 Location/Qualifiers
source                  1..5
                        mol_type = protein
                        organism = human immunodeficiency virus
SEQUENCE: 180
AVGMA                                                                5

SEQ ID NO: 181          moltype = AA  length = 5
FEATURE                 Location/Qualifiers
source                  1..5
                        mol_type = protein
                        organism = human immunodeficiency virus
SEQUENCE: 181
AVGFG                                                                5

SEQ ID NO: 182          moltype = AA  length = 5
FEATURE                 Location/Qualifiers
source                  1..5
                        mol_type = protein
                        organism = human immunodeficiency virus
SEQUENCE: 182
AVTLG                                                                5
```

```
SEQ ID NO: 183          moltype = AA  length = 5
FEATURE                 Location/Qualifiers
source                  1..5
                        mol_type = protein
                        organism = human immunodeficiency virus
SEQUENCE: 183
DLGLG                                                                    5

SEQ ID NO: 184          moltype = AA  length = 6
FEATURE                 Location/Qualifiers
source                  1..6
                        mol_type = protein
                        organism = human immunodeficiency virus
SEQUENCE: 184
AVVELG                                                                   6

SEQ ID NO: 185          moltype = AA  length = 5
FEATURE                 Location/Qualifiers
source                  1..5
                        mol_type = protein
                        organism = human immunodeficiency virus
SEQUENCE: 185
AVTIG                                                                    5

SEQ ID NO: 186          moltype = AA  length = 5
FEATURE                 Location/Qualifiers
source                  1..5
                        mol_type = protein
                        organism = human immunodeficiency virus
SEQUENCE: 186
AVGVG                                                                    5

SEQ ID NO: 187          moltype = AA  length = 6
FEATURE                 Location/Qualifiers
source                  1..6
                        mol_type = protein
                        organism = human immunodeficiency virus
SEQUENCE: 187
AVGMLG                                                                   6

SEQ ID NO: 188          moltype = AA  length = 6
FEATURE                 Location/Qualifiers
source                  1..6
                        mol_type = protein
                        organism = human immunodeficiency virus
SEQUENCE: 188
AVGIVG                                                                   6

SEQ ID NO: 189          moltype = AA  length = 6
FEATURE                 Location/Qualifiers
source                  1..6
                        mol_type = protein
                        organism = human immunodeficiency virus
SEQUENCE: 189
AVGGIG                                                                   6

SEQ ID NO: 190          moltype = AA  length = 6
FEATURE                 Location/Qualifiers
source                  1..6
                        mol_type = protein
                        organism = human immunodeficiency virus
SEQUENCE: 190
AVGGFG                                                                   6

SEQ ID NO: 191          moltype = AA  length = 5
FEATURE                 Location/Qualifiers
source                  1..5
                        mol_type = protein
                        organism = human immunodeficiency virus
SEQUENCE: 191
AMGIG                                                                    5

SEQ ID NO: 192          moltype = AA  length = 5
FEATURE                 Location/Qualifiers
source                  1..5
                        mol_type = protein
                        organism = human immunodeficiency virus
SEQUENCE: 192
AIGIG                                                                    5
```

```
SEQ ID NO: 193         moltype = AA  length = 4
FEATURE                Location/Qualifiers
source                 1..4
                       mol_type = protein
                       organism = human immunodeficiency virus
SEQUENCE: 193
AAIG                                                        4

SEQ ID NO: 194         moltype = AA  length = 5
FEATURE                Location/Qualifiers
source                 1..5
                       mol_type = protein
                       organism = human immunodeficiency virus
SEQUENCE: 194
AAGIG                                                       5

SEQ ID NO: 195         moltype = AA  length = 187
FEATURE                Location/Qualifiers
REGION                 1..187
                       note = Epitope Scaffold Protein
source                 1..187
                       mol_type = protein
                       organism = synthetic construct
SEQUENCE: 195
MDSKGSSQKG SRLLLLLVVS NLLLPQGVLA AVGIGAVFLG ITGTWYNQLG STFIVTAGAD  60
GALTGTYESA VGNAESRYVL TGRYDSAPAT DGSGTALGWT VAWKNNYRNA HSATTWSGQY  120
VGGAEARINT QWLLTSGTTE ANAWKSTLVG HDTFTKVKPS AASGGLVPRG SHHHHHHSAW  180
SHPQFEK                                                     187

SEQ ID NO: 196         moltype = AA  length = 96
FEATURE                Location/Qualifiers
REGION                 1..96
                       note = Recombinant antibody variable domain sequence
source                 1..96
                       mol_type = protein
                       organism = synthetic construct
SEQUENCE: 196
QVQLVQSGAE VKKPGASVKV SCKVSGYTLT ELSMHWVRQA PGKGLEWMGG FDPEDGETIY  60
AQKFQGRVTM TEDTSTDTAY MELSSLRSED TAVYYC                      96

SEQ ID NO: 197         moltype = AA  length = 93
FEATURE                Location/Qualifiers
REGION                 1..93
                       note = Recombinant antibody variable domain sequence
source                 1..93
                       mol_type = protein
                       organism = synthetic construct
SEQUENCE: 197
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYC                         93

SEQ ID NO: 198         moltype = AA  length = 452
FEATURE                Location/Qualifiers
REGION                 1..452
                       note = Tetanus Toxin heavy chain C fragment
source                 1..452
                       mol_type = protein
                       organism = synthetic construct
SEQUENCE: 198
MKNLDCWVDN EEDIDVILKK STILNLDINN DIISDISGFN SSVITYPDAQ LVPGINGKAI  60
HLVNNESSEV IVHKAMDIEY NDMFNNFTVS FWLRVPKVSA SHLEQYGTNE YSIISSMKKH  120
SLSIGSGWSV SLKGNNLIWT LKDSAGEVRQ ITFRDLPDKF NAYLANKWVF ITITNDRLSS  180
ANLYINGVLM GSAEITGLGA IREDNNITLK LDRCNNNNQY VSIDKFRIFC KALNPKEIEK  240
LYTSYLSITF LRDFWGNPLR YDTEYYLIPV ASSSKDVQLK NITDYMYLTN APSYTNGKLN  300
IYYRRLYNGL KFIIKRYTPN NEIDSFVKSG DFIKLYVSYN NNEHIVGYPK DGNAFNNLDR  360
ILRVGYNAPG IPLYKKMEAV KLRDLKTYSV QLKLYDDKNA SLGLVGTHNG QIGNDPNRDI  420
LIASNWYFNH LKDKILGCDW YFVPTDEGWT ND                          452
```

HIV-1 ENV FUSION PEPTIDE IMMUNOGENS AND THEIR USE

CROSS REFERENCE TO RELATED APPLICATIONS

This is a continuation of U.S. patent application Ser. No. 16/338,964, filed on Apr. 2, 2019, which is the U.S. National Stage of International Application No. PCT/US2017/054959, filed on Oct. 3, 2017, which was published in English under PCT Article 21(2), which in turn claims the benefit of U.S. Provisional Application No. 62/403,266, filed Oct. 3, 2016. Each of the above-listed applications is incorporated by reference herein in its entirety.

FIELD

This disclosure relates to immunogens based on the HIV-1 envelope (Env) fusion peptide for treatment and prevention of Human Immunodeficiency Virus type 1 (HIV-1) infection and disease.

BACKGROUND

Millions of people are infected with HIV-1 worldwide, and 2.5 to 3 million new infections have been estimated to occur yearly. Although effective antiretroviral therapies are available, millions succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection, proteases of the host cell cleave gp160 into gp120 and gp41. Gp41 is an integral membrane protein, while gp120 protrudes from the mature virus. Together gp120 and gp41 make up the HIV-1 Env spike, which is a target for neutralizing antibodies.

It is believed that immunization with an effective immunogen based on the HIV-1 Env glycoprotein can elicit a neutralizing response, which may be protective against HIV-1 infection. However, despite extensive effort, a need remains for agents capable of such action.

SUMMARY

This disclosure provides novel immunogens for eliciting an immune response to HIV-1 Env in a subject. In several embodiments, the immunogen comprise HIV-1 Env fusion peptide or portion thereof and can be used to elicit a neutralizing immune response to HIV-1 in a subject that targets the fusion peptide. As discussed in more detail below, in several embodiments, the disclosed immunogens can be used to elicit a surprisingly effective immune response that neutralizes diverse tier 2-strains of HIV-1.

In some embodiments, the immunogen comprises an immunogenic conjugate according to:

X-L-C wherein X is a polypeptide consisting of or consisting essentially of the amino acid sequence of residue 512 to one of residues 517-521 (HXB2 numbering) of a human immunodeficiency virus type 1 (HIV-1) Env protein, L is an optional linker, and C is a heterologous carrier. The X polypeptide can be directly covalently linked to the carrier, or indirectly linked to the carrier, for example via the optional linker. In several such embodiments, the carrier protein comprises tetanus toxin C fragment or diphtheria toxin variant CRM197 and the X polypeptide consists essentially of or consists of HIV-1 Env residues 512-519 (HXB2 numbering), for example, the X polypeptide consists essentially or consists of an amino acid sequence set forth as AVGIGAVF (residues 1-8 of SEQ ID NO: 1). In a non-limiting example, a peptide (such as AVGIGAVF peptide, residues 1-8 of SEQ ID NO: 1) is linked to a protein carrier by a linker including a heterologous cysteine residue fused to the C-terminal residue of the peptide by peptide bond and a, wherein the heterobifunctional moiety is linked to a lysine residue on the carrier and the cysteine residue. The immunogenic conjugate elicits a neutralizing immune response to HIV-1 in a subject.

In some embodiments, the immunogen comprises an epitope scaffold protein comprising, from N- to C-terminal, an amino acid sequence according to:

X-L-S wherein X is a polypeptide consisting of or consisting essentially of the amino acid sequence of residue 512 to one of residues 517-525 (HXB2 numbering) of an HIV-1 Env protein, L is an optional peptide linker, and S is a heterologous scaffold protein comprising, consisting essentially of, or consisting of the amino acid sequence of one of SEQ ID SEQ ID NOs: 13-31, or an amino acid sequence at least 90% identical thereto. In several such embodiments, the X polypeptide consists essentially of or consists of HIV-1 Env residues 512-519 (HXB2 numbering), for example, the X polypeptide consists essentially or consists of an amino acid sequence set forth as AVGIGAVF (residues 1-8 of SEQ ID NO: 1). In some embodiments, the epitope scaffold protein comprises an amino acid sequence set forth as any one of SEQ ID NOs: 32-58, or an amino acid sequence at least 90% identical thereto. The epitope scaffold protein elicits a neutralizing immune response to HIV-1 in a subject.

In some embodiments, the immunogen comprises a recombinant protein nanoparticle comprising a multimer of self-assembled fusion proteins comprising, from N- to C-terminal, an amino acid sequence according to:

X-L-N wherein X is a polypeptide consisting of or consisting essentially of the amino acid sequence of residue 512 to one of residues 517-525 (HXB2 numbering) of an HIV-1 Env protein, L is an optional peptide linker, and N is a subunit of a ferritin or lumazine synthase protein nanoparticle. In some embodiments, the lumazine synthase subunit comprises, consists essentially of, or consists of an amino acid sequence set forth as one of SEQ ID NOs: 84, or 87-88, or an amino acid sequence at least 90% identical thereto. In some embodiments, the ferritin subunit comprises, consists essentially of, or consists of an amino acid sequence set forth as one of SEQ ID NOs: 82-83 or 89-100, or an amino acid sequence at least 90% identical thereto. In several such embodiments, the X polypeptide consists essentially of or consists of HIV-1 Env residues 512-519 (HXB2 numbering), for example, the X polypeptide consists essentially or consists of an amino acid sequence set forth as AVGIGAVF (residues 1-8 of SEQ ID NO: 1). In some embodiments, the protein nanoparticle is a lumazine synthase nanoparticle and the self-assembled fusion proteins comprise an amino acid sequence set forth as any one of SEQ ID NOs: 101-103, or an amino acid sequence at least 90% identical thereto. In some embodiments, the protein nanoparticle is a ferritin nanoparticle and the self-assembled fusion proteins comprise an amino acid sequence set forth as any one of SEQ ID NOs: 104-122, or an amino acid sequence at least 90% identical thereto. The recombinant protein nanoparticle elicits a neutralizing immune response to HIV-1 in a subject.

In some embodiments, the immunogen comprises a recombinant HIV-1 Env ectodomain trimer. The trimer comprises three protomers, each comprising one or more amino acid substitutions to remove N-linked glycosylation sites at one or more of HIV-1 Env positions N88, N230, N241, and N611 (HXB2 numbering) of the protomer. The glycosylation sites are located near the fusion peptide in the HIV-1 Env ectodomain trimer, and their removal exposes the fusion peptide on the surface of the HIV-1 Env trimer to facilitate recognition of the fusion peptide by immune cells in a subject and elicitation of an immune response that targets the fusion peptide. In some embodiments, the protomers of the recombinant HIV-1 Env ectodomain trimer each further comprise a non-natural disulfide bond between cysteine substitutions at HIV-1 Env positions 201 and 433 to stabilize the recombinant HIV-1 Env ectodomain trimer in a prefusion mature closed conformation. In some embodiments, the protomers of the recombinant HIV-1 Env ectodomain trimer each further comprise non-natural disulfide bond between cysteine substitutions at positions 501 and 605, and a proline substitution at position 559, to stabilize the recombinant HIV-1 Env ectodomain trimer in a prefusion mature closed conformation. In some embodiments, the protomers of the recombinant HIV-1 Env ectodomain trimer each comprise a gp120 protein comprising HIV-1 Env positions 31-507 and a gp41 ectodomain comprising HIV-1 Env positions 512-664. In some embodiments, the protomers in the HIV-1 Env ectodomain trimer each comprise an amino acid sequence set forth as any one of SEQ ID NOs: 145-146 or 156-1570, or an amino acid sequence at least 90% identical thereto. In some embodiments, the HIV-1 Env ectodomain trimer can be soluble, or membrane anchored (for example, by linkage of a transmembrane to the C-terminus of the protomers of the trimer). The recombinant HIV-1 Env ectodomain trimer elicits a neutralizing immune response to HIV-1 in a subject.

Nucleic acid molecules encoding the disclosed immunogens and expression vectors (such as an inactivated or attenuated viral vector) including the nucleic acid molecules are also provided.

Compositions including the disclosed immunogens are also provided. The composition may be a pharmaceutical composition suitable for administration to a subject, and may also be contained in a unit dosage form. The compositions can further include an adjuvant. The immunogen can be further conjugated to a carrier to facilitate presentation to the immune system.

Methods of generating an immune response to HIV-1 Env protein in a subject are disclosed, as are methods of treating, inhibiting or preventing an HIV-1 infection in a subject. In such methods a subject, such as a human subject, is administered an effective amount of a disclosed immunogen to elicit the immune response. The subject can be, for example, a human subject at risk of or having an HIV-1 infection. In some embodiments, the methods comprise administration of a soluble HIV-1 Env trimer (such as a BG505.SOSIP-DS trimer with removal of N-linked glycan sequons at one or more of N88, N230, N241, and N611) followed by one or more administrations of the immunogenic conjugate according to X-L-C (such as FP8-TTHc). In some embodiments, the methods comprise one or more administrations of the immunogenic conjugate according to X-L-C (such as FP8-TTHc), followed by administration of a soluble HIV-1 Env trimer (such as a BG505.SOSIP-DS trimer with removal of N-linked glycan sequons at one or more of N88, N230, N241, and N611).

The foregoing and other features and advantages of this disclosure will become more apparent from the following detailed description of several embodiments which proceeds with reference to the accompanying figures.

BRIEF DESCRIPTION OF THE FIGURES

(FIG. 2A) Immunization scheme 1. At day 52, mouse spleens were harvested and hybridomas created. (FIG. 2B) ELISA and neutralization of serum from scheme 1-immunized mice. Protein probes used for ELISA are defined at top and include BG505 SOSIP.664, FP-epitope scaffold based on PDB 1M6T, and 1M6T scaffold with no FP. Columns 1 and 2 define mouse identification number, strain and adjuvant. ELISA data are shown as a function of serum dilution for pre-bleed, days 21, 35, and 52. Neutralization ($ID_{50}$, $ID_{50}$) values provided for day 52 serum; see supplemental for neutralization details. (FIG. 2C) Immunization scheme 2. At day 38, mouse spleens were harvested and hybridomas created. (FIG. 2D) ELISA and neutralization of serum from scheme 2-immunized mice, displayed as in (B).

FIGS. 3A-3C. First Generation vaccine-elicited antibodies targeting FP neutralize up to 10% of HIV-1. (FIG. 3A) Genetic characteristics of vaccine-elicited antibodies recognizing both HIV-1 Env and FP. Identity values are based on nucleotide sequence of the indicated heavy or light chain gene. (FIG. 3B) Heavy and light chain phylogenetic tree. (FIG. 3C) Neutralization dendrograms for vaccine-elicited antibodies vFP1.01, vFP5.01 and vFP7.04, with branches according to neutralization potency. Strains sensitive to V3-directed or CD4-induced antibodies are shown in italics.

FIGS. 4A-4E. FP Assumes disparate antibody-bound conformations, with neutralization restricted to a select angle of trimer approach. (FIG. 4A) Top panels, cryo-EM reconstruction at 8.6 Å resolution (gray) of Fab vFP1.01 in complex with BG505 DS-SOSIP trimer. Expanded view, crystal structure of Env trimer and FP-bound Fab vFP1.01 at 2.0 Å resolution, which was modeled into the cryo-EM map by rigid-body docking. Surface areas shown for N-terminal region of FP. (FIG. 4B) Same as (FIG. 4A). (FIG. 4C) Comparison of FP bound by vFP1.01 versus VRC34.01. (FIG. 4D) Same as (FIG. 4C), but for vFP5.01. (FIG. 4E) Angle of recognition and Fv-domain overlap for vFP1.01, vFP5.01, and VRC34.01. See also FIG. 11.

FIGS. 5A-5E. Second-Generation vaccine-elicited antibodies neutralize up to 31% of HIV-1. (FIG. 5A) 16 immunization schema (left), with neutralization (middle) and hybridoma-identified antibodies (right). Names for vFP1-class antibodies are italicized according to neutralization properties as indicated. (FIG. 5B) Trimer boost induced significantly higher serum neutralization titers. (FIG. 5C) Neutralization by $2^{nd}$ generation vaccine-elicited antibodies on 10 isolates, 5 with complete glycans around FP. (FIG. 5D) Neutralization by trimer-boosted sera on 10 isolates, 5 with complete glycans around FP, as in (FIG. 5A). (FIG. 5E) Neutralization dendrogram for vFP16.02 and vFP20.01, with branches according to neutralization potency.

(FIG. 6A) CryoEM map of quaternary complex with antibody 2712-vFP16.02, segmented by components at a contour level that allowed visualization of the entire complex, including less ordered antibody Fc domains. (FIG. 6B) Same as (A), but with 2716-vFP20.01. (FIG. 6C) Details of vFP16.02 interaction, with right panels showing experimental EM density in mesh, with contour level adjusted to allow visualizing of the partially ordered glycan. Residues altered by SHM highlighted. Antibody vFP16.02 recognizes both FP and neighboring glycan to achieve greater than 30% breadth. (FIG. 6D) Same as (FIG. 6C), but for vFP20.01. (FIG. 6E) Sequence alignment of vaccine-elicited FP-directed antibodies and origin genes. FP contacts, glycan contacts and SHM are highlighted. Additional Env contacts are highlighted by double underlining. Because the density from the cryo-EM reconstructions was not always sufficiently clear to allow atomic-level fitting, contacts shown with dotted rectangles are inferred.

FIGS. 7A-7F. Iterative structure-based vaccine design begins to achieve breadth observed with naturally elicited antibodies. (FIG. 7A) Dendrogram representing neutralization fingerprints shows vaccine-elicited antibodies to cluster with natural FP antibodies, though as a separate group. (FIG. 7B) Comparison of HIV-1-neutralization breadth and potency from natural and vaccine-elicited antibodies. (FIG. 7C) Neutralization breadth of FP-directed antibodies versus affinity for stabilized Env trimer. (FIG. 7D) Bar plot showing FP sequence association with neutralization data. Residue position 515 is significantly associated with large panel neutralization data for vFP1 class antibodies; a dotted line corresponds to an adjusted P-value of 0.05. (FIG. 7E) Sequence diversity of the first five residues of FP (residue 512 to 516) in the 208-virus panel ranked by their prevalence. The accumulative coverage of the sequence diversity of these five residues is also shown. (FIG. 7F) vFP-defined site of vulnerability allows for target-site conformational diversity.

FIGS. 8A-8H. Characteristics of FP immunogens. (FIG. 8A) Metric for antigenicity. The fraction of binding is derived from a panel of antibodies, and implemented as a Boolean variable where binding is true for KD tighter than a cutoff-value and false for KD weaker than the cutoff-value. In FIG. 1A, we chose a cutoff-value of 100 nM, for the antigenicity score, which was FP-specific. See FIG. 9C for $K_D$ data. (FIG. 8B) Antigenicity assessment of FP immunogens by BLI method with Octet. Examples of Octet-binding curves for FPKLH and FP-1M6T epitope scaffold are shown. (FIG. 8C) FP-immunogen antigenicity. FP-directed antibodies VRC34.01, VRC34.02, PGT151 and ACS202 were considered neutralizing, whereas CHO7 was considered weakly or non-neutralizing. (FIG. 8D) Amino acid sequences for FP scaffolds: FP-3HSH and FP-1SLF. Additional epitope scaffolds described in Kong et al. 2016. (FIG. 8E) Structural models of FP-3HSH and FP-1SLF. (FIG. 8F) Negative-stain EM images (inset shows 2D averages). (FIG. 8G) Physical stability of FP-coupled KLH. Fractional values refer to VRC34.01 reactivity retained after exposure to various physical extremes as compared to initial VRC34.01 binding level. Affinity measured by biolayer interferometry. (FIG. 8H) Binding of VRC34 Fab to FP-KLH illustrated by negative-stain electron microscopy. Examples of micrographs for FP-KLH (left) and FP-KLH mixed with VRC34 Fab at a molar ratio of 1:10 (right). Right panels: examples of raw particles for FP-KLH and FP-KLH-VRC34, respectively. White arrows indicate bound Fab fragments. Bottom panels: examples of 2D classes for FP-KLH and FP-KLH-VRC34 fab, respectively. White arrows indicate bound Fab fragments.

FIGS. 9A-9G. Neutralization characteristics of vFP sera and antibodies. (FIG. 9A) Neutralization assessment of sera from immunized mice in FIG. 1. (FIG. 9B-FIG. 9C) Neutralization assay for 1st-generation FP-directed antibodies. (FIG. 9B) Antibody neutralization of wildtype and glycan deleted Env-pseudotyped viruses. Five wildtype viruses and the corresponding single and double glycan removed mutants on glycan 88 and 611 were assessed. (FIG. 9C) Neutralization curves for antibodies vFP1.01, vFP7.04 and vFP7.05 on wildtype and glycan deleted Envpseudoviruses. The IC50 and IC80 values were assessed and are shown in (FIG. 9B). (FIG. 9D-FIG. 9E) Second-generation serum neutralization on 293T-derived HIV-1 Env-pseudotyped viruses in TZM-bl assay. (FIG. 9D) Serum neutralization curves of 5 immunized and 2 unimmunized control C57/BL6 mice, tested on 10 wildtype HIV-1 Env-pseudotyped viruses. SVA-MLV was assessed as control. Information on the viruses and ID50 titers are shown in FIG. 5E. (FIG. 9E) FP-competed neutralization curves of indicated immunized mice sera on HIV-1 strain 25710-2.43. Sera were pre-incubated with a nine amino acid FP, control peptide or control media before mixing with virus stock. ID50 titers are shown in the table. ID50 fold change was calculated as ID50[media]/ID50[peptide]. % inhibition of FP or control peptide was calculated as (1-ID50[peptide]/ID50[media])*100%. (FIG. 9F-FIG. 9G) Repeat immunization experiment of mouse ID #2716 with control. (FIG. 9F) Experimental schema and neutralization on D88+611 BG505 virus. (FIG. 9G) Statistical comparison. * Denotes P<0.01.

(FIG. 10A-FIG. 10B) vFP1.01 crystal structure with FP. (FIG. 10A) Interaction between vFP1.01 and FP (contacting residues are shown as sticks). (FIG. 10B) Ligplot showing the contact between vFP1.01 and FP. (FIG. 10C-FIG. 10D) vFP5.01 crystal structure with FP. (FIG. 10C) Interaction between vFP5.01 and FP (contacting residues are shown as sticks). (FIG. 10D) Ligplot showing the contact between vFP5.01 and FP. (FIG. 10E) Principal component analysis of FP conformation based on molecular dynamics simulations of fully glycosylated HIV-1-Env trimer. Principal component projections (in transparency) are shown for HIV-1-fusion peptides bound by antibody (or for clade G Env trimer-5FYJ). Four prevalent clusters of fusion-peptide conformations were observed. Most prevalent was a symmetrical U-shaped conformation, which was recognized by FP1.01 and also observed in the fully glycosylated Env trimer from a Clade G isolate. A J-shaped conformation, recognized by FP5.01, was also highly prevalent, as was the extended linear conformation, recognized by VRC34.01. A related extended conformation was also recognized by antibody PGT151, though the conformational space sampled by the PGT151-bound antibody was substantially less dense than the other antibody-recognized conformations. (FIG. 10F) Conformational superposition of the peptides analyzed in (FIG. 10E), along with the principal component projection (in transparency). Despite substantial difference in secondary structure, the two conformations share similar global shape. Thus, even though the FP-conformation in 5FYJ is slightly helical (one turn), both peptides adopt a symmetrical "U"-shape conformation. (FIG. 10G) Superimposition of vFP1-class antibodies in complex with FP (residues 512-519). Antibody variable regions of vFP1-class antibodies, including vFP1.01, vFP7.04, vFP16.02 and vFP20.01, were aligned structurally. (FIG. 10H) SA omit map of FP, in the crystal structure of vFP16.02 bound complex.

FIG. 11A-11B. Impact of Env-trimer prime on neutralization and vFP1-class antibody SHM. (FIG. 11A) FP-KLH mouse immunization experiment schemes with or without trimer prime. Sera neutralization and antibody isolation is shown. (FIG. 11B) Statistics comparison for the antibody SHM between two schemes.

FIGS. 12A-12B. Binding of vaccine-elicited antibodies to HIV-1 Env trimers and His-tagged FP. (FIG. 12A) SPR constants of all first and second generation vFPs Fabs binding to wild type, glycan-deleted BG505.DS-SOSIP, and FPs. (FIG. 12B) Pearson correlation between the log of BG505.DS-SOSIP KD and log of neutralization IC50 for wild type, delta glycan 88, and delta glycan 611. Vaccine elicited antibodies are shown in solid circles while VRC34.01 is shown in hollow circles.

FIGS. 13A-13H. Translatability of murine vFP1 antibodies to humans and elicitation of vFP antibodies in other standard vaccine-test species. (FIG. 13A) V-gene signature of vFP1 class antibodies. Signature residues for heavy chain (top) and light chain (bottom) are showed in sticks and labeled. (FIG. 13B) Comparisons of IGHV1-15 and IGKV1-117 to their respect human homologs identified by IMGT/V-QUEST and mutation profile of human gene IGHV1-24 and IGKV2-28. Compared to mouse IGHV1-15, human IGHV1-24 contains the H35 signature, and the A50 and A/V58 signatures can be reproduced by somatic hypermutation with high frequencies. This suggested similar key signatures may be reproduced by human antibodies. However, the alignment also showed multiple germline gene positions are diversified between the homolog genes, further investigations are required to understand whether they will affect FP recognition. The mouse IGKV1-117 was aligned to two human kappa chain genes, IGKV2-28 and IGKV2-40. Similar to mouse IGKV1-117, the IGKV2-28 also has a His-Ser-Asn motif in CDR L1. We built a substitution profile for IGKV2-28 using 104 antibody lineages derived from repertoires of three healthy human donors. The substitution profile showed that the key signatures of vFP1 antibodies, Y27d, Y32, and E34 are either germline residue or mutations with high frequency in human IGKV2-28 antibodies, suggesting the signatures observed in the vFP1 antibodies can be obtained with high frequency. V gene positions numbered using Kabat system. (FIGS. 13C-13D) Autoreactivity analysis of FP-directed antibodies. (FIG. 13C) ANA Hep-2 staining analysis showed none of the five FP-directed antibodies are autoreactive. Control antibodies with known autoreactivity are italicized. (FIG. 13D) Anti-cardiolipin ELISA showed that none of the three FP-directed antibodies are reactive. Controls are italicized as in (FIG. 13C). (FIG. 13E) Guinea pig FP immunization scheme. (FIG. 13F) Neutralization assay with guinea pig FP immunization study week 28 sera. (FIG. 13G) Rhesus macaque FP immunization scheme. (FIG. 13H) Neutralization assay with NHP FP immunization study week 26 sera.

FIGS. 14A-14B. Impact of alanine and glycine mutations at different FP residue positions on binding of FP-directed antibodies. The binding of indicated antibodies to alanine mutants (FIG. 14A) or glycine mutants (FIG. 14B) was normalized to binding to the wild-type FP sequence.

FIG. 15. vFP antibody neutralization statistics from the 208-virus isolate panel. Neutralization breadth of FP targeting neutralizing antibodies evaluated based on different virus panels: a 208-isolate panel evaluated in this study; the global panel; the tier 2 isolates in the 208-isolate panel (156 strains that were not neutralized by antibodies 17b, 48d, F105, 447-52D and 3074; the 58 strains in the 208-isolate panel that have the identical N-terminal 8-mer of the FP as BG505. Breadth statistics for $IC_{50}$<50 μg/ml is shown on the top and statistics for $IC_{50}$<100 μg/ml is shown at the bottom.

FIG. 16. Sensitivity/resistance analysis for FP-directed antibodies. FIG. 16A shows N-terminal fusion peptide residues (512-519) and their association with neutralization data from the 208-isolate panel for vFP7.04, vFP7.05, and vFP20.01. P-values are corrected for multiple testing using Hohm metric. Only entries with adjusted P-value<0.05 are displayed in the table. FIG. 16B shows FP-proximal N-glycan sequons (N88, N241, N448, and N611) and their association with neutralization data from the 208-isolate panel. P-values are corrected for multiple testing using Hohm metric. Only entries with adjusted P-value<0.05 are displayed in the table.

FIG. 17 shows a diagram and a graph illustrating design and VRC34 binding to epitope scaffold proteins containing the HIV-1 Env fusion peptide. The structure of the scaffold used for 3 designs that bound to VRC34 with high affinity is shown in the top panel. Corresponding scaffold proteins are provided herein as SEQ ID NO: 21 (glyc88_1M6T_A35N_A37S), SEQ ID NO: 22 (glyc88_1M6T_K42N), and SEQ ID NO: 23 (glyc88_1M6T_E49N_K51T). The N-terminus of the scaffold, where the fusion peptide was added to via a GGG linker. The scaffold sequence was modified to include N-linked glycosylation sites that minim the glycans found on the native HIV-1 Env trimer that are located near the fusion peptide. The sites where N-linked glycosylation were introduced are shown (K42N, A35N, E49N). ELISA analysis with VRC34.01 of the 1M6T-K42N scaffolds, with and without attaching the fusion peptide at the N-terminus, is shown in the lower panel.

FIGS. 18A-18D. Design, production, and antigenicity of lumazine synthase and ferritin nanoparticles that include the HIV-1 Env fusion peptide linked to the N-terminus of the nanoparticle subunits. (FIG. 18A) Illustration of design of lumazine synthase (1HQK) based nanoparticles. (FIG. 18B) Antigenic screening of FP-nanoparticles. (FIG. 18C) FP-LS produced in a HEK293 transient transfection system shows homogenous particle formation. The SEC profile of purified FP-LS nanoparticle shows that the nanoparticle forms one major peak in PBS buffer. SDS-PAGE analysis of purified nanoparticle protein with or without reducing agent shows the presence of 60mer and monomer. Negative stain electron microscopy analysis of the purified FP-LS nanoparticles showed that the sample contains well-assembled, round particles with a diameter of about 20 nm. 2D classification and averaging produced highly symmetrical classes. (FIG. 18D) Neutralizing antibodies that target the fusion peptide specifically bind to the purified FP-LS. Binding to FP-KLH and FP-1M6T is shown for comparison.

FIGS. 19A-19G. Diverse HIV-1 Env fusion peptides conjugated to several different carrier proteins induce neutralizing immune responses to HIV-1 in mice.

FIGS. 21A-21D. HIV-1 Env fusion peptides conjugated to several different carrier proteins in combination with HIV-1 Env trimers induce neutralizing immune responses to HIV-1 in Guinea pigs.

SEQUENCE LISTING

Figure 1:
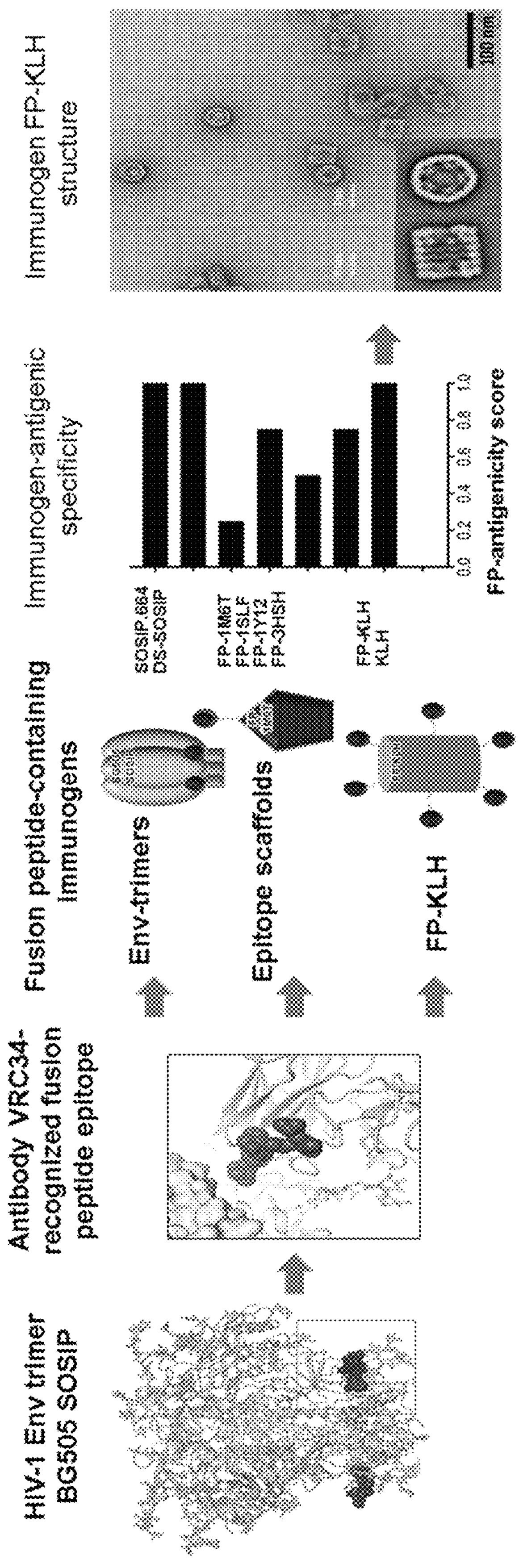
FIG. 1. Design and properties of FP immunogens based on the epitope of antibody VRC34.01. Structure-based design, antigenic characteristics, and EM structure of FP immunogens. FP antigenicity, as characterized by Octet and MSD, are shown in FIG. 8.

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an XML file in the form of the file named "4239-97661-12_Sequence.xml", which was created on Feb. 4, 2023, and has a file size of 266,240 bytes, and which is incorporated by reference herein.

DETAILED DESCRIPTION

As the HIV-1 pandemic continues to infect millions of people each year, the need for an effective vaccine increases. However the development of such a vaccine has been stymied due to the difficulty in developing an immunogen capable of eliciting broadly neutralizing antibodies. The current disclosure meets these needs.

One of the major hurdles to the construction of an effective HIV-1 vaccine is focusing the immune response to regions of HIV proteins which mostly produce broadly neutralizing antibodies. As disclosed herein, a series of immunogens that elicit immune responses to the HIV-1 Env fusion peptide has been constructed. Such molecules have utility as both potential vaccines for HIV and as diagnostic molecules (for example, to detect and quantify target antibodies in a polyclonal serum response).

One immunogen, a peptide including the N-terminal eight residues of the HIV-1-fusion peptide conjugated to carrier is shown to elicit antibodies that can neutralize diverse tier 2-strains of HIV-1, and up to 30% of HIV-1 strains in a standardized 208 pseudovirus panel, an elusive result sought for decades, but not achieved until now.

Further, immunization protocols comprising immunization with a peptide including the N-terminal eight residues of the HIV-1-fusion peptide conjugated to carrier, subsequently followed by immunization with HIV-1 Env trimer stabilized in a prefusion mature conformation elicited production of antibodies that neutralize over 30% of HIV-1 in a standardized 208 pseudovirus panel. Even more remarkable it that the immunization protocol elicited a neutralization response with considerable breadth, even though the overall neutralization titers are low. For example, immunization with peptide including the N-terminal eight residues of the BG505 HIV-1-fusion peptide conjugated to carrier, subsequently followed by immunization with BG505.SOSIP-DS trimer elicits an immune response that has relatively low binding activity for WT BG505, yet sera from immunized animals has clear cross-clade neutralization. Such low potency, high breadth is more typical of broadly neutralizing antibodies (see, for example, the breadth/potency curve for antibody 2G12), but very surprising to see for serum responses.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine, published by* Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided: Adjuvant: A vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJU-PLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, ASO1, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. Additional description of adjuvants can be found, for example, in Singh (ed.) Vaccine Adjuvants and Delivery Systems. Wiley-Interscience, 2007). Adjuvants can be used in combination with the disclosed immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid. In some examples, an amino acid in a polypeptide is substituted with an amino acid from a homologous polypeptide, for example, an amino acid in a recombinant Clade A HIV-1 Env polypeptide can be substituted with the corresponding amino acid from a Clade B HIV-1 Env polypeptide.

Antibody: An immunoglobulin, antigen-binding fragment, or derivative thereof, that specifically binds and recognizes an analyte (antigen), such as HIV-1 Env, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Carrier: An immunogenic molecule to which an antigen (such as the N-terminal portion of the HIV-1 Env fusion peptide) can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conjugate: A composition composed of at least two heterologous molecules (such as an HIV-1 Env fusion peptide and a carrier, such as a protein carrier) linked together. In a non-limiting example, a peptide (such as AVGIGAVF peptide, residues 1-8 of SEQ ID NO: 1) is linked to a protein carrier by a linker including a heterologous cysteine residue fused to the C-terminal residue of the peptide by peptide bond and a heterobifunctional moiety, wherein the heterobifunctional moiety is linked to a lysine residue on the carrier and the cysteine residue. In this example, the peptide is indirectly covalently linked to the carrier by the linker. Immunogenic conjugates are conjugates that are useful for eliciting a specific immune response to a molecule in the conjugate in a vertebrate. In some embodiments where the conjugate include a viral antigen, the immune response is protective in that it enables the vertebrate animal to better resist infection from the virus from which the antigen is derived.

Conservative variants: "Conservative" amino acid substitutions are those substitutions that do not substantially affect or decrease a function of a protein, such as the ability of the protein to elicit an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant Env protein, such as the ability to elicit an immune response when administered to a subject. For instance, if an amino acid residue is essential for a function of the protein, even an otherwise conservative substitution may disrupt that activity. Thus, a conservative substitution does not alter the basic function of a protein of interest.

Consists essentially of and Consists Of: A polypeptide comprising an amino acid sequence that consists essentially of a specified amino acid sequence does not include any additional amino acid residues. However, the residues in the polypeptide can be modified to include non-peptide components, such as labels (for example, fluorescent, radioactive, or solid particle labels), sugars or lipids, and the N- or C-terminus of the polypeptide can be joined (for example, by peptide bond) to heterologous amino acids, such as a cysteine (or other) residue in the context of a linker for conjugation chemistry. A polypeptide that consists of a specified amino acid sequence does not include any additional amino acid residues, nor does it include additional biological components, such as nucleic acids lipids, sugars, nor does it include labels. However, the N- or C-terminus of the polypeptide can be joined (for example, by peptide bond) to heterologous amino acids, such as a peptide tag, or a cysteine (or other) residue in the context of a linker for conjugation chemistry.

A polypeptide that consists or consists essentially of a specified amino acid sequence can be glycosylated or have an amide modification. A polypeptide that consists of or consists essentially of a particular amino acid sequence can be linked via its N- or C-terminus to a heterologous polypeptide, such as in the case of a fusion protein containing a first polypeptide consisting or a first sequence that is linked (via peptide bond) to a heterologous polypeptide consisting of a second sequence. In another example, the N- or C-terminus of a polypeptide that consists of or consists essentially of a particular amino acid sequence can be linked to a peptide linker (via peptide bond) that is further linked to one or more additional heterologous polypeptides. In a further example, the N- or C-terminus of a polypeptide that consists of or consists essentially of a particular amino acid sequence can be linked to one or more amino acid residues that facilitate further modification or manipulation of the polypeptide.

Control: A reference standard. In some embodiments, the control is a negative control sample obtained from a healthy patient. In other embodiments, the control is a positive control sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example, a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Covalent bond: An interatomic bond between two atoms, characterized by the sharing of one or more pairs of electrons by the atoms. The terms "covalently bound" or "covalently linked" refer to making two separate molecules into one contiguous molecule. The terms include reference to joining an antigen (such as an HIV-1 Env fusion peptide) either directly or indirectly to a carrier molecule, for example indirectly with an intervening linker molecule, such as a peptide or non-peptide linker.

Degenerate variant: In the context of the present disclosure, a "degenerate variant" refers to a polynucleotide encoding a polypeptide (such as a disclosed immunogen) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting: To identify the existence, presence, or fact of something. General methods of detecting may be supplemented with the protocols and reagents disclosed herein. For example, included herein are methods of detecting the level of a protein in a sample or a subject.

Effective amount: An amount of agent, such as an immunogen, that is sufficient to generate a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to generate a protective immune response.

In one example, a desired response is to induce an immune response that inhibits or prevents HIV-1 infection. The HIV-1 infected cells do not need to be completely eliminated or prevented for the composition to be effective. For example, administration of an effective amount of the immunogen can induce an immune response that decreases the number of HIV-1 infected cells (or prevents the infection of cells) by a desired amount, for example, by at least 50%, at least 60%, at least 70%, at least 80%, at least 90%, at least 95%, at least 98%, or even at least 100% (elimination or prevention of detectable HIV-1 infected cells), as compared to the number of HIV-1 infected cells in the absence of the immunization.

Epitope-Scaffold Protein: A chimeric protein that includes an epitope sequence fused to a heterologous "acceptor" scaffold protein. Design of the epitope-scaffold is performed, for example, computationally in a manner that preserves the native structure and conformation of the epitope when it is fused onto the heterologous scaffold protein. Several embodiments include an epitope scaffold protein with a HIV-1 Env fusion peptide or portion thereof included on a heterologous scaffold protein. When linked to the heterologous scaffold, the HIV-1 Env fusion peptide maintains a conformation similar to that of the HIV-1 Env fusion peptide in the HIV-1 Env ectodomain trimer. Accordingly, such epitope scaffold proteins can specifically bind to neutralizing antibodies that target the HIV-1 Env fusion peptide, such as VRC34.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include cosmids, plasmids (e.g., naked or contained in liposomes) and viruses (e.g., lentiviruses, retroviruses, adenoviruses, and adeno-associated viruses) that incorporate the recombinant polynucleotide.

Heterologous: Originating from a different genetic source. A nucleic acid molecule that is heterologous to a cell originated from a genetic source other than the cell in which it is expressed. Methods for introducing a heterologous nucleic acid molecule in a cell or organism include, for example, transformation with a nucleic acid, including electroporation, lipofection, particle gun acceleration, and homologous recombination.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus Type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HIV-1 envelope protein (Env): The HIV-1 Env protein is initially synthesized as a precursor protein of 845-870 amino acids in size. Individual precursor polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120-gp41 protomers within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a postfusion conformation. The HIV-1 Env ectodomain comprises the gp120 protein (approximately HIV-1 Env positions 31-511) and the gp41 ectodomain (approximately HIV-1 Env positions 512-644). An HIV-1 Env ectodomain trimer comprises a protein complex of three HIV-1 Env ectodomains. As used herein "HIV-1 Env ectodomain trimer" includes both soluble trimers (that is, trimers without gp41 transmembrane domain or cytoplasmic tail) and membrane anchored trimers (for example, trimers including a full-length gp41).

Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is an extracellular polypeptide that interacts with the gp41 ectodomain to form an HIV-1 Env protomer that trimerizes to form the HIV-1 Env ectodomain trimer. The mature gp120 wild-type polypeptide is heavily N-glycosylated, giving rise to an apparent molecular weight of 120 kD. Native gp120 includes five conserved regions ($C_1$-$C_5$) and five regions of high variability (V1-V5).

Mature gp41 includes approximately HIV-1 Env residues 512-860, and includes cytosolic-, transmembrane-, and ectodomains. The gp41 ectodomain (including approximately HIV-1 Env residues 512-644) can interact with gp120 to form an HIV-1 Env protomer that trimerizes to form the HIV-1 Env trimer.

The prefusion mature closed conformation of the HIV-1 Env ectodomain trimer is a structural conformation adopted by HIV-1 Env ectodomain trimer after cellular processing to a mature prefusion state with distinct gp120 and gp41 polypeptide chains, and before specific binding to the CD4 receptor. The three-dimensional structure of an exemplary HIV-1 Env ectodomain trimer in the prefusion mature closed conformation is known (see, e.g., Pancera et al., Nature, 514:455-461, 2014). In the prefusion mature closed conformation, the HIV-1 Env ectodomain trimer includes a V1V2 domain "cap" at its membrane distal apex, with the V1V2 domain of each Env protomer in the trimer coming together at the membrane distal apex. At the membrane proximal aspect, the prefusion mature closed conformation of the HIV-1 Env ectodomain trimer includes distinct α6 and α7 helices. CD4 binding causes changes in the conformation of the HIV-1 Env ectodomain trimer, including disruption of the V1V1 domain cap, which "opens" as each V1V2 domain moves outward from the longitudinal axis of the Env trimer, and formation of the HR1 helix, which includes both the α6 and α7 helices (which are no longer distinct). These conformational changes bring the N-terminus of the fusion peptide within close proximity of the target cell membrane, and expose "CD4-induced" epitopes (such as the 17b epitope) that are present in the CD4-bound open conformation, but not the mature closed conformation, of the HIV-1 Env ectodomain trimer.

Unless context indicates otherwise, the numbering used in the disclosed HIV-1 Env proteins and fragments thereof (such as a gp120 and gp41) is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, NM, which is incorporated by reference herein in its entirety. For reference, the amino acid sequence of HIV-1 Env of HXB2 is set forth as SEQ ID NO: 154 (GENBANK® GI:1906382, incorporated by reference herein as present in the database on Jun. 20, 2014).

```
HXB2 (Clade B, SEQ ID NO: 154):
MRVKEKYQHLWRWGWRWGTMLLGMLMICSATEKLWVTVYYGVPVWKEA

TTTLFCASDAKAYDTEVHNVWATHACVPTDPNPQEVVLVNVTENFNMW

KNDMVEQMHEDIISLWDQSLKPCVKLTPLCVSLKCTDLKNDTNTNSSS

GRMIMEKGEIKNCSFNISTSIRGKVQKEYAFFYKLDIIPIDNDTTSYK

LTSCNTSVITQACPKVSFEPIPIHYCAPAGFAILKCNNKTFNGTGPCT
```

-continued

```
NVSTVQCTHGIRPVVSTQLLLNGSLAEEEVVIRSVNFTDNAKTIIVQL

NTSVEINCTRPNNNTRKRIRIQRGPGRAFVTIGKIGNMRQAHCNISRA

KWNNTLKQIASKLREQFGNNKTIIFKQSSGGDPEIVTHSFNCGGEFFY

CNSTQLFNSTWFNSTWSTEGSNNTEGSDTITLPCRIKQIINMWQKVGK

AMYAPPISGQIRCSSNITGLLLTRDGGNSNNESEIFRPGGGDMRDNWR

SELYKYKVVKIEPLGVAPTKAKRRVVQREKRAVGIGALFLGFLGAAGS

TMGAASMTLTVQARQLLSGIVQQQNNLLRAIEAQQHLLQLTVWGIKQL

QARILAVERYLKDQQLLGIWGCSGKLICTTAVPWNASWSNKSLEQIWN

HTTWMEWDREINNYTSLIHSLIEESQNQQEKNEQELLELDKWASLWNW

FNITNWLWYIKLFIMIVGGLVGLRIVFAVLSIVNRVRQGYSPLSFQTH

LPTPRGPDRPEGIEEEGGERDRDRSIRLVNGSLALIWDDLRSLCLFSY

HRLRDLLLIVTRIVELLGRRGWEALKYWWNLLQYWSQELKNSAVSLLN

ATAIAVAEGTDRVIEVVQGACRAIRHIPRRIRQGLERILL
```

HIV-1 Env ectodomain trimer stabilized in a prefusion mature closed conformation: A HIV-1 Env ectodomain trimer having one or more amino acid substitutions, deletions, or insertions compared to a native HIV-1 Env sequence that provide for increased retention of the prefusion mature closed conformation upon CD4 binding compared to a corresponding native HIV-1 Env sequence. In some embodiments, the HIV-1 Env ectodomain trimer can include one or more cysteine substitutions that allow formation of a non-natural disulfide bond that stabilizes the HIV-1 Env ectodomain trimer in its prefusion mature closed conformation.

A HIV-1 Env ectodomain trimer stabilized in the prefusion mature closed conformation has at least 90% (such as at least 95% or at least 99%) reduced transition to the CD4-bound open conformation upon CD4 binding compared to a corresponding native HIV-1 Env sequence. The "stabilization" of the prefusion mature closed conformation by the one or more amino acid substitutions, deletions, or insertions can be, for example, energetic stabilization (for example, reducing the energy of the prefusion mature closed conformation relative to the CD4-bound open conformation) and/or kinetic stabilization (for example, reducing the rate of transition from the prefusion mature closed conformation to the prefusion mature closed conformation). Additionally, stabilization of the HIV-1 Env ectodomain trimer in the prefusion mature closed conformation can include an increase in resistance to denaturation compared to a corresponding native HIV-1 Env sequence.

Methods of determining if a HIV-1 Env ectodomain trimer is in the prefusion mature closed conformation are provided herein, and include (but are not limited to) negative stain electron microscopy and antibody binding assays using a prefusion mature closed conformation specific antibody, such as VRC26 or PGT145. Methods of determining if a HIV-1 Env ectodomain trimer is in the CD4-bound open conformation are also provided herein, and include (but are not limited to) negative stain electron microscopy and antibody binding assays using a CD4-bound open conformation specific antibody, such as 17b, which binds to a CD4-induced epitope. Transition from the prefusion mature closed conformation upon CD4 binding can be assayed, for example, by incubating a HIV-1 Env ectodomain trimer of interest that is in the prefusion mature closed conformation with a molar excess of CD4, and determining if the HIV-1 Env ectodomain trimer retains the prefusion mature closed conformation (or transitions to the CD4-bound open conformation) by negative stain electron microscopy analysis, or antigenic analysis.

HIV-1 gp140: A recombinant HIV Env polypeptide including gp120 and the gp41 ectodomain, but not the gp41 transmembrane or cytosolic domains. HIV-1 gp140 polypeptides can trimerize to form a soluble HIV-1 Env ectodomain trimer.

HIV-1 gp145: A recombinant HIV Env polypeptide including gp120, the gp41 ectodomain, and the gp41 transmembrane domain. HIV-1 gp145 polypeptides can trimerize to form a membrane-anchored HIV-1 Env ectodomain trimers.

HIV-1 gp160: A recombinant HIV Env polypeptide including gp120 and the entire gp41 protein (ectodomain, transmembrane domain, and cytosolic tail).

HIV-1 neutralizing antibody: An antibody that reduces the infectious titer of HIV-1 by binding to HIV-1 Env protein and inhibiting HIV-1 function. In some embodiments, neutralizing antibodies to HIV-1 can inhibit the infectivity of multiple strains of HIV-1, Teir-2 strain from multiple clades of HIV-1. In some embodiments, a disclosed immunogen can be administered to a subject to elicit an immune response that includes production of antibodies that specifically bind to the HIV-1 Env fusion peptide and neutralize Teir-2 strains of HIV-1 from multiple HIV-1 clades.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen.

Immunogenic composition: A composition comprising a disclosed immunogen, or a nucleic acid molecule or vector encoding a disclosed immunogen, that elicits a measurable CTL response against the immunogen, or elicits a measurable B cell response (such as production of antibodies) against the immunogen, when administered to a subject. It further refers to isolated nucleic acids encoding an immunogen, such as a nucleic acid that can be used to express the immunogen (and thus be used to elicit an immune response against this immunogen). For in vivo use, the immunogenic composition will typically include the protein or nucleic acid molecule in a pharmaceutically acceptable carrier and may also include other agents, such as an adjuvant.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker. In a non-limiting example, a peptide (such as AVGIGAVF peptide, residues 1-8 of SEQ ID NO: 1) is linked to a protein carrier by a linker including a heterologous cysteine residue fused to the C-terminal residue of the peptide by peptide bond and a heterobifunctional moiety, wherein the heterobifunctional moiety is linked to a lysine residue on the carrier and the cysteine residue.

N-linked glycan sequon: A triplet sequence of NX(S/T) of a protein, in which N is asparagine, X is any residue except proline, and (S/T) is a serine or threonine residue. Reference to an N-linked glycan sequon that begins at a particular residue position of a protein means that the asparagine of the sequon begins at that position.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired anti-HIV-1 immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost immunization: An immunotherapy including administration of multiple immunogens over a period of time to elicit the desired immune response.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a disclosed antigen (for example, a HIV-1 Env fusion peptide) and self-assembled into a protein nanoparticle presenting the disclosed antigens on its surface, which can be administered to a subject to stimulate an immune response to the antigen.

Recombinant: A recombinant nucleic acid is one that has a sequence that is not naturally occurring or has a sequence that is made by an artificial combination of two otherwise separated segments of sequence. This artificial combination can be accomplished, for example, the artificial manipulation of isolated segments of nucleic acids, for example, using genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Nati. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Homologs and variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of $10^{-20}$ amino acids, and may possess sequence identities of at least 85% or at least 90% or 95% depending on their similarity to the reference sequence. Methods for determining sequence identity over such short windows are available at the NCBI website on the internet. These sequence identity ranges are provided for guidance only; it is entirely possible that strongly significant homologs could be obtained that fall outside of the ranges provided.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-30 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as residues 1-30 of SEQ ID NO: 59.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, gp120) and does not bind in a significant amount to other proteins or polysaccharides present in the sample or subject. Specific binding can be determined by standard methods. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Subject: Living multicellular vertebrate organisms, a category that includes human and non-human mammals. In an example, a subject is a human. In a particular example, the subject is a newborn infant. In an additional example, a subject is selected that is in need of inhibiting of an HIV-1 infection. For example, the subject is either uninfected and at risk of HIV-1 infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane.

Under conditions sufficient for: A phrase that is used to describe any environment that permits a desired activity.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with HIV-1 infection and/or decreases the viral load compared to a control. In another non-limiting example, a vaccine reduces HIV-1 infection compared to a control.

Vector: An entity containing a DNA or RNA molecule bearing a promoter(s) that is operationally linked to the coding sequence of an immunogenic protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses.

A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. The presence of VLPs following recombinant expression of viral proteins can be detected using conventional techniques, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

VRC34: An antibody that binds to the fusion peptide of HIV-1 any neutralizing HIV-1 infection. VRC34. Unless context indicates otherwise, "VRC34" refers to the VRC34.01 antibody disclosed by Kong et al. (Science, 352, 828-833, 2016). Sequences of the heavy and light chain variable regions of the VRC34.01 antibody are available, for example, as GenBank Accession Nos. ANF29805.1 and ANF29798.1, respectively, each of which is incorporated by reference herein.

II. Immunogens

Embodiments of immunogens based on the HIV-1 Env fusion peptide and methods of their use and production are provided below. In several embodiments, the immunogens can be used to generate a neutralizing immune response to HIV-1 in a subject, for example, to treat or prevent an HIV-1 infection in the subject. As discussed in more detail below, the immunogens include, for example, immunogenic conjugates including the N-terminal residues of the HIV-1-fusion peptide conjugated to a carrier, epitope scaffold proteins including the N-terminal residues of the HIV-1-fusion peptide conjugated to a scaffold protein, protein nanoparticles including the N-terminal residues of the HIV-1-fusion peptide conjugated to subunits of the protein nanoparticle, and recombinant HIV-1 Env ectodomain trimers that have been selectively deglycosylated to expose the HIV-1 Env fusion peptide.

A. Immunogenic Conjugates

Immunogenic conjugates are provided that include between 6-10 amino acids (such as 6, 7, 8, 9, or 10 amino acids) from the N-terminus of the gp41 protein from HIV-1 (that is, the N-terminal portion of the HIV-1 Env fusion peptide). This corresponds to residue 512 to one of residues 517-521 of HIV-1 Env according to the HXB2 numbering system. The immunogenic conjugates have the general formula:

X-L-C wherein X is a polypeptide consisting of or consisting essentially of the amino acid sequence of residue 512 to one of residues 517-521 of a HIV-1 Env protein, L is an optional linker, and C is the heterologous carrier.

In some examples, the HIV-1 Env fusion peptide and the carrier protein are linked by a linker between a lysine amino acid residue present on the carrier protein and a cysteine amino acid residue fused (by a peptide bond) to the C-terminal residue of the HIV-1 Env fusion peptide and the conjugate has the formula:

X-Cys-L-Lys-C wherein X is a polypeptide consisting of or consisting essentially of the amino acid sequence of residue 512 to one of residues 517-521 of a HIV-1 Env protein, Cys is a cysteine residue fused by a peptide bond to the C-terminus of the X polypeptide, L is a linker, Lys is a lysine residue present on the carrier, and C is the heterologous carrier.

Suitable linkers include, but are not limited to, straight or branched-chain carbon linkers, heterocyclic carbon linkers or peptide linkers. For an immunogenic conjugate from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, a wide variety of linking groups may be employed. In some cases, the linking group can be designed to be either hydrophilic or hydrophobic in order to enhance the desired binding characteristics of the fusion peptide and the carrier. The covalent linkages should be stable relative to the solution conditions under which the conjugate is subjected.

In some embodiments, the linkers may be joined to the constituent amino acids through their side chains (such as through a disulfide linkage to cysteine) or to the alpha carbon, amino, and/or carboxyl groups of the terminal amino acids. In some embodiments, the linker, the X polypeptide, and the carrier can be encoded as a single fusion polypeptide such that the X polypeptide and the carrier are joined by peptide bonds.

The procedure for attaching a molecule to a polypeptide varies according to the chemical structure of the molecule. Polypeptides typically contain a variety of functional groups; for example, carboxylic acid (COOH), free amine (—$NH_2$) or sulfhydryl (—SH) groups, which are available for reaction with a suitable functional group on a polypeptide. Alternatively, the polypeptide is derivatized to expose or attach additional reactive functional groups. The derivatization may involve attachment of any of a number of linker molecules such as those available from Pierce Chemical Company, Rockford, IL.

In some embodiments, a sulfosuccinimidyl (4-iodoacetyl) aminobenzoate (Sulfo-SIAB) linker is used to link the X polypeptide to carrier. In some embodiments an m-maleimidobenzoyl-N-hydroxysuccinimide ester (MBS) linker is used to link the X polypeptide to carrier.

Any specific combination of HIV-1 Env fusion peptide and carrier may be selected from the specific HIV-1 Env fusion peptide and carriers that are listed below.

HIV-1 can be classified into four groups: the "major" group M, the "outlier" group O, group N, and group P. Within group M, there are several genetically distinct clades (or subtypes) of HIV-1. The HIV-1 Env fusion peptide included in the immunogenic conjugate can be derived from any subtype of HIV, such as groups M, N, O, or P or clade A, B, C, D, F, G, H, J or K and the like. The X polypeptide (including N-terminal residues of the HIV-1 Env fusion peptide) included in the immunogenic conjugate can consist essentially of or consist of residue 512 to one of residues 517-521 (such as residues 512-519) of HIV-1 Env (HXB2) numbering of the Env protein from any subtype of HIV, such as groups M, N, O, or P or clade A, B, C, D, F, G, H, J or K and the like. HIV Env fusion peptides from the different HIV clades, as well as nucleic acid sequences encoding such proteins and methods for the manipulation and insertion of such nucleic acid sequences into vectors, are known (see, e.g., HIV Sequence Compendium, Division of AIDS, National Institute of Allergy and Infectious Diseases (2003); HIV Sequence Database (hiv-web.lanl.gov/content/hiv-db/mainpage.html); Sambrook et al., Molecular Cloning, a Laboratory Manual, 2d edition, Cold Spring Harbor Press, Cold Spring Harbor, N. Y. (1989); Ausubel et al., Current Protocols in Molecular Biology, Greene Publishing Associates and John Wiley & Sons, New York, N. Y. (1994)).

In some embodiments, the X polypeptide (including HIV-1 Env residue 512 to one of residues 517-525) in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGAVFLG (SEQ ID NO: 1). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO:18.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGLGAVFLG (SEQ ID NO: 2). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 2.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGAMIFG (SEQ ID NO: 3). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 3.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGTIGAMFLG (SEQ ID NO: 4). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 4.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGAMFLG (SEQ ID NO: 5). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 5.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGALFLG (SEQ ID NO: 6). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 6.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AIGLGAMFLG (SEQ ID NO: 7). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 7.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGLGAVFIG (SEQ ID NO: 8). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 8.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGAVLLG (SEQ ID NO: 9). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 9.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AVGIGAVFIG (SEQ ID NO: 10). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 10.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AIGLGALFLG (SEQ ID NO: 11). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 11.

In some embodiments, the X polypeptide in the conjugate consists essentially of or consists of from 6 to 10 residues (such as 6, 7, 8, 9, or 10 residues or 7-9 residues or 8-10 residues or 6-8 residues) from the N-terminus of the amino acid sequence set forth as AALGAVFLG (SEQ ID NO: 12). These residues correspond to HIV-1 Env positions 512-521 (HXB2 numbering). In some embodiments, the X polypeptide in the conjugate consists essentially of or consists of the amino acid sequence set forth as residues 1-8 of SEQ ID NO: 12.

In some embodiments, the immunogenic conjugate comprises any of the above X polypeptides (such as AVGIGAVF, residues 1-8 of SEQ ID NO: 1) conjugated to KLH, wherein the X polypeptide is conjugated to KLH by a linker between a lysine residue on the KLH and a heterologous cysteine residue fused to a C-terminal residue of the X polypeptide.

In some embodiments, the immunogenic conjugate comprises any of the above X polypeptides (such as AVGIGAVF, residues 1-8 of SEQ ID NO: 1) conjugated to tetanus toxoid, wherein the X polypeptide is conjugated to tetanus toxoid by a linker between a lysine residue on the tetanus toxoid and a heterologous cysteine residue fused to a C-terminal residue of the X polypeptide.

In some embodiments, the immunogenic conjugate comprises any of the above X polypeptides (such as AVGIGAVF, residues 1-8 of SEQ ID NO: 1) conjugated to tetanus toxoid heavy chain C fragment, wherein the X polypeptide is conjugated to tetanus toxoid heavy chain C fragment by a linker between a lysine residue on the tetanus toxoid heavy chain C fragment and a heterologous cysteine residue fused to a C-terminal residue of the X polypeptide.

In some embodiments, the immunogenic conjugate comprises any of the above X polypeptides (such as AVGIGAVF, residues 1-8 of SEQ ID NO: 1) conjugated to H influenza protein D (HiD), wherein the X polypeptide is conjugated to H influenza protein D (HiD) by a linker between a lysine residue on the H influenza protein D (HiD) and a heterologous cysteine residue fused to a C-terminal residue of the X polypeptide.

In some embodiments, the immunogenic conjugate comprises any of the above X polypeptides (such as AVGIGAVF, residues 1-8 of SEQ ID NO: 1) conjugated to diphtheria toxoid or a variant thereof (such as CRM197), wherein the X polypeptide is conjugated to diphtheria toxoid or the variant thereof by a linker between a lysine residue on the diphtheria toxoid or the variant thereof and a heterologous cysteine residue fused to a C-terminal residue of the X polypeptide.

It can be advantageous to produce conjugates in which more than one X polypeptide (including N-terminal residues of the HIV-1 Env fusion peptide) as described herein is conjugated to a single carrier protein. In several embodiments, the conjugation of multiple X polypeptides to a single carrier protein is possible because the carrier protein has multiple lysine or cysteine side-chains that can serve as sites of attachment. The amount of X polypeptide reacted with the amount of carrier may vary depending upon the specific X polypeptide and the carrier protein. However, the respective amounts should be sufficient to introduce from 1-30 chains of X polypeptide onto the carrier protein. The resulting number of X polypeptides linked to a single carrier molecule may vary depending upon the specific X polypeptide and the carrier protein. In some embodiments, from 1 to 30, such as about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30× polypeptides can be linked to each carrier protein molecule. “About” in this context refers to plus or minus 5% when measuring an average number of X polypeptide molecules per carrier molecule in the conjugate. Thus, in some embodiments, the average ratio of X polypeptide (including N-terminal residues of the HIV-1 Env fusion peptide) molecules to carrier protein molecules is between about 1:1 and about 30:1, such as about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1, about 21:1, about 22:1, about 23:1, about 24:1, about 25:1, about 26:1, about 27:1, about 28:1, about 29:1, or about 30:1, for example, between about 1:1 and about 15:1, between about 5:1 and about 20:1, or between about 10:1 and about 30:1.

In some embodiments (such as when KLH is used as a carrier, from 1 to 1000, such as about 50, about 100, about 200, about 300, about 400, about 500, about 700, about 1000, about 9, about 10, about 11, about 12, about 13, about 14, about 15, about 16, about 17, about 18, or about 19× polypeptides can be linked to each carrier protein molecule. "About" in this context refers to plus or minus 5% when measuring an average number of X polypeptide molecules per carrier molecule in the conjugate. Thus, in some embodiments, the average ratio of X polypeptide (including N-terminal residues of the HIV-1 Env fusion peptide) molecules to carrier protein molecules is between about 1:1 and about 1000:1, such as between about 100:1 and about 500:1, between about 500:1 and about 10000:1, or between about 250:1 and about 750:1.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are available (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, Hum Vaccin Immunother., 9: 2505-2523, 2013, which is incorporated by reference herein in its entirety).

In some embodiments, the carrier is a tetanus toxin heavy chain C fragment comprising the amino acid sequence set forth as

```
                                          (SEQ ID NO: 198)
MKNLDCWVDNEEDIDVILKKSTILNLDINNDIISDISGFNSSVITYPD

AQLVPGINGKAIHLVNNESSEVIVHKAMDIEYNDMFNNFTVSFWLRVP

KVSASHLEQYGTNEYSIISSMKKHSLSIGSGWSVSLKGNNLIWTLKDS

AGEVRQITFRDLPDKFNAYLANKWVFITITNDRLSSANLYINGVLMGS

AEITGLGAIREDNNITLKLDRCNNNNQYVSIDKFRIFCKALNPKEIEK

LYTSYLSITFLRDFWGNPLRYDTEYYLIPVASSSKDVQLKNITDYMYL

TNAPSYTNGKLNIYYRRLYNGLKFIIKRYTPNNEIDSFVKSGDFIKLY

VSYNNNEHIVGYPKDGNAFNNLDRILRVGYNAPGIPLYKKMEAVKLRD

LKTYSVQLKLYDDKNASLGLVGTHNGQIGNDPNRDILIASNWYFNHLK

DKILGCDWYFVPTDEGWTND
```

Following conjugation of the HIV-1 Env fusion peptide to the carrier protein, the conjugate can be purified by appropriate techniques. One goal of the purification step is to separate the unconjugated HIV-1 Env fusion peptide or carrier from the conjugate. One method for purification, involving ultrafiltration in the presence of ammonium sulfate, is described in U.S. Pat. No. 6,146,902.

Alternatively, the conjugates can be purified away from unconjugated HIV-1 Env fusion peptide or carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry, for example.

In several embodiments, the disclosed immunogenic conjugates can be formulated into immunogenic composition (such as vaccines), for example by the addition of a pharmaceutically acceptable carrier and/or adjuvant.

B. Epitope Scaffold Proteins

In some embodiments, the immunogen comprises an epitope scaffold protein that includes one or more copies of the HIV-1 Env fusion peptide or portion thereof linked to a scaffold protein. The one or more copies of the HIV-1 Env fusion peptide or portion thereof are typically linked (directly, or indirectly via a peptide linker) to the N-terminus of the scaffold protein. Exemplary HIV-1 Env fusion peptides and scaffold proteins that can be combined to generate a disclosed epitope scaffold protein are provided below. When linked to the heterologous scaffold, the HIV-1 Env fusion peptide maintains a conformation similar to that of the HIV-1 Env fusion peptide in the HIV-1 Env ectodomain trimer. Accordingly, the disclosed epitope scaffold proteins can specifically bind to neutralizing antibodies that target the HIV-1 Env fusion peptide, such as VRC34. The disclosed epitope scaffold proteins can be used to elicit a neutralizing immune response to HIV-1 in a subject. Additionally, the disclosed epitope scaffold proteins can be used as probes to evaluate antibody binding to the HIV-1 Env fusion peptide.

In several embodiments, the epitope scaffold protein comprises, from N- to C-terminal, an amino acid sequence according to:

X-L-S wherein X is a polypeptide consisting of or consisting essentially of the amino acid sequence of residue 512 to one of residues 517-525 of HIV-1 Env (HXB2 numbering), L is an optional peptide linker, and S is the scaffold protein. The epitope scaffold protein can be used to elicit an immune response to HIV-1 Env protein in a subject.

In several embodiments, the optional peptide linker is a glycine linker, a serine linker, or a glycine-serine linker. The linker can be, for example, no more than 10 amino acids in length. For example, the X polypeptide (including HIV-1 Env residue 512 to one of residues 517-525) can be linked to any of the disclosed scaffold proteins by a glycine linker such as a glycine 6-mer. In additional embodiments, the X polypeptide (including HIV-1 Env residue 512 to one of residues 517-525) can be linked to any of the disclosed scaffold proteins by a glycine linker such as a glycine 2-mer.

The X polypeptide (including HIV-1 Env residue 512 to one of residues 517-525) included in the epitope scaffold protein can be derived from any subtype of HIV, such as groups M, N, O, or P or clade A, B, C, D, F, G, H, J or K and the like. The X polypeptide (including HIV-1 Env residue 512 to one of residues 517-525) included in the epitope scaffold protein can consist essentially of or consist of residue 512 to one of residues 517-525 (such as residues 512-519) of HIV-1 Env (HXB2) numbering of the Env protein from any subtype of HIV, such as groups M, N, O, or P or clade A, B, C, D, F, G, H, J or K and the like.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVFLG (SEQ ID NO: 1). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 1.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGLGAVFLG (SEQ ID NO: 2). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 2.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAMIFG (SEQ ID NO: 3). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 3.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGTIGAMFLG (SEQ ID NO: 4). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 4.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAMFLG (SEQ ID NO: 5). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 5.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGALFLG (SEQ ID NO: 6). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 6.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AIGLGAMFLG (SEQ ID NO: 7). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 7.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGLGAVFIG (SEQ ID NO: 8). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 8.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVLLG (SEQ ID NO: 9). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 9.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVFIG (SEQ ID NO: 10). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 10.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AIGLGALFLG (SEQ ID NO: 11). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 11.

In some embodiments, the X polypeptide (including HIV-1 Env residue 512 to one of residues 517-525) in the epitope scaffold protein comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AALGAVFLG (SEQ ID NO: 12). These residues correspond to HIV-1 Env positions 512-521 (HXB2 numbering). In some embodiments, the X polypeptide in the epitope scaffold protein comprises, consists essentially of, or consists of the amino acid sequence set forth as residues 1-8 of SEQ ID NO: 12.

In some embodiments the epitope scaffold protein can have a maximum length, such as no more than 200 or no more than 500 amino acids in length.

In several embodiments, the scaffold in the epitope scaffold protein comprises, consists essentially of, or consists of any one of the 1y12, 1M6T, 3HSH, or 1SLF scaffolds listed in the following table (showing SEQ ID NOs: 13-31), or a scaffold with an amino acid sequence at least 90% (such as at least 95%) identical to any one of SEQ ID NOs: 13-31. Any one of the embodiments of the X polypeptide (including HIV-1 Env residue 512 to one of residues 517-525) disclosed herein can be linked to the N-terminus of any one of the 1Y12, 1M6T, 3HSH, or 1SLF scaffolds listed in the following table (showing SEQ ID NOs: 13-31), or a scaffold with an amino acid sequence at least 90% (such as at least 95%) identical to SEQ ID NOs: 13-31. In some embodiments, two or more (such as two) of any of the embodiments of the X polypeptide (including HIV-1 Env residue 512 to one of residues 517-525) can be linked sequentially to the N-terminus of any one of the 1Y12, 1M6T, 3HSH, or 1SLF scaffolds listed in the following table (showing SEQ ID NOs: 13-31), or a scaffold with an amino acid sequence at least 90% (such as at least 95%) identical to SEQ ID NOs: 13-31. In such embodiments, the multiple copies of the X polypeptide can be linked by a peptide linker, such as a glycine linker (for example a glycine 6-mer). The linkage can be direct or indirect (by a peptide linker connecting the C-terminus of the X polypeptide and the N-terminus of the scaffold). The scaffold can include one or more N-linked glycosylation sites (N-X-[S/T]) that are glycosylated during production of the epitope scaffold protein in cells. The glycan moiety mimics the glycans near the fusion peptide on the HIV-1 Env trimer, such as HIV-1 Env glycans at positions N88, N230, N241, and N611. In the following table (showing SEQ ID NOs: 13-31), N-linked glycan sites are shown in bold text.

| SEQ ID NO | Name | Sequence |
|---|---|---|
| | | 1Y12 |
| 13 | 1Y12 | AVDMFIKIGDVKGESKDKTHAEEIDVLAWSWGMSQSGSMHMGGGGGAGKVNVQDLSF TKYIDKSTPNLMMACSSGKHYPQAKLTIRKAGGENQVEYLIITLKEVLVSSVSTGGS GGEDRLTE**NVT**LNFAQVQVDYQPQKADGAKDGGPVKYGWNIRQNVQA |
| 14 | 1y12-Gly1 | AVDMFIKIGDVKGESKDKTH**nst**IDVLAWSWGMSQSGSMHMGGGGGAGKVNVQDLSF TKYIDKSTPNLMMACSSGKHYPQAKLTIRKAGGENQVEYLIITLKEVLVSSVSTGGS GGEDRLTE**NVT**LNFAQVQVDYQPQKADGAKDGGPVKYGWNIRQNVQA |
| 15 | 1y12-Gly2 | AVDMFIKIGDVKGESKDKTHAEEIDVLAWSWGMSQSGSMHMGGGGGAGKVNVQDLSF TKYIDKSTPNLMMACSSGKHYPQAKLTIRKAGGENQVEYLIITLKEVLVSSVSTGGS GGEDRLTE**NVT**LNFAQVQVDYQPQ**nst**GAKDGGPVKYGWNIRQNVQA |
| 16 | 1y12-Gly1-2 | AVDMFIKIGDVKGESKDKTH**nst**IDVLAWSWGMSQSGSMHMGGGGGAGKVNVQDLSF TKYIDKSTPNLMMACSSGKHYPQAKLTIRKAGGENQVEYLIITLKEVLVSSVSTGGS GGEDRLTE**NVT**LNFAQVQVDYQPQ**nst**GAKDGGPVKYGWNIRQNVQA |

-continued

| SEQ ID NO | Name | Sequence |
|---|---|---|
| 17 | 1y12-cHis-R157c-g90c | AVDMFIKIGDVKGESKDKTHAEEIDVLAWSWGMSQSGSMHMGGGGGAGKVNVQDLSF<br>TKYIDKSTPNLMMACSSGKHYPQAKLTIRKAcGENQVEYLIITLKEVLVSSVSTGGS<br>GGEDRLTE**NVT**LNFAQVQVDYQPQKADGAKDGGPVKYGWNI**c**QNVQA |
| 18 | 1y12-Gly2-cHis-R157c-g90c | AVDMFIKIGDVKGESKDKTHAEEIDVLAWSWGMSQSGSMHMGGGGGAGKVNVQDLSF<br>TKYIDKSTPNLMMACSSGKHYPQAKLTIRKAcGENQVEYLIITLKEVLVSSVSTGGS<br>GGEDRLTE**NVT**LNFAQVQVDYQPQ**nst**GAKDGGPVKYGWNI**c**QNVQA |
| 19 | 1y12-Gly1-cHis-R157c-g90c | AVDMFIKIGDVKGESKDKTH**nst**IDVLAWSWGMSQSGSMHMGGGGGAGKVNVQDLSF<br>TKYIDKSTPNLMMACSSGKHYPQAKLTIRKAcGENQVEYLIITLKEVLVSSVSTGGS<br>GGEDRLTE**NVT**LNFAQVQVDYQPQKADGAKDGGPVKYGWNI**c**QNVQA |
| 20 | 1y12-Gly1-2-cHis-R157c-g90c | AVDMFIKIGDVKGESKDKTH**nst**IDVLAWSWGMSQSGSMHMGGGGGAGKVNVQDLSF<br>TKYIDKSTPNLMMACSSGKHYPQAKLTIRKAcGENQVEYLIITLKEVLVSSVSTGGS<br>GGEDRLTE**NVT**LNFAQVQVDYQPQ**nst**GAKDGGPVKYGWNI**c**QNVQA |
| | | 1M6T |
| 21 | glyc88_1M6T_A35N_A37S | ADLEDNWETLNDNLKVIEKADNAAQVKDALTKMR**nAs**LDAQKATPPKLEDKSPDSPE<br>MKDFRHGFDILVGQIDDALKLANEGKVKEAQAAAEQLKTTRNAYIQKYL |
| 22 | glyc88_1M6T_K42N | ADLEDNWETLNDNLKVIEKADNAAQVKDALTKMRAAALDAQ**nAT**PPKLEDKSPDSPE<br>MKDFRHGFDILVGQIDDALKLANEGKVKEAQAAAEQLKTTRNAYIQKYL |
| 23 | glyc88_1M6T_E49N_K51T | ADLEDNWETLNDNLKVIEKADNAAQVKDALTKMRAAALDAQKATPPKL**nDt**SPDSPE<br>MKDFRHGFDILVGQIDDALKLANEGKVKEAQAAAEQLKTTRNAYIQKYL |
| 24 | 1M6T | ADLEDNWETLNDNLKVIEKADNAAQVKDALTKMRAAALDAQKATPPKLEDKSPDSPE<br>MKDFRHGFDILVGQIDDALKLANEGKVKEAQAAAEQLKTTRNAYIQKYL |
| | | 3HSH |
| 25 | 3HSH | SGVRLWATRQAMLGQVHEVPEGWLIFVAEQEELYVRVQNGFRKVQLEARTPLPR |
| 26 | 3HSH_A11N_L13T | SGVRLWATRQ**nMt**GQVHEVPEGWLIFVAEQEELYVRVQNGFRKVQLEARTPLPR |
| 27 | 3HSH_Q15N_H17T | SGVRLWATRQAMLG**NVT**EVPEGWLIFVAEQEELYVRVQNGFRKVQLEARTPLPR |
| 28 | 3HSH_E18N_P20S | SGVRLWATRQAMLGQVH**nVs**EGWLIFVAEQEELYVRVQNGFRKVQLEARTPLPR |
| | | 1SLF |
| 29 | 1slf_P135N | AEAGITGTWYNQLGSTFIVTAGADGALTGTYESAVGNAESRYVLTGRYDSAPATDGS<br>GTALGWTVAWKNNYRNAHSATTWSGQYVGGAEARINTQWLLTSGTTEANAWKSTLVG<br>HDTFTKVK**nSs**AS |
| 30 | 1slf_A100N | EAGITGTWYNQLGSTFIVTAGADGALTGTYESAVGNAESRYVLTGRYDSAPATDGSG<br>TALGWTVAWKNNYRNAHSATTWSGQYVGG**nEs**RINTQWLLTSGTTEANAWKSTLVGH<br>DTFTKVKPSAAS |
| 31 | 1slf_T115N | EAGITGTWYNQLGSTFIVTAGADGALTGTYESAVGNAESRYVLTGRYDSAPATDGSG<br>TALGWTVAWKNNYRNAHSATTWSGQYVGGAEARINTQWLLTSGT**nEs**NAWKSTLVGH<br>DTFTKVKPSAAS |

In several embodiments, the epitope scaffold protein comprises, consists essentially of, or consists of the amino acid sequence of any one of epitope-scaffold proteins listed in the following table (showing SEQ ID NOs: 32-58), or an amino acid sequence at least 90% (such as at least 95%) identical to any one of SEQ ID NOs: 32-58. The scaffold can include one or more N-linked glycosylation sites (N-X-[IS/T]) that are glycosylated during production of the epitope scaffold protein in cells. The glycan moiety mimics the glycans near the fusion peptide on the HIV-1 Env trimer, such as HIV-1 Env glycans at positions N88, N230, N241, and N611. In the following table (showing SEQ ID NOs: 32-58), N-linked glycan sites are shown in bold text and HIV-1 Env fusion peptides are shown in bold text with underlining.

| SEQ ID NO | Name | Sequence |
|---|---|---|
| | | 1Y12 |
| 32 | Pep1-1y12 | **avgigavfl**gggGGGAVDMFIKIGDVKGESKDKTHAEEIDVLAWSWGMSQSGSMHMGGGGGAGK<br>VNVQDLSFTKYIDKSTPNLMMACSSGKHYPQAKLTIRKAGGENQVEYLIITLKEVLVSSVSTGG<br>SGGEDRLTE**NVT**LNFAQVQVDYQPQKADGAKDGGPVKYGWNIRQNVQA |

-continued

| SEQ ID NO | Name | Sequence |
|---|---|---|
| 33 | Pep1-2-1y12 | **avgigavfl**gggGGG**avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQKADGAKDGGPVKYGWNIRQNVQA |
| 34 | Pep1-1y12-Gly1 | **avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQKADGAKDGGPVKYGWNIRQNVQA |
| 35 | Pep1-1y12-Gly2 | **avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQ**nst**GAKDGGPVKYGWNIRQNVQA |
| 36 | Pep1-1y12-Gly1-2 | **avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQ**nst**GAKDGGPVKYGWNIRQNVQA |
| 37 | Pep1-2-1y12-Gly1 | **avgigavfl**gggGGG**avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQKADGAKDGGPVKYGWNIRQNVQA |
| 38 | Pep1-2-1y12-Gly2 | **avgigavfl**gggGGG**avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQ**nst**GAKDGGPVKYGWNIRQNVQA |
| 39 | Pep1-2-1y12-Gly1-2 | **avgigavfl**gggGGG**avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTE**NVT**LNFAQVQVDYQPQ**nst**GAKDGGPVKYGWNIRQNVQA |
| 40 | Pep1-1y12-cHis-R157c-g90c | **avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQKADGAKDGGPVKYGWNI**c**QNVQA |
| 41 | Pep1-2-1y12-cHis-R157c-g90c | **avgigavfl**gggGGG**avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQKADGAKDGGPVKYGWNI**c**QNVQA |
| 42 | Pep1-1y12-Gly1-cHis-R157c-g90c | **avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQKADGAKDGGPVKYGWNI**c**QNVQA |
| 43 | Pep1-1y12-Gly2-cHis-R157c-g90c | **avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQ**nst**GAKDGGPVKYGWNI**c**QNVQA |
| 44 | Pep1-1y12-Gly1-2-cHis-R157c-g90c | **avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQ**nst**GAKDGGPVKYGWNI**c**QNVQA |
| 45 | Pep1-2-1y12-Gly1-cHis-R157c-g90c | **avgigavfl**gggGGG**avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQKADGAKDGGPVKYGWNI**c**QNVQA |
| 46 | Pep1-2-1y12-Gly2-cHis-R157c-g90c | **avgigavfl**gggGGG**avgigavfl**gggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQ**nst**GAKDGGPVKYGWNI**c**QNVQA |
| 47 | Pep1-2-1y12-Gly1-2-cHis-R157c-g90c | **avgigavfl**gggGGG**avgigavfl**gggGGGAVDMFIKIGDVKGESKDKTH**nst**IDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTE**NVT**LNFAQVQVDYQPQ**nst**GAKDGGPVKYGWNI**c**QNVQA |
| | | 1M6T |
| 48 | FP_glyc88_1M6T_A35N_A37S | **avgigavfl**GGGADLEDNWETLNDNLKVIEKADNAAQVKDALTKMR**nAs**LDAQKATPPKLEDKSPDSPEMKDFRHGFDILVGQIDDALKLANEGKVKEAQAAAEQLKTTRNAYIQKYL |

-continued

| SEQ ID NO | Name | Sequence |
|---|---|---|
| 49 | FP_glyc88_1M6T_K42N | **avgigavfl**GGGADLEDNWETLNDNLKVIEKADNAAQVKDALTKMRAAALDAQ**nAT**PPKLEDKSPDSPEMKDFRHGFDILVGQIDDALKLANEGKVKEAQAAAEQLKTTRNAYIQKYL |
| 50 | FP_glyc88_1M6T_E49N_K51T | **avgigavfl**GGGADLEDNWETLNDNLKVIEKADNAAQVKDALTKMRAAALDAQKATPPKL**nDt**SPDSPEMKDFRHGFDILVGQIDDALKLANEGKVKEAQAAAEQLKTTRNAYIQKYL |
| 51 | FP_1M6T | **avgigavfl**GGGADLEDNWETLNDNLKVIEKADNAAQVKDALTKMRAAALDAQKATPPKLEDKSPDSPEMKDFRHGFDILVGQIDDALKLANEGKVKEAQAAAEQLKTTRNAYIQKYL |
| | | 3HSH |
| 52 | FP_3HSH | **avgigavflg**GGGSSGVRLWATRQAMLGQVHEVPEGWLIFVAEQEELYVRVQNGFRKVQLEARTPLPR |
| 53 | FP_3HSH_A11N_L13T | **avgigavflg**GGGSSGVRLWATRQ**nMt**GQVHEVPEGWLIFVAEQEELYVRVQNGFRKVQLEARTPLPR |
| 54 | FP_3HSH_Q15N_H17T | **avgigavflg**GGGSSGVRLWATRQAMLG**NVT**EVPEGWLIFVAEQEELYVRVQNGFRKVQLEARTPLPR |
| 55 | FP_3HSH_E18N_P20S | **avgigavflg**GGGSSGVRLWATRQAMLGQVH**nVs**EGWLIFVAEQEELYVRVQNGFRKVQLEARTPLPR |
| | | 1SLF |
| 56 | 1slf_P135N | **avgigavf**AEAGITGTWYNQLGSTFIVTAGADGALTGTYESAVGNAESRYVLTGRYDSAPATDGSGTALGWTVAWKNNYRNAHSATTWSGQYVGGAEARINTQWLLTSGTTEANAWKSTLVGHDTFTKVK**nSs**AS |
| 57 | 1slf_A100N | **avgigavf**EAGITGTWYNQLGSTFIVTAGADGALTGTYESAVGNAESRYVLTGRYDSAPATDGSGTALGWTVAWKNNYRNAHSATTWSGQYVGG**nEs**RINTQWLLTSGTTEANAWKSTLVGHDTFTKVKPSAAS |
| 58 | 1slf_T115N | **avgigav**EAGITGTWYNQLGSTFIVTAGADGALTGTYESAVGNAESRYVLTGRYDSAPATDGSGTALGWTVAWKNNYRNAHSATTWSGQYVGGAEARINTQWLLTSGT**nEs**NAWKSTLVGHDTFTKVKPSAAS |

The epitope scaffold protein can include various tags and sequences for production and purification of the epitope scaffold protein. Typically protein tags are linked to the C-terminus of the epitope scaffold protein and are ultimately removed (for example by selective protease cleave) from the epitope scaffold protein. For production in cells, the epitope scaffold protein can be initially synthesized with a signal peptide, for example, a signal peptide having the amino acid sequence set forth as MDSKGSSQKGSRLLLLLVVSNLLLPQGVLA (residues 1-30 of SEQ ID NO: 59). Exemplary sequences of epitope scaffold proteins that comprise a disclosed HIV-1 Env fusion peptide or portion thereof, as well as various signal peptides, and C-terminal protein tags, etc., for production and purification are provided below.

| SEQ ID NO | Name | Sequence |
|---|---|---|
| 59 | Pep1-1y12-cHis | MDSKGSSQKGSRLLLLLVVSNLLLPQGVLAavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQKADGAKDGGPVKYGWNIRQNVQAGGGSHHHHHHHH |
| 60 | Pep1-2-1y12-cHis | MDSKGSSQKGSRLLLLLVVSNLLLPQGVLAavgigavflgggGGavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQKADGAKDGGPVKYGWNIRQNVQAGGGSHHHHHHHH |
| 61 | Pep1-1y12-Gly1-cHis | MDSKGSSQKGSRLLLLLVVSNLLLPQGVLAavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQKADGAKDGGPVKYGWNIRQNVQAGGGSHHHHHHHH |
| 62 | Pep1-1y12-Gly2-cHis | MDSKGSSQKGSRLLLLLVVSNLLLPQGVLAavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQnstGAKDGGPVKYGWNIRQNVQAGGGSHHHHHHHH |

-continued

| SEQ ID NO | Name | Sequence |
|---|---|---|
| 63 | Pep1-1y12-Gly1-2-cHis | MDSKGSSQKGSRLLLLLVVSNLLLPQGVLAavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQnstGAKDGGPVKYGWNIRQNVQAGGGSHHHHHHHH |
| 64 | Pep1-2-1y12-Gly1-cHis | MDSKGSSQKGSRLLLLLVVSNLLLPQGVLAavgigavflgggGGGavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQKADGAKDGGPVKYGWNIRQNVQAGGGSHHHHHHHH |
| 65 | Pep1-2-1y12-Gly2-cHis | MDSKGSSQKGSRLLLLLVVSNLLLPQGVLAavgigavflgggGGGavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQnstGAKDGGPVKYGWNIRQNVQAGGGSHHHHHHHH |
| 66 | Pep1-2-1y12-Gly1-2-cHis | MDSKGSSQKGSRLLLLLVVSNLLLPQGVLAavgigavflgggGGGavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAGGENQVEYLIITLKEVLVSSVSTGGSGGEDRLTENVTLNFAQVQVDYQPQnstGAKDGGPVKYGWNIRQNVQAGGGSHHHHHHHH |
| 67 | Pep1-1y12-cHis-R157c-g90c | MDSKGSSQKGSRLLLLLVVSNLLLPQGVLAavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQKADGAKDGGPVKYGWNIcQNVQAGGGSHHHHHHHH |
| 68 | Pep1-2-1y12-cHis-R157c-g90c | MDSKGSSQKGSRLLLLLVVSNLLLPQGVLAavgigavflgggGGGavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQKADGAKDGGPVKYGWNIcQNVQAGGGSHHHHHHHH |
| 69 | Pep1-1y12-Gly1-cHis-R157c-g90c | MDSKGSSQKGSRLLLLLVVSNLLLPQGVLAavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQKADGAKDGGPVKYGWNIcQNVQAGGGSHHHHHHHH |
| 70 | Pep1-1y12-Gly2-cHis-R157c-g90c | MDSKGSSQKGSRLLLLLVVSNLLLPQGVLAavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQnstGAKDGGPVKYGWNIcQNVQAGGGSHHHHHHHH |
| 71 | Pep1-1y12-Gly1-2-cHis-R157c-g90c | MDSKGSSQKGSRLLLLLVVSNLLLPQGVLAavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQnstGAKDGGPVKYGWNIcQNVQAGGGSHHHHHHHH |
| 72 | Pep1-2-1y12-Gly1-cHis-R157c-g90c | MDSKGSSQKGSRLLLLLVVSNLLLPQGVLAavgigavflgggGGGavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQKADGAKDGGPVKYGWNIcQNVQAGGGSHHHHHHHH |
| 73 | Pep1-2-1y12-Gly2-cHis-R157c-g90c | MDSKGSSQKGSRLLLLLVVSNLLLPQGVLAavgigavflgggGGGavgigavflgggGGGAVDMFIKIGDVKGESKDKTHAEEIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQnstGAKDGGPVKYGWNIcQNVQAGGGSHHHHHHHH |
| 74 | Pep1-2-1y12-Gly1-2-cHis-R157c-g90c | MDSKGSSQKGSRLLLLLVVSNLLLPQGVLAavgigavflgggGGGavgigavflgggGGGAVDMFIKIGDVKGESKDKTHnstIDVLAWSWGMSQSGSMHMGGGGGAGKVNVQDLSFTKYIDKSTPNLMMACSSGKHYPQAKLTIRKAcGENQVEYLIITLKEVLVSSVSTGGSGGEDRLTENVTLNFAQVQVDYQPQnstGAKDGGPVKYGWNIcQNVQAGGGSHHHHHHHH |
| 75 | FP_glyc88_1M6T_A35N_A37S | MDSKGSSQKGSRLLLLLVVSNLLLPQGVLAavgigavflgGGADLEDNWETLNDNLKVIEKADNAAQVKDALTKMRnAsLDAQKATPPKLEDKSPDSPEMKDFRHGFDILVGQIDDALKLANEGKVKEAQAAAEQLKTTRNAYIQKYLGGGSLEVLFQGPGSGSAWSHPQFEKGSGHHHHHHHH |
| 76 | FP_glyc88_1M6T_K42N | MDSKGSSQKGSRLLLLLVVSNLLLPQGVLAavgigavflgGGADLEDNWETLNDNLKVIEKADNAAQVKDALTKMRAAALDAQnATPPKLEDKSPDSPEMKDFRHGFDILVGQIDDALKLANEGKVKEAQAAAEQLKTTRNAYIQKYLGGGSLEVLFQGPGSGSAWSHPQFEKGSGHHHHHHHH |
| 77 | FP_glyc88_1M6T_E49N_K51T | MDSKGSSQKGSRLLLLLVVSNLLLPQGVLAavgigavflgGGADLEDNWETLNDNLKVIEKADNAAQVKDALTKMRAAALDAQKATPPKLnDtSPDSPEMKDFRHGFDILVGQIDDALKLANEGKVKEAQAAAEQLKTTRNAYIQKYLGGGSLEVLFQGPGSGSAWSHPQFEKGSGHHHHHHHH |
| 78 | FP_3HSH | MDSKGSSQKGSRLLLLLVVSNLLLPQGVLAavgigavflgGGGSSGVRLWATRQAMLGQVHEVPEGWLIFVAEQEELYVRVQNGFRKVQLEARTPLPRGGGSLEVLFQGPGSGSAWSHPQFEKGSGHHHHHHHH |

-continued

| SEQ ID NO | Name | Sequence |
|---|---|---|
| 79 | FP_3HSH_ A11N_L13T | MDSKGSSQKGSRLLLLLVVSNLLLPQGVLAavgigavflgGGGSSGVRLWATRQnMtGQVHEV PEGWLIFVAEQEELYVRVQNGFRKVQLEARTPLPRGGGSLEVLFQGPGSGSAWSHPQFEKGSG HHHHHHHH |
| 80 | FP_3HSH_ Q15N_H17T | MDSKGSSQKGSRLLLLLVVSNLLLPQGVLAavgigavflgGGGSSGVRLWATRQAMLGNVTEV PEGWLIFVAEQEELYVRVQNGFRKVQLEARTPLPRGGGSLEVLFQGPGSGSAWSHPQFEKGSG HHHHHHHH |
| 81 | FP_3HSH_ E18N_P20S | MDSKGSSQKGSRLLLLLVVSNLLLPQGVLAavgigavflgGGGSSGVRLWATRQAMLGQVHnV sEGWLIFVAEQEELYVRVQNGFRKVQLEARTPLPRGGGSLEVLFQGPGSGSAWSHPQFEKGSG HHHHHHHH |

D. HIV-1 Env Fusion Peptide Protein Nanoparticles

In some embodiments a protein nanoparticle is provided that includes one or more of the disclosed HIV-1 Env fusion peptides or portion thereof. Non-limiting examples of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. To construct such protein nanoparticles the HIV-1 Env fusion peptide or portion thereof can be linked (directly, or indirectly via a peptide linker) to the N-terminus of a subunit of the protein nanoparticle (such as a ferritin protein, an encapsulin protein, a SOR protein, or a lumazine synthase protein) and expressed in cells under appropriate conditions. The fusion protein self-assembles into a nanoparticle and can be purified.

In some embodiments, any of the disclosed HIV-1 Env fusion peptides or portion thereof can be linked to a ferritin subunit to construct a ferritin nanoparticle. Ferritin nanoparticles and their use for immunization purposes (e.g., for immunization against influenza antigens) have been disclosed, for example, in Kanekiyo et al. (Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such ferritin subunit is represented by:

(SEQ ID NO: 82)
ESQVRQQFSKDIEKLLNEQVNKEMQSSNLYMSMSSWCYTHSLDGAGLFL

FDHAAEEYEHAKKLIIFLNENNVPVQLTSISAPEHKFEGLTQIFQKAYE

HEQHISESINNIVDHAIKSKDHATFNFLQWYVAEQHEEEVLFKDILDKI

ELIGNENHGLYLADQYVKGIAKSRKS

In some embodiments, any of the disclosed HIV-1 Env fusion peptides (or portion thereof) can be linked to a ferritin subunit including an amino acid sequence at least 80% (such as at least 85%, at least 90%, at least 95%, or at least 97%) identical to amino acid sequence set forth as SEQ ID NO: 82.

Another example of the amino acid sequence of a ferritin subunit is represented by:

(SEQ ID NO: 83)
MLSKDIIKLLNEQVNKEMQSSNLYMSMSSWCYTHSLDGAGLFLFDHAAE

EYEHAKKLIIFLNENNVPVQLTSISAPHHKFHGLTHIFHKAYHHEQHIS

ESINNIVDHAIKSKDHATFNFLQWYVAEQHEEEVLFKDILDKIELIGNE

NHGLYLADQYVKGIAKSRKS

In some embodiments, any of the disclosed HIV-1 Env fusion peptides (or portion thereof) can be linked to a ferritin subunit including an amino acid sequence at least 80% (such as at least 85%, at least 90%, at least 95%, or at least 97%) identical to amino acid sequence set forth as SEQ ID NO: 83. In some embodiments, any of the disclosed HIV-1 Env fusion peptides (or portion thereof) can be linked to a ferritin subunit including an amino acid sequence at least 80% (such as at least 85%, at least 90%, at least 95%, or at least 97%) identical to amino acids 5-171, 4-171, 3-171, or 2-171 of SEQ ID NO: 83.

Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are described, for example, in Zhang et al. (*Int. J. Mol. Sci.,* 12:5406-5421, 2011, which is incorporated herein by reference in its entirety) and are further described herein.

In some embodiments, any of the disclosed HIV-1 Env fusion peptides (or portion thereof) can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

(SEQ ID NO: 84)
MQIYEGKLTAEGLRFGIVASRFNHALVDRLVEGAIDAIVRHGGREEDIT

LVRVPGSWEIPVAAGELARKEDIDAVIAIGVLIRGATPHFDYIASEVSK

GLADLSLELRKPITFGVITADTLEQAIERAGTKHGNKGWEAALSAIEMA

NLFKSLR.

In some embodiments, any of the disclosed HIV-1 Env fusion peptides (or portion thereof) can be linked to a lumazine synthase subunit including an amino acid sequence at least 80% (such as at least 85%, at least 90%, at least 95%, or at least 97%) identical to amino acid sequence set forth as SEQ ID NO: 84.

In some embodiments, any of the disclosed HIV-1 Env fusion peptides (or portion thereof) can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as

```
                                        (SEQ ID NO: 85)
MEFLKRSFAPLTEKQWQEIDNRAREIFKTQLYGRKFVDVEGPYGWEYAA

HPLGEVEVLSDENEVVKWGLRKSLPLIELRATFTLDLWELDNLERGKPN

VDLSSLEETVRKVAEFEDEVIFRGCEKSGVKGLLSFEERKIECGSTPKD

LLEAIVRALSIFSKDGIEGPYTLVINTDRWINFLKEEAGHYPLEKRVEE

CLRGGKIITTPRIEDALVVSERGGDFKLILGQDLSIGYEDREKDAVRLF

ITETFTFQVVNPEALILLKF.
```

In some embodiments, any of the disclosed HIV-1 Env fusion peptides (or portion thereof) can be linked to an encapsulin subunit including an amino acid sequence at least 80% (such as at least 85%, at least 90%, at least 95%, or at least 97%) identical to amino acid sequence set forth as SEQ ID NO: 85.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are described, for example, in Sutter et al. (Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, any of the disclosed HIV-1 Env fusion peptides (or portion thereof) can be linked to a Sulfur Oxygenase Reductase (SOR) subunit to construct a recombinant SOR nanoparticle. In some embodiments, the SOR subunit can include the amino acid sequence set forth as

```
                                        (SEQ ID NO: 86)
MEFLKRSFAPLTEKQWQEIDNRAREIFKTQLYGRKFVDVEGPYGWEYAA

HPLGEVEVLSDENEVVKWGLRKSLPLIELRATFTLDLWELDNLERGKPN

VDLSSLEETVRKVAEFEDEVIFRGCEKSGVKGLLSFEERKIECGSTPKD

LLEAIVRALSIFSKDGIEGPYTLVINTDRWINFLKEEAGHYPLEKRVEE

CLRGGKIITTPRIEDALVVSERGGDFKLILGQDLSIGYEDREKDAVRLF

ITETFTFQVVNPEALILLKF.
```

In some embodiments, any of the disclosed HIV-1 Env fusion peptides (or portion thereo can be linked to a SOR subunit including an amino acid sequence at least 80% (such as at least 85%, at least 90%, at least 95%, or at least 97%) identical to amino acid sequence set forth as SEQ ID NO: 86.

SOR proteins are microbial proteins (for example from the thermoacidophilic archaeon *Acidianus ambivalens* that form 24 subunit protein assemblies. Methods of constructing SOR nanoparticles are described, for example, in Urich et al. (Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

The HIV-1 Env fusion peptide included in the protein nanoparticle can be derived from any subtype of HIV, such as groups M, N, O, or P or clade A, B, C, D, F, G, H, J or K and the like. The HIV-1 Env fusion peptide included in the protein nanoparticle can consist essentially of or consist of residue 512 to one of residues 517-525 (such as residues 512-519) of HIV-1 Env (HXB2) numbering of the Env protein from any subtype of HIV, such as groups M, N, O, or P or clade A, B, C, D, F, G, H, J or K and the like.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVFLG (SEQ ID NO: 1). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 1.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGLGAVFLG (SEQ ID NO: 2). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 2.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAMIFG (SEQ ID NO: 3). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 3.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGTIGAMFLG (SEQ ID NO: 4). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 4.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAMFLG (SEQ ID NO: 5). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 5.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGALFLG (SEQ ID NO: 6). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 6.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AIGLGAMFLG (SEQ ID NO: 7). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 7.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGLGAVFIG (SEQ ID NO: 8). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 8.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVLLG (SEQ ID NO: 9). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 9.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AVGIGAVFIG (SEQ ID NO: 10). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 10.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AIGLGALFLG (SEQ ID NO: 11). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 11.

In some embodiments, the HIV-1 Env fusion peptide linked to the N-terminus of the subunits of the protein nanoparticle comprises, consists essentially of, or consists of from 6 to 10 residues (such as 6, 7, 8, 9, or 10 residues or 7-9 residues or 8-10 residues or 6-8 residues) from the N-terminus of the amino acid sequence set forth as AALGAVFLG (SEQ ID NO: 12). These residues correspond to HIV-1 Env positions 512-521 (HXB2 numbering). In some embodiments, the HIV-1 Env fusion peptide linked to the N-terminus of the subunits of the protein nanoparticle comprises, consists essentially of, or consists of the amino acid sequence set forth as residues 1-8 of SEQ ID NO: 12.

For production purposes, the HIV-1 Env fusion peptide (or portion thereof) linked to the nanoparticle subunit can include an N-terminal signal peptide that is cleaved during cellular processing. The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

In some embodiments, the protein nanoparticle can comprise self-assembled ferritin or lumazine synthase monomers comprising, consisting essentially of, or consisting of an amino acid sequence as listed in the following table (shown as SEQ ID NOs: 87-100), or to a comprise, consist essentially of, or consist of an amino acid sequence at least 90% (such as at least 95%) identical to any one of SEQ ID NOs: 87-100. Any one of the disclosed HIV-1 Env fusion peptides, or portion thereof, can be linked to the N-terminus of any one of the ferritin or lumazine synthase monomers comprising, consisting essentially of, or consisting of an amino acid sequence as listed in the following table (shown as SEQ ID NOs: 87-100), or to a ferritin or lumazine synthase monomer comprising, consisting essentially of, or consisting of an amino acid sequence at least 90% (such as at least 95%) identical to any one of SEQ ID NOs: 87-100. In some embodiments, two or more (such as two) of any of the disclosed HIV-1 Env fusion peptides, or portion thereof, can be linked sequentially to the N-terminus of any one of the ferritin or lumazine synthase monomers comprising, consisting essentially of, or consisting of an amino acid sequence as listed in the following table (shown as SEQ ID NOs: 87-100), or to a ferritin or lumazine synthase monomer comprising, consisting essentially of, or consisting of an amino acid sequence at least 90% (such as at least 95%) identical to any one of SEQ ID NOs: 87-100. In such embodiments, the multiple copies of the HIV-1 Env fusion peptide (or portion thereof) can be linked by a peptide liner, such as a glycine linker (for example a glycine 6-mer). The linkage can be direct or indirect (by a peptide linker connecting the C-terminus of the HIV-1 Env fusion peptide and the N-terminus of the nanoparticle monomer). The monomers of the protein nanoparticle can include one or more N-linked glycosylation sites (N-X-[IS/T]) that are glycosylated during production of the protein nanoparticle in cells. In several embodiments, the glycan moiety mimics the glycans near the fusion peptide on the HIV-1 Env trimer, such as HIV-1 Env glycans at positions N88, N230, N241, and N611. In the following table (showing SEQ ID NOs: 87-100), N-linked glycan sites, as well as engineered HIS tags embedded in the monomer sequence are shown in bold text.

| SEQ ID NO | Name | Sequence |
|---|---|---|
| | | Lumazine Synthase |
| 87 | 1hqk G12N R14S | MQIYEGKLTAE**nLs**FGIVASRFNHALVDRLVEGAIDAIVRHGGREEDITLVRVPGSWEIPVAAGELARKEDIDAVIAIGVLIRGATPHFDYIASEVSKGLADLSLELRKPITFGVITADTLEQAIERAGTKHGNKGWEAALSAIEMANLFKSLR |
| 88 | 1hqk D71N D73S | MQIYEGKLTAEGLRFGIVASRFNHALVDRLVEGAIDAIVRHGGREEDITLVRVPGSWEIPVAAGELARKE**nIs**AVIAIGVLIRGATPHFDYIASEVSKGLADLSLELRKPITFGVITADTLEQAIERAGTKHGNKGWEAALSAIEMANLFKSLR |
| | | Ferritin |
| 89 | Ferr | DIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 90 | Ferr-gly1 | DIIKLLNEQVN**net**QSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 91 | Ferr-gly2 | DIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINN**It**DHAIKSKDHATFNFLQWYVAEQHEEEVLFKDILDKIELIGNENHGLYLADQYVKGIAKSRKS |
| 92 | Ferr-gly1-gly2 | DIIKLLNEQVN**net**QSSNLYMSMSSWCYTHSLDGAGLFLFDHAAEEYEHAKKLIIFLNENNVPVQLTSISAPHHKFHGLTHIFHKAYHHEQHISESIN**NIt**DHAIKSKDHATFNFLQWYVAEQHEEEVLFKDILDKIELIGNENHGLYLADQYVKGIAKSRKS |
| 93 | 3egm N148S | MLSKDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIG**NEs**HGLYLADQYVKGIAKSRKS |
| 94 | 3egm N148S HIS | MLSKDIIKLLNEQVNKEMQSSNLYMSMSSWCYTHSLDGAGLFLFDHAAEEYEHAKKLIIFLNENNVPVQLTSIS**hhhHhh**EGLTQIFQKAYEHEQHISESINNIVDHAIKSKDHATFNFLQWYVAEQHEEEVLFKDILDKIELIG**NEs**HGLYLADQYVKGIAKSRKS |
| 95 | 3egm K79N E81T HIS | MLSKDIIKLLNEQVNKEMQSSNLYMSMSSWCYTHSLDGAGLFLFDHAAEEYEHAKKLIIFLNENNV**hhhhhh**ISAPEH**nFs**GLTQIFQKAYEHEQHISESINNIVDHAIKSKDHATFNFLQWYVAEQHEEEVLFKDILDKIELIGNENHGLYLADQYVKGIAKSRKS |
| 96 | 3egm Q69N HIS | MLSKDIIKLLNEQVNKEMQSSNLYMSMSSWCYTHSLDGAGLFLFDHAAEEYEHAKKLIIFLNENNVPV**nLT**SIS**hhhHhh**EGLTQIFQKAYEHEQHISESINNIVDHAIKSKDHATFNFLQWYVAEQHEEEVLFKDILDKIELIGNENHGLYLADQYVKGIAKSRKS |
| 97 | 3egm S72N | MLSKDIIKLLNEQVNKEMQSSNLYMSMSSWCYTHSLDGAGLFLFDHAAEEYEHAKKLIIFLNENNVPV**nLT**SISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 98 | 3egm S72N HIS | MLSKDIIKLLNEQVNKEMQSSNLYMSMSSWCYTHSLDGAGLFLFDHAAEEYEHAKKLIIFLNENNVPVQLT**nIShhhHhh**EGLTQIFQKAYEQHISESINNIVDHAIKSKDHATFNFLQWYVAEQHEEEVLFKDILDKIELIGNENHGLYLADQYVKGIAKSRKS |
| 99 | 3egm H96N | MLSKDIIKLLNEQVNKEMQSSNLYMSMSSWCYTHSLDGAGLFLFDHAAEEYEHAKKLIIFLNENNVPVQLTSISAPHHKFHGLTHIFHKAYHHEQ**nIS**ESINNIVDHAIKSKDHATFNFLQWYVAEQHEEEVLFKDILDKIELIGNENHGLYLADQYVKGIAKSRKS |
| 100 | 3egm H96N HIS | MLSKDIIKLLNEQVNKEMQSSNLYMSMSSWCYTHSLDGAGLFLFDHAAEEYEHAKKLIIFLNENNVPVQLTSIS**hhhHhh**EGLTQIFQKAYEHEQ**nIS**ESINNIVDHAIKSKDHATFNFLQWYVAEQHEEEVLFKDILDKIELIGNENHGLYLADQYVKGIAKSRKS |

In several embodiments, the monomers of the protein nanoparticle (including HIV-1 Env fusion peptide linked to nanoparticle subunit) comprise, consist essentially of, or consist of the amino acid sequence of any one of protein nanoparticle monomers listed in the following table (showing SEQ ID NOs: 101-122), or an amino acid sequence at least 90% (such as at least 95%) identical to any one of SEQ ID NOs: 101-122. In several embodiments, the glycan moiety mimics the glycans near the fusion peptide on the HIV-1 Env trimer, such as HIV-1 Env glycans at positions N88, N230, N241, and N611. In the following table (showing SEQ ID NOs: 101-122), N-linked glycan sites, as well as engineered HIS tags embedded in the monomer sequence are shown in bold text, and HIV-1 Env fusion peptides are shown in bold text with underlining.

| SEQ ID NO | Name | Sequence |
|---|---|---|
| | | Lumazine Synthase |
| 101 | HIV_FP-LS | **avgigavflg**sgMQIYEGKLTAEGLSFGIVASRFNHALVDRLVEGAIDAIVRHGGREEDITLVRVPGSWEIPVAAGELARKEDIDAVIAIGVLIRGATPHFDYIASEVSKGLADLSLELRKPITFGVITADTLEQAIERAGTKHGNKGWEAALSAIEMANLFKSLR |
| 102 | HIV_FP 1hqk G12N R14S | **avgigavflg**sgMQIYEGKLTAE**nLs**FGIVASRFNHALVDRLVEGAIDAIVRHGGREEDITLVRVPGSWEIPVAAGELARKEDIDAVIAIGVLIRGATPHFDYIASEVSKGLADLSLELRKPITFGVITADTLEQAIERAGTKHGNKGWEAALSAIEMANLFKSLR |
| 103 | HIV_FP 1hqk D71N D73S | **avgigavflg**sgsaMQIYEGKLTAEGLRFGIVASRFNHALVDRLVEGAIDAIVRHGGREEDITLVRVPGSWEIPVAAGELARKE**nIs**AVIAIGVLIRGATPHFDYIASEVSKGLADLSLELRKPITFGVITADTLEQAIERAGTKHGNKGWEAALSAIEMANLFKSLR |
| | | Ferritin |
| 104 | Pep1_Ferr-His06 | **avgigavfl**SGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 105 | Pep1-2_Ferr-His06 | **avgigavfl**SGG**avgigavfl**SGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 106 | Pep1_Ferr-His06-gly1 | **avgigavfl**SGGDIIKLLNEQVN**net**QSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 107 | Pep1_Ferr-His06-gly2 | **avgigavfl**SGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESIN**NIt**DHAIKSKDHATFNFLQWYVAEQHEEEVLFKDILDKIELIGNENHGLYLADQYVKGIAKSRKS |
| 108 | Pep1-2_Ferr-His06-gly1 | **avgigavfl**SGG**avgigavfl**SGGDIIKLLNEQVN**net**QSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 109 | Pep1-2_Ferr-His06-gly2 | **avgigavfl**SGG**avgigavfl**SGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESIN**NIt**DHAIKSKDHATFNFLQWYVAEQHEEEVLFKDILDKIELIGNENHGLYLADQYVKGIAKSRKS |
| 110 | Pep1-2_Ferr-His 06-gly1-2 | **avgigavfl**SGG**avgigavfl**SGGDIIKLLNEQVN**net**QSSNLYMSMSSWCYTHSLDGAGLFLFDHAAEEYEHAKKLIIFLNENNVPVQLTSISAPHHKFHGLTHIFHKAYHHEQHISESIN**NIt**DHAIKSKDHATFNFLQWYVAEQHEEEVLFKDILDKIELIGNENHGLYLADQYVKGIAKSRKS |
| 111 | Pep1-2_Ferr-His06-gly1-2 | **avgigavfl**SGG**avgigavfl**SGGDIIKLLNEQVN**nEt**QSSNLYMSMSSWCYTHSLDGAGLFLFDHAAEEYEHAKKLIIFLNENNVPVQLTSISAPHHKFHGLTHIFHKAYHHEQHISESIN**NIt**DHAIKSKDHATFNFLQWYVAEQHEEEVLFKDILDKIELIGNENHGLYLADQYVKGIAKSRKS |
| 112 | HIV_FP 3egm N148S | **avgigavflg**SQDPMLSKDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIG**NEs**HGLYLADQYVKGIAKSRKS |
| 113 | HIV_FP 3egm-2 N148S | **avgigavflg**SgDPMLSKDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIG**NEs**HGLYLADQYVKGIAKSRKS |
| 114 | HIV_FP 3egm N148S HIS1 | **avgigavflg**SQDPMLSKDIIKLLNEQVNKEMQSSNLYMSMSSWCYTHSLDGAGLFLFDHAAEEYEHAKKLIIFLNENNVPVQLTSIS**hhhHhh**EGLTQIFQKAYEHEQHISESINNIVDHAIKSKDHATFNFLQWYVAEQHEEEVLFKDILDKIELIG**NEs**HGLYLADQYVKGIAKSRKS |
| 115 | HIV_FP 3egm-2 N148S HIS1 | **avgigavflg**SgDPMLSKDIIKLLNEQVNKEMQSSNLYMSMSSWCYTHSLDGAGLFLFDHAAEEYEHAKKLIIFLNENNVPVQLTSIS**hhhHhh**EGLTQIFQKAYEHEQHISESINNIVDHAIKSKDHATFNFLQWYVAEQHEEEVLFKDILDKIELIG**NEs**HGLYLADQYVKGIAKSRKS |

-continued

| SEQ ID NO | Name | Sequence |
|---|---|---|
| 116 | HIV_FP<br>3egm K79N<br>E81T HIS1 | avgigavflgQDPMLSKDIIKLLNEQVNKEMQSSNLYMSMSSWCYTHSLDGAGLFLFDHAAEEY<br>EHAKKLIIFLNENNVhhhhhhISAPEHnFsGLTQIFQKAYEHEQHISESINNIVDHAIKSKDHA<br>TFNFLQWYVAEQHEEEVLFKDILDKIELIGNENHGLYLADQYVKGIAKSRKS |
| 117 | HIV_FP<br>3egm-2<br>K79N E81T<br>HIS1 | avgigavflgMLSKDIIKLLNEQVNKEMQSSNLYMSMSSWCYTHSLDGAGLFLFDHAAEEYEHA<br>KKLIIFLNENNVhhhhhhISAPEHnFsGLTQIFQKAYEHEQHISESINNIVDHAIKSKDHATFN<br>FLQWYVAEQHEEEVLFKDILDKIELIGNENHGLYLADQYVKGIAKSRKS |
| 118 | HIV_FP<br>3egm Q69N<br>HIS1 | avgigavflgMLSKDIIKLLNEQVNKEMQSSNLYMSMSSWCYTHSLDGAGLFLFDHAAEEYEHA<br>KKLIIFLNENNVPVnLTSIShhhHhhEGLTQIFQKAYEHEQHISESINNIVDHAIKSKDHATFN<br>FLQWYVAEQHEEEVLFKDILDKIELIGNENHGLYLADQYVKGIAKSRKS |
| 119 | HIV_FP<br>3egm S72N | avgigavflgMLSKDIIKLLNEQVNKEMQSSNLYMSMSSWCYTHSLDGAGLFLFDHAAEEYEHA<br>KKLIIFLNENNVPVnLTSISAPHHKFHGLTHIFHKAYHHEQHISESINNIVDHAIKSKDHATFN<br>FLQWYVAEQHEEEVLFKDILDKIELIGNENHGLYLADQYVKGIAKSRKS |
| 120 | HIV_FP<br>3egm S72N<br>HIS1 | avgigavflgsgMLSKDIIKLLNEQVNKEMQSSNLYMSMSSWCYTHSLDGAGLFLFDHAAEEYE<br>HAKKLIIFLNENNVPVQLTnIShhhHhhEGLTQIFQKAYEQHISESINNIVDHAIKSKDHATFN<br>FLQWYVAEQHEEEVLFKDILDKIELIGNENHGLYLADQYVKGIAKSRKS |
| 121 | HIV_FP<br>3egm H96N | avgigavflgsgMLSKDIIKLLNEQVNKEMQSSNLYMSMSSWCYTHSLDGAGLFLFDHAAEEYE<br>HAKKLIIFLNENNVPVQLTSISAPHHKFHGLTHIFHKAYHHEQnISESINNIVDHAIKSKDHAT<br>FNFLQWYVAEQHEEEVLFKDILDKIELIGNENHGLYLADQYVKGIAKSRKS |
| 122 | HIV_FP<br>3egm H96N<br>HIS1 | avgigavflgsgMLSKDIIKLLNEQVNKEMQSSNLYMSMSSWCYTHSLDGAGLFLFDHAAEEYE<br>HAKKLIIFLNENNVPVQLTSIShhhHhhEGLTQIFQKAYEHEQnISESINNIVDHAIKSKDHAT<br>FNFLQWYVAEQHEEEVLFKDILDKIELIGNENHGLYLADQYVKGIAKSRKS |

The monomers of the protein nanoparticle can include various tags and sequences for production and purification of the epitope scaffold protein. Typically such protein tags are linked to the C-terminus of the monomer and are ultimately removed (for example by selective protease cleave) from the monomer. For production in cells, the monomers of the protein nanoparticle can be initially synthesized with a signal peptide, for example, a signal peptide having the amino acid sequence set forth as MDSKGSSQKGSRLLLLLVVSNLLLPQGVLA (residues 1-30 of SEQ ID NO: 59). Exemplary sequences of protein nanoparticle subunits comprising a disclosed HIV-1 Env fusion peptide or portion thereof, as well as various signal peptides, and C-terminal protein tags, etc., for production and purification are provided below.

| | | |
|---|---|---|
| | | Lumazine synthase |
| 123 | HIV_FP-LS | MDSKGSSQKGSRLLLLLVVSNLLLPQGVVGavgigavflgsgMQIYEGKLTAEnLsFGIVASR<br>FNHALVDRLVEGAIDAIVRHGGREEDITLVRVPGSWEIPVAAGELARKEDIDAVIAIGVLIRG<br>ATPHFDYIASEVSKGLADLSLELRKPITFGVITADTLEQAIERAGTKHGNKGWEAALSAIEMA<br>NLFKSLR |
| 124 | HIV_FP<br>1hqk<br>G12N R14S | MDSKGSSQKGSRLLLLLVVSNLLLPQGVVGavgigavflgsgMQIYEGKLTAEnLsFGIVASR<br>FNHALVDRLVEGAIDAIVRHGGREEDITLVRVPGSWEIPVAAGELARKEDIDAVIAIGVLIRG<br>ATPHFDYIASEVSKGLADLSLELRKPITFGVITADTLEQAIERAGTKHGNKGWEAALSAIEMA<br>NLFKSLR |
| 125 | HIV_FP<br>1hqk<br>D71N D73S | MDSKGSSQKGSRLLLLLVVSNLLLPQGVVGavgigavflgsgsaMQIYEGKLTAEGLRFGIVA<br>SRFNHALVDRLVEGAIDAIVRHGGREEDITLVRVPGSWEIPVAAGELARKEnIsAVIAIGVLI<br>RGATPHFDYIASEVSKGLADLSLELRKPITFGVITADTLEQAIERAGTKHGNKGWEAALSAIE<br>MANLFKSLR |
| | | Ferritin |
| 126 | HIV_FP<br>3egm<br>N148S | MDSKGSSQKGSRLLLLLVVSNLLLPQGVVGavgigavflgSQDPMLSKDIIKLLNEQVNKEMQ<br>SSNLYMSMSSWCYTHSLDGAGLFLFDHAAEEYEHAKKLIIFLNENNVPVQLTSISAPHHKFHG<br>LTHIFHKAYHHEQHISESINNIVDHAIKSKDHATFNFLQWYVAEQHEEEVLFKDILDKIELIG<br>NEsHGLYLADQYVKGIAKSRKS |
| 127 | HIV_FP<br>3egm-2<br>N148S | MDSKGSSQKGSRLLLLLVVSNLLLPQGVVGavgigavflgSgDPMLSKDIIKLLNEQVNKEMQ<br>SSNLYMSMSSWCYTHSLDGAGLFLFDHAAEEYEHAKKLIIFLNENNVPVQLTSISAPHHKFHG<br>LTHIFHKAYHHEQHISESINNIVDHAIKSKDHATFNFLQWYVAEQHEEEVLFKDILDKIELIG<br>NEsHGLYLADQYVKGIAKSRKS |
| 128 | HIV_FP<br>3egm<br>N148S HIS1 | MDSKGSSQKGSRLLLLLVVSNLLLPQGVVGavgigavflgSQDPMLSKDIIKLLNEQVNKEMQ<br>SSNLYMSMSSWCYTHSLDGAGLFLFDHAAEEYEHAKKLIIFLNENNVPVQLTSIShhhHhhEG<br>LTQIFQKAYEHEQHISESINNIVDHAIKSKDHATFNFLQWYVAEQHEEEVLFKDILDKIELIG<br>NEsHGLYLADQYVKGIAKSRKS |

-continued

| | | |
|---|---|---|
| 129 | HIV_FP 3egm-2 N148S HIS1 | MDSKGSSQKGSRLLLLLVVSNLLLPQGVVGavgigavflgSgDPMLSKDIIKLLNEQVNKEMQSSNLYMSMSSWCYTHSLDGAGLFLFDHAAEEYEHAKKLIIFLNENNVPVQLTSIShhhHhhEGLTQIFQKAYEHEQHISESINNIVDHAIKSKDHATFNFLQWYVAEQHEEEVLFKDILDKIELIGNEsHGLYLADQYVKGIAKSRKS |
| 130 | HIV_FP 3egm K79N E81T HIS1 | MDSKGSSQKGSRLLLLLVVSNLLLPQGVVGavgigavflgQDPMLSKDIIKLLNEQVNKEMQSSNLYMSMSSWCYTHSLDGAGLFLFDHAAEEYEHAKKLIIFLNENNVhhhhhhISAPEHnFsGLTQIFQKAYEHEQHISESINNIVDHAIKSKDHATFNFLQWYVAEQHEEEVLFKDILDKIELIGNENHGLYLADQYVKGIAKSRKS |
| 131 | HIV_FP 3egm-2 K79N E81T HIS1 | MDSKGSSQKGSRLLLLLVVSNLLLPQGVVGavgigavflgMLSKDIIKLLNEQVNKEMQSSNLYMSMSSWCYTHSLDGAGLFLFDHAAEEYEHAKKLIIFLNENNVhhhhhhISAPEHnFsGLTQIFQKAYEHEQHISESINNIVDHAIKSKDHATFNFLQWYVAEQHEEEVLFKDILDKIELIGNENHGLYLADQYVKGIAKSRKS |
| 132 | HIV_FP 3egm Q69N HIS1 | MDSKGSSQKGSRLLLLLVVSNLLLPQGVVGavgigavflgMLSKDIIKLLNEQVNKEMQSSNLYMSMSSWCYTHSLDGAGLFLFDHAAEEYEHAKKLIIFLNENNVPVnLTSIShhhHhhEGLTQIFQKAYEHEQHISESINNIVDHAIKSKDHATFNFLQWYVAEQHEEEVLFKDILDKIELIGNENHGLYLADQYVKGIAKSRKS |
| 133 | HIV_FP 3egm S72N | MDSKGSSQKGSRLLLLLVVSNLLLPQGVVGavgigavflgMLSKDIIKLLNEQVNKEMQSSNLYMSMSSWCYTHSLDGAGLFLFDHAAEEYEHAKKLIIFLNENNVPVnLTSISAPHHKFHGLTHIFHKAYHHEQHISESINNIVDHAIKSKDHATFNFLQWYVAEQHEEEVLFKDILDKIELIGNENHGLYLADQYVKGIAKSRKS |
| 134 | HIV_FP 3egm S72N HIS1 | MDSKGSSQKGSRLLLLLVVSNLLLPQGVVGavgigavflgsgMLSKDIIKLLNEQVNKEMQSSNLYMSMSSWCYTHSLDGAGLFLFDHAAEEYEHAKKLIIFLNENNVPVQLTnIShhhHhhEGLTQIFQKAYEQHISESINNIVDHAIKSKDHATFNFLQWYVAEQHEEEVLFKDILDKIELIGNENHGLYLADQYVKGIAKSRKS |
| 135 | HIV_FP 3egm H96N | MDSKGSSQKGSRLLLLLVVSNLLLPQGVVGavgigavflgsgMLSKDIIKLLNEQVNKEMQSSNLYMSMSSWCYTHSLDGAGLFLFDHAAEEYEHAKKLIIFLNENNVPVQLTSISAPHHKFHGLTHIFHKAYHHEQnISESINNIVDHAIKSKDHATFNFLQWYVAEQHEEEVLFKDILDKIELIGNENHGLYLADQYVKGIAKSRKS |
| 136 | HIV_FP 3egm H96N HIS1 | MDSKGSSQKGSRLLLLLVVSNLLLPQGVVGavgigavflgsgMLSKDIIKLLNEQVNKEMQSSNLYMSMSSWCYTHSLDGAGLFLFDHAAEEYEHAKKLIIFLNENNVPVQLTSIShhhHhhEGLTQIFQKAYEHEQnISESINNIVDHAIKSKDHATFNFLQWYVAEQHEEEVLFKDILDKIELIGNENHGLYLADQYVKGIAKSRKS |
| 137 | Pep1_Ferr-His06 | MDSKGSSQKGSRLLLLLVVSNLLLPQGVLAavgigavflSGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKSGS |
| 138 | Pep1-2_ Ferr-His06 | MDSKGSSQKGSRLLLLLVVSNLLLPQGVLAavgigavflSGGavgigavflSGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKSGS |
| 139 | Pep1_Ferr-His06-gly1 | MDSKGSSQKGSRLLLLLVVSNLLLPQGVLAavgigavflSGGDIIKLLNEQVNnetQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKSGS |
| 140 | Pep1_Ferr-His06-gly2 | MDSKGSSQKGSRLLLLLVVSNLLLPQGVLAavgigavflSGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNItDHAIKSKDHATFNFLQWYVAEQHEEEVLFKDILDKIELIGNENHGLYLADQYVKGIAKSRKSGS |
| 141 | Pep1-2_ Ferr-His06-gly1 | MDSKGSSQKGSRLLLLLVVSNLLLPQGVLAavgigavflSGGavgigavflSGGDIIKLLNEQVNnetQSSNLYMSMSSWCYTHSLDGAGLFLFDHAAEEYEHAKKLIIFLNENNVPVQLTSISAPHHKFHGLTHIFHKAYHHEQHISESINNIVDHAIKSKDHATFNFLQWYVAEQHEEEVLFKDILDKIELIGNENHGLYLADQYVKGIAKSRKSGS |
| 142 | Pep1-2_ Ferr-His06-gly2 | MDSKGSSQKGSRLLLLLVVSNLLLPQGVLAavgigavflSGGavgigavflSGGDIIKLLNEQVNKEMQSSNLYMSMSSWCYTHSLDGAGLFLFDHAAEEYEHAKKLIIFLNENNVPVQLTSISAPHHKFHGLTHIFHKAYHHEQHISESINNItDHAIKSKDHATFNFLQWYVAEQHEEEVLFKDILDKIELIGNENHGLYLADQYVKGIAKSRKSGS |
| 143 | Pep1-2_ Ferr-His06-gly1-2 | MDSKGSSQKGSRLLLLLVVSNLLLPQGVLAavgigavflSGGavgigavflSGGDIIKLLNEQVNnetQSSNLYMSMSSWCYTHSLDGAGLFLFDHAAEEYEHAKKLIIFLNENNVPVQLTSISAPHHKFHGLTHIFHKAYHHEQHISESINNItDHAIKSKDHATFNFLQWYVAEQHEEEVLFKDILDKIELIGNENHGLYLADQYVKGIAKSRKSGS |

-continued

| | | |
|---|---|---|
| 144 | Pep1-2_ Ferr-His06- gly1-2 | MDSKGSSQKGSRLLLLLVVSNLLLPQGVLAavgigavflSGGavgigavflSGGDIIKLLNEQ VNnEtQSSNLYMSMSSWCYTHSLDGAGLFLFDHAAEEYEHAKKLIIFLNENNVPVQLTSISAP HHKFHGLTHIFHKAYHHEQHISESINNItDHAIKSKDHATFNFLQWYVAEQHEEEVLFKDILD KIELIGNENHGLYLADQYVKGIAKSRKSGS |

F. Recombinant HIV-1 Env Ectodomain Trimers

Also provided herein are recombinant HIV-1 Env ectodomain trimers comprising protomers (each comprising a gp120 protein and a gp41 ectodomain) that are modified from a native form (e.g., by introduction of one or more amino acid substitutions) to lack N-linked glycosylation sites near the HIV-1 Env fusion peptide in the trimer (such as N88, N230, N241, and/or N611 glycosylation sites, HXB2 numbering). Selective deglycosylation of these N-linked glycosylation sites increases exposure of the HIV-1 Env fusion peptide to the immune system to promote a neutralizing immune response.

In some embodiments, the protomers of the recombinant HIV-1 Env ectodomain trimer comprise one more amino acid substitutions to remove the N88 N-linked glycosylation site. In some embodiments, the protomers of the recombinant HIV-1 Env ectodomain trimer comprise one more amino acid substitutions to remove the N230 N-linked glycosylation site. In some embodiments, the protomers of the recombinant HIV-1 Env ectodomain trimer comprise one more amino acid substitutions to remove the N241 N-linked glycosylation site. In some embodiments, the protomers of the recombinant HIV-1 Env ectodomain trimer comprise one more amino acid substitutions to remove the N611 N-linked glycosylation site. In some embodiments the protomers of the recombinant HIV-1 Env ectodomain trimer comprise one more amino acid substitutions to remove two or more, such as three or all four) of the N88, N230, N241, and N611 N-linked glycosylation sites. The amino acid substitutions to remove the glycosylation site can include a substitution of the asparagine residue or the serine/threonine residue of the N-X-[S/T] consensus. Typical substitutions include an asparagine to glutamine substitution, a serine to cysteine or methionine substitution, or a threonine to cysteine or methionine substitution, although any substitution that removes the N-linked glycosylation site can be used if it does not disrupt the structure (for example, prefusion mature closed conformation) or function (for example, VRC34 binding) of the recombinant HIV-1 Env ectodomain trimer.

In several embodiments, the protomers of the recombinant HIV-1 Env ectodomain trimer comprise one more additional amino acid substitutions that stabilize the recombinant HIV-1 Env ectodomain trimer in a prefusion mature closed conformation. In some embodiments, the gp120 protein of the protomers of the HIV-1 Env ectodomain trimer can include a non-natural disulfide bond between HIV-1 Env positions 201 and 433. For example, the non-natural disulfide bond can be introduced by including cysteine substitutions at positions 201 and 433 (e.g., I201C and A433C substitutions). The presence of the non-natural disulfide bond between residues 201 and 433 contributes to the stabilization of the HIV-1 Env ectodomain trimer in the prefusion mature closed conformation (see, e.g., Kwon et al., Nat. Struct. Biol., 22(7), 522-531, 2015, incorporated by reference herein). In some embodiments, the HIV-1 Env ectodomain trimer can include protomers that including the "SOSIP" substitutions, which include a non-natural disulfide bond between cysteine residues introduced at HIV-1 Env positions 501 and 605 (for example, by A501C and T605C substitutions), and a proline residue introduced at HIV-1 Env positions 559 (for example, by an I559P substitution). The presence of the non-natural disulfide bond between positions 501 and 605 and the proline residue at position 559 contributes to the stabilization of the HIV-1 Env ectodomain trimer in the prefusion mature closed conformation (see, e.g., Kwon et al., Nat. Struct. Biol., 22(7), 522-531, 2015). In several embodiments, the protomers of the recombinant HIV-1 Env ectodomain trimer can include a non-natural disulfide bond between HIV-1 Env positions 201 and 433 (e.g., by introduction of I201C and A433C substitutions) and the SOSIP mutations to stabilize the HIV-1 Env ectodomain trimer in the prefusion mature closed conformation.

The prefusion mature closed conformation of the HIV-1 Env trimer has been disclosed, for example, in Pancera et al., Nature, 514, 455-461, 2014 and PCT App. No. PCT/US2015/048729, each of which is incorporated by reference herein in its entirety. In some embodiments, the protomers of the HIV-1 Env ectodomain trimers disclosed herein can further include one of more modifications as disclosed in PCT App. No. PCT/US2015/048729 to stabilize the recombinant HIV-1 Env ectodomain trimer in the prefusion mature closed conformation. For example, the HIV-1 Env ectodomain trimer can include a prefusion mature closed conformation wherein the V1V2 domain of each Env ectodomain protomer in the trimer comes together at the membrane distal apex. At the membrane proximal aspect, the HIV-1 Env ectodomain trimer in the prefusion mature closed conformation includes distinct α6 and α7 helices; the α7 helix does not start until after residue 570. For example, in the prefusion mature closed conformation, the interprotomer distance between residues 200 and 313 can be less than 5 Angstroms.

In additional embodiments, any of the recombinant HIV-1 ectodomain trimers disclosed in PCT App. No. PCT/US2015/048729 (incorporated by reference herein in its entirety) can be further modified by removing N-linked glycosylation sites near the HIV-1 Env fusion peptide in the trimer (such as N88, N230, N241, and/or N611 glycosylation sites, HXB2 numbering). Selective deglycosylation of these N-linked glycosylation sites increases exposure of the HIV-1 Env fusion peptide to the immune system to promote a neutralizing immune response.

In some embodiments, the protomers of the recombinant HIV-1 Env ectodomain trimer can include an amino acid sequence of a native protomer of a HIV-1 Env ectodomain trimer (including gp120 and the gp41 ectodomain), for example, from genetic subtype A-F as available in the HIV Sequence Database (hiv-web.lanl.gov/content/hiv-db/main-page.html), or an amino acid sequence at least 90% (such as at least 95%, at least 96%, at least 97%, at least 98% or at least 99%) identical thereto, that has been modified by one or more amino acid substitutions as discussed herein, for example, to remove one or more of the N88, N230, N241, and N611 N-linked glycosylation sites or to stabilize the HIV-Env ectodomain trimer in the prefusion mature closed conformation.

In some examples, the protomers of the HIV-1 Env ectodomain trimer can comprise the sequence of BG505.SOSIP-DS modified to remove one or more glycan residues to expose the fusion peptide, such as one or more of the N88, N230, N241, and N611 glycan sequons. The BG505.SOSIP-DS sequence is set forth as:

BG505 SOSIP-DS (BG505.SOSIP.R6.664.T332N_I201C/A433C) (SEO ID NO: 155)

AENLWVTVYYGVPVWKDAETTLFCASDAKAYETEKHNVWATHACVPTDP
NPQEIHLENVTEEFNMWKNNMVEQMHTDIISLWDQSLKPCVKLTPLCVT
LQCTNVTNNITDDMRGELKNCSFNMTTELRDKKQKVYSLFYRLDVVQIN
ENQGNRSNNSNKEYRLINCNTSAcTQACPKVSFEPIPIHYCAPAGFAIL
KCKDKKFNGTGPCPSVSTVQCTHGIKPVVSTQLLLNGSLAEEEVMIRSE
NITNNAKNILVQFNTPVQINCTRPNNNTRKSIRIGPGQAFYATGDIIGD
IRQAHCNVSKATWNETLGKVVKQLRKHFGNNTIIRFANSSGGDLEVTTH
SFNCGGEFFYCNTSGLFNSTWISNTSVQGSNSTGSNDSITLPCRIKQII
NMWQRIGQcMYAPPIQGVIRCVSNITGLILTRDGGSTNSTTETFRPGGG
DMRDNWRSELYKYKVVKIEPLGVAPTRCKRRVVGRRRRRRAVGIGAVFL
GFLGAAGSTMGAASMTLTVQARNLLSGIVQQQSNLLRAPEAQQHLLKLT
VWGIKQLQARVLAVERYLRDQQLLGIWGCSGKLICCTNVPWNSSWSNRN
LSEIWDNMTWLQWDKEISNYTQIIYGLLEESQNQQEKNEQDLLALD

The above BG505.SOSIP-DS sequence is truncated at position 664, and includes T332N and R6 substitutions. Membrane-bound forms of these sequence can be readily generated by attaching a transmembrane domain and cytosolic tail to C-terminal residue of the sequence.

In some embodiments, the protomers of the HIV-1 Env ectodomain trimer can comprise an amino acid sequence set forth as one of:

BG505.SOSIP-DS degly4 (removal of N611, N241, N230, N88 glycan sequons) (SEQ ID NO: 156)

AENLWVTVYYGVPVWKEAKTTLFCASDAKAYEKEVHNVWATHACVPTDP
NPQEMVLKQVTENFNMWKNDMVDQMHEDVISLWDQSLKPCVKLTPLCVT
LNCTNATASNSSIIEGMKNCSFNITTELRDKREKKNALFYKLDIVQLDG
NSSQYRLINCNTSVCTQACPKVSFDPIPIHYCAPAGYAILKCNQKTFTG
TGPCNQVSTVQCTHGIKPVVSTQLLLNGSLAEGEIIIRSENITNNVKTI
IVHLNESVKIECTRPNNKTRTSIRIGPGQAFYATGQVIGDIREAYCNIN
ESKWNETLQRVSKKLKEYFPHKNITFQPSSGGDLEITTHSFNCGGEFFY
CNTSSLFNRTYMANSTDMANSTETNSTRTITIHCRIKQIINMWQEVGRC
MYAPPIAGNITCISNITGLLLTRDGGKNNTETFRPGGGNMKDNWRSELY
KYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARV
LAVERYLRDQQLLGIWGCSGKLICCTNVPWQSSWSNRNLSEIWDNMTWL
QWDKEISNYTQIIYGLLEESQNQQEKNEQDLLALD

BG505.SOSIP-DS degly3 (removal of N611, N241, N230 glycan sequons) (SEQ ID NO: 157)

AENLWVTVYYGVPVWKEAKTTLFCASDAKAYEKEVHNVWATHACVPTDP
NPQEMVLKNVTENFNMWKNDMVDQMHEDVISLWDQSLKPCVKLTPLCVT
LNCTNATASNSSIIEGMKNCSFNITTELRDKREKKNALFYKLDIVQLDG
NSSQYRLINCNTSVCTQACPKVSFDPIPIHYCAPAGYAILKCNQKTFTG
TGPCNQVSTVQCTHGIKPVVSTQLLLNGSLAEGEIIIRSENITNNVKTI
IVHLNESVKIECTRPNNKTRTSIRIGPGQAFYATGQVIGDIREAYCNIN
ESKWNETLQRVSKKLKEYFPHKNITFQPSSGGDLEITTHSFNCGGEFFY
CNTSSLFNRTYMANSTDMANSTETNSTRTITIHCRIKQIINMWQEVGRC
MYAPPIAGNITCISNITGLLLTRDGGKNNTETFRPGGGNMKDNWRSELY
KYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARV
LAVERYLRDQQLLGIWGCSGKLICCTNVPWQSSWSNRNLSEIWDNMTWL
QWDKEISNYTQIIYGLLEESQNQQEKNEQDLLALD

In some examples, the protomers of the HIV-1 Env ectodomain trimer can comprise the sequence of a/BG505 chimera including the SOSIP, R6, T332N, and DS modifications (CH505.SOSIP-DS) that is further modified to remove one or more glycan residues to expose the fusion peptide, such as one or more of the N88, N230, N241, and N611 glycan sequons. The CH505.SOSIP-DS sequence is set forth as: CH505.SOSIP-DS (SEQ ID NO: 158)

AENLWVTVYYGVPVWKEAKTTLFCASDAKAYEKEVHNVWATHACVPTDP
NPQEMVLKNVTENFNMWKNDMVDQMHEDVISLWDQSLKPCVKLTPLCVT
LNCTNATASNSSIIEGMKNCSFNITTELRDKREKKNALFYKLDIVQLDG
NSSQYRLINCNTSVCTQACPKVSFDPIPIHYCAPAGYAILKCNNKTFTG
TGPCNNVSTVQCTHGIKPVVSTQLLLNGSLAEGEIIIRSENITNNVKTI
IVHLNESVKIECTRPNNKTRTSIRIGPGQAFYATGQVIGDIREAYCNIN
ESKWNETLQRVSKKLKEYFPHKNITFQPSSGGDLEITTHSFNCGGEFFY
CNTSSLFNRTYMANSTDMANSTETNSTRTITIHCRIKQIINMWQEVGRC
MYAPPIAGNITCISNITGLLLTRDGGKNNTETFRPGGGNMKDNWRSELY
KYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARV
LAVERYLRDQQLLGIWGCSGKLICCTNVPWNSSWSNRNLSEIWDNMTWL
QWDKEISNYTQIIYGLLEESQNQQEKNEQDLLALD

In some embodiments, the protomers of the HIV-1 Env ectodomain trimer can comprise an amino acid sequence set forth as one of:

CH505.SOSIP-DS degly4 (removal of N611, N241, N230, N88 glycan sequons) (SEQ ID NO: 145)

CH505.SOSIP-DS degly3 removal of N611, N241, N230 glycan sequons) (SEQ ID NO: 146)

AENLWVTVYYGVPVWKEAKTTLFCASDAKAYEKEVHNVWATHACVPTDP

NPQEMVLKQVTENFNMWKNDMVDQMHEDVISLWDQSLKPCVKLTPLCVT

LNCTNATASNSSIIEGMKNCSFNITTELRDKREKKNALFYKLDIVQLDG

NSSQYRLINCNTSVCTQACPKVSFDPIPIHYCAPAGYAILKCNQKTFTG

TGPCNQVSTVQCTHGIKPVVSTQLLLNGSLAEGEIIIRSENITNNVKTI

IVHLNESVKIECTRPNNKTRTSIRIGPGQAFYATGQVIGDIREAYCNIN

ESKWNETLQRVSKKLKEYFPHKNITFQPSSGGDLEITTHSFNCGGEFFY

CNTSSLFNRTYMANSTDMANSTETNSTRTITIHCRIKQIINMWQEVGRC

MYAPPIAGNITCISNITGLLLTRDGGKNNTETFRPGGGNMKDNWRSELY

KYKVVKIEPLGVAPTRCKRRVVGRRRRRRAVGIGAVFLGFLGAAGSTMG

AASMTLTVQARNLLSGIVQQQSNLLRAPEAQQHLLKLTVWGIKQLQARV

LAVERYLRDQQLLGIWGCSGKLICCTNVPWQSSWSNRNLSEIWDNMTWL

QWDKEISNYTQIIYGLLEESQNQQEKNEQDLLALD

AENLWVTVYYGVPVWKEAKTTLFCASDAKAYEKEVHNVWATHACVPTDP

NPQEMVLKNVTENFNMWKNDMVDQMHEDVISLWDQSLKPCVKLTPLCVT

LNCTNATASNSSIIEGMKNCSFNITTELRDKREKKNALFYKLDIVQLDG

NSSQYRLINCNTSVCTQACPKVSFDPIPIHYCAPAGYAILKCNQKTFTG

TGPCNQVSTVQCTHGIKPVVSTQLLLNGSLAEGEIIIRSENITNNVKTI

IVHLNESVKIECTRPNNKTRTSIRIGPGQAFYATGQVIGDIREAYCNIN

ESKWNETLQRVSKKLKEYFPHKNITFQPSSGGDLEITTHSFNCGGEFFY

CNTSSLFNRTYMANSTDMANSTETNSTRTITIHCRIKQIINMWQEVGRC

MYAPPIAGNITCISNITGLLLTRDGGKNNTETFRPGGGNMKDNWRSELY

KYKVVKIEPLGVAPTRCKRRVVGRRRRRRAVGIGAVFLGFLGAAGSTMG

AASMTLTVQARNLLSGIVQQQSNLLRAPEAQQHLLKLTVWGIKQLQARV

LAVERYLRDQQLLGIWGCSGKLICCTNVPWQSSWSNRNLSEIWDNMTWL

QWDKEISNYTQIIYGLLEESQNQQEKNEQDLLALD

Any of the HIV-1 Env trimers disclosed herein can further comprise one or more amino acid substitutions to the fusion peptide sequence (e.g., HIV-1Env residues 512-519) to change the sequence to that of the fusion peptide from a heterologous HIV-1 strain. For example, the native fusion peptide sequence of BG505 is AVGIGAVF (residues 1-8 of SEQ ID NO: 1); this sequence could be modified to AVGLGAVF (residues 1-8 of SEQ ID NO: 2) to match that of other HIV-1 strains. To generate a set of HIV-1 Env trimer with diverse fusion peptide sequences, the first eight amino acid residues of the BG505 fusion peptide can be mutated as needed to match the fusion peptide sequence of other HIV-1 strains of interest. In some embodiments, a "cocktail" of soluble HIV-1 Env trimers is provided that contain fusion peptide sequence representation many different HIV-1 strains, such as shown in FIG. 7E.

In several embodiments, the N-terminal residue of the recombinant gp120 protein included in the protomers of the HIV-1 Env ectodomain trimer is one of HIV-1 Env positions 1-35, and the C-terminal residue of the recombinant gp120 protein is one of HIV-1 Env positions 503-511. In some embodiments, the N-terminal residue of the recombinant gp120 protein included in protomers of the HIV-1 Env ectodomain trimer is HIV-1 Env position 31 and the C-terminal residue of the recombinant gp120 protein is HIV-1 Env position 511 or position 507. In some embodiments, the recombinant gp120 protein included in protomers of the HIV-1 Env ectodomain trimer comprises or consists of HIV-1 Env positions 31-507 (HXB2 numbering).

In the protomers of the purified trimer, the recombinant gp120 protein typically does not include a signal peptide (for example, the recombinant gp120 protein typically does not include HIV-1 Env positions 1-30), as the signal peptide is proteolytically cleaved during cellular processing. Additionally, in several embodiments, the gp41 ectodomain included in the protomers of the trimer includes the extracellular portion of gp41 (e.g., positions 512-664). In embodiments including a soluble recombinant HIV-1 Env ectodomain trimer, the gp41 ectodomain is not linked to a transmembrane domain or other membrane anchor. However, in embodiments including a membrane anchored recombinant HIV-1 Env ectodomain trimer, the C-terminus of the gp41 ectodomain can be linked to a transmembrane domain (such as, but not limited to, an HIV-1 Env transmembrane domain). In several embodiments, in the protomers of the HIV-1 Env ectodomain trimer:

- the N-terminal residue of the gp120 protein is one of HIV-1 Env positions 1-35;
- the C-terminal residue of the gp120 protein is one of HIV-1 Env positions 503-511;
- the N-terminal residue of the gp41 ectodomain is one of HIV-1 Env positions 512-522; and/or
- the C-terminal residue of the gp41 ectodomain is one of HIV-1 Env positions 624-705.

In some embodiments, the N-terminal residue of the recombinant gp120 protein is HIV-1 Env position 31; the C-terminal residue of the recombinant gp120 protein is HIV-1 Env position 507 or 511; the N-terminal residue of the gp41 ectodomain is HIV-1 Env position 512; and the C-terminal residue of the gp41 ectodomain is HIV-1 Env position 664. In some embodiments, the N-terminal residue of the recombinant gp120 protein is HIV-1 Env position 31; the C-terminal residue of the recombinant gp120 protein is HIV-1 Env position 507; the N-terminal residue of the gp41 ectodomain is HIV-1 Env position 512; and the C-terminal residue of the gp41 ectodomain is HIV-1 Env position 664. In some embodiments, the C-terminal residue of the recombinant HIV-1 Env ectodomain is position 683 (the entire ectodomain, terminating just before the transmembrane domain). In additional embodiments, the C-terminal residue of the recombinant HIV-1 Env ectodomain is position 707 (the entire ectodomain, terminating just after the transmembrane domain).

Stabilization of the recombinant HIV-1 Env ectodomain trimer or immunogenic fragment in the prefusion mature closed conformation prevents transition of the HIV-1 Env ectodomain to the CD4-bound open conformation. Thus, recombinant HIV-1 Env ectodomain trimers that are stabilized in this conformation can be specifically bound by an antibody that is specific for the mature closed conformation of HIV-1 Env (e.g., VRC26, PGT151, PGT122, or PGT145), but are not specifically bound by an antibody specific for the CD4-bound open conformation, of HIV-1 Env (e.g., 17b mAb in the presence of sCD4). Methods of determining if a recombinant HIV-1 Env ectodomain trimer includes a CD4-induced epitope are described, for example, in PCT App. No. PCT/US2015/048729. For example, the antibody binding assay can be conducted in the presence of a molar excess of soluble CD4 as described in Sanders et al. (*Plos Pathogens,* 9, e1003618, 2013).

In some embodiments, the recombinant HIV-1 Env trimer specifically binds to an antibody that targets the HIV-1 Env fusion peptide, such as VRC34, with a dissociation constant of less than $10^{-6}$ Molar, such as less than $10^{-7}$ Molar, less than $10^{-8}$ Molar, or less than $10^{-9}$ Molar. In some embodiments, the recombinant HIV-1 Env ectodomain trimers can be specifically bound by an antibody that specifically binds to the V1V2 domain on a HIV-1 Env trimer, but not an Env monomer. Exemplary antibodies with such antigen binding characteristics include the PGT141, PGT142, PGT143, PGT144, PGT145, and VRC26 antibodies. Additional examples include the PG9, PG16, and CH01-CH04 antibodies. Accordingly, in some embodiments the recombinant HIV-1 Env ectodomain trimer specifically binds to an antibody (such as a PGT141, PGT142, PGT143, PGT144, PGT145, and VRC26 antibody) that specifically binds to the VIV2 domain of a HIV-1 Env in its trimeric, but not monomeric, form with a dissociation constant of less than $10^{-6}$ Molar, such as less than $10^{-7}$ Molar, less than $10^{-8}$ Molar, or less than $10^{-9}$ Molar. The determination of specific binding may readily be made by using or adapting routine procedures, such as ELISA, immunocompetition, surface plasmon resonance, or other immunosorbant assays (described in many standard texts, including Greenfield, Antibodies, A Laboratory Manual, 2nd ed. Cold Spring Harbor Laboratory Press, New York (2014).

Several embodiments include a multimer of the recombinant HIV-1 Env ectodomain trimer, for example, a multimer including 2, 3, 4, 5, 6, 7, 8, 9, or 10, or more of the recombinant HIV-1 Env ectodomain trimers or immunogenic fragment thereof.

In some embodiments, the recombinant gp120 protein in the protomers of any of the disclosed HIV-1 Env ectodomain trimers disclosed herein can further include an N-linked glycosylation site at HIV-1 Env position 332 (if not already present on the ectodomain). For example, by T332N substitution in the case of BG505-based immunogens. The presence of the glycosylation site at N332 allows for binding by 2G12 antibody.

In some embodiments, the recombinant gp120 protein in the protomers of any of the disclosed HIV-1 Env ectodomain trimers disclosed herein can include a lysine residue at HIV-1 Env position 168 (if not already present on the ectodomain). For example, the lysine residue can be added by amino acid substitution (such as an E168K substitution in the case of the JR-FL based immunogens). The presence of the lysine residue at position 168 allows for binding of particular broadly neutralizing antibodies to the V1V2 loop of gp120.

Native HIV-1 Env sequences include a furin cleavage site between positions 508 and 512 (HXB2 numbering), that separates gp120 and gp41. Any of the disclosed recombinant HIV-1 Env ectodomains can further include an enhanced cleavage site between gp120 and gp41 proteins. The enhanced cleavage cite can include, for example, substitution of six arginine resides for the four residues of the native cleavage site (e.g., REKR (SEQ ID NO: 147) to RRRRRR (SEQ ID NO: 148). It will be understood that protease cleavage of the furin or enhanced cleavage site separating gp120 and gp41 can remove a few amino acids from either end of the cleavage site.

In view of the conservation and breadth of knowledge of HIV-1 Env sequences, corresponding HIV-1 Env amino acid positions between different HIV-1 Env strains and subtypes can be readily identified. The HXB2 numbering system has been developed to assist comparison between different HIV-1 amino acid and nucleic acid sequences (see, e.g., Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, NM, which is incorporated by reference herein in its entirety). The numbering of amino acid substitutions disclosed herein is made according to the HXB2 numbering system, unless context indicates otherwise.

It is understood that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques. Examples of such techniques are found in see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013, both of which are incorporated herein by reference in their entirety.

The protomers of the recombinant HIV-1 Env ectodomain trimer can include modifications of the native HIV-1 sequence, such as amino acid substitutions, deletions or insertions, glycosylation and/or covalent linkage to unrelated proteins (e.g., a protein tag), as long as the protomers can form the trimer.

In several embodiments, the recombinant HIV-1 Env ectodomain trimer is soluble in aqueous solution. In some embodiments, the recombinant HIV-1 Env ectodomain trimer dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in phosphate buffered saline (pH 7.4) at room temperature (e.g., 20-22 degrees Celsius) and remains dissolved for at least for at least 12 hours (such as at least 24 hours, at least 48 hours, at least one week, at least two weeks, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). Determining if a protein remains in solution over time can be accomplished using appropriate techniques. For example, the concentration of the protein dissolved in an aqueous solution can be tested over time using standard methods.

The recombinant HIV-1 Env ectodomain trimer can be derivatized or linked to another molecule (such as another peptide or protein). In general, the recombinant HIV-1 Env ectodomain trimer is derivatized such that the binding to broadly neutralizing antibodies to the trimer is not affected adversely by the derivatization or labeling. For example, the recombinant HIV-1 Env ectodomain trimer can be functionally linked (by chemical coupling, genetic fusion, noncovalent association or otherwise) to one or more other molecular entities, such as an antibody or protein or detection tag.

HIV-1 Env Ectodomain Trimers Linked to a Transmembrane Domain

In some embodiments, the HIV-1 Env ectodomain trimer is membrane anchored, for example, the protomers in the trimer can each be linked to a transmembrane domain. Typically, the transmembrane domain is linked to the C-terminal residue the gp41 ectodomain in the protomers of the HIV-1 Env ectodomain trimer. One or more peptide linkers (such as a gly-ser linker, for example, a 10 amino acid glycine-serine peptide linker, such as a peptide linker comprising the amino acid sequence set forth as SEQ ID NO: 149 (GGSGGGGSGG) can be used to link the transmembrane domain and gp41 ectodomain. In some embodiments a native HIV-1 Env MPER sequence can be used to link the transmembrane domain and the gp41 protein.

Non-limiting examples of transmembrane domains for use with the disclosed embodiments include the BG505 TM domain (KIFIMIVGGLIGLRIVFAVLSVIHRVR, SEQ ID NO: 150), the Influenza A Hemagglutinin™ domain (ILAIYSTVASSLVLLVSLGAISF, SEQ ID NO: 151), and the Influenza A Neuraminidase™ domain (IITIGSICMVVGIISLILQIGNIISIWVS, SEQ ID NO: 152).

The recombinant HIV-1 Env ectodomain linked to the transmembrane domain can include any of the mutations provided herein for removing N-linked glycosylation sites near the HIV-1 Env fusion peptide, or stabilizing the HIV-1 Env trimer in the prefusion mature closed conformation (or combinations thereof) as long as the recombinant HIV-1 Env ectodomain linked to the transmembrane domain retains the desired properties (e.g., the HIV-1 Env prefusion mature closed conformation).

HIV-1 Env Ectodomain Trimers Linked to a Trimerization Domain

In several embodiments, the HIV-1 Env ectodomain trimer can be linked to a trimerization domain, for example, the C-terminus of the gp41 ectodomains included in the protomers of the HIV-1 Env ectodomain trimer can be linked to the trimerization domain. The trimerization domain can promote trimerization of the three protomers of the recombinant HIV-1 Env protein. Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344:191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to the recombinant HIV-1 Env ectodomain (e.g., by linkage to the C-terminus of the gp41 polypeptide to promote trimerization of the recombinant HIV-1 protein, as long as the recombinant HIV-1 Env ectodomain retains specific binding activity for a mature closed conformation specific antibody, prefusion-specific antibody (e.g., PGT122), and/or includes a HIV-1 Env mature closed conformation.

In some examples, the protomers in the recombinant HIV-1 Env ectodomain can be linked to a T4 fibritin Foldon domain, for example, the recombinant HIV-1 Env ectodomain can include a gp41 polypeptide with a Foldon domain linked to its C-terminus. In specific examples, the T4 fibritin Foldon domain can include the amino acid sequence GYIPEAPRDGQAYVRKDGEWVLLSTF (SEQ ID NO: 153), which adopts a β-propeller conformation, and can fold and trimerize in an autonomous way (Tao et al. 1997 *Structure* 5:789-798).

Typically, the heterologous trimerization domain is positioned C-terminal to the gp41 protein. Optionally, the heterologous trimerization is connected to the recombinant HIV-1 Env ectodomain via a linker, such as an amino acid linker. Exemplary linkers include Gly or Gly-Ser linkers, such as SEQ ID NO: 149 (GGSGGGGSGG). Some embodiments include a protease cleavage site for removing the trimerization domain from the HIV-1 polypeptide, such as, but not limited to, a thrombin site between the recombinant HIV-1 Env ectodomain and the trimerization domain.

HIV-1 Env Ectodomain Trimer Protein Nanoparticles

In some embodiments a protein nanoparticle is provided that includes one or more of the disclosed HIV-1 Env fusion peptides (or portion thereof). Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. To construct such protein nanoparticles, a protomer of a disclosed HIV-1 Env ectodomain trimer can be linked (directly, or indirectly via a peptide linker) to the N-terminus of a subunit of the protein nanoparticle (such as a ferritin protein, an encapsulin protein, a SOR protein, or a lumazine synthase protein) and expressed in cells under appropriate conditions. The fusion protein self-assembles into a nanoparticle and can be purified.

In some embodiments, a protomer of any of the disclosed recombinant HIV-1 Env ectodomain trimers can be linked to a ferritin subunit to construct a ferritin nanoparticle. Examples of the ferritin subunit amino acid sequences include SEQ ID NO: 83 and 83. In some embodiments, a protomer of any of the disclosed recombinant HIV-1 Env ectodomain trimers can be linked to a ferritin subunit including an amino acid sequence at least 80% (such as at least 85%, at least 90%, at least 95%, or at least 97%) identical to amino acid sequence set forth as any one of SEQ ID NOs: 82 or 83.

In some embodiments, a protomer of any of the disclosed recombinant HIV-1 Env ectodomain trimers can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as SEQ ID NO: 84. In some embodiments, a protomer of any of the disclosed recombinant HIV-1 Env ectodomain trimers can be linked to a lumazine synthase subunit including an amino acid sequence at least 80% (such as at least 85%, at least 90%, at least 95%, or at least 97%) identical to amino acid sequence set forth as SEQ ID NO: 84.

In some embodiments, a protomer of any of the disclosed recombinant HIV-1 Env ectodomain trimers can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as SEQ ID NO: 85. In some embodiments, a protomer of any of the disclosed recombinant HIV-1 Env ectodomain trimers can be linked to an encapsulin subunit including an amino acid sequence at least 80% (such as at least 85%, at least 90%, at least 95%, or at least 97%) identical to amino acid sequence set forth as SEQ ID NO: 85.

In some embodiments, a protomer of any of the disclosed recombinant HIV-1 Env ectodomain trimers can be linked to a Sulfur Oxygenase Reductase (SOR) subunit to construct a recombinant SOR nanoparticle. In some embodiments, the SOR subunit can include the amino acid sequence set forth as SEQ ID NO: 86. In some embodiments, a protomer of any of the disclosed recombinant HIV-1 Env ectodomain trimers can be linked to a SOR subunit including an amino acid sequence at least 80% (such as at least 85%, at least 90%, at least 95%, or at least 97%) identical to amino acid sequence set forth as SEQ ID NO: 86.

SOR proteins are microbial proteins (for example from the thermoacidophilic archaeon *Acidianus ambivalens* that form 24 subunit protein assemblies. Methods of constructing SOR nanoparticles are described, for example, in Urich et al. (Science, 311:996-1000, 2006, which is incorporated by reference herein in its entirety).

For production purposes, the protomer of the recombinant HIV-1 Env ectodomain trimer can include an N-terminal signal peptide that is cleaved during cellular processing. For example, the protomer linked to the protein nanoparticle subunit can include a signal peptide at its N-terminus including, for example, a native HIV-1 Env signal peptide. The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

III. Polynucleotides and Expression

Polynucleotides encoding a disclosed immunogen are also provided. These polynucleotides include DNA, cDNA and RNA sequences which encode the antigen. The genetic code can be used to construct a variety of functionally equivalent nucleic acids, such as nucleic acids which differ in sequence but which encode the same protein sequence, or encode a conjugate or fusion protein including the nucleic acid sequence.

In several embodiments, the nucleic acid molecule encodes a precursor of a disclosed immunogen, such as an epitope scaffold protein, a subunit of a self-assembling protein nanoparticle or a protomer of a recombinant HIV-1 Env ectodomain trimer, that, when expressed in cells under appropriate conditions, is processed into the active form of the immunogen. For example, the nucleic acid molecule can encode a recombinant HIV-1 Env ectodomain including a N-terminal signal sequence for entry into the cellular secretory system that is proteolytically cleaved in the during processing of the HIV-1 Env protein in the cell. In some embodiments, the signal peptide includes the amino acid sequence set forth as residues 1-30 of SEQ ID NO: 59.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signals for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques. In some embodiments, if the host is prokaryotic, such as, but not limited to, *E. coli*, competent cells which are capable of DNA uptake can be prepared from cells harvested after exponential growth phase and subsequently treated by the $CaCl_2$ method. Alternatively, $MgCl_2$ or RbCl can be used.

Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines can be utilized.

In one non-limiting example, a disclosed immunogen is expressed using the pVRC8400 vector (described in Barouch et al., J. Virol, 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Non-limiting examples of such modifications include termination codons, a methionine added at the amino terminus to provide an initiation site, additional amino acids placed on either terminus to create conveniently located restriction sites, or additional amino acids (such as poly His) to aid in purification steps.

IV. Viral Vectors

A nucleic acid molecule encoding a disclosed immunogen can be included in a viral vector, for example, for expression of the immunogen in a host cell, or for immunization of a subject as disclosed herein. In some embodiments, the viral vectors are administered to a subject as part of a prime-boost immunization. In several embodiments, the viral vectors used in a prime-boost immunization protocol to prime an immune response to HIV-1 Env or boost an immune response to HIV-1 Env.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158:39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, Curr. Top. *Microbiol. Immunol.,* 158:91-123; On et al., 1990, *Gene,* 89:279-282), herpes viruses including HSV and EBV (Margolskee, 1992, *Curr. Top. Microbiol. Immunol.,* 158: 67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, Curr. Top. *Microbiol. Immunol.,* 158:1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed immunogen. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Replication competent and deficient adenoviral vectors (including singly and multiply replication deficient adenoviral vectors) can be used. Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/02231 1.

V. Virus-Like Particles

In some embodiments, a virus-like particle (VLP) is provided that includes a disclosed immunogen. VLPs lack the viral components that are required for virus replication and thus represent a highly attenuated, replication-incompetent form of a virus. However, the VLP can display a polypeptide (e.g., a recombinant HIV-1 Env protein) that is analogous to that expressed on infectious virus particles and should be equally capable of eliciting an immune response to HIV when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

VI. Pharmaceutical Compositions

Immunogenic compositions comprising a disclosed immunogen and a pharmaceutically acceptable carrier are also provided. Such pharmaceutical compositions can be administered to subjects by a variety of administration modes, for example, intramuscular, subcutaneous, intravenous, intra-arterial, intra-articular, intraperitoneal, or parenteral routes. In several embodiments, pharmaceutical compositions including one or more of the disclosed immunogens are immunogenic compositions. Actual methods for preparing administrable compositions are described in more detail in such publications as *Remingtons Pharmaceutical Sciences,* $19^{th}$ Ed., Mack Publishing Company, Easton, Pennsylvania, 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA) may also be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which elicits an immune response without significant, adverse side effects. In some embodiments, the composition can be provided in unit dosage form for use to elicit an immune response in a subject, for example, to prevent HIV-1 infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VII. Therapeutic Methods

The disclosed immunogens, polynucleotides and vectors encoding the disclosed immunogens, and compositions including same, can be administered to a subject to induce an immune response to HIV-1 to prevent, inhibit, and/or treat an HIV-1 infection. The immune response can be a protective immune response, for example a response that prevents or reduces subsequent infection with HIV-1. Elicitation of the immune response can also be used to treat or inhibit infection and illnesses associated with HIV-1 infection. Thus, the disclosed immunogens, polynucleotides and vectors encoding the disclosed immunogens, and compositions including same can be used in methods of preventing, inhibiting and treating an HIV-1 infection. In several embodiments, an effective amount of an immunogenic composition including one or more of the disclosed immunogens can be administered to a subject in order to generate a neutralizing immune response to HIV-1.

When inhibiting, treating, or preventing HIV-1 infection, the methods can be used either to avoid infection in an HIV-1 seronegative subject (e.g., by inducing an immune response that protects against HIV-1 infection), or to treat existing infection in an HIV-1 seropositive subject. The HIV-1 seropositive subject may or may not carry a diagnosis of AIDS. Hence in some embodiments the methods involve selecting a subject at risk for contracting HIV-1 infection, or a subject at risk of developing AIDS (such as a subject with HIV-1 infection), and administering a disclosed immunogen to the subject to elicit an immune response to HIV-1 in the subject.

Treatment of HIV-1 by inhibiting HIV-1 replication or infection can include delaying the development of AIDS in a subject. Treatment of HIV-1 can also include reducing signs or symptoms associated with the presence of HIV-1 (for example, by reducing or inhibiting HIV-1 replication). In some examples, treatment using the methods disclosed herein prolongs the time of survival of the subject.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject.

These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize HIV-1 infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The disclosed immunogens can be used in coordinate (or prime-boost) immunization protocols or combinatorial formulations. In certain embodiments, novel combinatorial immunogenic compositions and coordinate immunization protocols employ separate immunogens or formulations, each directed toward eliciting an anti-HIV-1 immune response, such as an immune response to HIV-1 Env protein. Separate immunogenic compositions that elicit the anti-HIV-1 immune response can be combined in a polyvalent immunogenic composition administered to a subject in a single immunization step, or they can be administered separately (in monovalent immunogenic compositions) in a coordinate immunization protocol.

In one embodiment, a suitable immunization regimen includes at least two separate inoculations with one or more immunogenic compositions including a disclosed immunogen, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the immunization parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that immunization is suboptimal, the subject can be boosted with an additional dose of immunogenic composition, and the immunization parameters can be modified in a fashion expected to potentiate the immune response. Thus, for example, a dose of a disclosed immunogen can be increased or the route of administration can be changed.

It is contemplated that there can be several boosts, and that each boost can be a different disclosed immunogen. It is also contemplated in some examples that the boost may be the same immunogen as another boost, or the prime.

In some embodiments, the prime comprises administration of an immunogenic conjugate as described herein, and the boost (or boosts) comprises administration of a selectively deglycosylated recombinant HIV-1 Env ectodomain trimer as described herein, or a recombinant HIV-1 Env ectodomain trimer that is stabilized in a prefusion mature closed conformation as described in PCT App. No. PCT/US2015/048729 (incorporated by reference herein in its entirety). In some embodiments, the prime comprises administration of a selectively deglycosylated recombinant HIV-1 Env ectodomain trimer as described herein, or a recombinant HIV-1 Env ectodomain trimer that is stabilized in a prefusion mature closed conformation as described in PCT App. No. PCT/US2015/048729 (incorporated by reference herein in its entirety), and the boost (or boosts) comprises administration of an immunogenic conjugate as described herein.

In some embodiments, the immunization protocol can comprise administering one:

(a) a soluble HIV-1 envelope trimer (such as a selectively deglycosylated recombinant HIV-1 Env ectodomain trimer as described herein, or a recombinant HIV-1 Env ectodomain trimer that is stabilized in a prefusion mature closed conformation as described in PCT App. No. PCT/US2015/048729) to the subject one or more times;

(b) the immunogenic conjugate according to X-L-C to the subject one or more times;

(c) the epitope scaffold protein according to X-L-S to the subject one or more times;

(d) the protein nanoparticle according to X-L-N to the subject one or more times; or (e) a combination of (a) and (b); (a) and (c); (a) and (d); (b) and (c); (b) and (d); (c) and (d); (a), (b), and (c); (a), (b), and (d); (a), (c), and (d); (b), (c), and (d); (a), (b), (c), and (d).

In some embodiments, the immunization protocol can comprise:

(A) administering the soluble HIV-1 envelope trimer to the subject one or more times, then administering the immunogenic conjugate according to X-L-C to the subject one or more times;

(B) administering the immunogenic conjugate according to X-L-C to the subject one or more times, then administering the soluble HIV-1 envelope trimer to the subject one or more times; or (C) administering the soluble HIV-1 envelope trimer to the subject one or more times, then administering the immunogenic conjugate according to X-L-C to the subject one or more times, then administering the soluble HIV-1 envelope trimer to the subject one or more times.

(D) administering the soluble HIV-1 envelope trimer to the subject one or more times, then administering the epitope scaffold protein according to X-L-S to the subject one or more times;

(E) administering the epitope scaffold protein according to X-L-S to the subject one or more times, then administering the soluble HIV-1 envelope trimer to the subject one or more times; or (F) administering the soluble HIV-1 envelope trimer to the subject one or more times, then administering the epitope scaffold protein according to X-L-S to the subject one or more times, then administering the soluble HIV-1 envelope trimer to the subject one or more times.

(G) administering the soluble HIV-1 envelope trimer to the subject one or more times, then administering the protein nanoparticle according to X-L-N to the subject one or more times;

(H) administering the protein nanoparticle according to X-L-N to the subject one or more times, then administering the soluble HIV-1 envelope trimer to the subject one or more times;

(I) administering the soluble HIV-1 envelope trimer to the subject one or more times, then administering the protein nanoparticle according to X-L-N to the subject one or more times, then administering the soluble HIV-1 envelope trimer to the subject one or more times; or (J) co-administering the soluble HIV-1 envelope trimer and the immunogenic conjugate according to X-L-C to the subject two or more times;

(J) co-administering the soluble HIV-1 envelope trimer and the epitope scaffold protein according to X-L-S to the subject two or more times;

(J) co-administering the soluble HIV-1 envelope trimer and the protein nanoparticle according to X-L-N to the subject two or more times;

(J) co-administering the soluble HIV-1 envelope trimer and the immunogenic conjugate according to X-L-C to the subject one or more times; then administering the soluble HIV-1 envelope trimer to the subject one or more times;

(J) co-administering the soluble HIV-1 envelope trimer and the epitope scaffold protein according to X-L-S to the subject one or more times; then administering the soluble HIV-1 envelope trimer to the subject one or more times; or (J) co-administering the soluble HIV-1 envelope trimer and the protein nanoparticle according to X-L-N to the subject one or more times; then administering the soluble HIV-1 envelope trimer to the subject one or more times.

In any of the above embodiments, the soluble HIV-1 envelope trimer can comprise protomers comprising the amino acid sequence of one of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In any of the above embodiments, the immunogenic conjugate according to X-L-C can be FP8-TT or FP8-CRm197.

In a non-limiting example, the immunization protocol comprises one or more (such as 2, 3, or 4) administrations of an immunogenic conjugate comprising any of the recited X polypeptides (such as AVGIGAVF, residues 1-8 of SEQ ID NO: 1) conjugated to KLH, wherein the X polypeptide is conjugated to KLH by a linker between a lysine residue on the KLH and a heterologous cysteine residue fused to a C-terminal residue of the X polypeptide; followed by one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In a non-limiting example, the immunization protocol comprises one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide; followed by one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In a non-limiting example, the immunization protocol comprises one or more (such as 2, 3, or 4) administrations of an immunogenic conjugate comprising any of the recited X polypeptides (such as AVGIGAVF, residues 1-8 of SEQ ID NO: 1) conjugated to tetanus toxoid, wherein the X polypeptide is conjugated to tetanus toxoid by a linker between a lysine residue on the tetanus toxoid and a heterologous cysteine residue fused to a C-terminal residue of the X polypeptide; followed by one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In a non-limiting example, the immunization protocol comprises one or more (such as 2, 3, or 4) administrations of an immunogenic conjugate comprising any of the recited X polypeptides (such as AVGIGAVF, residues 1-8 of SEQ ID NO: 1) conjugated to tetanus toxin heavy chain C fragment, wherein the X polypeptide is conjugated to tetanus toxin heavy chain C fragment by a linker between a lysine residue on the tetanus toxin heavy chain C fragment and a heterologous cysteine residue fused to a C-terminal residue of the X polypeptide; followed by one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to KLH, wherein the X polypeptide is conjugated to KLH by a linker between a lysine residue on the KLH and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid, wherein the X polypeptide is conjugated to tetanus toxoid by a linker between a lysine residue on the tetanus toxoid and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid heavy chain C fragment, wherein the X polypeptide is conjugated to tetanus toxoid heavy chain C fragment by a linker between a lysine residue on the tetanus toxoid heavy chain C fragment and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to KLH, wherein the X polypeptide is conjugated to KLH by a linker between a lysine residue on the KLH and a heterologous cysteine residue fused to a C-terminal residue of the X polypeptide; followed by one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158).

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide; In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid, wherein the X polypeptide is conjugated to tetanus toxoid by a linker between a lysine residue on the tetanus toxoid and a heterologous cysteine residue fused to a C-terminal residue of the X polypeptide; In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid heavy chain C fragment, wherein the X polypeptide is conjugated to tetanus toxoid heavy chain C fragment by a linker between a lysine residue on the tetanus toxoid heavy chain C fragment and a heterologous cysteine residue fused to a C-terminal residue of the X polypeptide. In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to diphtheria toxin variant CRM197, wherein the X polypeptide is conjugated to diphtheria toxin variant CRM197 by a linker between a lysine residue on the diphtheria toxin variant CRM197 and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid, wherein the X polypeptide is conjugated to tetanus toxoid by a linker between a lysine residue on the tetanus toxoid and a heterologous cysteine residue fused to a C-terminal residue of the X polypeptide.

In a non-limiting example, the immunization protocol comprises one or more (such as 2 or 3) administrations of a recombinant HIV-1 Env ectodomain trimer comprising protomers comprising the amino acid sequence of CH505.SOSIP-DS degly4 (SEQ ID NO: 145), CH505.SOSIP-DS degly3 (SEQ ID NO: 146), BG505.SOSIP-DS degly4 (SEQ ID NO: 156), BG505.SOSIP-DS degly3 (SEQ ID NO: 157), or a BG505 or CH505 Env ectodomain trimer comprising the SOSIP substitutions and the non-natural disulfide bond between cysteine substitutions at HIV-1 Env positions 201 and 433 to stabilize the recombinant HIV-1 Env ectodomain trimer in a prefusion mature closed conformation (such as trimers with protomers set forth as SEQ ID NOs: 155 or 158); followed by one or more (such as 2, 3, or 4) administrations of an immunogenic conjugate comprising any of the recited X polypeptides (such as AVGIGAVF, residues 1-8 of SEQ ID NO: 1) conjugated to tetanus toxoid heavy chain C fragment, wherein the X polypeptide is conjugated to tetanus toxoid heavy chain C fragment by a linker between a lysine residue on the tetanus toxoid heavy chain C fragment and a heterologous cysteine residue fused to a C-terminal residue of the X polypeptide.

The prime and the boost can be administered as a single dose or multiple doses, for example, two doses, three doses, four doses, five doses, six doses or more can be administered to a subject over days, weeks or months. Multiple boosts can also be given, such one to five, or more. Different dosages can be used in a series of sequential inoculations. For example, a relatively large dose in a primary inoculation and then a boost with relatively smaller doses. The immune response against the selected antigenic surface can be generated by one or more inoculations of a subject.

In several embodiments, a disclosed immunogen can be administered to the subject simultaneously with the administration of an adjuvant. In other embodiments, the immunogen can be administered to the subject after the administration of an adjuvant and within a sufficient amount of time to elicit the immune response.

Determination of effective dosages in this context is typically based on animal model studies followed up by human clinical trials and is guided by administration protocols that significantly reduce the occurrence or severity of targeted disease symptoms or conditions in the subject, or that elicit a desired response in the subject (such as a neutralizing immune response). Suitable models in this regard include, for example, murine, rat, porcine, feline, ferret, non-human primate. Alternatively, effective dosages can be determined using in vitro models (for example, immunologic and histopathologic assays). Using such models, only ordinary calculations and adjustments are required to determine an appropriate concentration and dose to administer an effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, trans-epidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A non-limiting range for an effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 μg, for example, a dosage of about 1, 2, 3, 4, 5, 6, 7, 8, 9, 10, 15, 20, 30, 40, 50, 60, 70, 80, 90, 100, 150, 200, 250, or about 300 μg.

The dosage and number of doses will depend on the setting, for example, in an adult or anyone primed by prior HIV-1 infection or immunization, a single dose may be a sufficient booster. In naïve subjects, in some examples, at least two doses would be given, for example, at least three doses. In some embodiments, an annual boost is given, for example, along with an annual influenza vaccination.

For any application, treatment with a disclosed immunogen can be combined with anti-retroviral therapy, such as HAART. Antiretroviral drugs are broadly classified by the phase of the retrovirus life-cycle that the drug inhibits. The therapeutic agents can be administered before, during, concurrent to and/or after retroviral therapy. In some embodiments, the therapeutic agents are administered following a course of retroviral therapy. The disclosed therapeutic agents can be administered in conjunction with nucleoside and nucleotide reverse transcriptase inhibitors (nRTI), non-nucleoside reverse transcriptase inhibitors (NNRTI), protease inhibitors, Entry inhibitors (or fusion inhibitors), Maturation inhibitors, or a broad spectrum inhibitors, such as natural antivirals. Exemplary agents include lopinavir, ritonavir, zidovudine, lamivudine, tenofovir, emtricitabine and efavirenz.

HIV-1 infection does not need to be completely eliminated or reduced or prevented for the methods to be effective. For example, elicitation of an immune response to HIV-1 with one or more of the disclosed immunogens can reduce or inhibit HIV-1 infection by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 infected cells), as compared to HIV-1 infection in the absence of the therapeutic agent. In additional examples, HIV-1 replication can be reduced or inhibited by the disclosed methods. HIV-1 replication does not need to be completely eliminated for the method to be effective. For example, the immune response elicited using one or more of the disclosed immunogens can reduce HIV-1 replication by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 replication), as compared to HIV-1 replication in the absence of the immune response.

To successfully reproduce itself, HIV-1 must convert its RNA genome to DNA, which is then imported into the host cell's nucleus and inserted into the host genome through the action of HIV-1 integrase. Because HIV-1's primary cellular target, CD4+ T-Cells, can function as the memory cells of the immune system, integrated HIV-1 can remain dormant for the duration of these cells' lifetime. Memory T-Cells may survive for many years and possibly for decades. This latent HIV-1 reservoir can be measured by co-culturing CD4+ T-Cells from infected patients with CD4+ T-Cells from uninfected donors and measuring HIV-1 protein or RNA (See, e.g., Archin et al., *AIDS,* 22:1131-1135, 2008). In some embodiments, the provided methods of treating or inhibiting HIV-1 infection include reduction or elimination of the latent reservoir of HIV-1 infected cells in a subject. For example, a reduction of at least 10%, at least 20%, at least 50%, at least 60%, at least 70%, at least 80%, at least 90%, at least 95%, at least 98%, or even at least 100% (elimination of detectable HIV-1) of the latent reservoir of HIV-1 infected cells in a subject, as compared to the latent reservoir of HIV-1 infected cells in a subject in the absence of the treatment with one or more of the provided immunogens.

Following immunization of a subject, serum can be collected from the subject at appropriate time points, frozen, and stored for neutralization testing. Methods to assay for neutralization activity and include, but are not limited to, plaque reduction neutralization (PRNT) assays, microneutralization assays, flow cytometry based assays, single-cycle infection assays (e.g., as described in Martin et al. (2003) *Nature Biotechnology* 21:71-76), and pseudovirus neutralization assays (e.g., as described in Georgiev et al. (Science, 340, 751-756, 2013), Seaman et al. (J. Virol., 84, 1439-1452, 2005), and Mascola et al. (J. Virol., 79, 10103-10107, 2005), each of which is incorporated by reference herein in its entirety. In some embodiments, the serum neutralization activity can be assayed using a panel of HIV-1 pseudoviruses as described in Georgiev et al., Science, 340, 751-756, 2013 or Seaman et al. J. Virol., 84, 1439-1452, 2005. Briefly, pseudovirus stocks are prepared by co-transfection of 293T cells with an HIV-1 Env-deficient backbone and an expression plasmid encoding the Env gene of interest. The serum to be assayed is diluted in Dulbecco's modified Eagle medium-10% FCS (Gibco®) and mixed with pseudovirus. After 30 min, 10,000 TZM-bl cells are added, and the plates are incubated for 48 hours. Assays are developed with a luciferase assay system (Promega®, Madison, WI), and the relative light units (RLU) are read on a luminometer (Perkin-Elmer®, Waltham, MA). To account for background, a cutoff of $ID_{50}$≥40 can be used as a criterion for the presence of serum neutralization activity against a given pseudovirus.

In some embodiments, administration of an effective amount of one or more of the disclosed immunogen to a subject (e.g., by a prime-boost administration of a DNA vector encoding a disclosed immunogen (prime) followed by a protein nanoparticle including a disclosed immunogen (boost)) elicits a neutralizing immune response in the subject, wherein serum from the subject neutralizes, with an $ID_{50}$≥40, at least 10% (such as at least 15%, at least 20%, at least 30%, at least 40%, at least 50%, or at least 70%) of pseudoviruses is a panel of pseudoviruses including the HIV-1 Env proteins listed in Table S5 or Table S6 of Georgiev et al. (Science, 340, 751-756, 2013), or Table 1 of Seaman et al. (J. Virol., 84, 1439-1452, 2005).

One approach to administration of nucleic acids is direct immunization with plasmid DNA, such as with a mammalian expression plasmid. Immunization by nucleic acid constructs is taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, Immunol. Today 12:383, 1991). Doses of antigen as low as 1 g encapsulated in ISCOMS™ have been found to produce Class I mediated CTL responses (Takahashi et al., Nature 344:873, 1990).

In some embodiments, a plasmid DNA vaccine is used to express a disclosed immunogen in a subject. For example, a nucleic acid molecule encoding a disclosed immunogen can be administered to a subject to elicit an immune response to HIV-1 gp120. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed immunogen (such as a protomer of a HIV-1 Env ectodomain trimer) can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed immunogen (such as a protomer of a HIV-1 Env ectodomain trimer) is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

EXAMPLES

The following examples are provided to illustrate particular features of certain embodiments, but the scope of the claims should not be limited to those features exemplified.

Example 1. Vaccine Elicitation of Fusion Peptide-Directed Antibodies that Neutralize HIV-1

This example shows that focusing the immune response to the exposed N-terminal residues of the Env-fusion peptide elicits monoclonal antibodies in mice capable of neutralizing up to 31% of a cross-clade panel of 208 HIV-1 isolates. Crystal and cryo-EM structures of elicited antibodies, in complexes with fusion peptide and Env trimer, respectively, revealed diversity in target-site conformation, which likely played a crucial role in eliciting cross-clade neutralizing antibodies. These data show that the fusion peptide of HIV-1 Env is a vaccine target for eliciting broadly reactive neutralizing antibodies.

Since crossing from chimpanzees ~100 years ago, HIV-1 has evolved to be one of the most diverse viruses to infect humans, and—with over 40 million people currently infected—the global diversity of HIV-1 continues to rise. While antibodies capable of neutralizing ~50% of circulating HIV-1 strains arise in half those infection, the vaccine elicitation of antibodies capable of neutralizing divergent strains of HIV-1 remains an unsolved problem: antibodies elicited by the best current vaccine regimes in standard vaccine-test species generally fail to neutralize more than a small fraction of the primary isolates that typify transmitted strains of HIV-1.

Antibody identification has been coupled with structural characterization to delineate sites of Env vulnerable to broadly neutralizing antibody. Dozens of structurally defined epitopes have been determined that can be categorized into a handful of Env regions. Virtually all involve sites of vulnerability that appear less than optimal for elicitation by immunization, including the CD4-binding site (Chen et al. (2009) Science 326, 1123-1127), where extensive somatic hypermutation (SHM) appears to be required (Scheid et al. (2011) Science 333, 1633-1637; Wu et al. (2010) Science 329, 856-861; Wu et al. (2011) Science 333, 1593-1602), a quaternary site at the trimer apex (Doria-Rose et al. (2014) Nature 509, 55-62; Gorman et al. (2016) Nat Struct Mol Biol 23, 81-90; McLellan et al. (2011) Nature 480, 336-343; Walker et al. (2009) Science 326, 285-289), where unusual recombination appears to be required (Andrabi et al. (2015) Immunity 43, 959-973; Briney et al. (2012) PLoS One 7, e36750; Doria-Rose et al. (2014) Nature 509, 55-62; Gorman et al. (2016) Nat Struct Mol Biol 23, 81-90), a glycan-V3 supersite (Kong et al. (2013) Nat Struct Mol Biol 20, 796-803; Pejchal et al. (2011) Science 334, 1097-1103; Walker et al. (2011) Nature 477, 466-470), where antibodies appear to require co-recognition of peptide and N-linked glycan (Garces et al. (2015) Immunity 43, 1053-1063; Kong et al. (2013) Nat Struct Mol Biol 20, 796-803; Pejchal et al. (2011) Science 334, 1097-1103), and the membrane-proximal external region (Huang et al. (2012) Nature 491, 406-412; Muster et al. (1994) J Virol 68, 4031-4034; Muster et al. (1993) J Virol 67, 6642-6647; Stiegler et al. (2001) AIDS Res Hum Retroviruses 17, 1757-1765), where antibodies appear to require co-recognition of membrane (Irimia et al. (2016) Immunity 44, 21-31; Ofek et al. (2010) J Virol 84, 2955-2962; Ofek et al. (2004) J Virol 78, 10724-10737) and are subjected to immune tolerance (Haynes et al. (2005) Hum Antibodies 14, 59-67).

Antibody N123-VRC34.01 (Kong et al. (2016b) Science 352, 828-833) is named for donor (N123), lineage (VRC34) and clone number (01), and hereafter referenced without the donor prefix. VRC34.01 targets primarily the conserved N-terminal region of the HIV-1-fusion peptide (FP), a critical component of the HIV-1 type 1 fusion machinery, the hydrophobic harpoon cast into the target cell membrane by prefusion to postfusion rearrangements (Carr and Kim. (1993) Cell 73, 823-832). FP had been thought to be poorly immunogenic: hidden from the immune system in the prefusion state and buried in membrane in the postfusion state.

VRC34.01 directs the majority of its binding energy to the N-terminal residues of FP, with the rest coming from interactions with Env including glycan N88 (Kong et al. (2016b) Science 352, 828-833). By contrast, other FP-interacting antibodies such as CHO7, PGT151, and ACS202 do not show tight FP binding. The ability to neutralize HIV-1 through recognition of a linear peptide, which is both conserved in sequence and exposed in the prefusion-closed conformation of Env, suggests that the VRC34.01 epitope might be amenable to epitope-focusing approaches of vaccine elicitation. In this example, two rounds of iterative structure-based vaccine design were employed to elicit FP-directed antibodies of promising breadth. Beginning with the epitope of VRC34.01, immunogens were engineered with antigenic specificity for FP-directed antibodies, immunized C57BL/6 mice, and analyzed the resultant $1^{st}$-generation antibodies; based on this analysis, $2^{nd}$-generation immunogens and immunization regimes were devised. The resultant $2^{nd}$-generation antibodies showed neutralizing breadths that begin to approach the level achieved by naturally elicited broadly neutralizing antibodies. The results achieve a key breakthrough, the vaccine elicitation of antibodies in a standard vaccine-test species capable of neutralizing a substantial fraction of the diverse neutralization resistant strains of HIV-1 that typify natural transmission.

Fusion Peptide Antigens and Their Antigenic Assessment

Figure 8B:
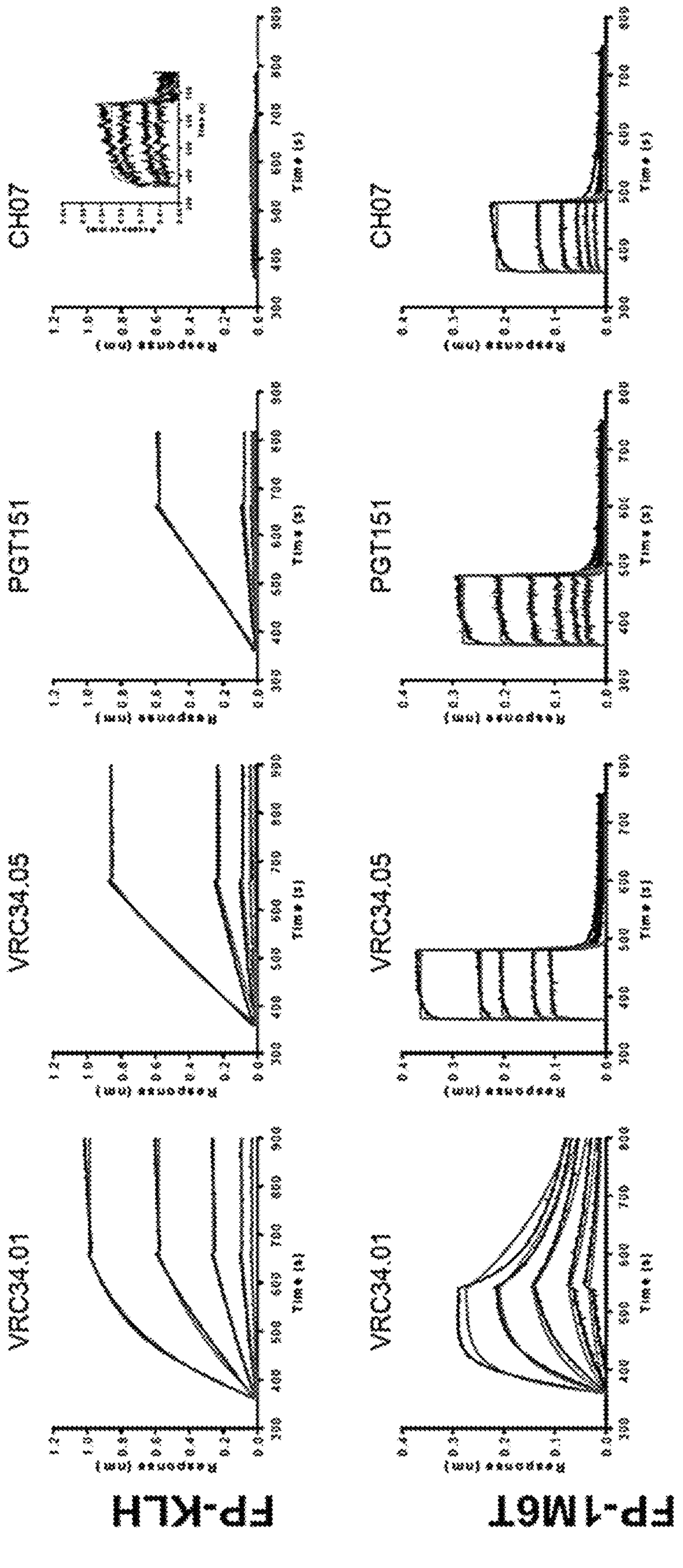

The N-terminal eight residues of FP were chosen as an initial vaccine target. To focus the immune response, structure-based design was utilized to engineer FP-containing immunogens and to assess their antigenic specificity against a panel of antibodies encompassing both broadly neutralizing antibodies and poorly or non-neutralizing antibodies (with an emphasis on antibodies reported to engage FP as part of their recognized epitope) (FIG. 1). An antigenicity score was used to estimate the epitope-specific antigenic suitability of each immunogen (FIGS. 8A-8C).

Figure 8E:
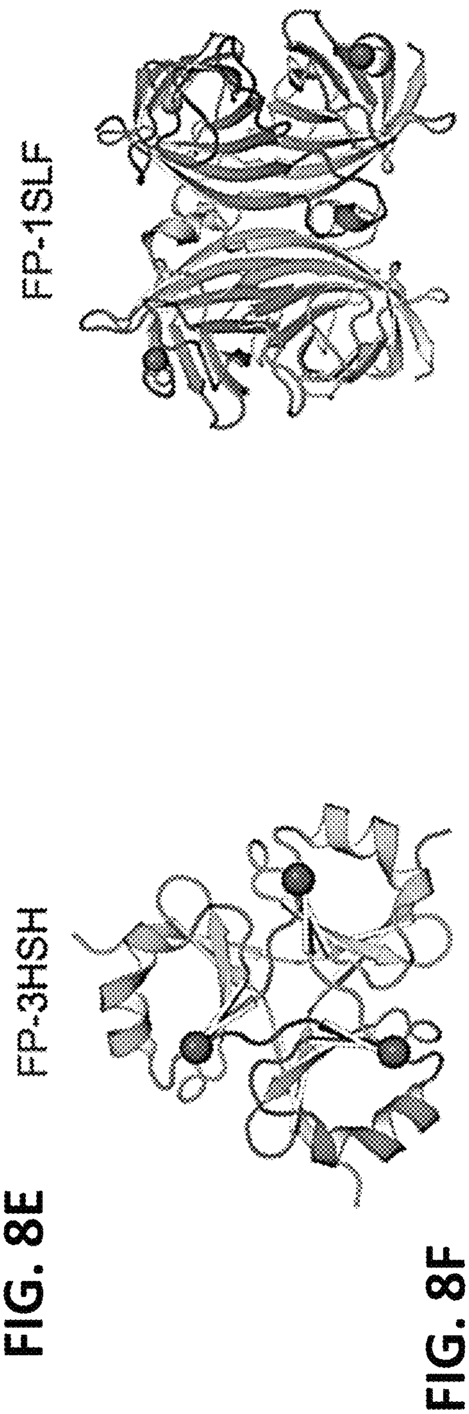
Figure 8F:
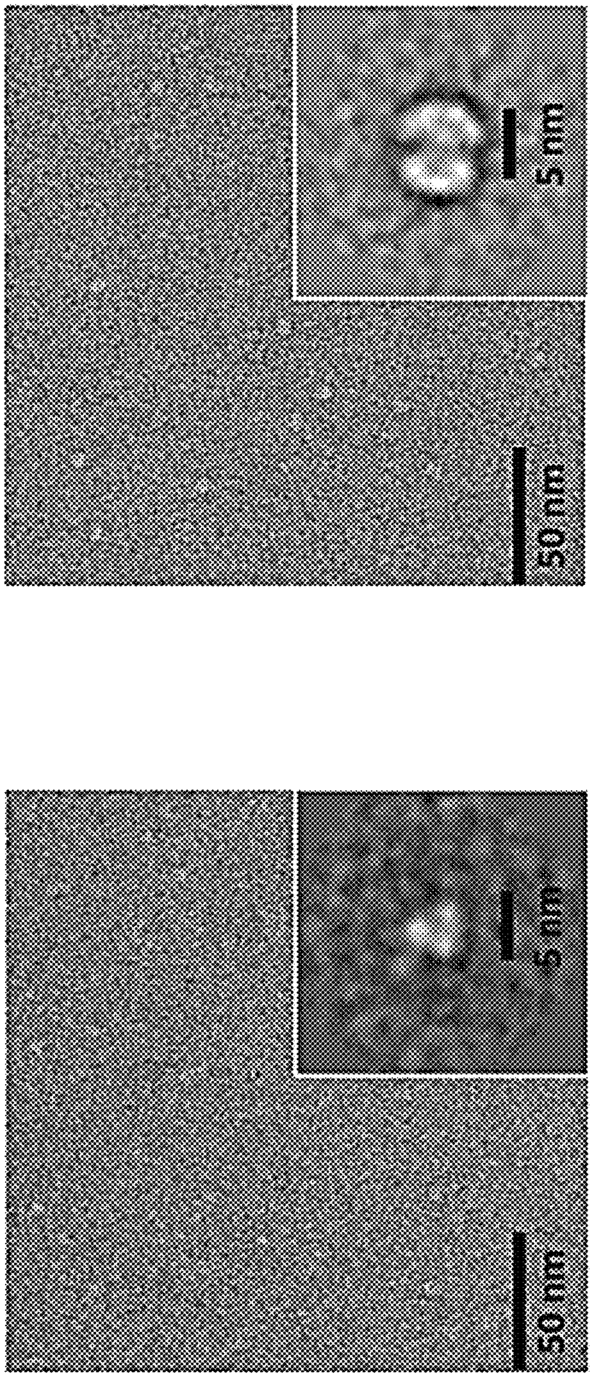

Epitope scaffolds incorporated the N-terminal 8 amino acids of FP, and in some cases, included added sites of N-linked glycosylation, which were positioned analogously to FP and glycan N88 in the VRC34.01 epitope. Initial assessment of these epitope scaffolds involved ELISA screening in a 96-well format. Two scaffolds based on proteins deposited as PDB 3HSH (Boudko et al. (2009) J Mol. Biol. 392, 787-802), and 1SLF (Tan et al. (2002) J cell biol 159, 373-382), which were trimeric and tetrameric, respectively (FIGS. 8D-8F) were further characterized. Epitope scaffolds engineered from proteins deposited as PDB 1M6T (Chu et al. (2002) J Mol. Biol. 323, 253-262) and from PDB 1Y12 (Mougous et al. (2006) Science 312, 1526-1530) were also assessed.

An FP-carrier protein conjugate was also created, by coupling the eight N-terminal residues of FP with an appended C-terminal cysteine to lysine residues in keyhole limpet hemacyanin (KLH). The resultant FP-KLH was stable to extremes of temperature and osmolality, and at pH 10.0, but not at pH 3.5. Negative stain-EM revealed the FP conjugated KLH to retain the barrel shape of KLH (FIGS. 8G, 8H). When assessed with the FP-antigenicity score (FIG. 1), FP-KLH showed antigenicity superior to that of the FP-epitope scaffolds and similar to that of the stabilized Env trimers, such as the SOSIP.664 (Sanders et al. (2013) PLoS pathogens 9, e1003618) or DS-SOSIP (Kwon et al. (2015) Nat Struct Mol Biol 22, 522-53) trimers from the clade A strain BG505.

Figure 2A:
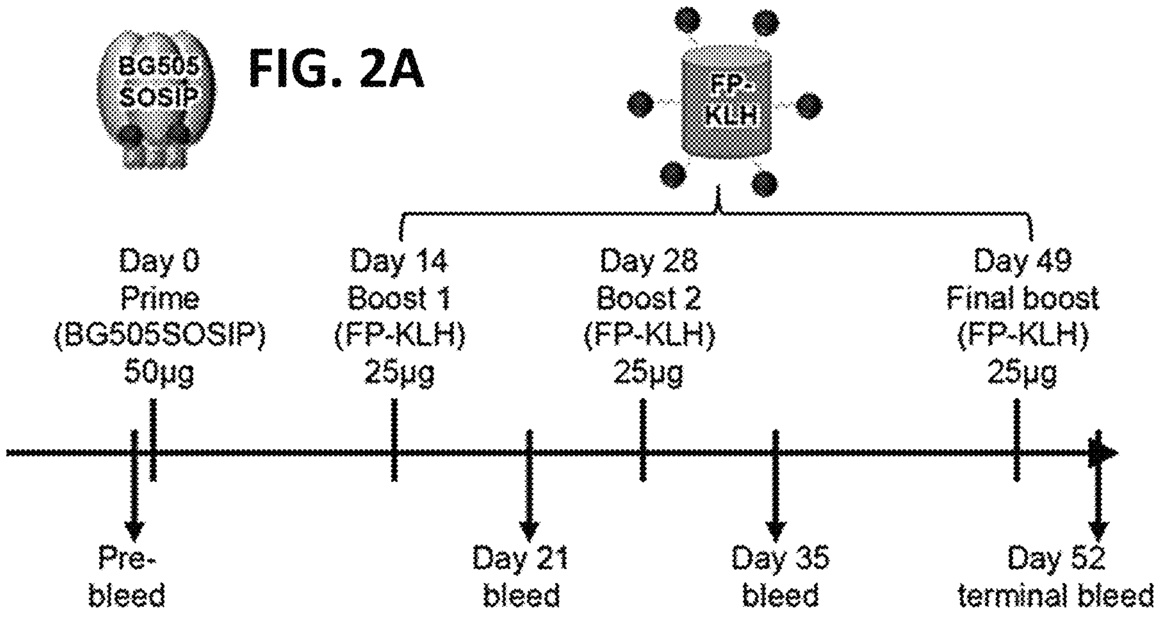
FIGS. 2A-2D. Immunogenicity of $1^{st}$-generation FP Immunogens.
Figure 2B:
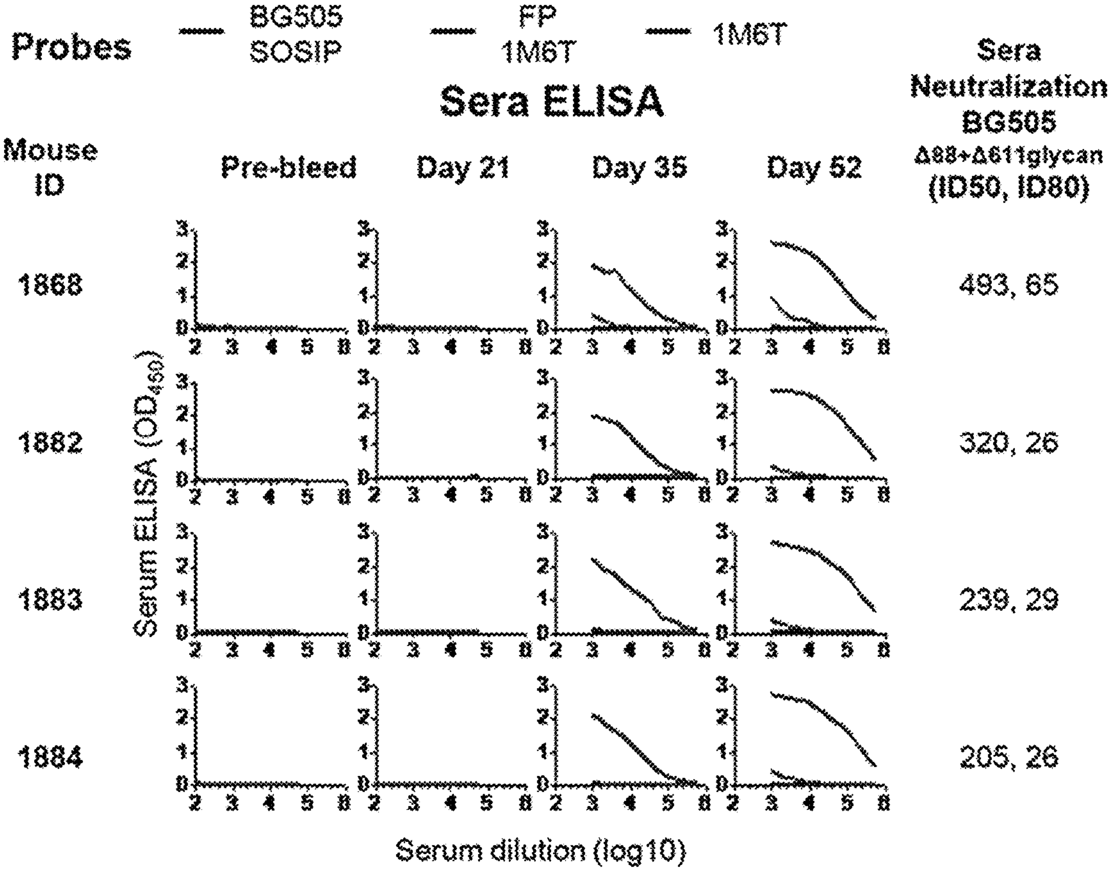

Immunogens with High FP-Antigenic Specificity Induce FP-Directed Neutralizing Responses To assess the ability of these $1^{st}$-generation FP-containing immunogens to elicit neutralizing responses, two immunization regimens were tested using the two immunogens with the highest FP-antigenicity scores: FP-KLH and stabilized Env trimer. For the first regimen, four C57BL/6 mice each received 50 µg of BG505 SOSIP Env trimer and were boosted with 25 µg of FP-KLH at day 14 (FIG. 2A). After a second boost at day 28, strong fusion peptide-ELISA responses were observed at day 35. Day 52 serum was tested for neutralization of the Env-pseudovirus BG505, and also of BG505 Env variants missing glycans at positions 88 or 611, as these viral variants are more sensitive to fusion peptide-directed antibodies (Kong et al. (2016b) Science 352, 828-833). While sera neutralization of wild-type BG505 generally did not pass our $ID_{50}$ threshold for neutralization (at least 1:40 and at least 2-fold the level of MuLv), unambiguous neutralization for the A88+611 glycan-deleted variant of BG505 was observed with all four of the mice (FIGS. 2B and 9A).

Figure 2C:
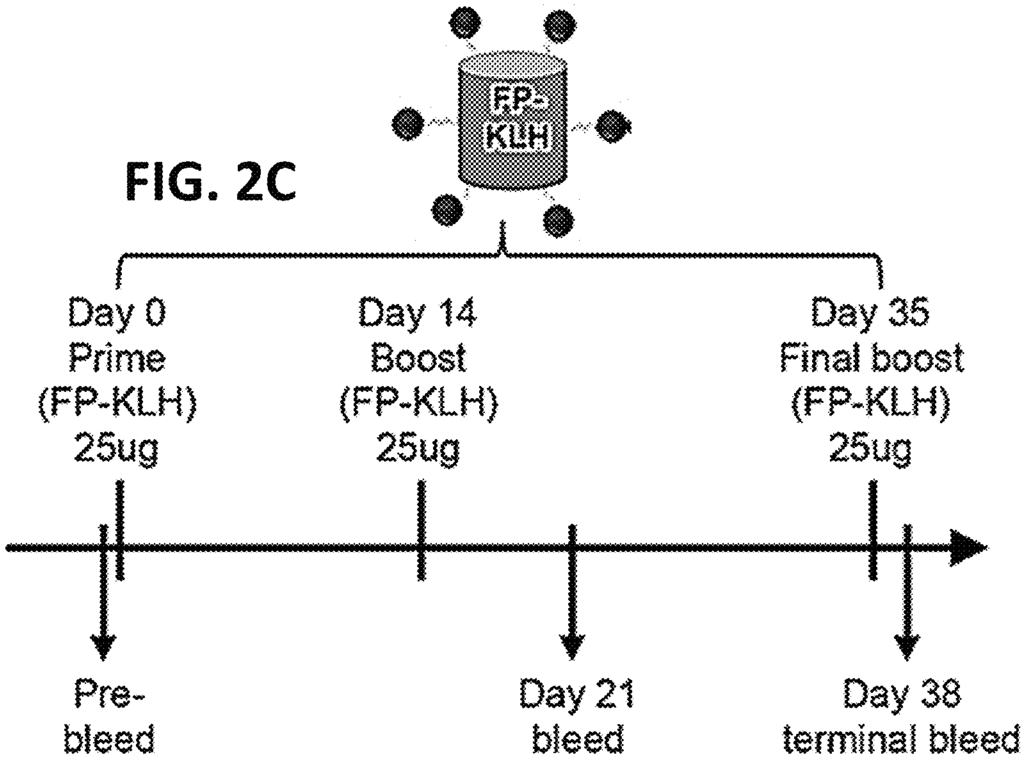
Figure 2D:
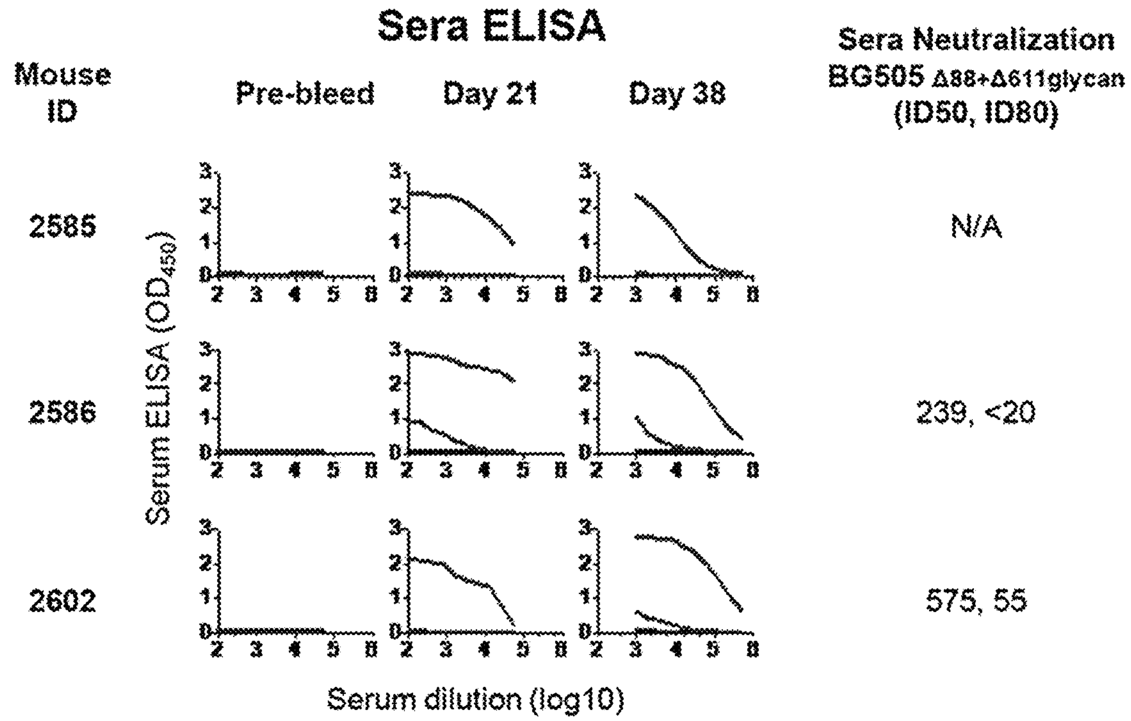

For the second regimen, three mice each received 25 µg of FP-KLH, followed by boosts at day 14 and day 35 (FIG. 2C). Serum ELISAs revealed Env trimer recognition in mouse 2586 at days 21 and 38, which also appeared in a second mouse after the third boost. Day 38 serum was tested and neutralization for the A88+611 glycan-deleted variant of BG505 was observed with two of the mice (FIGS. 2D and 9A).

First Generation vFP-Directed Antibodies Neutralize Up to 10% of HIV-1 Strains

Figure 3B:
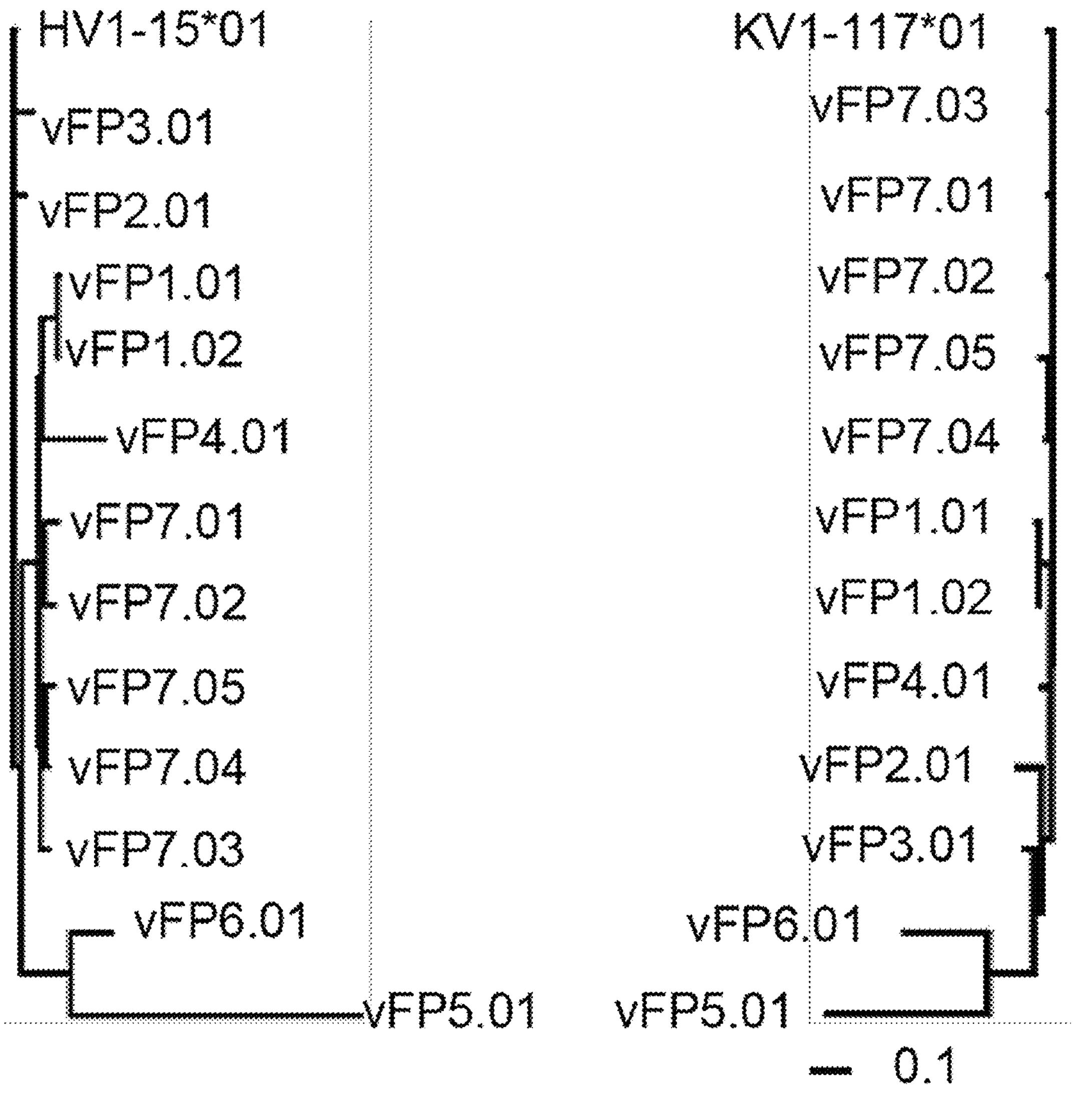

To provide insight into the antibodies elicited by FP-containing immunogens, hybridomas capable of binding both the BG505 SOSIP trimer and the FP-1M6T epitope scaffold from mouse 1868 (immunized with Env trimer and FP-KLH) and mouse 2586 (immunized with FP-KLH only) were selected. Sequences of eight hybridomas from mouse 1868 and five hybridomas from mouse 2586 revealed seven antibody lineages (vFP1-vFP7), which segregated into three classes, each with a defined mode of recognition and similar B cell pathway of development; the classes were named vFP1, vFP5, and vFP6, after the first identified member of each class (FIG. 3A).

Figure 3C:
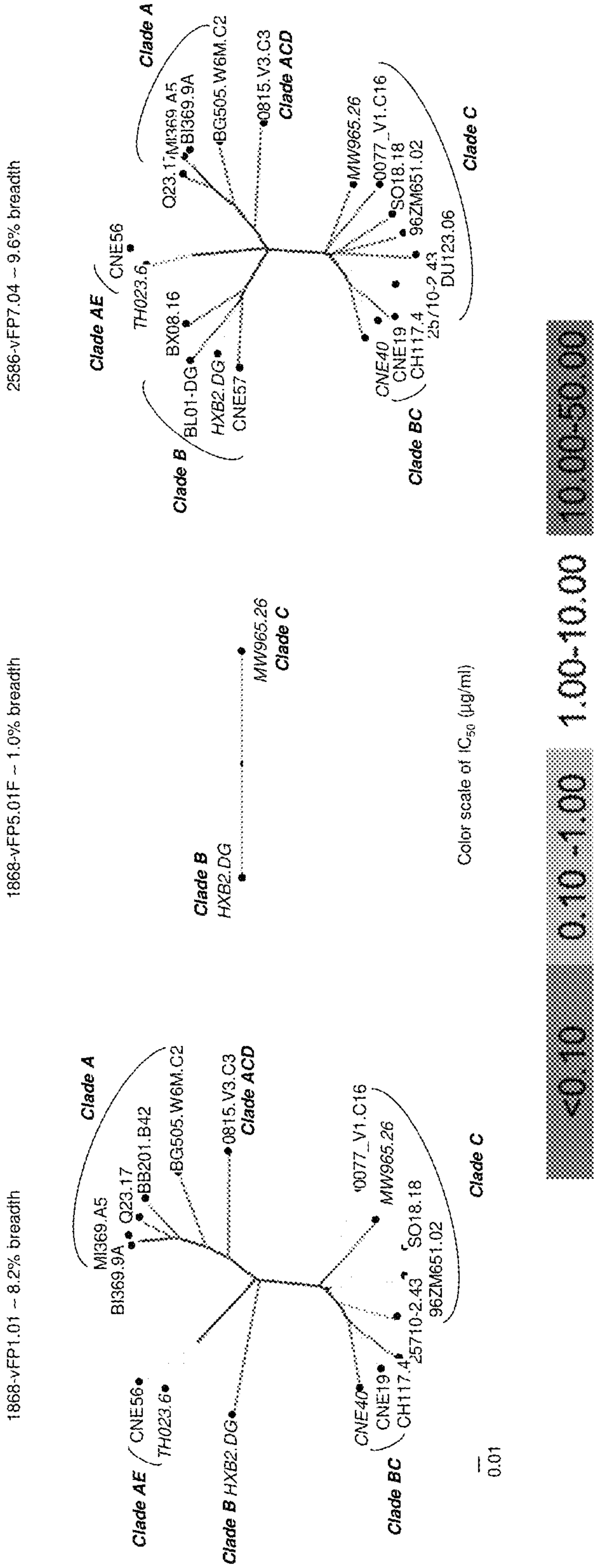
Figure 9C:
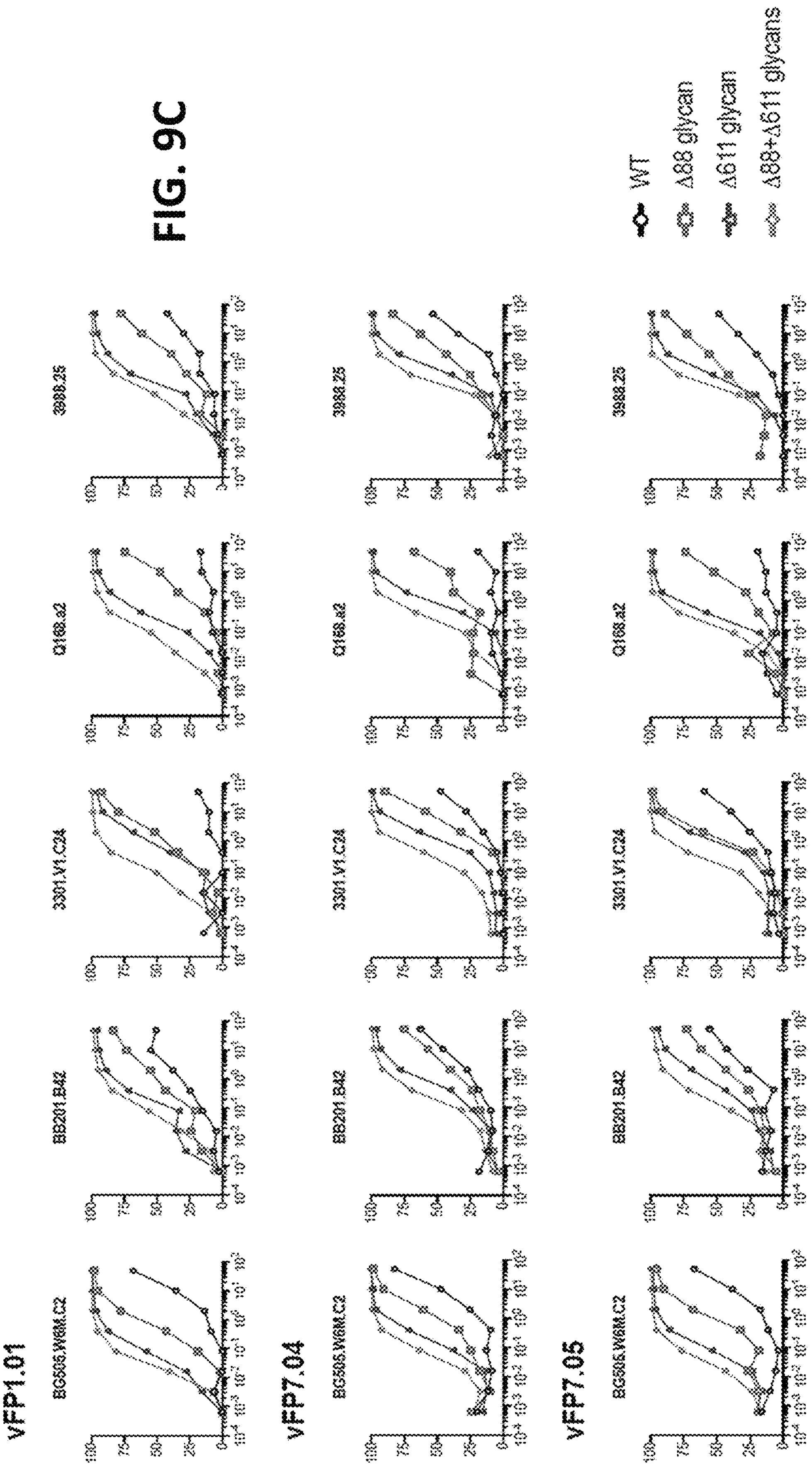

Neutralization for the 12 vFP antibodies was tested on a panel of wild-type and glycan-deleted HIV-1 variants. Clear neutralization of wild-type HIV-1 strains was observed with only a few of the vFP1-class antibodies (vFP1.01, vFP7.04 and vFP7.05), while the other vFP antibodies failed to neutralize or only neutralized glycan-deleted viruses (FIGS. 9B-9C). To characterize neutralization further, the three best vFP1 antibodies along with antibody vFP5.01 were assessed on a 208-isolate panel (Seaman et al. (2010) J Virol 84, 1439-1452), encompassing diverse viruses from all of the major clades (FIG. 3C). Notably, vFP1.01 and vFP7.05 both neutralized 18 strains at 50 µg/ml (8.2% breadth), while vFP7.04 neutralized 20 strains at 50 µg/ml (9.6% breadth). vFP5.01, by contrast, neutralized only two strains, both tier 1 isolates. Overall, neutralization was sparse and of less than optimal potency, although the best vFP antibodies did neutralize selected strains of diverse HIV-1.

Disparate Antibody-Bound FP Conformations

Figure 4B:
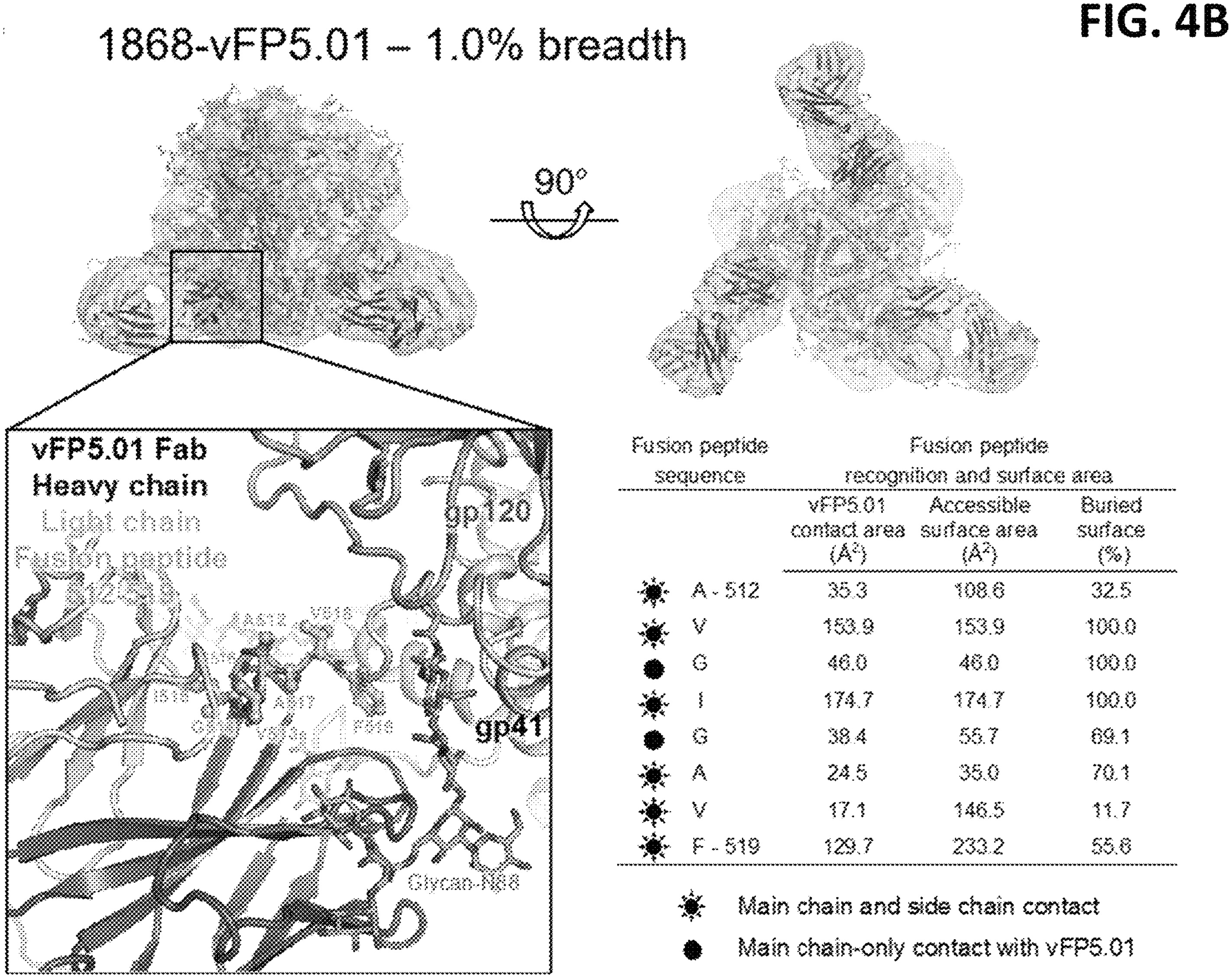
Figure 10A:
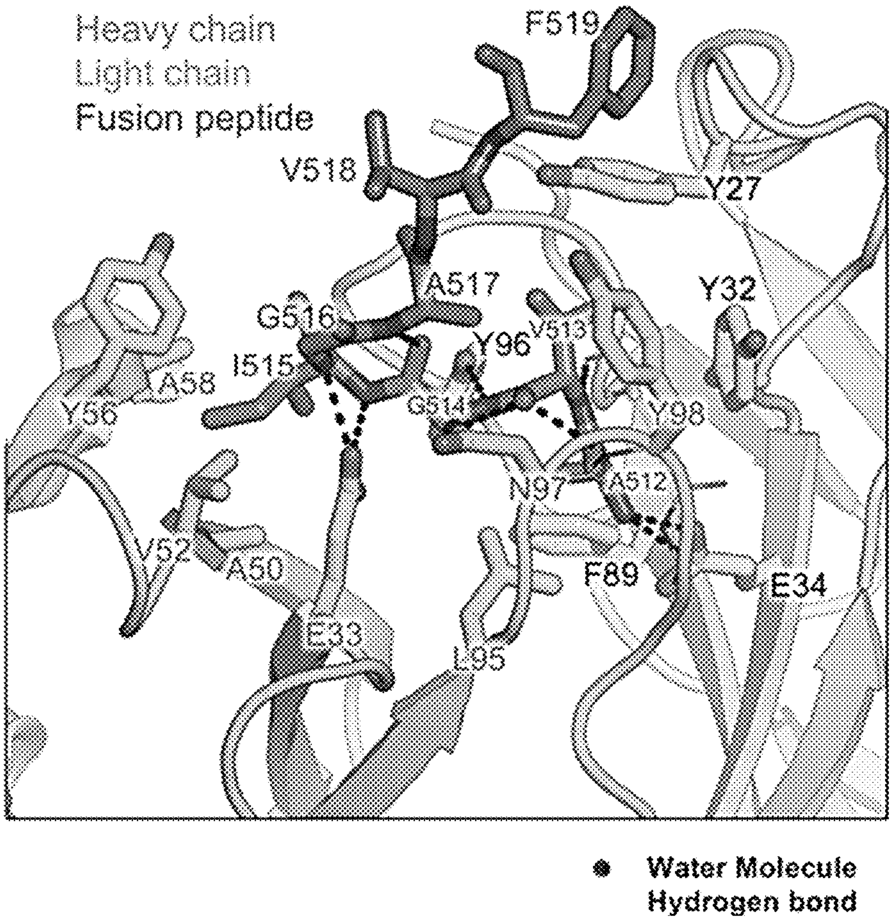
FIG. 10A-10H. Structural details of FP-conformational diversity and recognition by antibody.
Figure 10B:
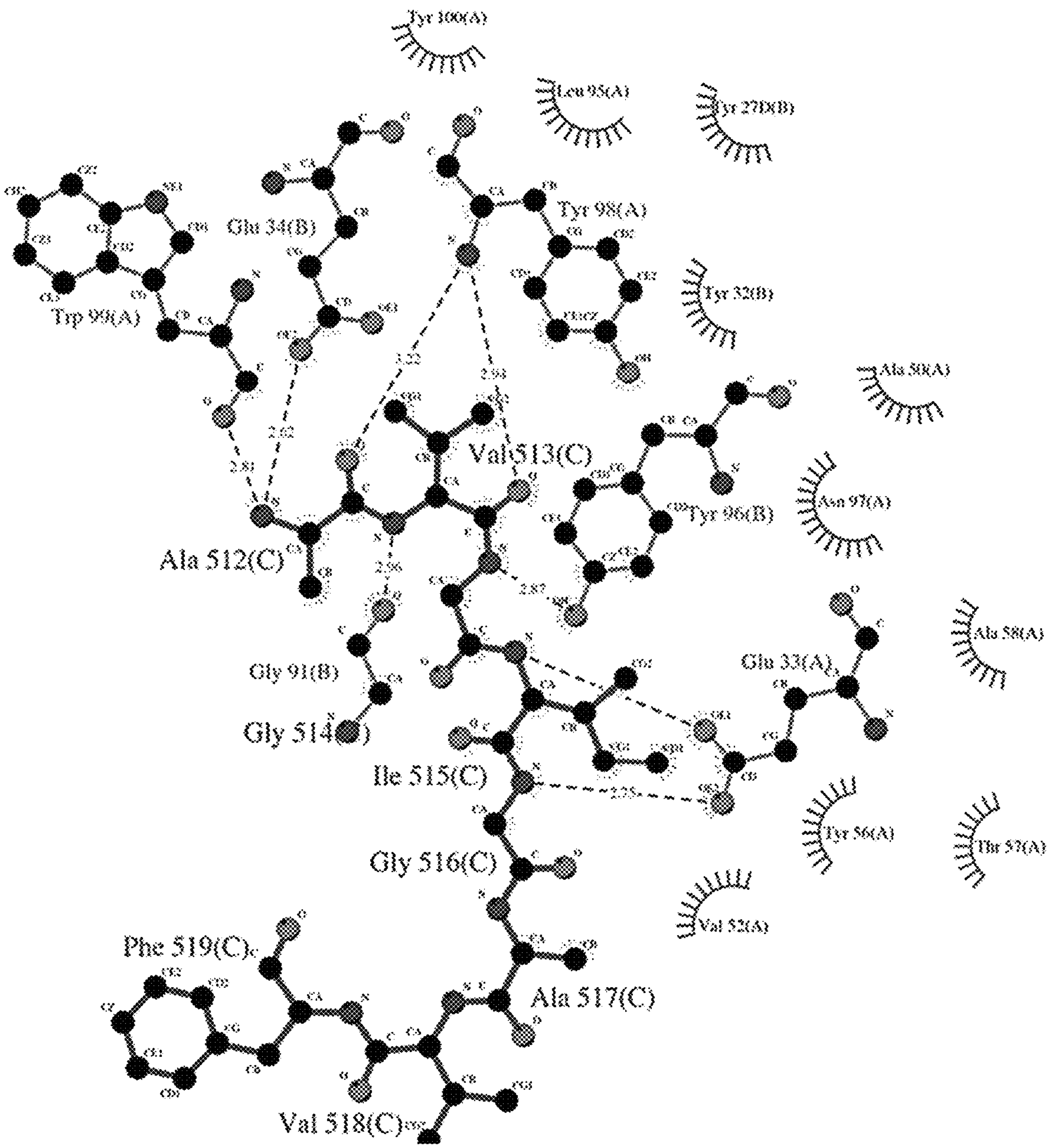

To provide insight into the structural basis for neutralization by these vaccine-elicited antibodies, crystal structures were determined for the antigen-binding fragment (Fab) of vFP1.01 and vFP5.01 antibodies in complex with the N-terminal eight residues of FP (Ala512-Phe519) at 2.0- and 1.5-Å resolution, respectively (FIGS. 4A, 4B). The vFP1.01 co-crystals with FP were orthorhombic with four molecules per asymmetric unit, and in all four independent copies, Fab and FP assumed similar conformations, with FP adopting a curved structure, with no intrachain-backbone hydrogen bonds. The N-terminus of FP (Ala512) was buried between heavy and light chains, with the amino terminus forming a buried salt bridge with $Glu34_{vFp1.01\text{-}LC}$, which was germline encoded and shielded from solvent by a tetra-tyrosine cage, comprising tyrosines at residues $27D_{vFP1.01\text{-}LC}$, $32_{vFP1.01\text{-}LC}$, $96_{vFP1.01\text{-}LC}$, and $98_{vFP1.01\text{-}HC}$ (for clarity, we reference the molecule as a subscript for all molecules other than HIV Env by antibody name and HC or LC for heavy or light chain, respectively). The FP-main chain paralleled the curvature of the vFP1.01 CDR H3, albeit with opposite orientation, up to residue Ile515, which packed against the body of the heavy chain, before extending from antibody into the main body of the trimer with Gly516-Phe519 (FIG. 10A, 10B).

Figure 10C:
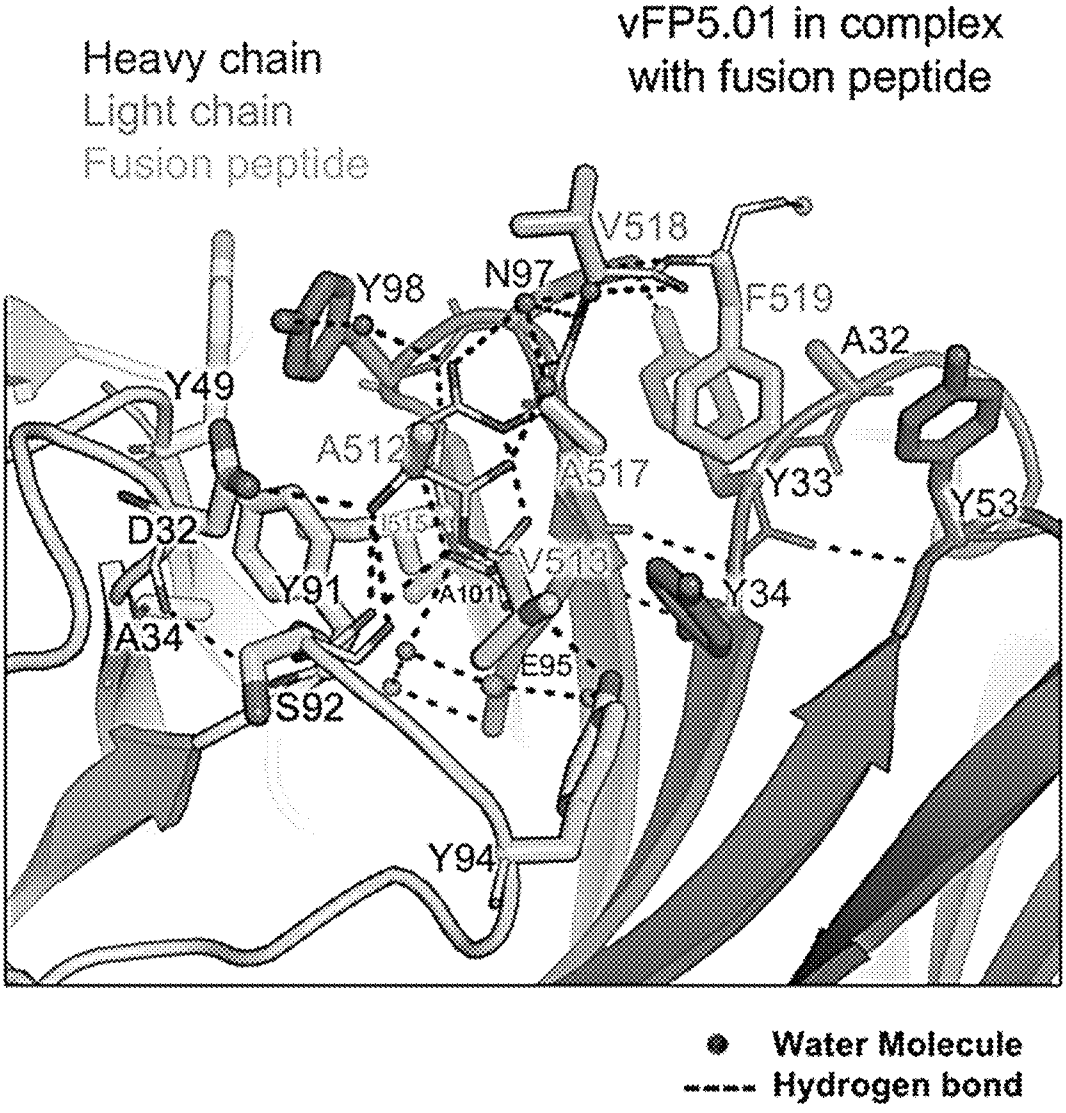
Figure 10D:
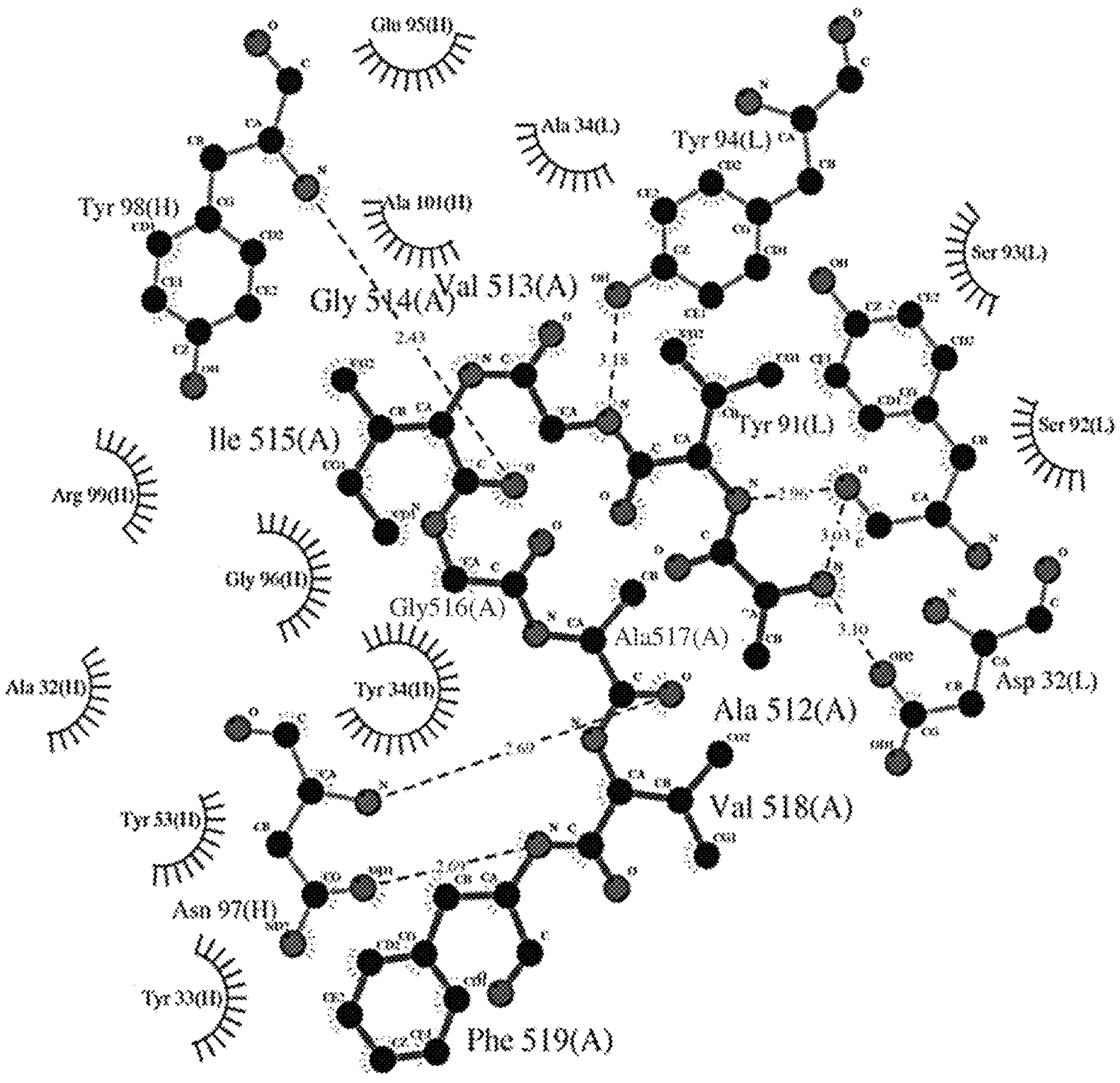

The vFP5.01 co-crystals with fusion peptide were monoclinic, with one molecule per asymmetric unit. vFP5.01 bound FP at the interface of heavy and light chains with the peptide adopting an overall hook structure: starting with a surface-exposed Ala512, dipping into the hydrophobic antibody interface with aliphatic side chains of Va1513 and Ile515 anchoring the FP-N terminus, before turning at Gly516, and extending from antibody towards Env (FIG. 10C,10D).

Figure 4C:
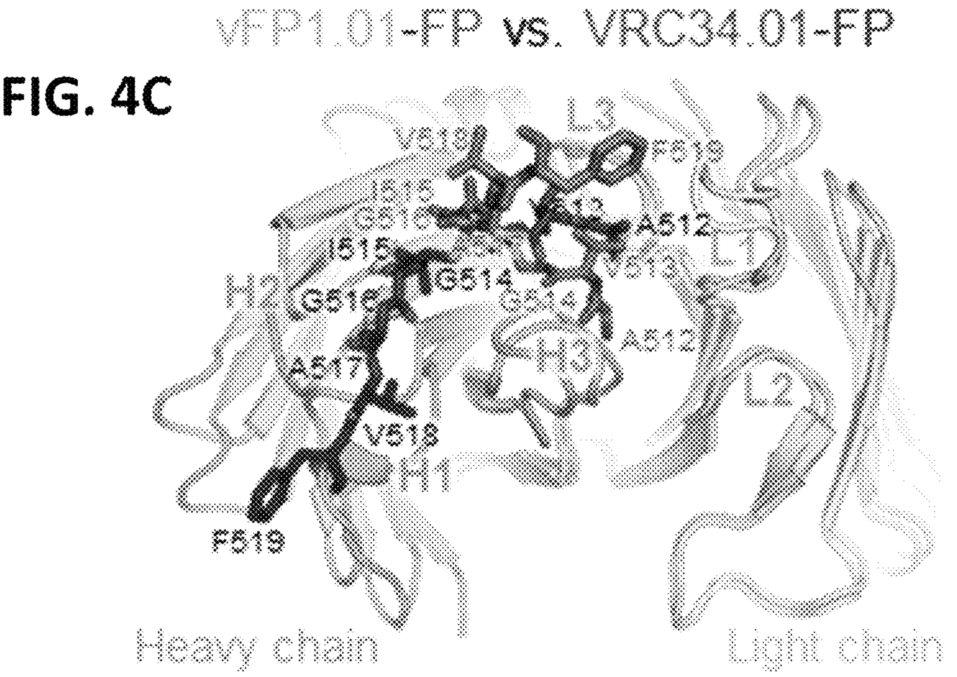
Figure 4D:
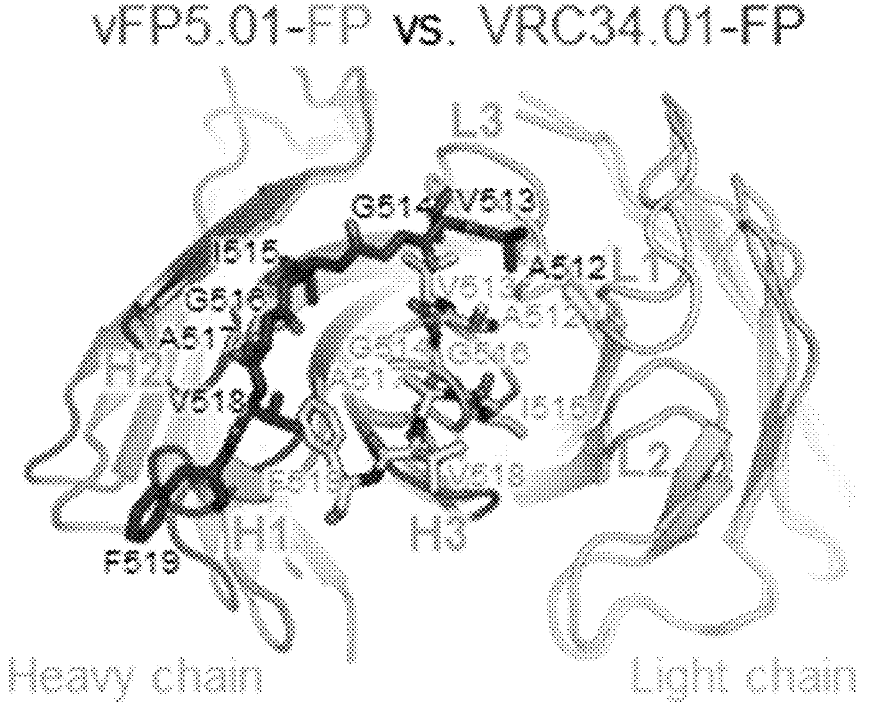
Figure 10E:
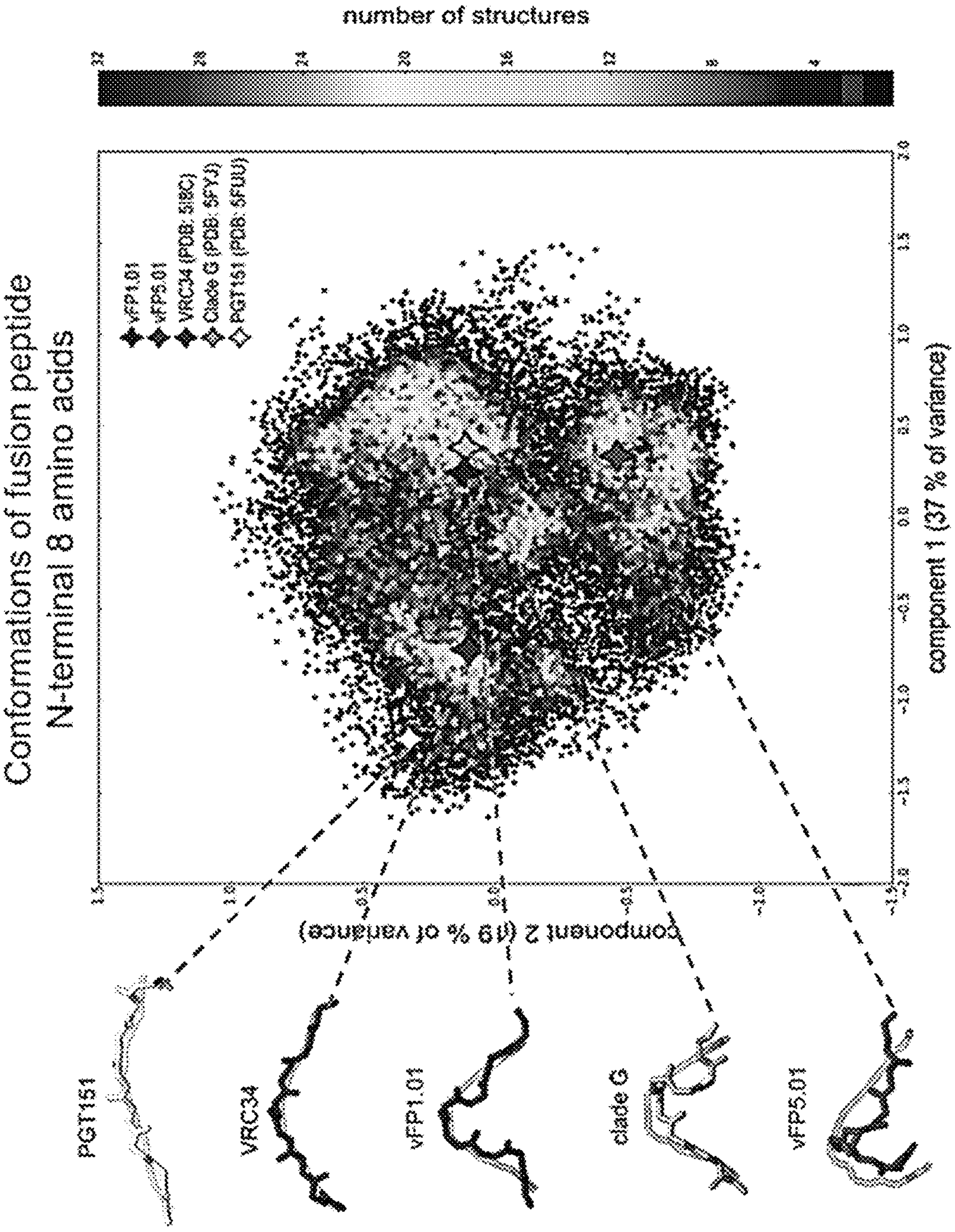
Figure 10F:
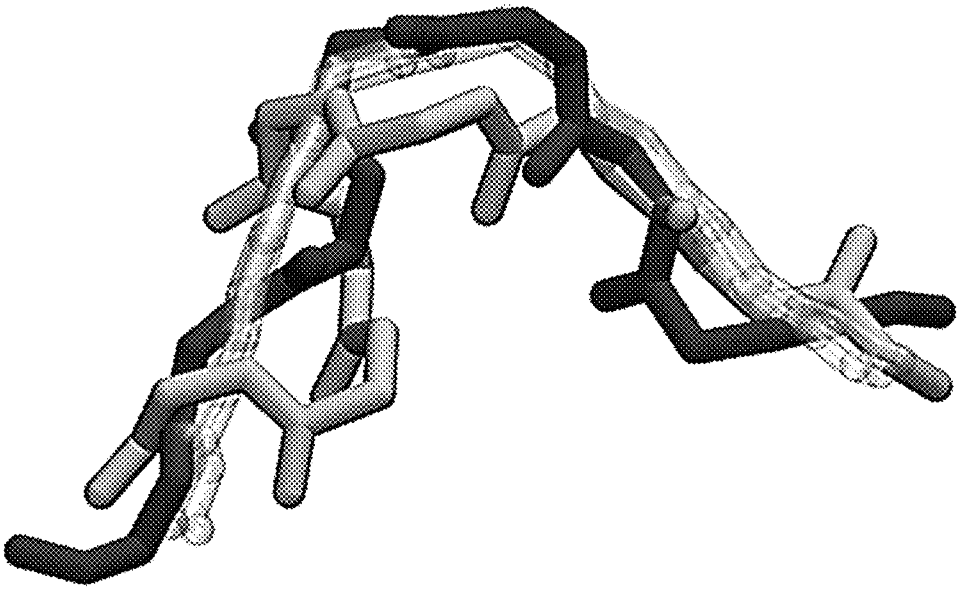

Comparison of antibody-bound crystal structures indicated substantial differences in FP conformation (FIG. 4C, 4D). While all three antibodies recognized the N-terminus of the fusion peptide with a similar region of the antibody at the CDR H3-CDR L3 interface, the conformations of the antibody-bound FP were substantially different: the vFP1.01-bound FP formed a U-shaped structure focused at the heavy-light interface, the FP5.01-bound FP extended to interact with CDR H3, and the VRC34.01-bound FP extended to interact with CDR H1. To place these disparate antibody-recognized conformations of FP into a more general context, principle component analysis was used to cluster N-terminal FP conformations from a molecular dynamics simulation of fully glycosylated HIV-1 Env. Four prevalent clusters of fusion-peptide conformations were observed (FIG. 10E). Overall, FP-directed antibodies were observed to recognize disparate but prevalent conformations of FP.

Restricted Angle of Approach for FP-Directed Neutralization

To position the vFP1.01 and vFP5.01 structures with FP into the context of the HIV-1-Env trimer, cryo-electron microscopy (cryo-EM) data was collected for these FP-directed antibodies complexed to the BG505 SOSIP trimer. With Fab vFP1.01, approximately 14,000 particles yielded an 8.6-Å resolution reconstruction after three-fold averaging; the resulting structure (FIG. 4A) showed three Fabs laterally interacting with the Env trimer. With Fab vFP5.01, several particle classes were observed yielding 14.7- and 19.6-Å resolution reconstructions; these asymmetric reconstructions indicated each of the vFP5.01 Fabs to approach Env differently (FIG. 4B).

Figure 4E:
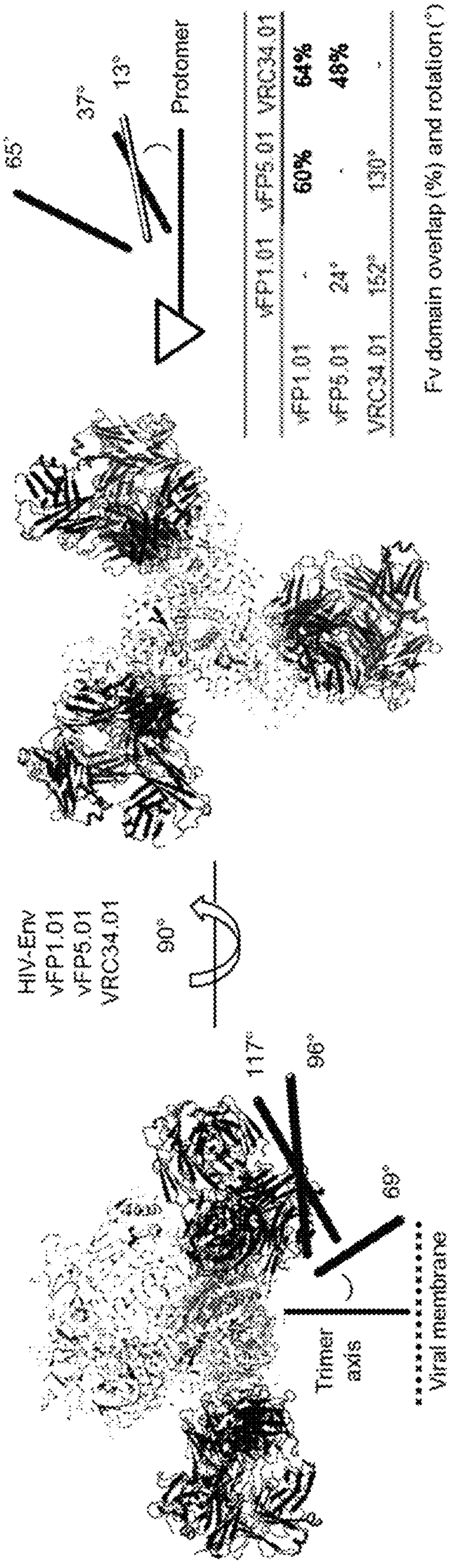

To provide insight into recognition of the Env trimer, the approach angle of the FP-recognizing antibodies was analyzed. Relative to the angle between trimer axis and membrane (FIG. 4E, left), vFP1.01 and VRC34.01 approached the Env trimer from similar angles of 96° and 117°, respectively, with vFP5.01 utilizing a more divergent ~69° angle of approach. Relative to the equatorial angle around the trimer axis (FIG. 4E, right), vFP1.01 and VRC34.01 approached from similar angles of 130 and 37°, respectively (though with relative heavy and light chain orientations swapped) with FP5.01 approaching the trimer from a more divergent 65° angle. Calculation of volume overlap for the variable domains indicated vFP1.01 and VRC34.01 to be most similar (64% overlap) and vFP5.01 to be more divergent (FIG. 4E, right). Approach angles for PGT151 and ACS202 were also analyzed. Overall, the trimer approach of antibodies directed primarily to FP and capable of neutralizing diverse HIV-1 strains (e.g. antibodies vFP1.01, VRC34, and ACS202) was highly similar, suggesting restrictions on trimer approach for effective FP-directed neutralization.

Considerations for Improved Second Generation Immunizations

Analysis of the 1$^{st}$-generation antibodies indicated effective FP-directed neutralization to occur preferentially at a restricted angle of approach, thereby suggesting that boosting with Env trimer might elicit improved neutralization. Additional clues were sought from analysis of the 1$^{st}$-generation FP-directed antibodies to improve FP immunization.

To provide insight into sequence requirements for neutralization, a panel of peptides comprising Ala and Gly mutants of the fusion peptide N terminus was created and screened for recognition by vaccine-elicited antibodies and by VRC34.01 (FIG. 14). The Ala/Gly mutants only affected vFP1.01 recognition if they occurred within the first four residues of the fusion peptide (512-515). For vFP5.01, a more extensive range was observed, with alterations to Ala/Gly at residues 513, 514, 515, 516, and 519 affecting recognition. VRC34.01 recognition by comparison was intermediate between vFP1.01 and vFP5.01, being sensitive to changes at 513, 515, and 516, and partially sensitivity to changes at 518 and 519. Overall, these results indicated a preference for N-terminal residues for effective neutralization, thereby suggesting that N-terminal focusing might improve neutralization of the vaccine-elicited antibodies.

Figure 11B:
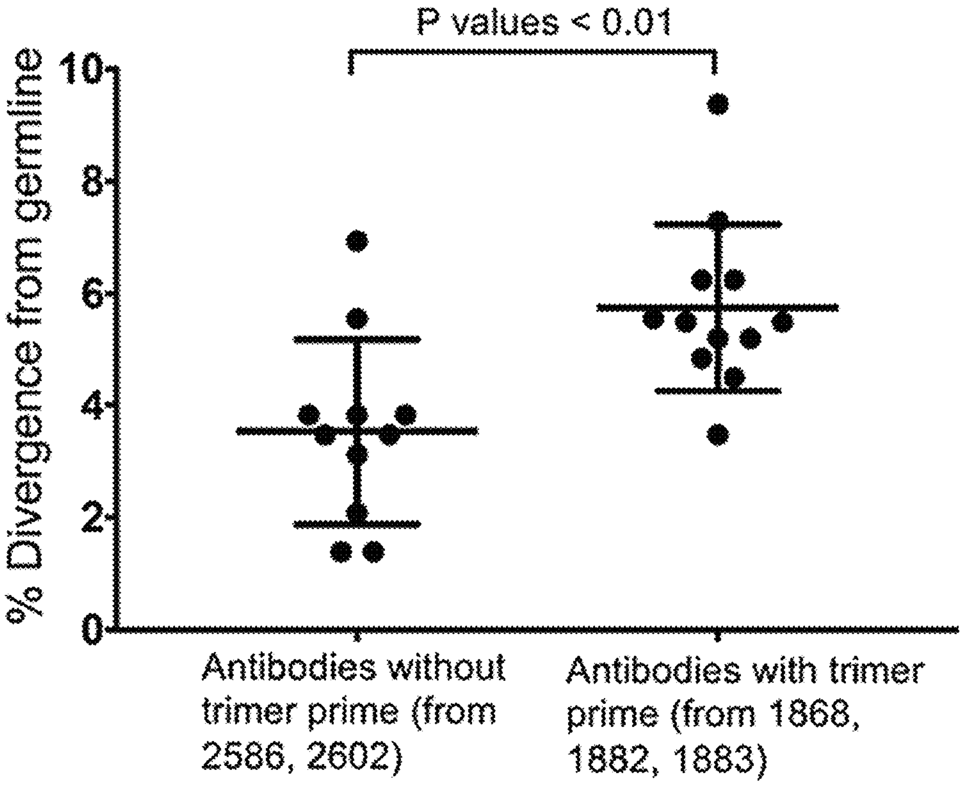

Although a significant improvement in neutralization titers upon Env priming was not observed in initial assays (FIG. 2), the degree of affinity maturation for vFP1-class antibodies was analyzed as this would lend insight into the induction of these antibodies. vFP1-class antibodies were identified from three additional mice, two of them (1882 and 1883), primed with Env trimer, and one (2602), immunized with only FP-KLH (FIG. 11). Notably, vFP1-class antibodies primed with Env trimer showed significantly higher somatic hypermutation (SHM). Thus, while Env-trimer priming did not improve neutralization, it did appear to prime vFP1-class antibodies.

Second Generation FP-Directed Antibodies Neutralize Up to >30% of HIV-1 Strains

Figure 5B:
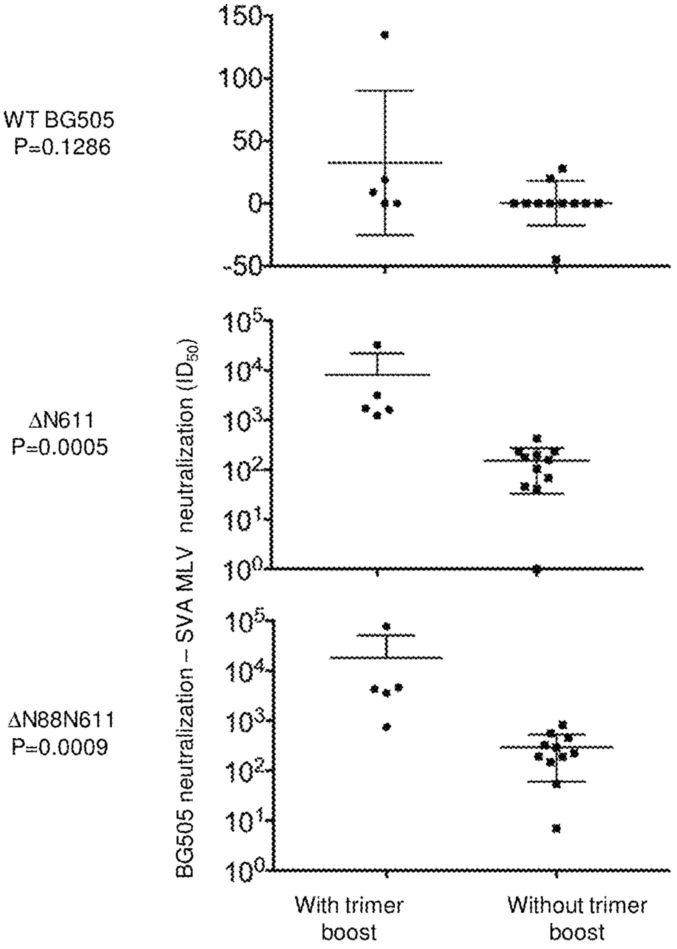

To elicit improved FP-directed antibodies, 16 different vaccine regimens were tested in C57BL/6 mice (FIG. 5A). These comprised a BG505 SOSIP trimer prime, various FP-KLH boosts, and a subset of five mice with a BG505 DS-SOSIP boost. The FP-KLH boosts utilized different lengths of FP, ranging from FP6 through FP10, which incorporated 6 through 10 residues from the N-terminal FP sequence of strain BG505. Neutralization as assessed on sera 68-92 days post T1-trimer prime. Sera were negative for MuLV neutralization, except for animals boosted three times with FP10. Only a few sera showed wild-type BG505. By contrast, nearly all of the sera displayed substantial titers against Δ611 or Δ88+611 glycan-deleted variants of BG505. Titers for the five trimer-boosted animals were especially improved, reaching an $ID_{50}$ as high as 77,379 for Δ88+611 BG505 with the trimer-boosted FP8, FP7, and FP6 regimen of mouse 2716 (FIG. 4A). To augment these individual animal results, an FP8-8-8 versus an FP8-7-6 regimen was tested with five C57BL/6 mice per group; average $ID_{50}$ titers of over 1000 against Δ88+611 BG505 with both regimens were observed versus an $ID_{50}<20$ for KLH with no FP; however, significant differences were not observed between the FP8-8-8 and FP8-7-6 regimes (FIG. 9F,9G). Indeed, analysis of factors influencing elicited neutralization did not reveal the length of FP used in the FP-KLH immunizations to be significant; however trimer boost yielded significantly higher titers, though only when assessed against Δ611 or Δ88+611 glycan-deleted variants of BG505 (FIG. 5B, 9).

For each of the 16 vaccine regimens, 67 antibodies were isolated and characterized that could be parsed into 21 lineages, vFP12-vFP32. Each of these 67 vFP antibodies was assessed against two wild-type viruses, the clade A BG505 and the clade B 3988.25. Neutralization with 24 of the vFP antibodies was observed against at least one of the two viruses, and these 24 antibodies were assessed against 8 additional viruses, 4 with complete glycan around the FP site and 4 missing select FP glycans—all 8 of which were resistant to neutralization by CD4-induced or V3-directed antibodies. Notably, substantial neutralization breadth was observed, with most of the 24 assessed antibodies neutralizing 70% or more of the 10-selected wild-type isolates, which were from divergent HIV-1 clades (FIG. 5C).

Figures 5D, 5E:
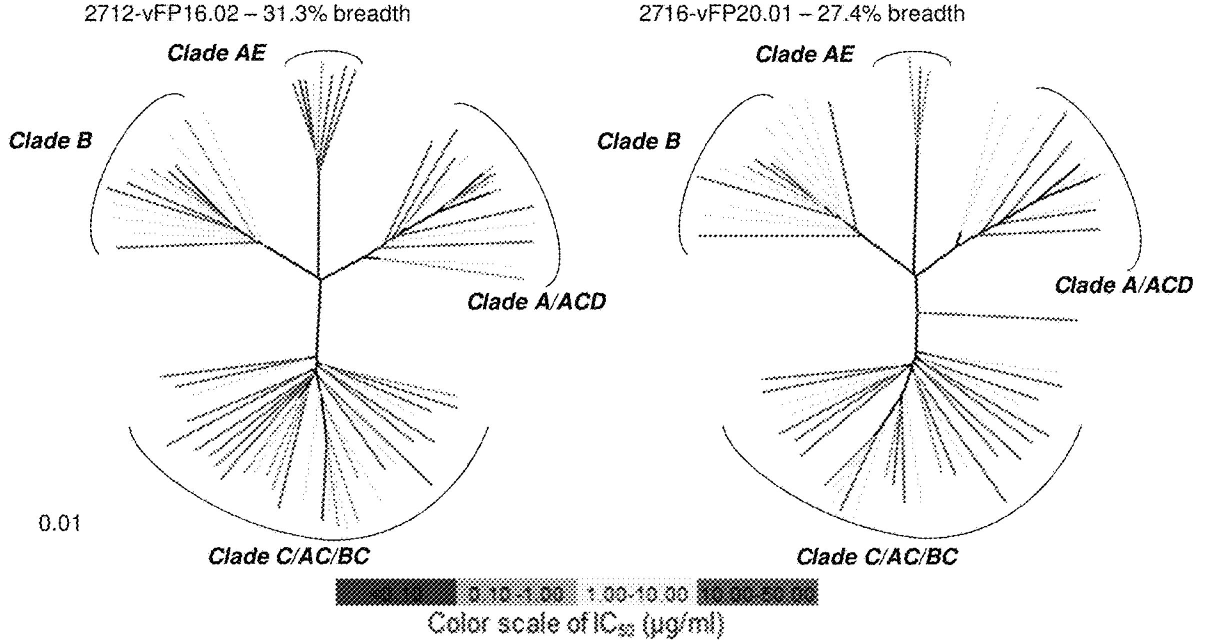
Figure 9D:
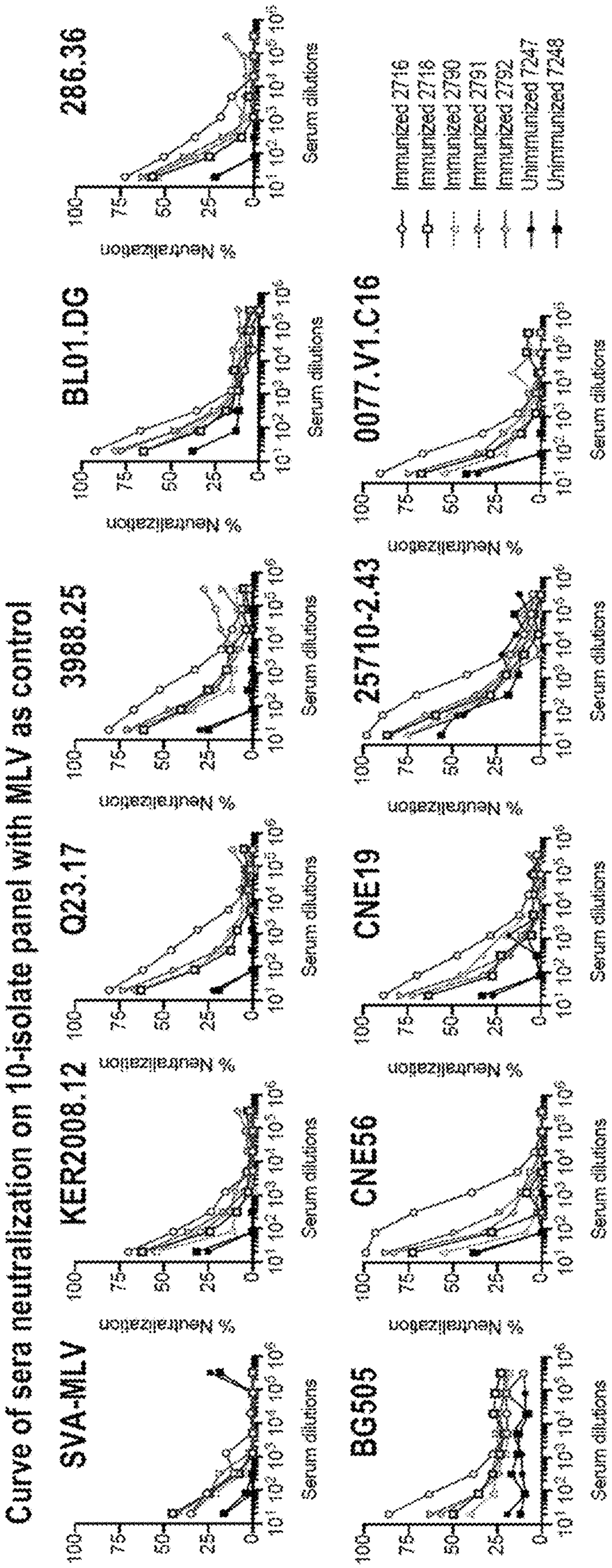
Figure 9E:
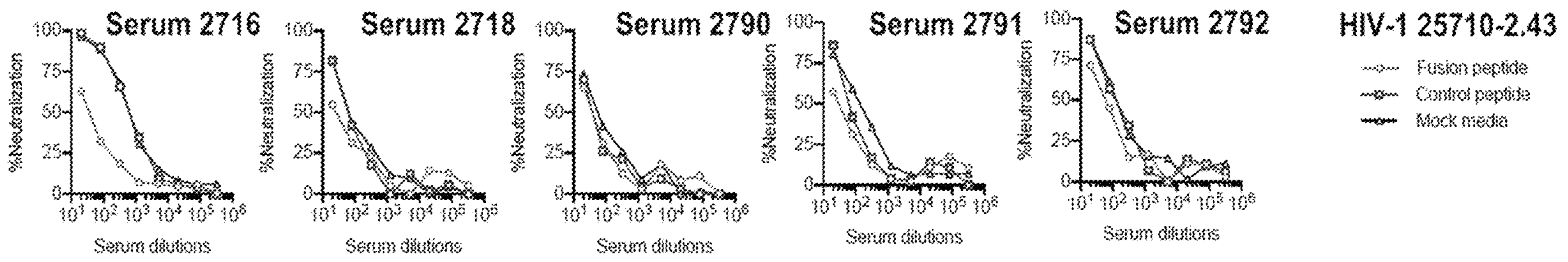
Figures 9F, 9G:
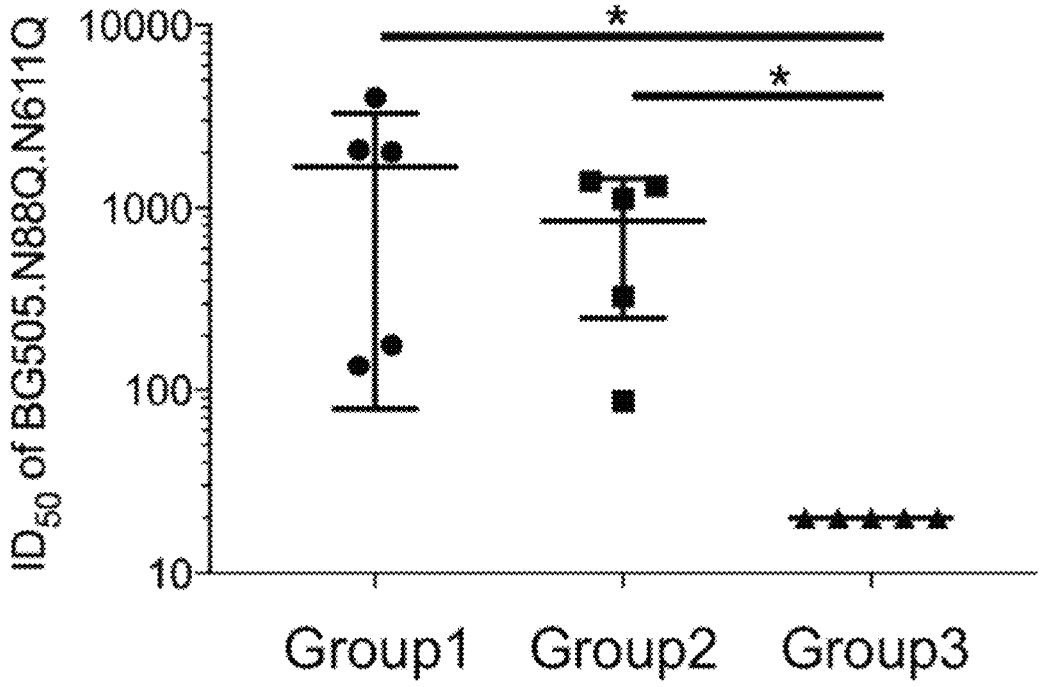

Serum neutralization for the 5 trimer-boosted animals was also tested on the 10-selected wild-type isolates (FIG. 5D, 9D). While weak neutralization from these five sera was observed against most of the selected isolates, sera from mouse 2716 achieved $ID_{50}$ levels of neutralization against all of the viruses. Notably, further analysis by peptide competition indicated neutralization of this sera to be targeted primarily to the FP (FIG. 9E).

Finally, two antibodies, 2712-vFP16.02 and 2716-vFP20.01, were selected for further assessment (vaccine-elicited FP antibodies were named for mouse ID-lineage-.clone, with antibody 2716-vFP20.01 being clone 01 from lineage vFP20 isolated from mouse ID 2716). Notably, on the 208-isolate panel, these two antibodies achieved 31.3 and 27.4% neutralization breadth, when assessed at a maximum $IC_{50}$ level of 50 μg/ml (FIG. 5E).

vFP16.02 and vFP20.01 Structures and Env Interaction

Figure 10G:
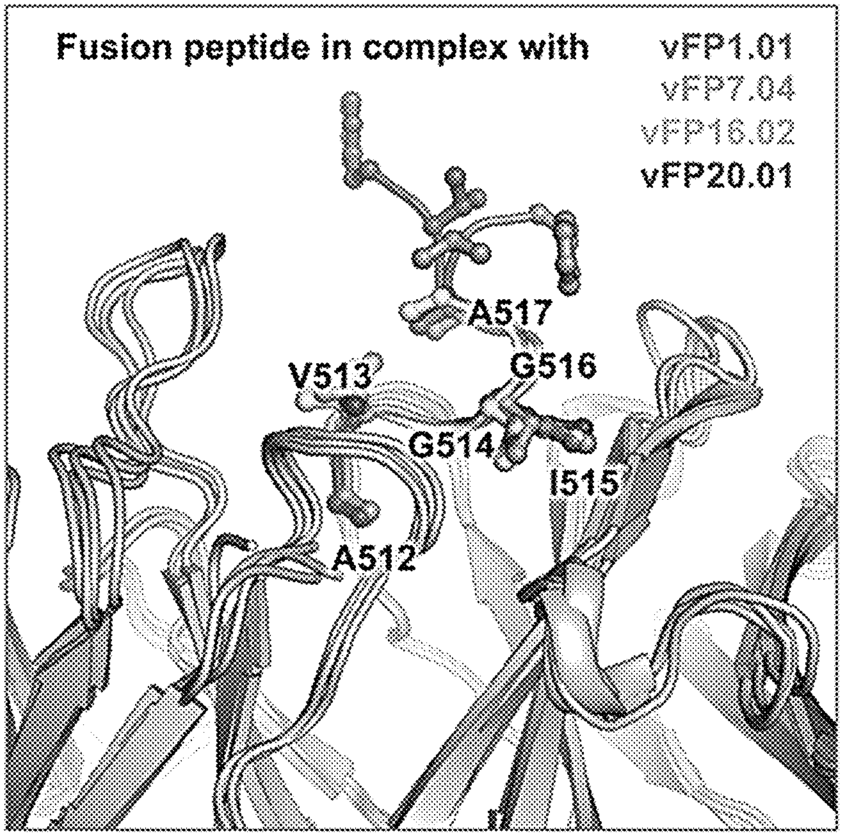
Figure 10H:
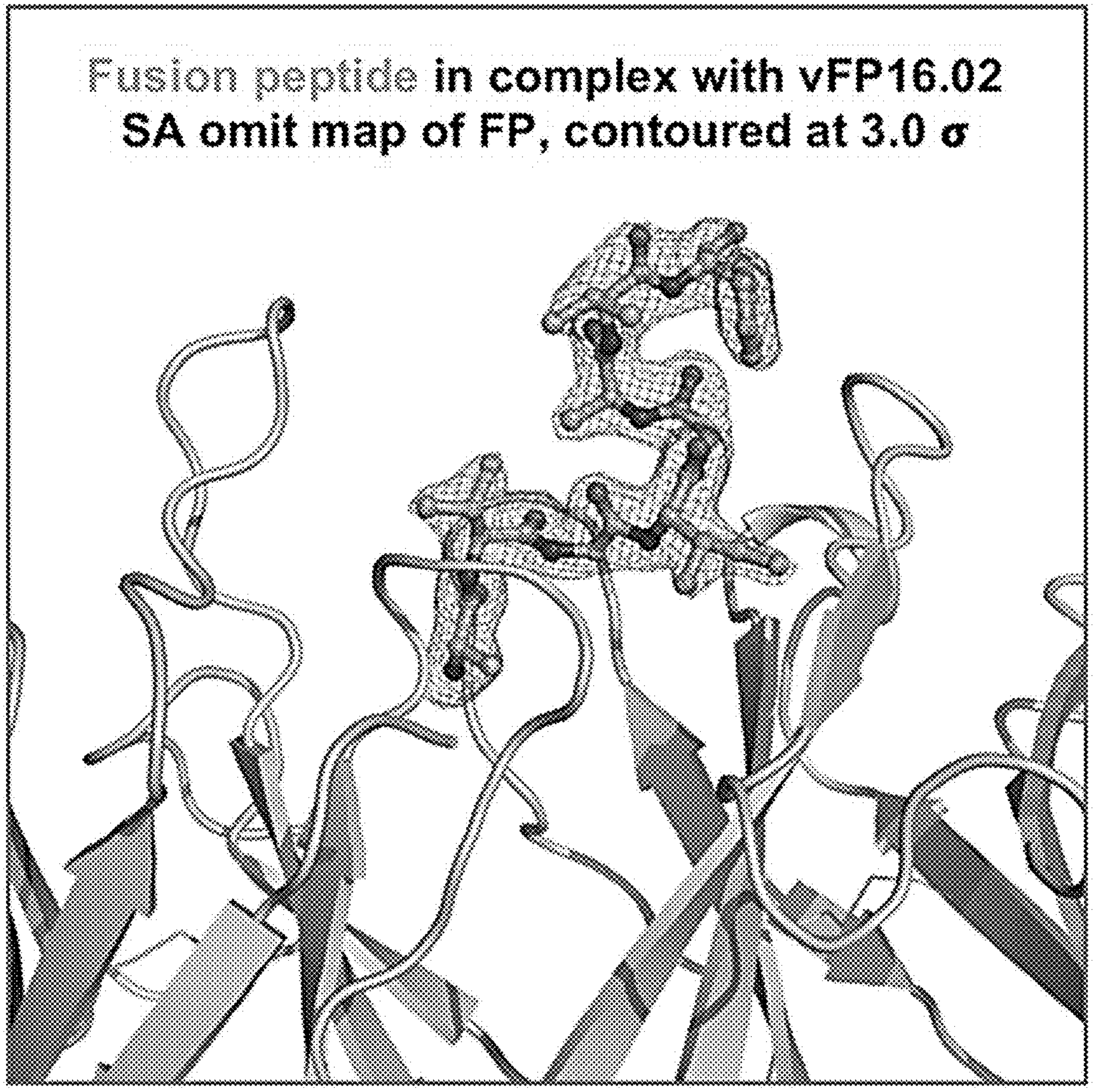

To gain insight into the promising breadth observed with vFP16.02 and vFP20.01 antibodies, their crystal structures in complex with FP and their cryo-EM structures in complex with HIV-1 Env were determined. Crystal structures with fusion peptide at 2.1- and 2.5-Å resolution revealed highly similar recognition of residues 512-517, with the vFP1-class antibodies constraining little of the FP conformation beyond residue 517 (FIGS. 10G, 10H). In the context of only FP, structural constraints for the modestly neutralizing antibodies vFP1.01 and vFP7.04 appeared similar to those of the more broadly neutralizing vFP16.02 and vFP20.01.

To provide structural information on the interaction of these antibodies with Env trimer, cryo-EM data on a quaternary complex with BG505 SOSIP trimer bound by antibodies PGT122 and VRC03 were collected, in addition to vFP16.02 or vFP20.01; the added antibodies increased the size of the particles and provided fiducial markers allowing better particle visualization and alignment. The resultant reconstructions displayed resolutions of 3.7- and 4.0-Å, respectively, as calculated using soft-edged masks that encompassed the entire structure including less ordered regions such as antibody constant regions; these improved to 3.6- and 3.7-Å, respectively, when flexible constant regions were removed from the mask, according to the FSC 0.143 gold-standard criterion (FIG. 6). Notably, in the reconstructions, the bound antibodies displayed variable levels of electron density. At a contour level for which pitch and side chains of gp41 helices could be resolved, only the regions of vFP16.02 and vFP20.01 in contact with Env were well-defined, with density becoming weaker, farther from the Env-binding site. By contrast, this decrease in level of electron density was not observed for the entire variable regions of both VRC03 and PGT122, though lower density levels were observed for parts of the PGT122 constant region. These results suggest that, despite the restricted angles of approach for the vFP antibodies, binding incorporated substantial flexibility in their position relative to the Env site of recognition.

Figure 6A:
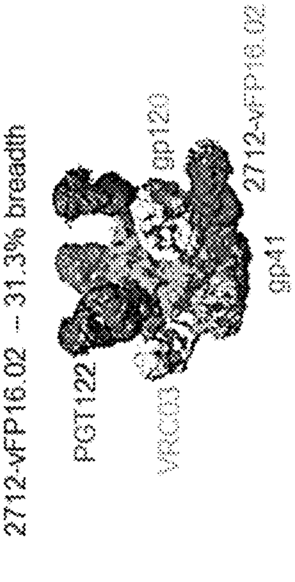
FIGS. 6A-6E. Multiple maturation pathways for and substantial glycan interactions by effective FP-directed antibodies.
Figure 6B:
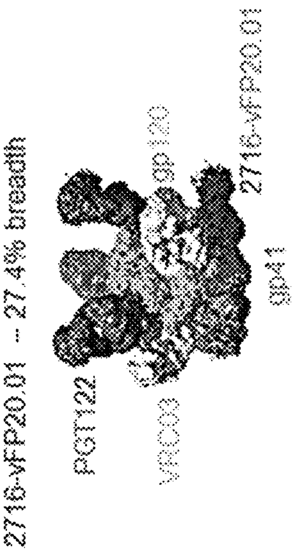
Figure 6C:
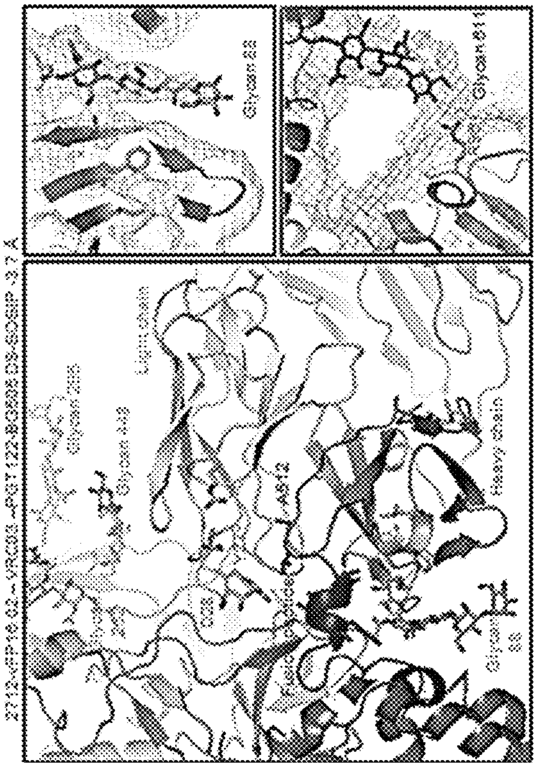
Figure 6D:
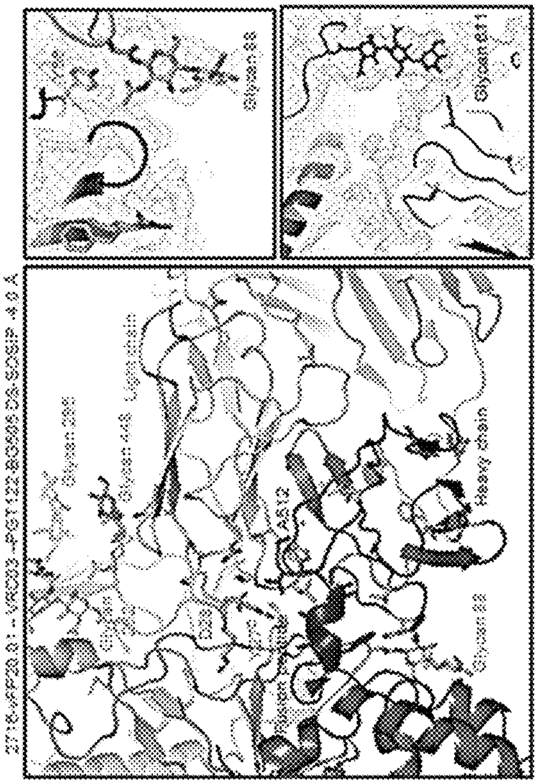

Substantial glycan interactions between vFP antibodies and Env trimer were observed (FIGS. 6C, 6D). In both antibody-Env complexes, glycans N448 and N611 displayed similar orientations, with glycan N448 buttressed by the light chain on one side and by glycan N295 on the other and with glycan N611 projecting from a neighboring Env protomer directly toward the antibody heavy chain. Glycan N88 also displayed ordered density in the protein proximal sugars, though this differed in the two antibody complexes: in vFP16.02, substantial ordering was observed, with the glycan lodged between gp41 and the heavy chain (FIG. 6C); in vFP20.01, glycan N88 was less ordered and assumed a substantially different conformation to accommodate the SHM-altered Gly56Tyr$_{vFP20.01\text{-}HC}$ side chain (FIG. 6D). Overall, the structures indicate vFP antibodies with promising breadth to substantially accommodate, if not partially recognize, FP-proximal N-linked glycan.

Figure 6E:
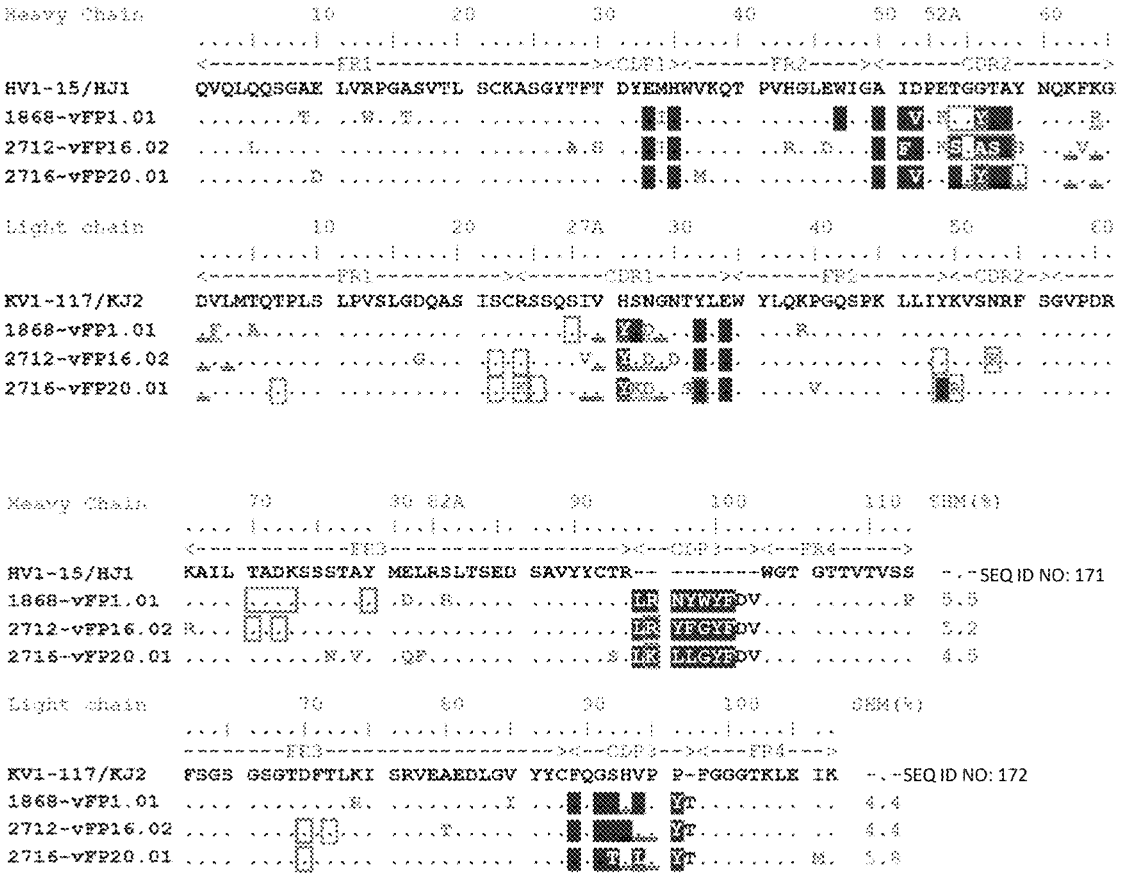

Second Generation Antibodies Use Diverse Pathways to Achieve Neutralization Breadth Both vFP16.02 and vFP20.01 showed ~5% SHM in both heavy and light chains, about the same level of SHM as antibody vFP1.01 (FIG. 6E). However, in the cases of vFP16.02 and vFP20.01, the SHM led to ~30% neutralization breadth, whereas the breadth of vFP1.01 was only 8%. The differences in SHM were thus examined to determine clues to induction of breadth. Few sites of SHM were observed to overlap between vFP16.02 and vFP20.01; indeed, only two sites of shared SHM were observed, His31Tyr$_{vFP\text{-}LC}$ and Asn33Asp$_{vFP\text{-}LC}$ in the CDR L1 region, both of which were also observed in vFP1.01. These two residues were located at the interface between antibody, gp120 and FP, and differed in orientation in the different FP-antibody complexes (FIGS. 6C, 6D).

A cluster of SHM was also observed in both vFP16.02 and vFP20.01 in the CDR H2 region. The CDR H2 SHM cluster was more extensive with vFP16.02, altering the interface with both FP and glycan N88. With vFP20.01, CDR H2 SHM altered only two residues, Asp52Val$_{vFP20.01\text{-}HC}$ and Gly57Tyr$_{vFP20.01\text{-}HC}$, both of which were also altered in vFP1.01 (FIG. 6C,6 D). Altogether SHM was observed to occur preferentially at the interface with Env, especially involving interactions with FP and with N-linked glycan. However, SHM was minimally conserved between the antibodies with greatest breadth, vFP16.02 and vFP20.01, indicating that divergent maturation pathways can achieve promising breadth with vFP1-class antibodies.

Figure 7A:
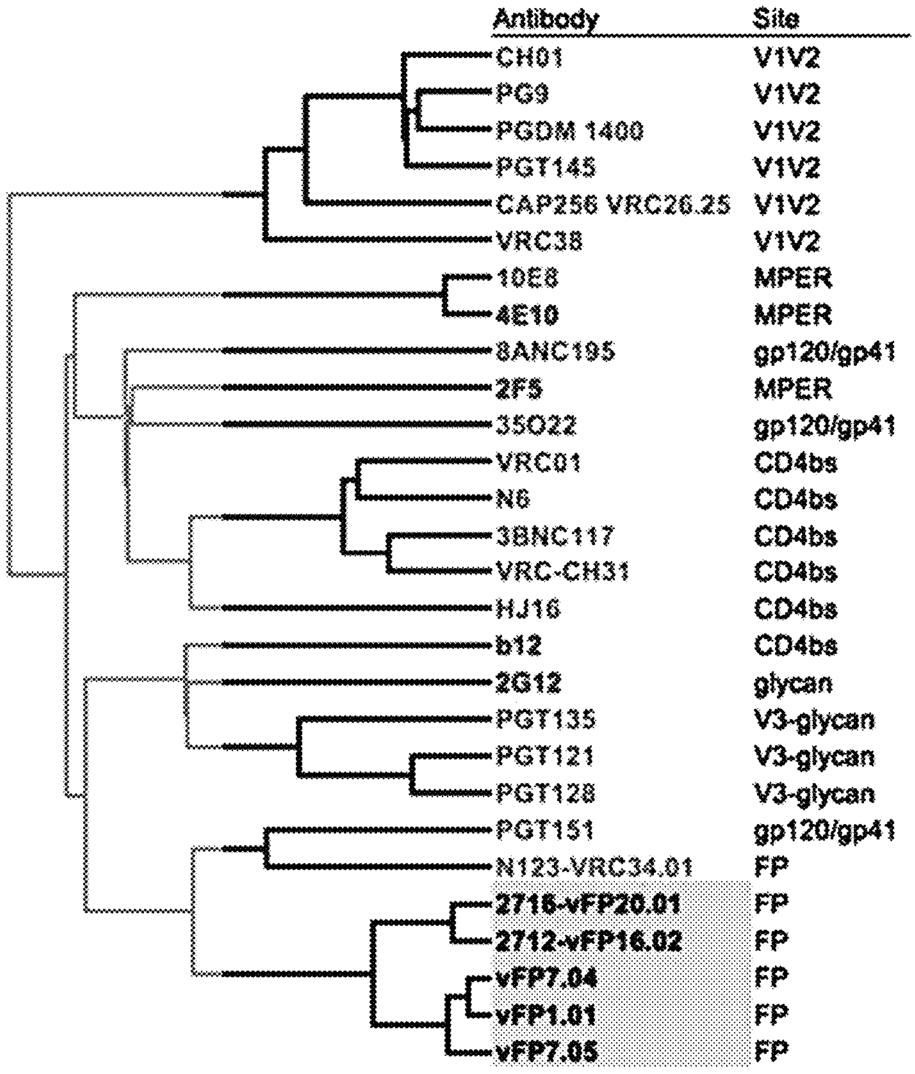

Fp-Directed Antibodies Begin to Achieve Breadth of Naturally Elicited Antibodies To provide insight into the neutralization characteristics of the FP antibodies and to allow comparison with antibodies elicited by natural infection, neutralization fingerprints were calculated (Georgiev et al. (2013) Science 340, 751-756) for the vaccine-elicited FP-directed antibodies. Notably, all of the FP-directed antibodies, both vaccine and naturally elicited, clustered in a neutralization-fingerprint dendrogram (FIG. 7A). The broadest vaccine-elicited antibodies, vFP16.02 and vFP20.01, were positioned closely in the dendrogram, despite not sharing much SHM, and the less broad antibodies, vFP1.01, vFP7.04 and vFP7.05, were also positioned closely. The naturally elicited antibodies, meanwhile, were more distantly positioned, with VRC34 and PGT151 positioned closer than the vaccine-elicited antibodies. Other gp120-gp41 interface antibodies such as 8ANC195 and 35O22 segregated to other regions of the dendrogram, indicating interface antibodies to have different neutralization characteristics. Overall, the FP-directed antibodies appeared to share neutralization characteristics, with vaccine-elicited antibodies more similar to each other than to the naturally elicited ones.

Figure 7B:
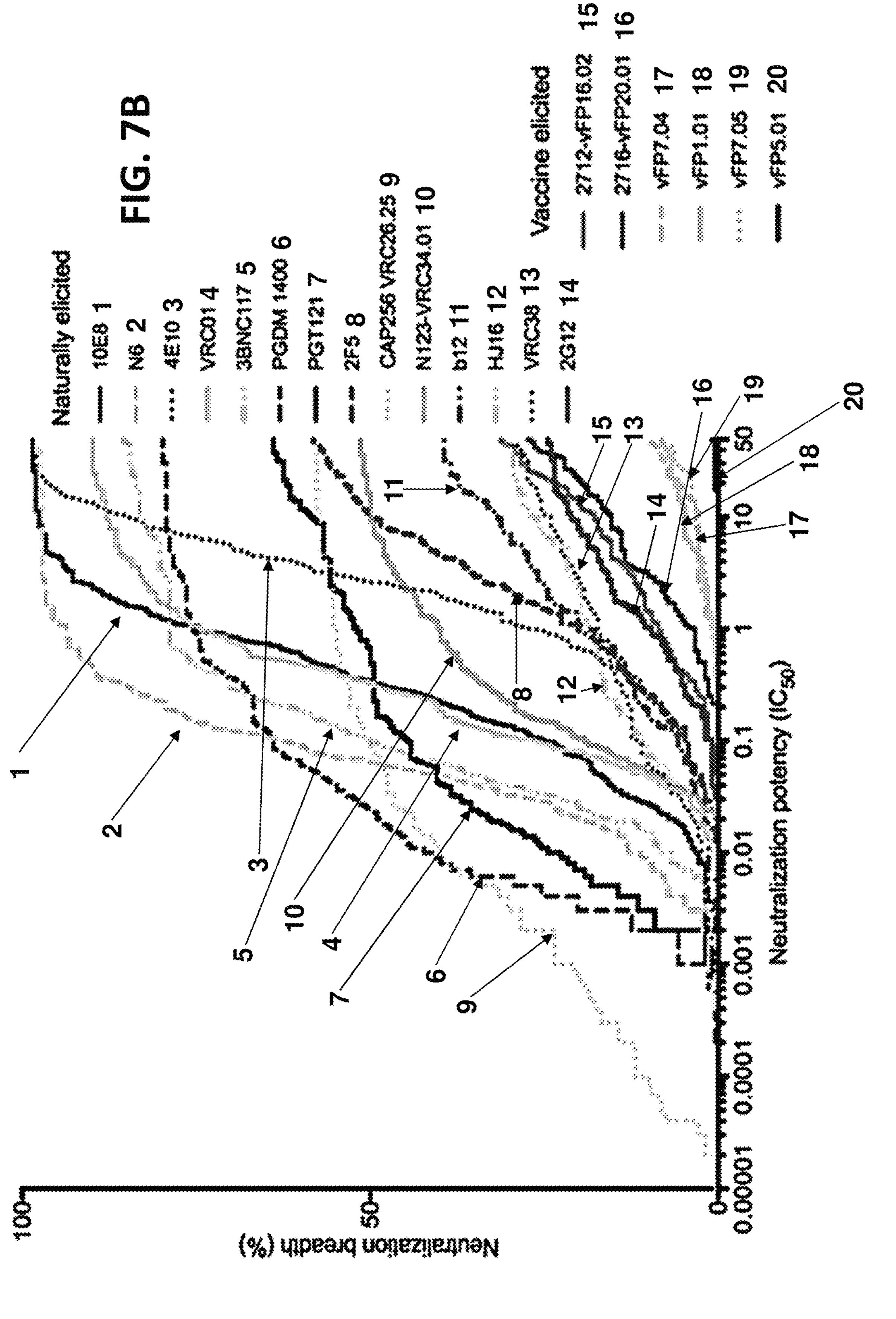

Breadth-potency analysis was also carried out with data from the 208-isolate virus panel comparing vaccine-elicited and naturally elicited antibodies (FIG. 7B). Notably these breadth-potency curves showed the best vaccine-elicited antibodies to exhibit higher breadth than naturally elicited antibodies such as 2G12, HJ16 and VRC38, with the potency of the vFP16.02 antibody similar to that of 2G12, which has been shown to delay rebound and to induce sieving of HIV-1 virus when passively infused (Trkola et al. (2005) Nat Med 11, 615-622; Trkola et al. (2008) J Virol 82, 1591-1599; Trkola et al. (1996) J Virol 70, 1100-1108). Thus, the $2^{nd}$-generation FP-directed antibodies achieve a level of breadth previously observed only with naturally elicited antibodies.

Figure 12B:
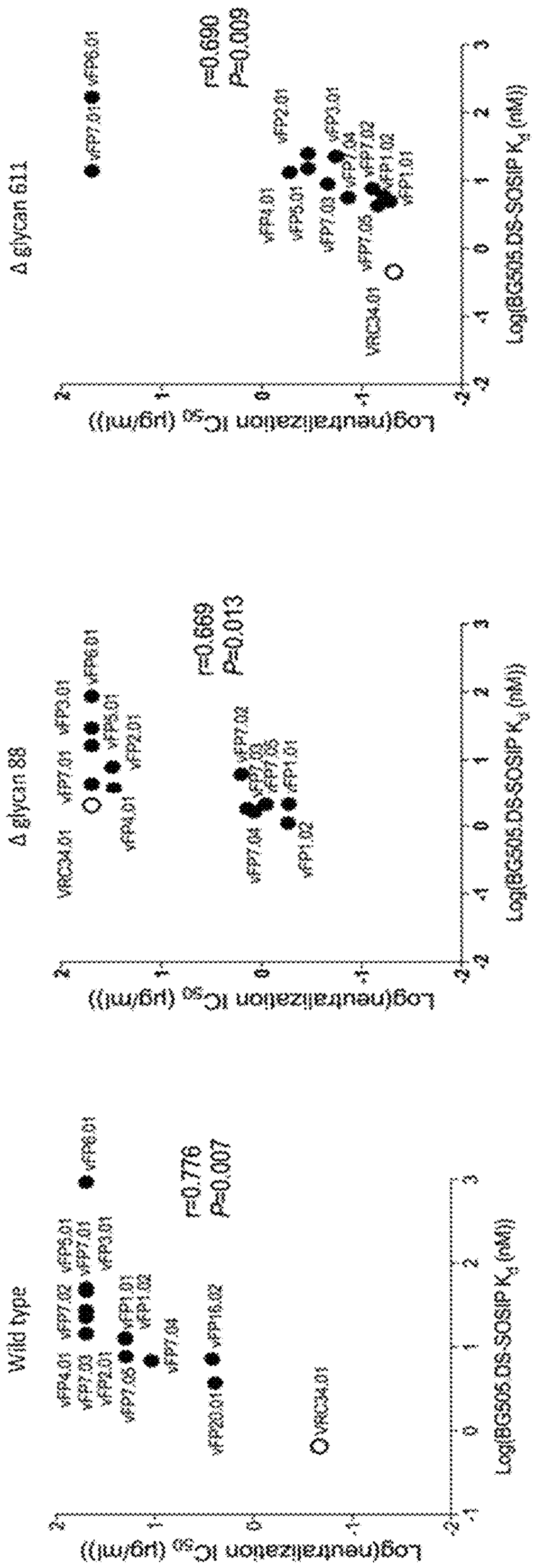

Iterative Structure-Based Optimization: Improving $2^{nd}$-Generation Antibodies The iterative process of structure-based optimization that was used to elicit antibodies of promising breadth relies on information gleaned from the analysis of elicited antibodies to identify ways to improve the subsequent generation of immunizations. How might the $2^{nd}$-generation antibodies be improved? We analyzed factors affecting neutralization breadth of the $2^{nd}$ generation FP-directed antibodies. The affinity between vaccine-elicited antibodies and FP or Env trimer lacked strong correlation with BG505 neutralization (FIG. 12). While the vaccine-elicited antibodies showed subnanomolar affinity to FP peptides, FP affinity did not correlate with neutralization breadth. Importantly, however, strong correlation was observed between Env trimer affinity and neutralization breadth (FIG. 7C), suggesting that enhancements of Env trimer affinity should lead to increased neutralization breadth.

Analysis of the FP sequences of sensitive and resistant strains indicated sequence variation at the $2^{nd}$ and $4^{th}$ positions of FP (residues 513 and 515, respectively) to impact significantly neutralization breadth for vFP1-class antibodies (FIG. 7D and FIG. 16). In particular, Va1513 and Ile515 were associated with sensitivity, while I1e513 and Leu515 were associated with resistance. By contrast, VRC34.01 tolerated changes at positions 513 and 515. The contribution of glycan to neutralization resistance was also analyzed. For vFP1.01, the presence of a glycan at N241 was observed to lead to neutralization resistance, whereas for the more broadly neutralizing vFP16.02 and vFP20.01, the presence of FP-proximal glycans did not negatively impact neutralization (FIG. 16). Thus, the primary restraint on vFP1-class neutralization breadth appeared to be tolerance to variation in the FP sequence itself. Fortunately, the FP sequence is quite conserved: if variation in only the first 5 amino acids is considered (as these are the primary FP residues recognized by the vFP1 class of antibodies), then only 4 sequences would be required to cover 80% of the isolates in the 208-isolate panel (FIG. 7E).

DISCUSSION

The vaccine elicitation of antibodies capable of neutralizing diverse strains of HIV-1 has been a goal of HIV-1 research for over 30 years. While substantial strides have been made in the creation of prefusion-stabilized Env trimers, responses elicited by these trimers in standard vaccine-test species have been primarily strain-specific. This example shows that focusing the immune response to the exposed N-terminal residues of the fusion peptide succeeds in eliciting HIV-1-neutralizing antibodies of promising breadth. Several factors led to this breakthrough. The characteristics of the target site—the FP N-terminus—a conserved and exposed site of vulnerability, which is not constrained in conformation, facilitated induction of antibodies of HIV-1-neutralization breadth (FIG. 7F).

Analysis of strains that share the identical sequence to the immunized eight amino acids of FP (comprising 58 strains of the 208-isolate panel) indicated vFP16.02 to neutralize 72.4% of these strains and vFP20.01 to neutralize 74.1% (FIG. 15). Thus, for strains with the same sequence as used in the FP immunizations, there does not appear to be an intrinsic limit to FP-directed breadth, with FP1-class antibodies having already achieved substantial breadth and VRC34.01 neutralizing 94.8% of these isolates.

Figure 13A:
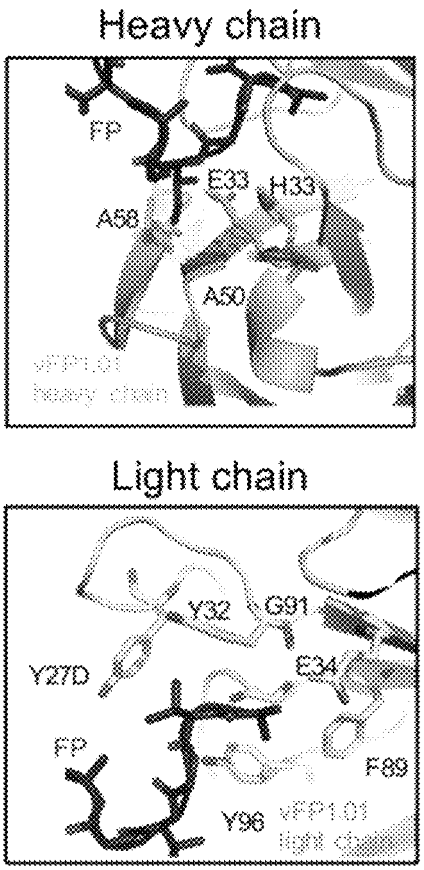
Figure 13B:
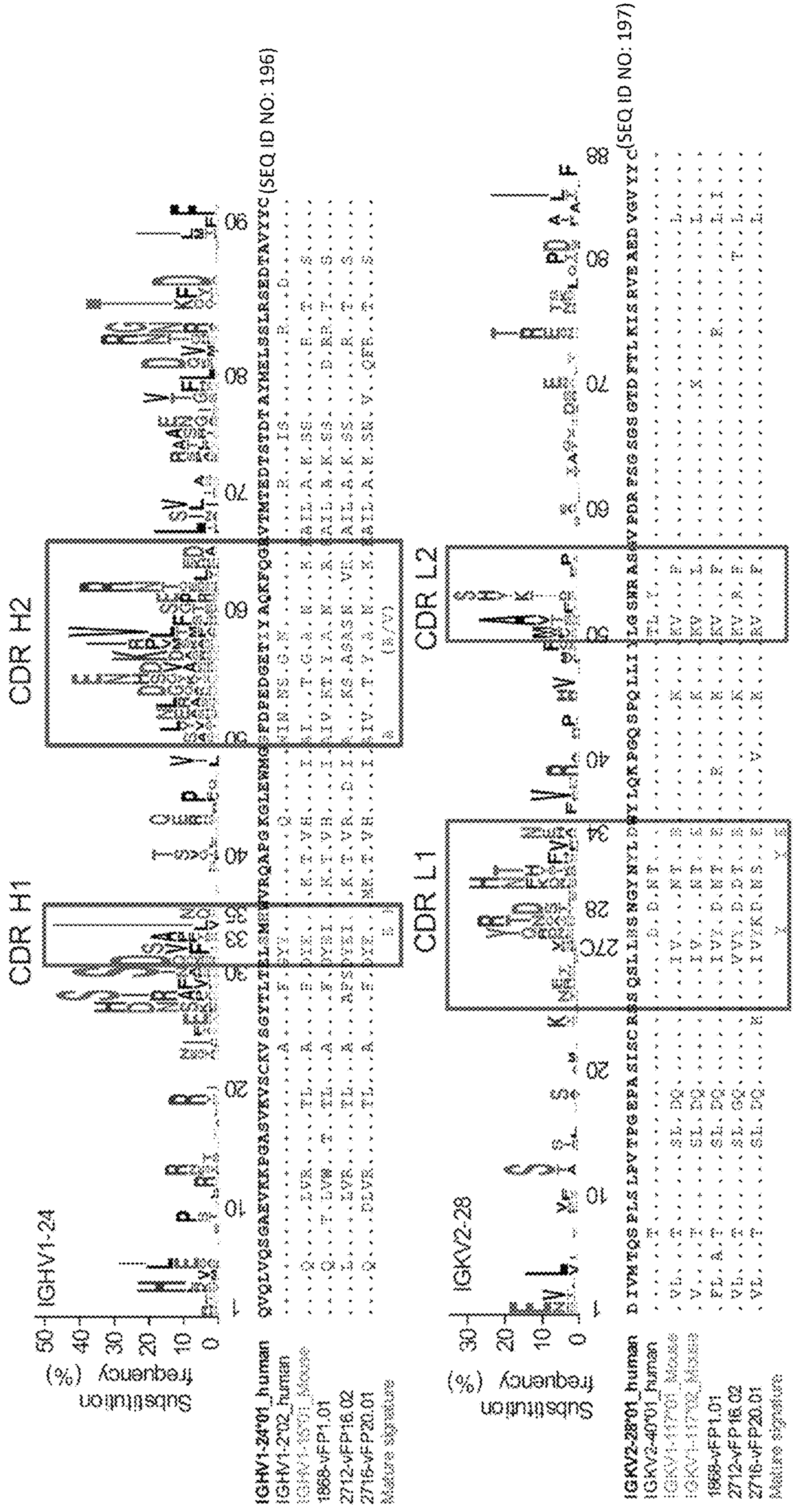
Figure 13C:
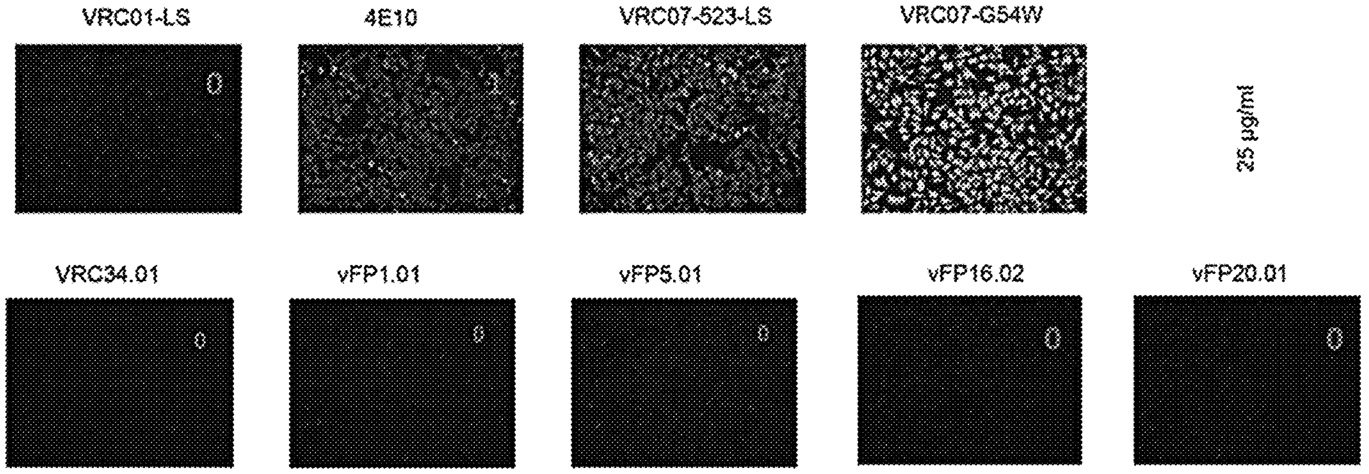
Figure 13E:
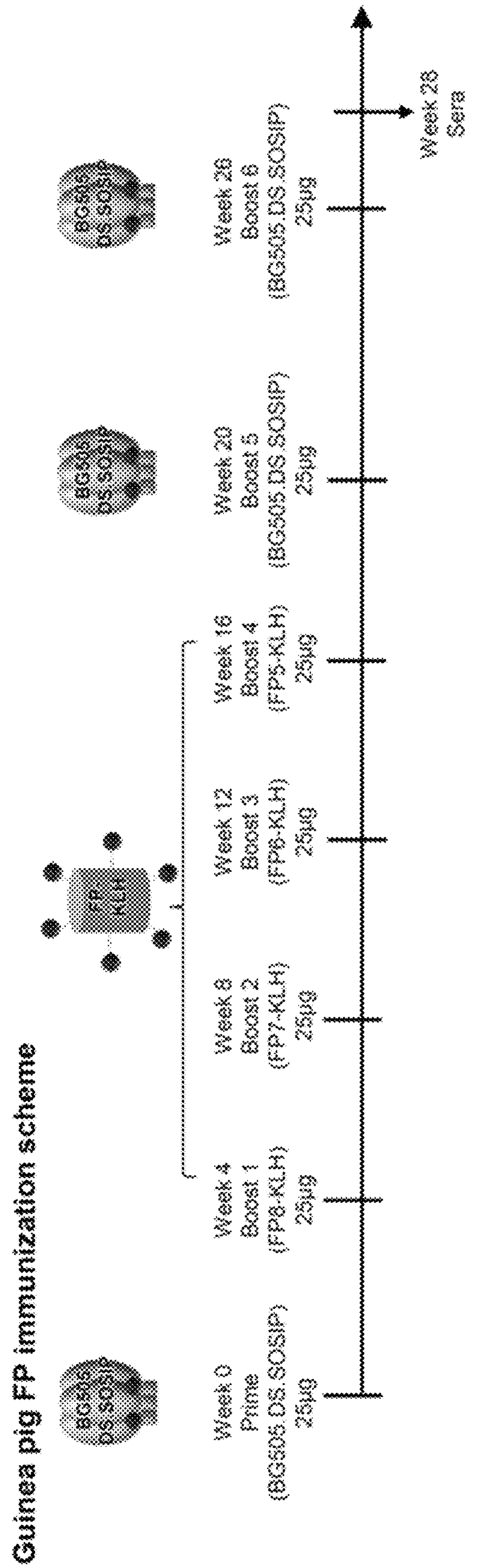
Figure 13G:
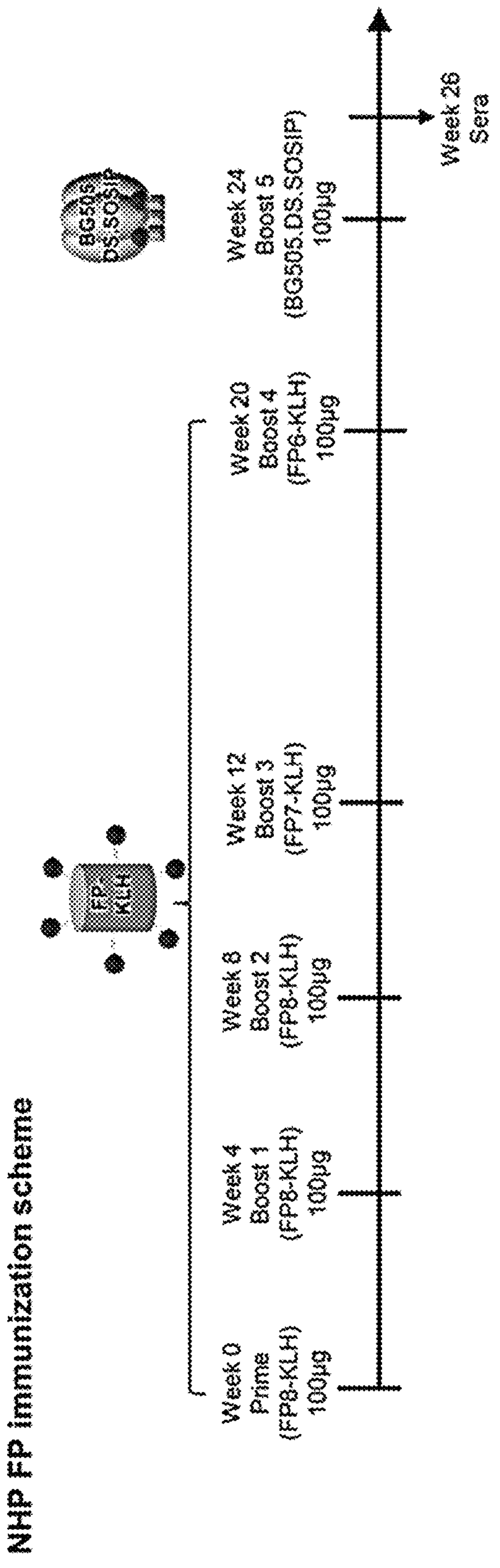

Genetic analysis indicates humans to have V-genes with similarity to the germline genes of the vFP1 class (FIGS. 13A, 13B), FP-directed antibodies can often be detected in HIV-1-infected donors by ELISA (Kong et al. (2016b) Science 352, 828-833), and vFP antibodies show no evidence of polyreactivity (FIGS. 13C, 13D). Moreover, we observed FP-KLH immunization followed by trimer boost to induce high neutralization titers against the glycan-deleted BG505 virus in guinea pigs and rhesus macaques (FIGS. 13E-13H), suggesting targeting of the FP region. Importantly, weak but cross clade neutralization of wild-type viruses from the 10-isolate panel was observed in a subset of sera. Overall, these results provide proof-of-principle for the ability of FP targeting to induce FP-directed antibodies with promising neutralization breadth.

Experimental Procedures

Peptide synthesis and peptide-carrier protein conjugate preparation. HIV-1 fusion peptides were each synthesized (GenScript®) with a free amine on the N-terminus. To prepare peptide-carrier protein conjugates (FP-KLH), peptides each with a cysteine residue added to the C-terminus were conjugated to the carrier protein keyhole limpet hemocyanin (KLH) (Thermo-Scientific®) using m-maleimidobenzoyl-N-hydroxysuccinimide ester (MBS) following the manufacturer's protocol. FP His-tagged peptides were each synthesized (GenScript®) with six histidine residues fused to the C-terminus of FP.

Protein expression and purification. BG505 SOSIP, BG505 DS-SOSIP and their glycan-deficient variants were expressed and purified using previously described protocols for expression and purification of HIV-1 Env trimers (Kwon et al. (2015) Nat Struct Mol Biol 22, 522-531). FP-epitope scaffold proteins, including FP-1M6T, FP-1Y12, FP-3HSH and FP-1SLF were expressed and purified using standard methods. The FP-1M6T-K42N epitope scaffold was designed by connecting the BG505 fusion peptide (512-519) to the N-terminus of a four helix bundle using a "GGG" linker, with a N-linked glycosylation sequon introduced at residue 42 of the scaffold (K42N). A control scaffold (1M6T-K42N) with the glycan introduced but without the fusion peptide (512-519) was also used. vFP1.01, vFP7.04, vFP16.02 and vFP20.01 antibodies used for structure determination were prepared as below. Heavy chain plasmids, encoding the chimera of mouse variable domain and human constant domain, with HRV3C cleavage site in the hinge region; and light chain plasmids, encoding the chimera of mouse variable domain and human constant domain were co-transfected in Expi293F cells (Thermo Fisher®) using Turbo293® transfection reagent (SPEED BioSystem®) according to the manufacturer's protocol. Transfected cells were incubated in shaker incubators at 120 rpm, 37° C., 9% $CO_2$ overnight. On the second day, one tenth culture volume of AbBooster® medium (ABI scientific) was added to each flask of transfected cells and cell cultures were incubated at 120 rpm, 33° C., 9% $CO_2$ for an additional 5 days. 6 days post-transfection, cell culture supernatants were harvested. IgGs were purified from the supernatant using protein-A column. After PBS wash and low pH glycine elution, eluate was collected with an addition of 10% volume of 1M Tris buffer pH 8.0 to neutralize the protein solution. Fabs were obtained either by HRV3C cleavage or Papain digestion. The fragmented Fabs were further purified by SEC in a Superdex® 200 column (GE®) with a buffer containing 5 mM HEPES, pH 7.5, 150 mM NaCl.

Negative-stain electron microscopy. Samples were diluted with a buffer containing 20 mM HEPES, pH 7.0, 150 mM NaCl, adsorbed to a freshly glow-discharged carbon-film grid, washed with the above buffer, and stained with 0.7% uranyl formate. Images were collected semi-automatically at a magnification of 100,000 using Serial_EM on a FEI Tecnai® T20 microscope equipped with a 2 k×2 k Eagle® CCD camera and operated at 200 kV. The pixel size was 0.22 nm/px. Particles were picked manually using the swarm mode in e2boxer from the EMAN2™ software package. Reference-free 2D classification was performed using EMAN2™ and SPIDER™

Antigenic characteristics of fusion peptide immunogens. Antigenic characteristics of KLH-coupled fusion peptide immunogens and FP scaffolds to various antibodies were assessed by Bio Layer Interferometry (BLI) method: A fort6Bio® Octet Red384 instrument was used to measure the apparent $K_D$ between antibodies and antigens, with antibodies (as IgG) immobilized on the chip surface.

Mouse immunization (GenScript®). Mice (C57BL/6) were immunized in two-week intervals with either HIV-1 Env trimer or FP-KLH, using Adjuplex as adjuvant (Sigma®) for trimer or GS-adjuvant (GenScript®) for FP-KLH. 50 µg of immunogens were used for prime immunization and 25 µg immunogens were used in boost immunization. Intraperitoneal (IP) route was used for all mice immunization. Sera were drawn either 7 days or 14 days after each immunization for ELISA and other analyses.

All experiments were performed in accordance with protocols reviewed by the Association for Assessment and Accreditation of Laboratory Animal Care International (AAALAC International). All mice were housed and cared for in an AAALAC-accredited facility at Genscript.

Hybridoma creation and monoclonal antibody production (GenScript®). Terminal boost was performed three weeks after the last immunization. Mice spleens were then harvested, and hybridomas were created for monoclonal antibody selection.

Guinea Pig and NHP Protocol and Immunization

For immunization studies, all animals were housed and cared for in accordance with local, state, federal, and institute policies in an American Association for Accreditation of Laboratory Animal Care-accredited facility at the Vaccine Research Center, NIAID, NIH or at a contract facility (Bioqual Inc, MD). All animal experiments were reviewed and approved by the Animal Care and Use Committee of the Vaccine Research Center, NIAID, NIH, and covered under protocol VRC 13-431.

Female Hartley guinea pigs with body weights of 300 grams were purchased from Charles River Laboratories, MA. For each immunization, 400 μl of immunogen mix, containing 25 μg of specified, filter-sterilized protein immunogen and 80 μl of Adjuplex (Sigma-Aldrich Inc, MO) in PBS, was injected into muscles of the two hind legs. While the animals were under anesthesia, blood was collected through retro-orbital bleeding for serological analyses.

Female and male Indian rhesus macaques with body weights of 2-9 kg were used for immunization studies. For each immunization, 1 ml of immunogen mix, containing 100 μg of specified, filter-sterilized protein immunogen and 200 μl of Adjuplex (Sigma-Aldrich Inc, MO) in PBS, was injected via a needle syringe into the caudal thighs of the two hind legs. Blood was collected for serological analyses.

ELISA. Fusion peptide ELISAs: 96-well plates (Costar® High Binding Half-Area, Corning, Kennebunk, ME) were coated with 50 μl/well of 2 μg/ml 1M6T or FP-1M6T scaffold proteins in PBS overnight at 4° C. Between subsequent steps, plates were washed 5 times with PBS-T (PBS+0.05% Tween) and incubated at 37° C. for 1 hour. After coating, plates were blocked with 100 l/well of blocking buffer (B3T: 150 mM NaCl, 50 mM Tris-HCl, 1 mM EDTA, 3.3% fetal bovine serum, 2% bovine albumin, 0.07% Tween 20, 0.02% Thimerosal). Next, 50 μl/well of 1:20 (for prebleed) and 1:1000 (for week 34) B3T-diluted guinea pig sera were added to the plate's first row, followed by a 5-fold serial dilution performed row by row. Afterward, 1:5000-diluted goat anti-guinea pig IgG secondary antibody (HRP-conjugated, KPL, Cat #14-17-06) was added at 50 μl/well. Plates were developed with tetramethylbenzidine (TMB) substrate (SureBlue™, KPL, Gaithersburg, MD) for 10 minutes before adding 1 N sulfuric acid (Fisher Chemical) to stop the reaction. Plates were read at 450 nm (Molecular Devices, SpectraMax® using SoftMax® Pro 5 software) and the optical densities (OD) were recorded.

BG505 SOSIP D7324 Capture ELISAs: 96-well plates (Costar® High Binding Half-Area, Corning, Kennebunk, ME) were coated with 50 μl/well of 2 μg/ml of sheep D7324 antibody (AALTO Bio Reagents) in PBS overnight at 4° C. Between subsequent steps, except for addition of trimer, plates were washed 5 times with PBS-T (PBS+0.05% Tween) and incubated at room temperature (RT) for 1 hr. After coating, plates were blocked with 100 l/well of blocking buffer (5% Skim Milk, 2% bovine albumin, 0.1% Tween 20 in TBS). Next, 50 μl/well of 0.5 μg/ml D7324-tagged BG505 SOSIP trimer diluted in 10% fetal bovine serum in PBS were added and incubated at RT for 2 hours. Next, 50 μl/well of 1:100 diluted guinea pig sera in blocking buffer were added to the first row of the plate, followed by a 5-fold serial dilution performed row by row. Afterward, 1:5000-diluted goat anti-guinea pig IgG secondary antibody (HRP-conjugated, KPL, Cat #14-17-06) was added at 50 μl/well. Plates were developed with tetramethylbenzidine (TMB) substrate (SureBlue™, KPL, Gaithersburg, MD) for 10 minutes before adding 1 N sulfuric acid (Fisher Chemical) to stop the reaction. Plates were read at 450 nm (Molecular Devices, SpectraMax® using SoftMax® Pro 5 software) and the optical densities (OD) were recorded.

Endpoint titers were deduced by selecting the highest reciprocal dilution that still yielded an OD>0.1 and were plotted using PRISM (PRISM 7 GraphPad Software for Mac OS X). Statistical analyses were assessed using Mann-Whitney tests with a cutoff for statistical significance set at two-tailed $p<0.05$.

Antibody Octet analysis. Binding of the vaccine elicited mouse vFP antibodies to sixteen His-tagged fusion peptide (residue 512-521), including wildtype and alanine/glycine mutants, was assessed using a fortéBio Octet Red384 instrument. Briefly, the sixteen peptides at 50 μg/ml in PBS were loaded onto Ni-NTA biosensors using their C-terminal histidine tags for 60 s. Typical capture levels were between 1.1 and 1.3 nm and variability within a row of eight tips did not exceed 0.1 nm. These peptide-bound biosensors were equilibrated in PBS for 60 s followed by capture of the antigen binding fragments (Fabs, 250 nM) of the vaccine elicited vFP antibodies, VRC34.01 and an RSV F antibody Motavizumab for 120 s and a subsequent dissociation step in PBS.

In all Octet measurements, parallel correction to subtract systematic baseline drift was carried out by subtracting the measurements recorded for a loaded sensor incubated in PBS. Data analysis was carried out using Octet software, version 9.0. The normalized responses obtained from one or triplicate data sets were plotted using PRISM® (PRISM 7 GraphPad® Software for Mac OS X).

Genetic assignment of antibodies. Antibody sequences were submitted to the ImMunoGeneTics information System® (IMGT, imgt.org) and subjected to variable (V), diverse(D) and joining(J) genes identification by alignment with the mouse germline sequences of the IMGT reference directory, and IMGT/JunctionAnalysis for a detailed analysis of the V-J and V-D-J junctions. We only considered the confirmed functional germline genes in the assigned germline. Clustal Omega™ software was used to prepare multiple sequence alignment of antibody sequences for maximum likelihood phylogenetic tree construction using DNAML™ program in the PHYLIP™ package version 3.69 (evolution-.genetics.washington.edu/phylip.html). The calculations were performed based on empirical base frequencies with transition/transversion (Ti/Tv) ratio of 2.0. Dendroscope 3 (dendroscope.org) was used to visualize phylogenetic trees. The amino acid sequence alignments were visualized using BioEdit v7.2.5 editing software. To calculate the minimal mutations required to switch between two different unmutated common ancestors, the unmutated common ancestor sequence was prepared by reverting the assigned V(D)J gene sequences into their corresponding germline sequences. Differences between unmutated common ancestor sequences were counted as the minimal mutations required to switch from one unmutated common ancestor to another.

Surface plasmon resonance assay. Binding affinities and kinetics of antibodies to HIV-1 DS-SOSIP trimers and His-tagged fusion peptide were assessed by surface plasmon resonance on a Biacore T-200 (GE Healthcare) at 25° C. To test antibody binding with HIV-1 DS-SOSIP trimers, 2G12 IgG was first immobilized on flow cells of a CM5 chip at ~3000-8000 response unit. BG505 DS-SOSIP trimer and its glycan-deleted mutants, BG505 DS-SOSIP.Δ88 and BG505 DS-SOSIP.Δ611, at 500 nM in HBS-EP+ buffer (10 mM HEPES, pH 7.4, 150 mM NaCl, 3 mM EDTA and 0.05% surfactant P-20) were then captured onto 2G12 of one flow cell by flowing the protein solution for 60 s at a flow rate of 6 μl/min. Serial diluted antibody Fab solutions starting at 200 nM were flowed through the 2G12-captured trimer channel and a 2G12-only reference channel for 180 s before a 300 s dissociation phase at 30 μl/min. The surface was regenerated by flowing 3M $MgCl_2$ solution for 30 s at a flow rate of 50 μl/min. Blank sensorgrams were obtained by injection of the same volume of HBS-EP+ buffer in place of antibody Fab solution. Sensorgrams of the concentration series were corrected with corresponding blank curves and fitted globally with Biacore T200 evaluation software using a 1:1 Langmuir model of binding.

Affinity of antibody Fab to the His-tagged fusion peptide was measured on a Ni-NTA sensor chip (GE Healthcare). The Ni-NTA surface was activated by injection of 5 mM of $Ni_2SO_4$ in HBS-P+ buffer (10 mM HEPES, pH 7.4, 150 mM NaCl and 0.05% surfactant P-20) for 60 s at 6 μl/min and then stabilized by washing with HBS-EP+ buffer containing 3 mM EDTA for 60 s at 30 μl/min. Fusion peptide with His-tag at 20 ng/ml was captured at 6 μl/min flow rate for 60 s over one nickel activated sensor surface. Serial diluted antibody Fab solutions starting at 200 nM were flowed through fusion peptide channel and a reference channel for 180 s seconds before a 300 s dissociation phase at 30 μl/min. The surface was regenerated by flowing 300 mM imidazole to both channels at 6 μl/min for 60 s. Sensorgrams of the concentration series were corrected with corresponding blank curves and fitted globally with Biacore T200 evaluation software using a 1:1 Langmuir model of binding.

HIV-1 Env mutagenesis. Site-directed mutagenesis on HIV-1 Env plasmids was performed through GeneImmune Biotechnology LLC, NY. T90A and S613A mutations were created to remove glycan 88 and 611, respectively.

HIV-1 Env-pseudotyped virus. 293T-grown HIV-1 Env-pseudotyped virus stocks were generated by cotransfection of the wildtype or mutant Env expression plasmids with a pSG3ΔEnv backbone (Wu et al. (2010). Science 329, 856-861).

Neutralization assays. A single round of entry neutralization assays using TZM-bl target cells were performed to assess monoclonal antibody (mAb) neutralization as described (Wu et al. (2010). Science 329, 856-861). Briefly, the mAbs were tested via 5-fold serial dilutions starting at 200 μg/ml. mAbs were mixed with the virus stocks in a total volume of 50 μl and incubated at 37° C. for 1 hr. 20 μl of TZM-bl cells (0.5 million/ml) were then added to the mixture and incubated at 37° C. overnight. 130 μl cDMEM was added on day 2, and cells were lysed on day 3 and assessed for luciferase activity (RLU). The 50% and 80% inhibitory concentrations ($IC_{50}$ and $IC_{50}$) were determined using a hill slope regression analysis as described (Wu et al. (2010). Science 329, 856-861).

To assess the mAb neutralization on a panel of 208 HIV-1 Env-pseudotyped viruses, an automated 384-well microneutralization assay was performed as described previously (Sarzotti-Kelsoe et al. (2014). J Immunol Methods 409, 131-146). Serum neutralization was also assessed in the single round of entry neutralization assays using TZM-bl target cells, as described above. Before evaluation, all sera from immunized and control mice were heat-inactivated at 56° C. for 1 hr. All sera were tested via 4-fold serial dilutions starting at 1:20 dilution.

Protein complex preparation. Antibody Fab and fusion peptide (residue 512-518) complexes were prepared by first dissolving fusion peptide into 100% DMSO at 50 mg/ml concentration, then mixing with Fab solution in 10:1 molar ratio.

Crystal screening. Antibody Fab and fusion peptide (residue 512-518) complexes were screened for crystallization from JCSG1-4 protein crystal screening kits using a Cartesian Honeybee crystallization robot as described previously (McLellan et al. (2011). Nature 480, 336-343) and a mosquito robot. Crystals initially observed from the wells were manually reproduced. vFP1.01/FP complex crystal grew in 0.2 M $AmSO_4$, 0.1 M NaoAc pH 4.6; vFP7.04/FP complex crystal grew in 0.1 M MES pH 6.0, 30% PEG 6000; vFP16.02/FP complex crystal grew in 0.1 M NaoAc pH 4.5, 2 M $AmSO_4$; vFP20.01/FP complex crystal grew in 0.1 M Citric acid pH 3.5, 2 M $AmSO_4$; vFP5.01/FP complex crystals grew in 0.2 M $MgCl_2$, 0.1 M Tris-HCl pH 8.5, 20% PEG 8000.

X-ray data collection, structure solution and model building. The crystals were cryoprotected in 20% glycerol and flash-frozen in liquid nitrogen. Data were collected at a wavelength of 1.00 Å at the SER-CAT beamline ID-22 (Advanced Photon Source, Argonne National Laboratory). Diffraction data was processed with the HKL2000 suite. Structure solution was obtained by molecular replacement with Phaser using homologous Fab structures (PDB ID: 3BKY for vFP1-class antibody complex and 3LEY for vFP5.01 antibody complex) as search models. Refinement was carried out with Phenix. Model building was carried out with Coot. Structural figures were prepared with PyMOL (pymol.org).

Cryo-EM data collection and processing. To prepare Env complexes, BG505 DS-SOSIP at a final concentration of 0.3-0.5 mg/ml was incubated with 4-5-fold molar excess of the antibody Fab fragments for 30-60 minutes. To prevent aggregation during vitrification, the sample was incubated in 0.085 mM dodecyl-maltoside (DDM). The vFP1.01 and vFP5.01 bound complexes were vitrified by applying 3 μl of sample to freshly plasma-cleaned C-flat holey carbon grids (CF-1.2/1.3-4C) (EMS, Hatfield, PA) for vFP1.01 and gold grids for vFP5.01, allowing the sample to adsorb to the grid for 60 s, followed by blotting with filter paper and plunge-freezing into liquid ethane using the CP3 cryo-plunger (Gatan, Inc.) (20° C., 85-90% relative humidity).

The vFP16.02 and vFP20.01 bound complexes were vitrified using a semi-automated Spotiton V1.0 robot The grids used were specially designed Nanowire self-blotting grids with a Carbon Lacey supporting substrate. Sample was dispensed onto these nanowire grids using a picoliter piezo dispensing head. A total of ~5 nl sample was dispensed in a stripe across each grid, followed by a pause of a few milliseconds, before the grid was plunged into liquid ethane.

Data was acquired using the Leginon system installed on Titan Krios electron microscopes operating at 300 kV and fitted with Gatan K2 Summit direct detection device. The dose was fractionated over 50 raw frames and collected over a 10 s exposure time. Individual frames were aligned and dose-weighted.

CTF was estimated using the GCTF package. Particles were picked using DoG Picker within the Appion pipeline. 2D and 3D classifications were performed using RELION. A map of unliganded BG505 SOSIP.664 (EMDB ID 5782), low-pass filtered to 60 Å was used as the starting point of 3D classification followed by 3D refinement in either RELION or cryoSparc. For the vFP16.02 and vFP20.01 complexes, after 3D classification in RELION, an additional step of ab initio reconstruction was performed using cryoSparc.

Modelfitting. Fits of HIV-1 trimer and Fab to the cryo-EM reconstructed maps were performed using Chimera. Glycosylated BG505 SOSIP trimer structure (PDB ID: 5YFL) was used for the trimer fits. For antibody fitting, we used the fusion peptide-bound coordinates of vFP1.01 and vFP5.01. For the antibody Fabs, both orientations rotated ~180° about the Fab longitudinal axis were tested, and the optimal fit was decided based on map-to-model correlation and positioning of the fusion peptide bound to the Fab relative to Env. For the vFP16.02 and vFP20.01 bound complexes, the coordinates were further fit to the electron density by an iterative process of manual fitting using Coot and real space refinement within Phenix. Molprobity and EMRinger were used to check geometry and evaluate structures at each iteration step. Figures were generated in UCSF Chimera and Pymol. Map-fitting cross correlations were calculated using Fit-in-Map feature in UCSF Chimera. Map-to-model FSC curves were generated using EMAN2.

Defining vFPJ class antibody V-gene sequence signature. The V-gene sequence signature for vFP1 class antibodies were defined by examining the vFP1 class antibody sequences listed in FIG. 5C that neutralize at least seven out of the ten tested isolates and the structures of FP in complex with vFP1.01, vFP16.02, and vFP20.01. A residue position was considered as part of the sequence signature if at least one side chain heavy atom was within five angstroms from any fusion peptide heavy atom for all three complex structures, and no more than three similar amino acid types have a combined prevalence of more than 90%, and each of these amino acid types had a prevalence of more than 10%.

Molecular Dynamics of mannose 5 Env trimer model. Using the BG505 SOSIP.664 Env trimer structure (PDB ID: 4TVP) as a starting template, we modeled in a fully extended mannose 5 moiety at each N-linked glycosylation sequon using our in-house software glycosylator. The fusion peptide structure was then grafted onto our full mannose 5 model followed by 5000 steps of conjugate gradient energy minimization in implicit solvent using NAMD. The obtained structure was then solvated in a 17 Å padding water box, neutralized by the addition of NaCl at a concentration of 150 mM. The CHARMM36 force field was used for the parameterization of the protein (including CMAP corrections) and the mannose 9. TIP3P water parameterization was used to describe the water molecules.

Two independent molecular simulation were carried out using ACEMD molecular dynamics software on a METROCUBO workstation. The system was minimized for 2000 steps, followed by equilibration using the NPT ensemble for 50 ns at 1 atm and 300 K using a time-step of 2 fs. We also used rigid bonds and cutoff of 9 Å using PME for long range electrostatics. During the equilibration phase, heavy atoms on the protein were constrained by a 1 kcal/molA-2 spring constant and slowly relaxed over the first 5 ns. Following the relaxation phase, the protein was allowed to move freely and simulated for 500 ns under the NVT ensemble using ACEMD's NVT ensemble with a Langevin thermostat. To achieve a time-step of 4 ps, we used damping at 0.1 ps-1 and a hydrogen mass repartitioning scheme. Each simulation ran up to 500 ns.

The conformations of the fusion peptide (residue 512-519) were extracted from the MD simulations every 100 ps, producing an ensemble of 30'000 structures. Prody was used to perform the principal component analysis of backbone atoms. The conformations of five crystalized fusion peptides were then projected into the eigenspace defined by the first two components: vFP1.01, vFP5.01, PGT-151 (PDB: 5FUU), VRC34 (PDB: 5I8H) and clade G (PDB: 5FYJ).

Analysis of antibody angle of approach to HIV-1 Env. To compare modes of antibody recognition of HIV-1 Env by vaccine elicited fusion peptide antibodies and VRC34.01, structural models of antibody in complex with HIV-1 Env derived from x-ray crystallography and EM were superposed by aligning the Env sequences. Antibody binding modes relative to the trimer axis and to the major interacting Env protomer were compared between different trimer-bound antibodies. The trimer axis was defined by two points, each with x, y, z coordinates obtained by averaging the coordinates of the Ca atom of a residue and its 3-fold symmetry mates on the same trimer. The protomer axis was defined by a line perpendicular to the trimer axis that passes the center of the protomer. The long axis of each antibody Fab was defined by two points, one point from the variable domain with x, y, z coordinates obtained by averaging the coordinates of the Ca atom of the 4 conserved Cys (Cys 22 and Cys92 of heavy chain, and Cys23 and Cys88 of light chain), and the other from the constant domain with x, y, z coordinates obtained by averaging the coordinates of the Ca atom of the 4 conserved Cys (Cys 140 and Cys196 of heavy chain, and Cys134 and Cys194 of light chain). The short axis of an antibody was defined by a line connected by Ca atom of heavy chain Cys22 and light chain Cys23. The angle of antibody approach to trimer axis was the angle between trimer axis and antibody long axis. The angle of antibody to its major interacting protomer was the angle between the protomer axis and antibody long axis. The relative orientation of antibody variable domains was compared by angles between antibody short axes. The axes can be visualized in PyMOL by placing their coordinates in PDB format.

Autoreactivity assay. Antibodies were assessed for autoreactivity by testing for binding to HEp2 cells by indirect immunofluorescence (Zeus Scientific, ANA HEp2 test system) and cardiolipin by ELISA (Inova Diagnostics, QUANTA Lite ACA IgG III), per the manufacturer's instructions. On HEp2 cells, antibodies were assigned a score between 0 and 3+ using control antibodies as reference. In the cardiolipin binding assay, OD values were converted to GPLs using standard samples provided in the kit. mAbs that scored greater than 20 GPLs at 33 μg/ml were considered autoreactive.

Neutralizationfingerprinting analysis. The neutralization fingerprint of a monoclonal antibody is defined as the potency pattern with which the antibody neutralizes a set of diverse viral strains. The neutralization fingerprints of a set of monoclonal antibodies were compared and clustered according to fingerprint similarity, as described previously (Georgiev et al. (2013) Science 340, 751-756). A set of 132 strains was used in the neutralization fingerprint analysis.

Data and Software Availability. The crystal structures reported in the paper are in the process of being deposited with the PDB. All software used in crystal structure determination (Phenix, Pymol and Coot) are accessible via the Structural Biology Grid (SBGrid). Cryo-EM maps and fitted/refined models are in the process of being deposited with the EMDB.

Example 2. Epitope Scaffold Proteins

This example illustrates the design and production of epitope scaffold proteins that include the HIV-1 Env fusion peptide linked to the N-terminus of the scaffold protein. When linked to the heterologous scaffold, the HIV-1 Env fusion peptide maintains a conformation similar to that of the HIV-1 Env fusion peptide in the HIV-1 Env ectodomain trimer. Accordingly, such epitope scaffold proteins can specifically bind to neutralizing antibodies that target the HIV-1 Env fusion peptide, such as VRC34.

VRC34-Epitope Scaffold Design

VRC34-epitope scaffold constructs were designed by adding fusion peptide (residues 512-519) to the N-terminus of various scaffold proteins (FIG. 18). An N-linked glycosylation site was also introduced to some of the constructs to resemble glycan N88 on HIV-1 Env protein. Sequences of epitope scaffold proteins (including HIV-1 Env fusion peptide linked to the scaffold, as well as processing and purification sequences, such as signal peptides and purification tags) are provided herein as SEQ ID NOs: 23-81. One exemplary epitope scaffold protein, FP-1M6T-K42N (SEQ ID NO: 49), was designed by connecting the BG505 fusion peptide (512-519) to the N-terminus of a four helix bundle (see Chu et al., Redesign of a four-helix bundle protein by phage display coupled with proteolysis and structural characterization by NMR and x-ray crystallography. *J. Mol. Biol.* 323, 253-262, 2002) using a "GGG" linker, with an N-linked glycosylation sequon introduced at residue 42 of the scaffold (K42N). A control scaffold (1M6T-K42N) with the glycan introduced but without the fusion peptide (512-519) was also used in binding assays.

Screening of Fusion Peptide-Based Immunogen

High throughput ELISA analysis was performed to identify VRC34-epitope scaffolds with a superior combination of expression level and affinity to VRC34.01 mAb. In detail, a 96-well microplate-formatted transient gene expression approach was used to achieve high-throughput expression of various design constructs as described previously (Pancera et al., PLOS ONE, 8, e55701, 2013). Briefly, 24 hours prior to DNA-transient transfection, 100 μl per well of physiologically growing HEK 293T cells were seeded into a 96-well microplate at a density of 2.5×105 cells/ml in expression medium (Dulbecco's Modified Eagle Medium and GlutaMAX, supplemented with 6% Fetal Bovine Serum and ix-Non-Essential Amino Acids) (Invitrogen, CA), and incubated at 37° C., 5% CO2. Two hours prior to transfection, 100 μl per well of spent medium was replaced with 60 μl of fresh expression medium. For transient transfection, DNA-TrueFect-Max complex per well was prepared by mixing 0.25 g plasmid DNA in 10 μl of Opti-MEM transfection medium (Invitrogen, CA) with 0.75 μl of TrueFect-Max (United BioSystems, VA) in 10 μl of Opti-MEM, and incubating for 15 min, and then mixed with growing cells in the 96-well plate and incubated at 37° C., 5% CO2. One day post transfection, 25 μl per well of enriched medium, ProBooster Protein Expression Enhancer for Adherent cell (ABI, VA) was fed. On day three and four post transfection, 96-well culture plate was exposed to oxygen in the sterilized air hood once per day. Five days after transfection, the antigenicity of expressed in the 96-well microplate was diluted with 70 μl of PBS in a Nickel coated 96-well ELISA plate (Thermo, IL) and incubated for two hours at room temperature (RT). After washing with PBS+0.05% Tween 20, 100 μl per well of primary antibody at a concentration of 10 μg/ml in PBS with 0.5% (W/V) dry milk and 0.02% tween 20 was incubated for 1 hour at RT. After washing, 100 μl per well of Horseradish peroxidase (HRP)-conjugated goat anti-human IgG antibody (Jackson ImmunoResearch Laboratories Inc., PA) at 1:10,000 in PBS with 1.0% (W/V) dry milk and 0.02% tween 20 was incubated for 30 min at RT. After washing, the reaction signal was developed using BioFX-TMB (SurModics, MN) at RT for 10 min, and then stopped with 1 N $H_2SO_4$. The readout was measured at a wavelength of 450 nm.

Of more than 30 epitope scaffold proteins tested, three constructs based on the 1M6T scaffold were identified as having the best combination of expression and VRC34 binding. These constructs are provided as FP_glyc88_1M6T_A35N_A37S (SEQ ID NO: 32), FP_glyc88_1M6T_K42N (SEQ ID NO: 33), and FP_glyc88_1M6T_E49N_K51T (SEQ ID NO: 34). SEQ ID NOs: 32-33 include signal peptide sequences and purification tags, etc. The core fusion peptide linked to scaffold sequence for each of these constructs is provided as SEQ ID NOs: 102-104. ELISA analysis with VRC34 of the 1M6T-K42N scaffold, with and without attaching the fusion peptide at the N-terminus, shows that the scaffold with the HIV-1 Env fusion peptide bound to VRC34 (FIG. 18).

Example 3. Protein Nanoparticles

Protein nanoparticles including the HIV-1 Env fusion peptide were designed by adding fusion peptide (e.g., HIV-1 Env residues 512-521) to the N-terminus of ferritin (PDB ID: 3EGM) and lumazine synthase (LS, PDB ID: 1HQK) subunits. In some examples, an N-linked glycosylation site was also introduced to resemble glycan N88 on HIV-1 Env protein. Sequences of the nanoparticle (including an N-terminal fusion to the HIV-1 Env fusion peptide), as well as processing and purification sequences, such as signal peptides and purification tags) are provided herein as SEQ ID NOs: 17-24, and 59-71.

Exemplary fusion peptide—lumazine synthase nanoparticle subunits are provided as SEQ ID NOs: 59 and 60. These subunits include amino acid substitutions to introduce an N-linked glycosylation site to resemble HIV-1 Env glycan N88.

Designed constructs were synthesized and cloned into the pVRC8400 expression vector. The resultant plasmids were transfected into adherent 293 cells in a 96-well plate format. Transfected supernatants were assessed by ELISA for N123-VRC34.01 and N123-VRC34.05 binding (FIG. 18B).

Several proteins with good expression and binding activity were expressed in HEK 293 cells at 1 liter volumes and purified by IMAC and size-exclusion chromatography. Size-exclusion chromatography analysis and negative-strain electron microscopy revealed that the immunogen FP-LS assembled into a homogenous nanoparticle (FIG. 18C). The matrix of fusion peptides enables high binding avidity to a panel of fusion peptide-targeting antibodies including N123-VRC34.01, N123-VRC34.05, vFP1.01, vFP1.05, and PGT151 (FIG. 18D). Binding affinities are comparable to KLH conjugated fusion peptide immunogens and superior to monomeric immunogens.

Accordingly, the FP-LS construct provides a multivalent platform with superior binding capability for engaging FP-directed bNAbs and can be used as an immunogen for both protein subunit and genetic immunization regimens, such as DNA/RNA or vector-based systems. DNA or RNA based immunization regimens allow a faster means to test candidate immunogens in human subjects by avoiding time-consuming manufacture of recombinant proteins. The structure-based design also includes glycan N88 as part of the displayed immunogen which is not always available using peptide conjugation methods. The involvement of glycan in the epitope may be relevant for stimulating potency of neutralizing antibodies.

Example 4. Antigenicity of Fusion Peptide Immunogens

This example provides results of binding assays for several of the disclosed immunogens to anit-HIV-1 Env antibodies that target fusion peptide. Apparent $K_D$ values were assessed using standard methods. As shown in the following table, the FPs-KLH immunogen showed superior antigenicity in terms of tight binding to antibodies VRC34.01, PGT151 and CHO7, which are known to bind to the HIV-1 Env fusion peptide.

| Construct | Scaffold configuration (EM) | Apparent $K_D$ value (nM) | | | | | |
|---|---|---|---|---|---|---|---|
| | | VRC34.01 | VRC34.05 | PGT151 | CH07 | FP1.01 | FP1.05 |
| FP8-KLH | KLH particle | <0.001 | <0.001 | <0.001 | 5.8* | N.D. | N.D. |
| FP8-1M6T | Monomer | 5.6 | 2365 | 2725 | 2739 | N.D. | N.D. |
| FP8-1HQK | 60-mer nanoparticle (lumazine synthase) | <0.001 | 0.002 | <0.001 | N.B. | <0.001 | <0.001 |
| FP8-3HSH | Trimer | <0.001 | N.B. | <0.001 | N.B. | <0.001 | <0.001 |
| FP8-1Y12 | Multimer | 3.7 | N.B. | <0.001 | N.B. | 1.0 | 0.007 |
| FP8-1LSF | Tetramer | 0.007 | 1.0 | 6.1 | N.B. | <0.001 | 10.7 |

N.B., no binding;
N.D., not determined;
*Response level low

Example 5. HIV-1 Env Fusion Peptide-Carrier Conjugates as Immunogens

As discussed above, naturally elicited antibodies VRC34.01 and ACS202 identified the N-terminus of the fusion peptide as an Env site of vulnerability, with molecular dynamics of the target region in the context of the pre-fusion closed Env trimer indicating substantial molecular flexibility of the fusion peptide N-terminus. An immunogen comprising the N-terminal eight amino acids of the fusion peptide, coupled to keyhole limpet hemocyanin (KLH), elicited fusion peptide-directed antibodies capable of neutralizing select tier-2 strains of HIV-1 from clades A, B and C. This example provides results using various HIV-1 Env fusion peptide sequences linked to three additional carrier proteins: CRM197 (the cross-reactive component of diphtheria toxin), tetanus toxin C fragment (tetanus toxin heavy chain fragment C or "TTHc"), and HiD (Haemophilus influenza protein D), each of which has been approved for use in humans. These three carriers as well as KLH were coupled to the first 8 residues (HXB2 numbering) of the four most commonly observed fusion peptide sequences. Sequences and carriers are show in FIG. 19A.

The FP peptides were linked to carrier proteins using standard cross-linking protocols with sulfo-SIAB cross-linker to link the primary amine of lysine residues in the carrier to a C-terminal cysteine linked to the FP peptide.

Figure 19C:
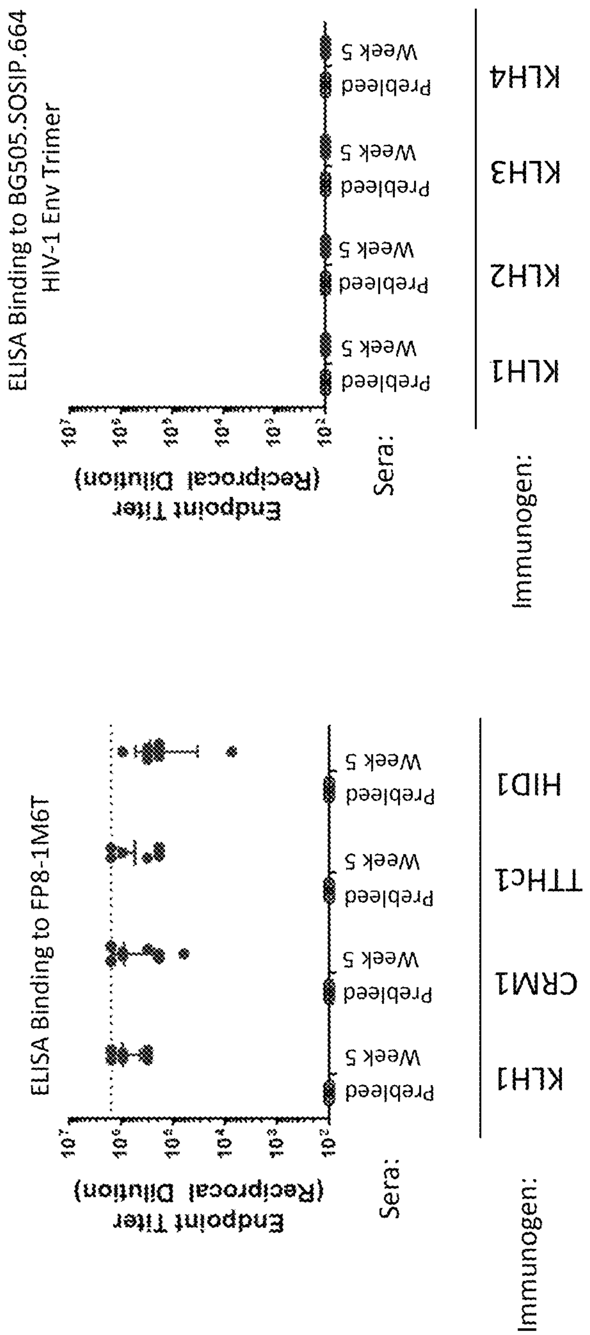
Figure 19D:
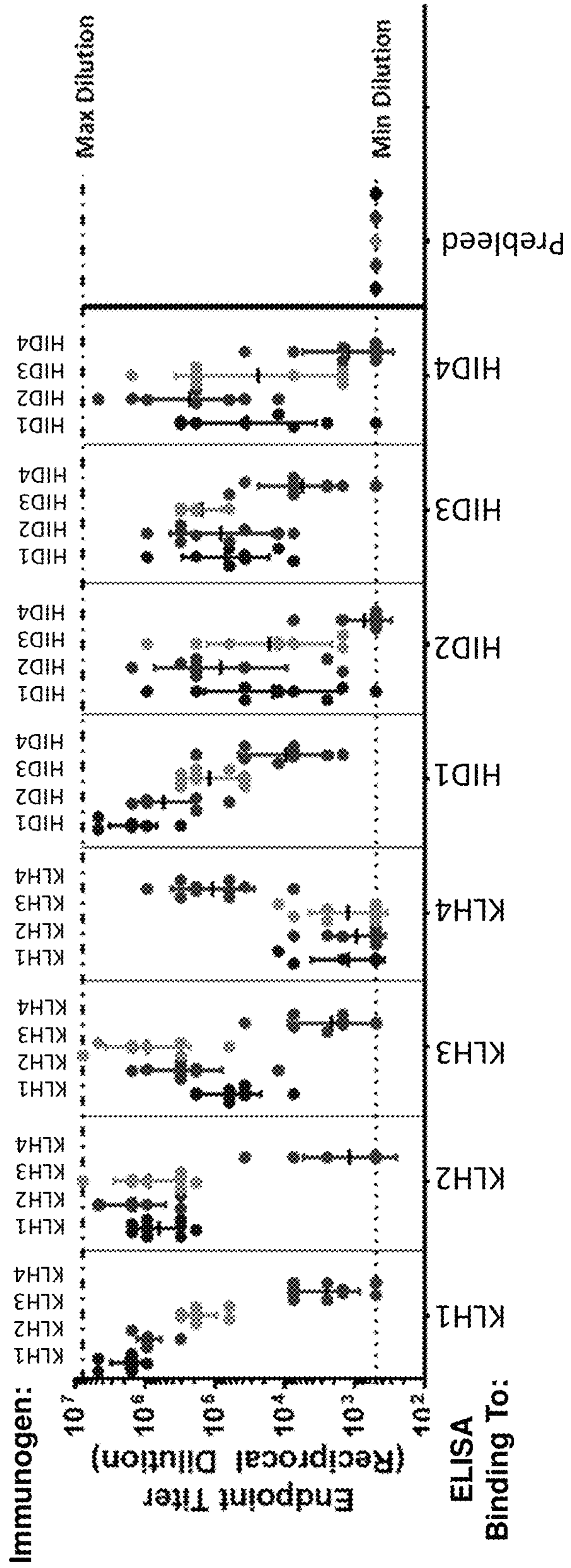
Figure 19E:
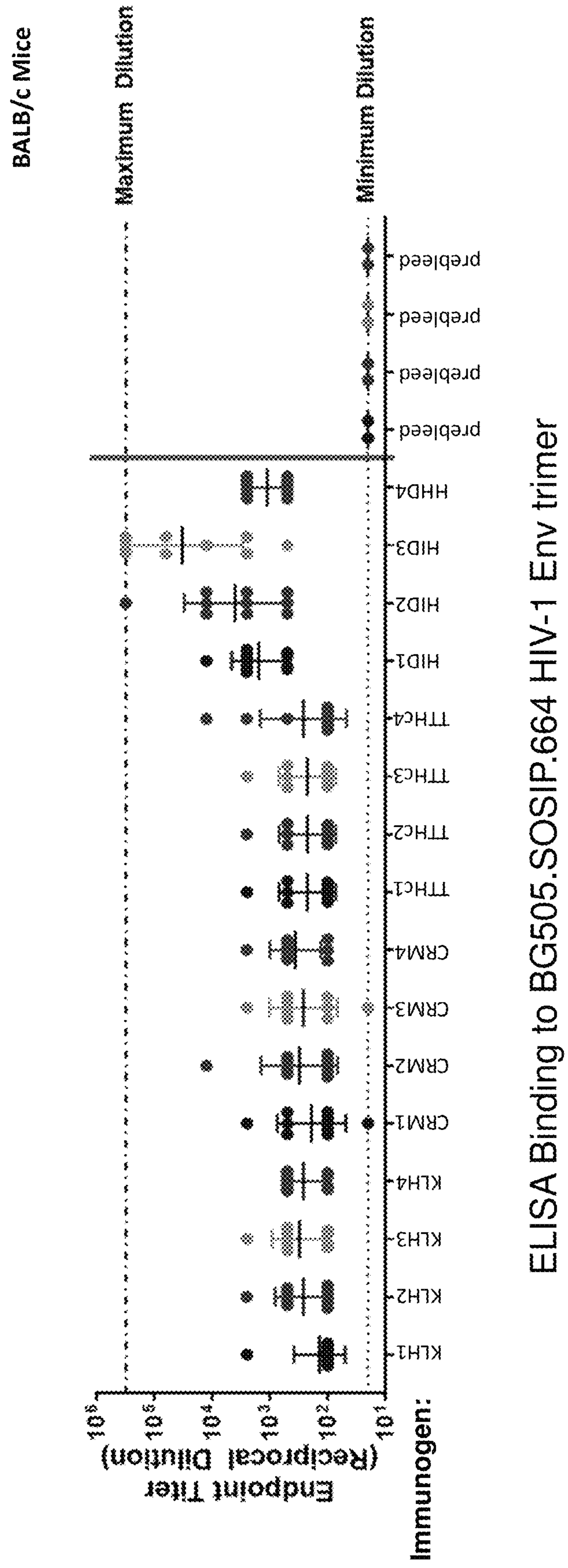
Figure 19F:
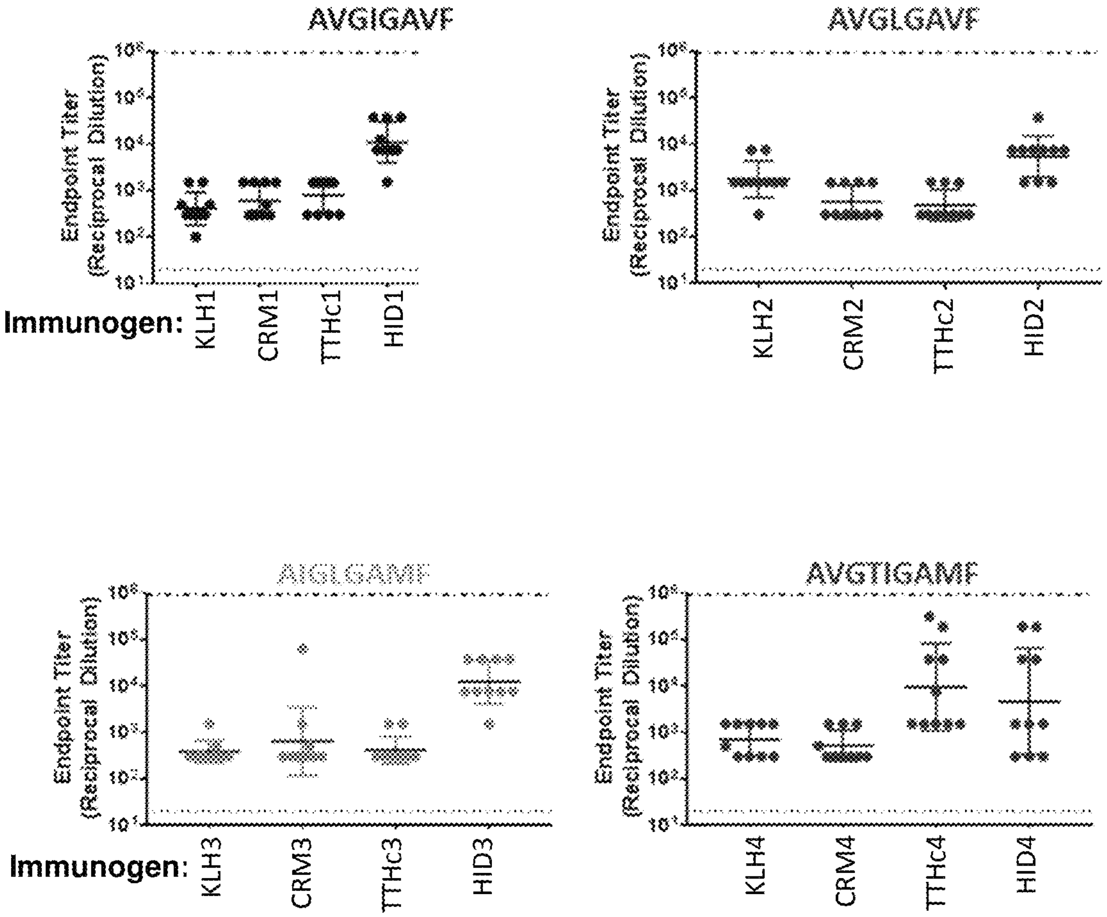
Figure 19G:
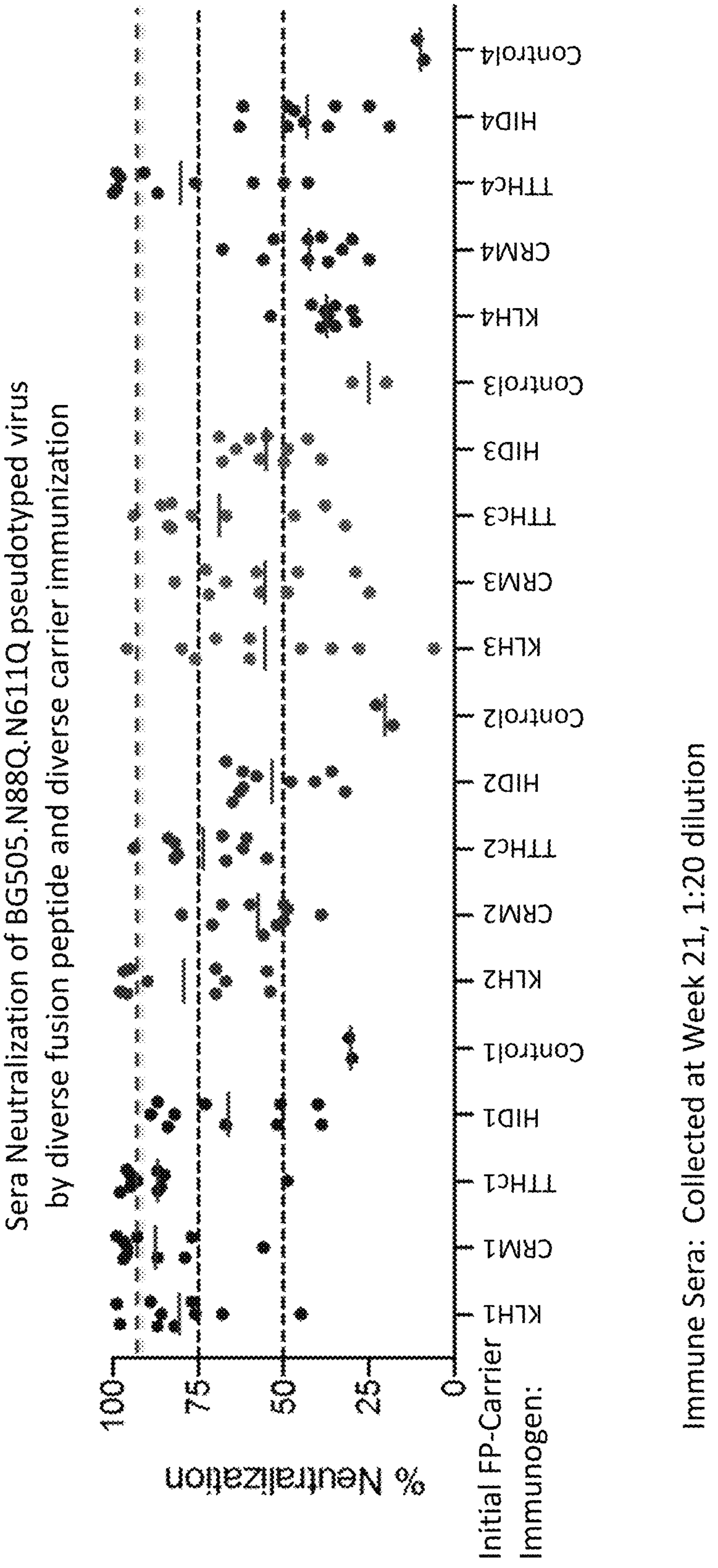

16 groups of mice were immunized with the resultant 4-carrier by 4-fusion peptide matrix. The immunization scheme is shown in FIG. 19B. ADJUPLEX™ was used as the adjuvant. After two immunizations, strong responses were observed in all mice against epitope scaffolds incorporating fusion peptides, but not against HIV-1 Env trimer (FIG. 19C). All the immunogens elicited an immune response that targeted diverse fusion peptide sequences (FIG. 19D). After a third immunization, responses to HIV-1 Env trimers were observed with all the immunogens, with the HiD carrier protein eliciting the highest response (FIG. 19E). Following the first trimer boost (week 21 sera, post-6$^{th}$ immunization) the ELISA endpoint titers were further increased (FIG. 19F). Finally, after completion of the immunization scheme detailed in FIG. 19B, sera was drawn and tested for neutralization of BG505 N88Q/N611Q pseudotyped virus. As shown in FIG. 19G, each immunization protocol elicited an immune response that neutralized the BG505 N88Q/N611Q virus. Tetanus toxoid as a carrier provided similar results as KLH, and elicited a neutralizing immune response for each fusion peptide sequence tested. These studies provide proof-of-principle for the utility of peptide-coupled carrier proteins as an immunogen platform to focus the immune response to the fusion-peptide site of vulnerability.

Example 6. Production of Fusion Peptide Linked to Tetanus Toxin Carrier

Figure 20:
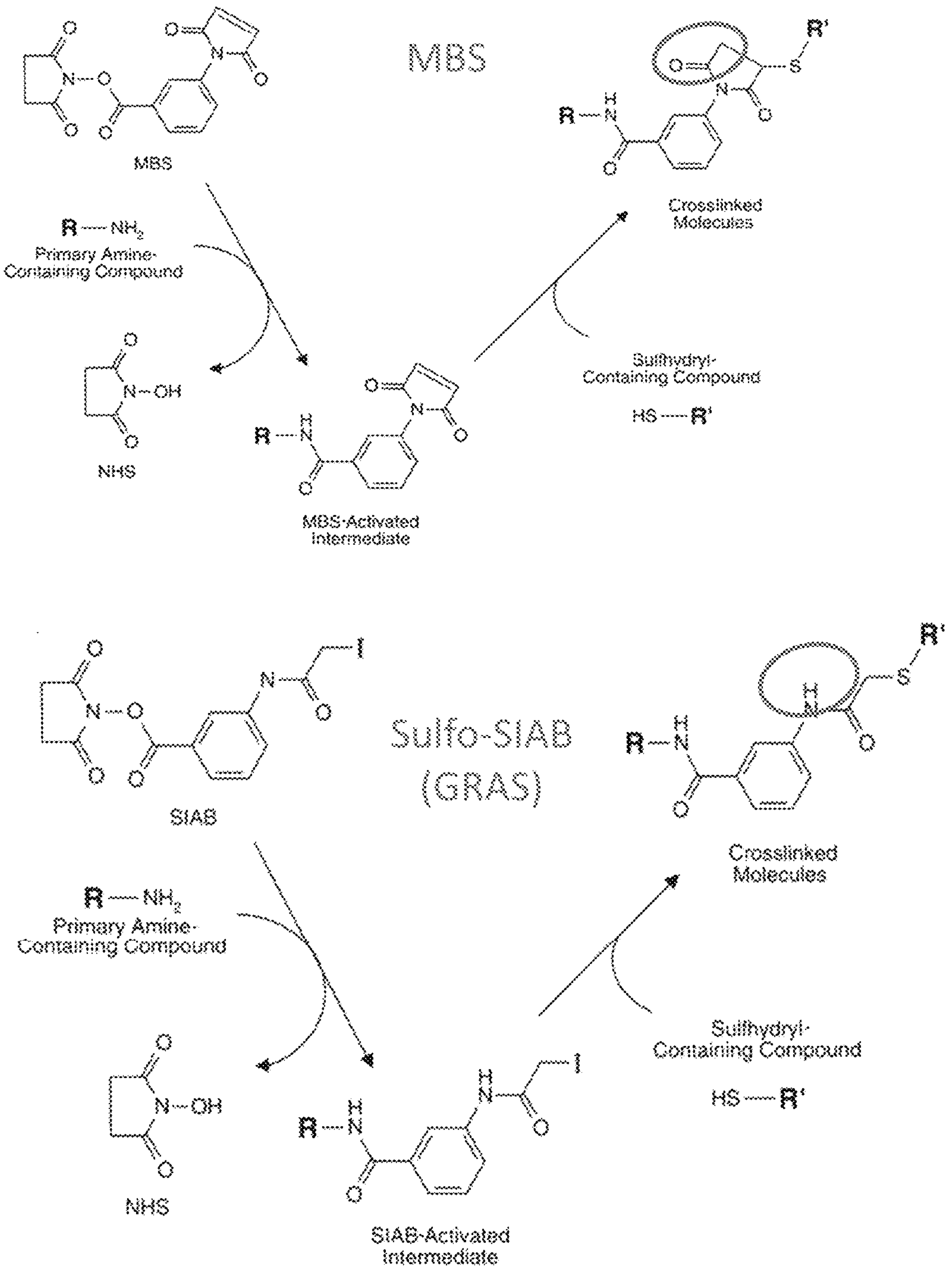
FIG. 20 shows peptide conjugation chemistry using sulfo-succinimidyl (4-iodoacetyl)aminobenzoate (Sulfo-SIAB) and m-maleimidobenzoyl-N-hydroxysuccinimide ester (MBS) linkers.

This provides a non-limiting example of a method of linking a HIV-1 Env fusion peptide (FP8, AVGIGAVF, residues 1-8 of SEQ ID NO: 1) to a tetanus toxin C fragment carrier (TTHc) via a sulfosuccinimidyl (4-iodoacetyl)aminobenzoate (Sulfo-SIAB) linker or a m-maleimidobenzoyl-N-hydroxysuccinimide ester (MBS) linker. The linkers and conjugation chemistry are illustrated in FIG. 20. The protocol used to link the fusion peptide to carrier was performed according to standard methods (see, e.g., Hermanson. Bioconjugation Techniques, 3$^{rd}$ ed., Chap. 6, p. 306-308. Academic Press, 2013).

Briefly, the conjugation protocol included:

Activation of TTHc (Tetanus Toxin Heavy Chain Fragment C) Carrier Protein:

1. Prepare 10 mM stock of sulfo-SIAB crosslinker. (Dissolved 5.04 mg of sulfo-SIAB in 1 mL water.)
2. Prepare a 1 mg/mL TTHc stock (from FinaBio, MW=51949.89 g/mol) in conjugation buffer (10% glycerol, 50 mM Na/$KPO_4$ buffer, pH 8.5, 1 mM EDTA). (Dissolved 10 mg TTHc in final volume of 10 ml buffer.)
3. Add sulfo-SIAB to TTHc using a 1:1 molar ratio of crosslinker to total Lys on carrier (32 Lys residues per TTHc): 1 mg/ml TTHc=19.2 uM×32 Lys residues=614.4 uM Lys (614 µl of 10 mM sulfo-SIAB mixed with 10 ml of 1 mg/ml TTHc)
4. Let reaction proceed at 25° C. (room temperature) for 1 hr.

5. At 4° C., pass through a 10 ml Zebra Spin Desalting Column, 7K MWCO (Thermofisher) to remove low molecular weight compounds.

Conjugation of Peptide to Activated Carrier:

1. Prepare a 12 mM stock of FP8 peptide. (Dissolved 10 mg of peptide in 1 ml of DMSO)
2. Allow activated TTHc carrier to warm up to 25° C. (room temperature). Gradually add peptide to activated carrier using a 1:1 (w/w) ratio [Added 1 mg of 12 mM peptide (100 l) to 1 mg activated TTHc protein (1 ml)]. Mix by inverting tube.
3. Spin for 2 min; use supernatant and discard precipitate.
4. Incubate reaction supernatant at 4° C. overnight.
5. Use a 10 ml Zebra Spin Desalting Column, 7K MWCO (Thermofisher) to remove low molecular weight compounds.
6. Dialyze conjugate against 1×PBS.
7. Analyze product: degree of conjugation by mass spectrometry and antigenic properties by Octet.

Following purification of the FP8-TTHc immunogens, antigenicity was assessed by binding to fusion peptide specific antibodies VRC34.01, VRC34.05, and PGT151. KD values (nM) are shown in the following table:

| | VRC34.01 | VRC34.05 | PGT151 |
|---|---|---|---|
| FP8-TTHc (MBS activation, 1:1 molar ratio*) | 0.3 | 1.3 | 2.3 |
| FP8-TTHc (sulfo-SIAB activation, 1:1 molar ratio) | 0.9 | 2.3 | 2.8 |
| FP8-TTHc (sulfo-SIAB activation, 0.5:1 molar ratio) | 1.0 | 3.0 | 3.6 |

(*ratio of crosslinker to Lys on carrier)

The conjugation protocol and chemistry illustrated in this example can readily be extended to other fusion peptide sequences and other carrier proteins.

Example 7. Immunogens for Eliciting an Immune Response to HIV-1 Env Fusion Peptide This example illustrates induction of an anit-HIV-1 Env fusion peptide immune response in Guinea pigs using several of the disclosed immunogens.

Figure 21D:
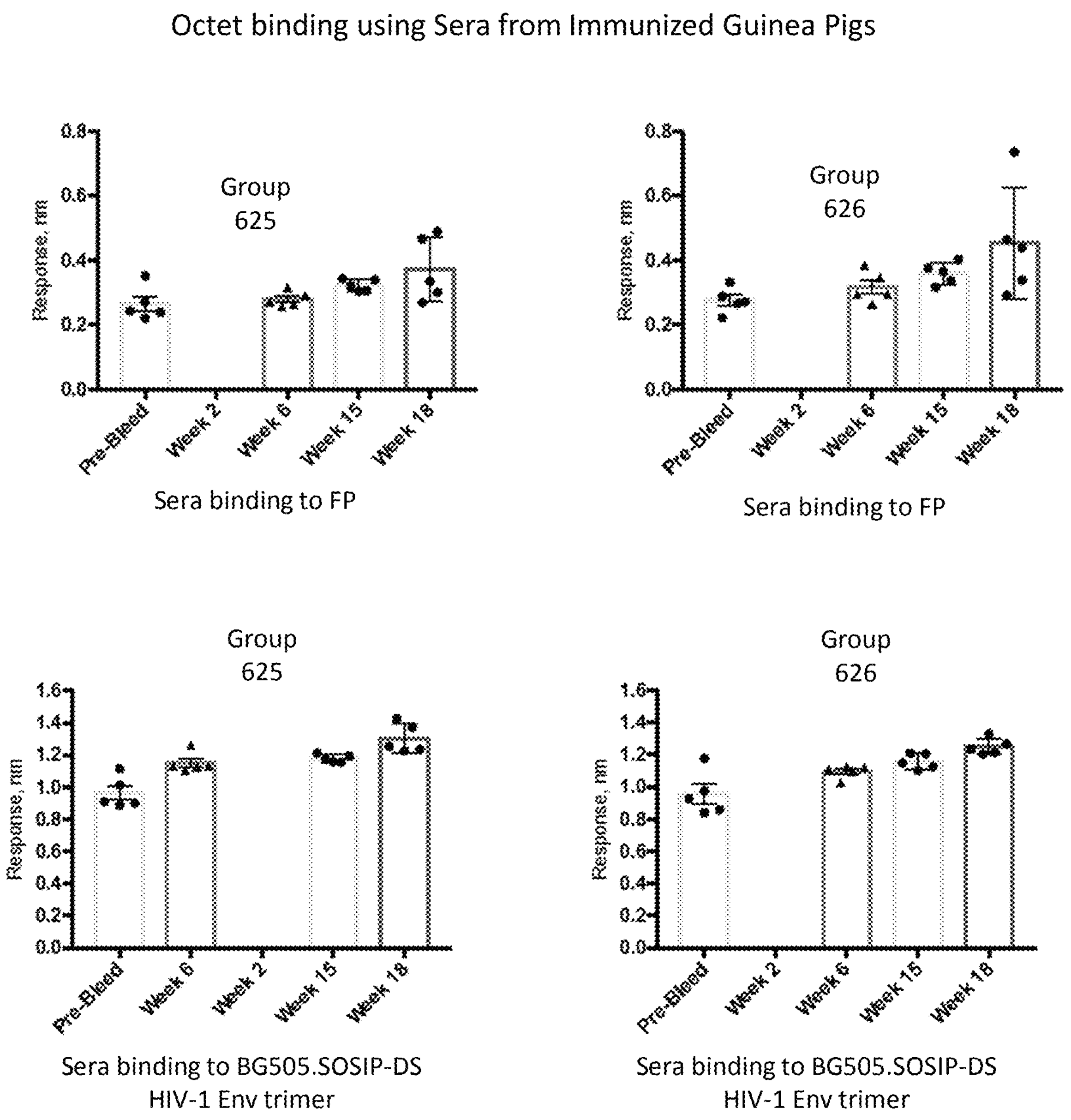

Two assays were performed each with three different immunization protocols (5 animals per group) were immunized at weeks 0, 4, 16, 28, 40, and 48, as shown in FIG. 21A. FP4, FP5, FP6, FP7, FP8 refer to peptides with the first 4, 5, 6, 7, or 8 amino acids of the HIV-1 Env fusion peptide (from the N-terminus) sequence set forth as AVGIGAVFLG (SEQ ID NO: 1). KLH refers to Keyhole Limpet Hemocyanin. Individual immunizations were performed with 25 g immunogen and ADJUPLEX™ as adjuvant.

Sera was collected from the immunized animals and assayed for neutralization of pseudotyped virus expressing HIV-1 Env proteins as indicated in FIGS. 21A and 21B. The assay results show that a neutralizing immune response was generated in each animal, and that boosting with a HIV-1 Env trimer enhances the immune response. Further analysis of the sera collected from these animals was done using Octet analysis of sera binding response to the FP8 fusion peptide (residues 1-8 of SEQ ID NO: 1) and the BG505.SOSIP-DS HIV-1 Env trimer (SEQ ID NO: 155). Sera were diluted 1:200 in 1% BSA, FP8 (His tag) was loaded at 50 μg/mL, and BG505.SOSIP-DS was loaded at 100 μg/mL. The results show that the binding response to FP8 was relatively low compared to the binding response to BG505.SOSIP-DS, indicating that the antibodies elicited by these immunization protocols preferentially bind to HIV-1 Env trimer over the isolated fusion peptide. Finally ELISA binding of diluted sera to FP8-1M6T epitope scaffold was performed to confirm that the elicited immune response targeted the fusion peptide. Immune sera collected at week 18 from all animals in Groups 625 and 626 bound to FP8-1M6T, but not corresponding scaffold protein without FP8. However, immune sera collected at weeks 2, 6, 15, and 18 from all animals in Group 611 bound poorly to FP8-1M6T, indicating that priming the immune response with HIV-1 Env trimer containing the delgy3 or delgy4 modification facilitated immune-focusing towards the fusion peptide.

It will be apparent that the precise details of the methods or compositions described may be varied or modified without departing from the spirit of the described embodiments. We claim all such modifications and variations that fall within the scope and spirit of the claims below.

It is claimed:

1. An immunogen, comprising a human immunodeficiency virus type 1 (HIV-1) Env fusion peptide conjugated to a carrier protein by a heterologous linker, wherein:

the HIV-1 Env fusion peptide consists of the amino acid sequence of AVGIGAV (residues 1-7 of SEQ ID NO: 1) or AVGIGAL (residues 1-7 of SEQ ID NO: 6); and the immunogen elicits a neutralizing immune response to HIV-1 in a subject.

2. The immunogen of claim 1, wherein the HIV-1 Env fusion peptide consists of the amino acid sequence of AVGIGAV (residues 1-7 of SEQ ID NO:

1).

3. The immunogen of claim 1, wherein the HIV-1 Env fusion peptide consists of the amino acid sequence of AVGIGAL (residues 1-7 of SEQ ID NO: 6).

4. The immunogen of claim 1, the HIV-1 Env fusion peptide is conjugated to the carrier by a linker between a lysine residue on the carrier and a heterologous cysteine residue fused to the C-terminal residue of the HIV-1 Env fusion peptide.

5. The immunogen of claim 4, wherein the average molar ratio of the HIV-1 Env fusion peptide to the carrier in the immunogenic conjugate is between about 1:1 and 1000:1.

6. The immunogen of claim 1, wherein the linker is a Sulfo-SIAB linker.

7. The immunogen of claim 1, wherein the carrier is a tetanus toxoid heavy chain C fragment.

8. The immunogen of claim 7, wherein the tetanus toxoid heavy chain C fragment comprises the amino acid sequence set forth as SEQ ID NO: 198.

9. The immunogen of claim 1, wherein the carrier is tetanus toxoid heavy chain C fragment comprising the amino acid sequence set forth as SEQ ID NO: 198, and the linker is a Sulfo-SIAB linker.

10. The immunogen of claim 1, wherein the carrier is a tetanus toxoid heavy chain C fragment;

the linker is a Sulfo-SIAB linker; and the HIV-1 Env fusion peptide is conjugated to the carrier by a linker between a lysine residue on the carrier and a heterologous cysteine residue fused to the C-terminal residue of the HIV-1 Env fusion peptide.

11. The immunogen of claim 1, wherein the immunogen specifically binds to a VRC34 antibody.

12. An immunogenic composition comprising the immunogen of claim 1, and a pharmaceutically acceptable carrier.

13. The immunogenic composition of claim 12, further comprising an adjuvant.

14. The immunogenic composition of claim 13, wherein the adjuvant is a saponin adjuvant or a carbomer-lecithin adjuvant.

15. A method for generating an immune response to HIV-1 in a subject, comprising administering to the subject an effective amount of the immunogen of claim 1 to generate the immune response.

16. The method of claim 15, wherein generating the immune response to HIV-1 in the subject comprises a prime-boost immunization comprising administering the immunogen to the subject one or more times followed by administering a soluble HIV-1 envelope trimer to the subject one or more times.

17. The method of claim 15, wherein the soluble HIV-1 envelope trimer is stabilized in a prefusion conformation by one or more amino acid substitutions.

18. The method of claim 15, wherein the soluble HIV-1 envelope trimer comprises one or more amino acid substitutions to remove an N-linked glycan sequon at one or more of HXB2 positions N88, N230, N241, and N611.

19. The method of claim 15, wherein the immune response treats or inhibits HIV-1 infection in the subject.

20. The method of claim 15, wherein the immune response inhibits HIV-1 replication in the subject.

* * * * *